(12) United States Patent  
Marshall et al.

(10) Patent No.: US 9,964,538 B2
(45) Date of Patent: May 8, 2018

(54) METHODS AND COMPOSITIONS FOR ENZYME LINKED IMMUNO AND HYBRIDIZATION MASS SPECTROMETRIC ASSAY

(71) Applicant: YYZ Pharmatech, Inc., Toronto (CA)

(72) Inventors: John G. Marshall, Toronto (CA); Angelica Kirsten Florentinus, Richmond Hill (CA)

(73) Assignee: YYZ Pharmatech, Inc., Toronto (CA)

( * ) Notice: Subject to any disclaimer, the term of this patent is extended or adjusted under 35 U.S.C. 154(b) by 104 days.

(21) Appl. No.: 14/947,696

(22) Filed: Nov. 20, 2015

(65) Prior Publication Data

US 2016/0223530 A1 Aug. 4, 2016

Related U.S. Application Data

(63) Continuation of application No. PCT/CA2014/000454, filed on May 23, 2014.
(Continued)

(51) Int. Cl.
*G01N 33/543* (2006.01)
*G01N 30/72* (2006.01)
(Continued)

(52) U.S. Cl.
CPC ....... *G01N 33/54306* (2013.01); *G01N 30/72* (2013.01); *G01N 33/543* (2013.01);
(Continued)

(58) Field of Classification Search
None
See application file for complete search history.

(56) References Cited

U.S. PATENT DOCUMENTS 7,108,974 B2 9/2006 Ecker et al.
7,217,510 B2 5/2007 Ecker et al.
(Continued)

FOREIGN PATENT DOCUMENTS

CA 2107113 A1 9/1992
CA 2311502 A1 6/1999

OTHER PUBLICATIONS

Bowden, Peter et al. Quantitative Statistical Analysis of Standard and Human Blood Proteins from Liquid Chromatography, Electrospray Ionization, and Tandem Mass Spectrometry. Journal of proteome research. American Chemical Society. Apr. 6, 2012, vol. 11, No. 4, pp. 2032-2047.
(Continued)

*Primary Examiner* — Changhwa J Cheu
(74) *Attorney, Agent, or Firm* — Bereskin & Parr LLP; Carmela De Luca

(57) ABSTRACT

Disclosed are sensitive methods for detecting a target substance in low concentrations. The method can include immobilizing a target substance to a solid phase; incubating the immobilized target substance with a reporter enzyme detection probe in solution under conditions for forming target: enzyme detection probe complexes; washing the solid phase to remove any unbound reporter enzyme detection probe; incubating the target: enzyme detection probe complex with a reporter enzyme detection probe substrate in substrate reaction solution to generate one or more ionizable products; and detecting one or more of the one or more ionizable products using mass spectrometry (MS).

28 Claims, 79 Drawing Sheets

Related U.S. Application Data

(60) Provisional application No. 61/826,796, filed on May 23, 2013.

(51) Int. Cl.
*G01N 33/58* (2006.01)
*G01N 33/68* (2006.01)

(52) U.S. Cl.
CPC ....... *G01N 33/581* (2013.01); *G01N 33/6848* (2013.01); *G01N 2560/00* (2013.01)

(56) References Cited

U.S. PATENT DOCUMENTS

| | | |
|---|---|---|
| 7,226,739 B2 | 6/2007 | Ecker et al. |
| 7,255,992 B2 | 8/2007 | Ecker et al. |
| 7,339,051 B2 | 3/2008 | Crooke et al. |
| 7,666,588 B2 | 2/2010 | Ecker et al. |
| 7,666,592 B2 | 2/2010 | Ecker et al. |
| 7,718,354 B2 | 5/2010 | Ecker et al. |
| 7,741,036 B2 | 6/2010 | Ecker et al. |
| 7,781,162 B2 | 8/2010 | Ecker et al. |
| 7,956,175 B2 | 6/2011 | Sampath et al. |
| 8,013,142 B2 | 9/2011 | Sampath et al. |
| 8,017,322 B2 | 9/2011 | Ecker et al. |
| 8,017,358 B2 | 9/2011 | Ecker et al. |
| 8,017,743 B2 | 9/2011 | Ecker et al. |
| 8,026,084 B2 | 9/2011 | Ecker et al. |
| 8,046,171 B2 | 10/2011 | Ecker et al. |
| 8,057,993 B2 | 11/2011 | Ecker et al. |
| 8,071,309 B2 | 12/2011 | Ecker et al. |
| 8,073,627 B2 | 12/2011 | Ecker et al. |
| 8,088,582 B2 | 1/2012 | Sampath et al. |
| 8,163,895 B2 | 4/2012 | Sampath et al. |
| 8,187,814 B2 | 5/2012 | Ecker et al. |
| 8,198,407 B1 | 6/2012 | Burton et al. |
| 8,206,901 B2 | 6/2012 | Freskgard et al. |
| 8,214,154 B2 | 7/2012 | Ecker et al. |
| 8,242,254 B2 | 8/2012 | Sampath et al. |
| 8,265,878 B2 | 9/2012 | Ecker et al. |
| 8,268,565 B2 | 9/2012 | Ecker et al. |
| 8,288,523 B2 | 10/2012 | Sampath et al. |
| 8,298,760 B2 | 10/2012 | Ecker et al. |
| 8,380,442 B2 | 2/2013 | Ecker et al. |
| 8,394,945 B2 | 3/2013 | Sampath et al. |
| 8,407,010 B2 | 3/2013 | Hofstadler et al. |
| 8,465,951 B2 | 6/2013 | Rao et al. |
| 8,551,738 B2 | 10/2013 | Ecker et al. |
| 8,563,250 B2 | 10/2013 | Ecker et al. |
| 8,722,583 B2 | 5/2014 | Gouliaev et al. |
| 8,802,372 B2 | 8/2014 | Ecker et al. |
| 8,808,984 B2 | 8/2014 | Pedersen et al. |
| 8,815,513 B2 | 8/2014 | Ecker et al. |
| 8,822,156 B2 | 9/2014 | Ecker et al. |
| 8,921,047 B2 | 12/2014 | Ecker et al. |
| 9,109,248 B2 | 8/2015 | Freskgard et al. |
| 9,121,110 B2 | 9/2015 | Gouliaev et al. |
| 9,149,473 B2 | 10/2015 | Ecker et al. |
| 9,284,600 B2 | 3/2016 | Freskgard et al. |
| 2012/0309636 A1 | 12/2012 | Gibbons et al. |
| 2013/0095502 A1* | 4/2013 | Tao ............ G01N 33/587 435/7.4 |

OTHER PUBLICATIONS

Florentinus, Angelica K. et al. The Fc receptor-cytoskeleton complex from human neutrophils. Journal of Proteomics 75, 2011, pp. 450-468.

Florentinus, Angelica K. et al. Identification and quantification of peptides and proteins secreted from prostate epithelial cells by unbiased liquid chromatography tandem mass spectrometry using goodness of fit and analysis of variance. Journal of Proteomics 75, 2012, pp. 1303-1317.

Hempen, Christel et al. Liquid chromatographic/mass spectrometric investigation on the reaction products in the peroxidase-catalyzed oxidation of o-phenylenediamine by hydrogen peroxide. Anal Bioanal Chem, 2005, vol. 382, pp. 234-238.

Pris, Andrew D., et al. Improved Specific Biodetection with Ion Trap Mobility Spectrometry (ITMS): A 10-min, Multiplexed, Immunomagnetic ELISA. Anal. Chem., 2009, vol. 81, pp. 9948-9954.

Florentinus-Mefailoski, Angelique, et al. Enzyme Linked Immuno Mass Spectrometric Assay (ELIMSA). Journal of Proteomics 96, 2014, pp. 343-352.

\* cited by examiner

A

AS-MX Naphthol phosphate

AP

+

| PSA (ng/100ul) | std | Sample 1-8 | Sample 9-16 | Sample 17-24 | Sample 25-30 |
|---|---|---|---|---|---|
| 0 | 0.065 | 0.055 | 0.057 | 0.079 | 0.168 |
| 0.1 | 0.066 | 0.057 | 0.084 | 0.092 | 0.188 |
| 0.5 | 0.067 | 0.055 | 0.072 | 0.083 | 0.182 |
| 1 | 0.068 | 0.055 | 0.085 | 0.098 | 0.192 |
| 2.5 | 0.164 | 0.054 | 0.072 | 0.116 | 0.22 |
| 5 | 0.216 | 0.058 | 0.077 | 0.149 | 0.222 |
| 7.5 | 0.281 | 0.055 | 0.076 | 0.133 | |
| 10 | 0.309 | 0.06 | 0.089 | 0.138 | | para-nitrophenyl phosphate (pNPP)

4-Nitrophenol

+

A

B

C

MS

MS/MS

Phosphotyrosine 17 and 18 with enzyme AP. MW of T17 = 1518.7 , MW of pT18 = 1463.7

METHODS AND COMPOSITIONS FOR ENZYME LINKED IMMUNO AND HYBRIDIZATION MASS SPECTROMETRIC ASSAY

RELATED APPLICATIONS

This is a continuation application of International Application No. PCT/CA2014/000454, filed on May 23, 2014, and claims the benefit of 35 U.S.C. § 119 and/or 120 based on the priority of U.S. Provisional Patent Application No. 61/826,796, filed May 23, 2013 each of these applications being incorporated herein by reference in their entirety.

INCORPORATION OF SEQUENCE LISTING

A computer readable form of the Sequence Listing "P43997US01_SL.txt" (8,192 bytes), submitted via EFS-WEB and created on Nov. 20, 2015, is herein incorporated by reference.

FIELD

The disclosure pertains to a sensitive method of measuring the amount of a target substance and particularly to a method of measuring the amount of a target substance using immunological method and a MS method.

BACKGROUND

ELISA

ELISA is a specific and sensitive method for quantifying proteins and detecting particular antigens or antibodies in solutions [2, 3]. ELISA is typically performed in 96-well polystyrene plates and consists of the stepwise binding of capture antibodies, the target analyte and detection antibodies with washing steps to separate bound and free sample components and incubation in an enzyme reaction buffer (e.g. substrate reaction solution) to create a detectable product in the soluble phase [15]. The most commonly used reporter enzyme are horseradish peroxidase HRP and alkaline phosphatase (AP) [2, 3]. A large selection of substrates are available including chromogenic, fluorescent and chemiluminescent compounds [15]. Complete ELISA kits are also commercially available for detection of specific cytokines and other targets. Reporter enzyme such as AP and HRP can be covalently attached to streptavidin [16] that binds with a high affinity to biotin which can be covalently attached to the detection antibody using NHS coupling [17]. The detection limits for ELISAs are usually in the lower nanogram (ng) range.

RIA

In a related method termed radio immunometric assay (RIA), the capture antibody may be saturated with a radioactive analyte that is displaced by the sample analyte and the released radioactivity measured from the liquid phase [18]. At present the RIA is a most sensitive technology for detecting well characterized molecules but requires the use of radioisotopes that increase the administrative burden and cost of performing assays while limiting their broad application. RIA can reach sensitivities limited only by the background radioactivity and can commonly reach pico mol and even as low as femto mol levels.

LC-MS/MS

Many compounds may enter the gas phase by electrospray ionization [19]. Where pure compounds are available, the direct use of mass spectrometry may reach the atto mol levels [20, 21]. For complex biological samples, detection of the parent ions by SIM, or of the fragment ions by SRM, has been shown to provide sensitivity as low as ng/ml [22, 23]. However most of the protein assays by SRM are of relatively high abundance in the micrograms per ml (µg/ml) [24] well above the concentrations typically reached by ELISA with ECL or colorimetric detection and the SRM method frequently suffers a lack of sensitivity in complex samples [25]. A liquid chromatography column coupled to an electrospray source or nanospray source or MALDI source for a tandem mass spectrometer can directly measure ionized peptides or small molecules with a sensitivity of about 1 µg or less in the low femto mol to pico mol range depending on the molecule [26].

There remains a need to measure molecules such as proteins that are present in low concentrations below those detectable by enzyme linked Immuno absorbent assays (ELISA).

SUMMARY

An aspect of the disclosure includes a method of detecting a target substance comprising the steps: immobilizing the target substance to a solid phase; incubating the immobilized target substance with a reporter enzyme detection probe in solution under conditions for forming target: enzyme detection probe complexes; washing the solid phase to remove any unbound reporter enzyme detection probe; incubating the target: enzyme detection probe complex with a reporter enzyme detection probe substrate in substrate reaction solution to generate one or more ionizable products; and detecting one or more of the one or more ionizable products using mass spectrometry (MS).

In an embodiment, the target substance is immobilized by directly binding the solid phase, optionally by adsorption to the solid phase. In another embodiment, the target substance is immobilized to the solid phase indirectly by a capture molecule, optionally a capture antibody or binding fragment thereof, coupled to the solid phase that specifically binds the target substance. In a further embodiment, the solid phase is a reaction vessel, optionally a bead or plate, optionally having a polystyrene surface.

In some embodiments, the step of incubating the immobilized target substance with a reporter enzyme detection probe is preceded by incubating the immobilized target substance with a primary detection agent specific for the immobilized target substance prior to incubating with the reporter enzyme detection probe to form the target: enzyme detection probe complex. In this embodiment, the target: enzyme detection probe complex comprises 1) target substance which is immobilized to the solid phase, 2) primary detection agent specific for the immobilized target substance and 3) reporter enzyme detection probe, wherein the detection probe moiety of the reporter enzyme detection probe optionally comprises a secondary target binding moiety that is specific for the primary detection agent. In such embodiments, the reporter enzyme detection probe indirectly binds the immobilized target substance through the primary detection agent.

In an embodiment, the one or more ionizable products are separated prior to detection using mass spectrometry (MS). In another embodiment, the separation is by liquid chromatography, optionally isocratic normal phase chromatography. In yet another embodiment, the liquid chromatography is high-performance liquid chromatography (HPLC). In an embodiment, the HPLC is nanoflow liquid chromatography. In another embodiment, the HPLC can be reverse phase HPLC, ion exchange HPLC or normal phase HPLC. The chromatography mobile phase can for example be isopropyl alcohol (IPA), methanol, ethanol, propanol, or acetonitrile. The stationary phase can for example be silica based or polymer based, for example silica particles modified with octadecyl carbon chain (C18).

In an embodiment, the step of detecting the one or more ionizable products using MS comprises ionizing the one or more ionizable products, optionally by electrospray ionization (ESI) to produce one or more product ions with a selected signal to noise ratio, and subjecting the one or more product ions to MS optionally tandem MS (MS/MS). In another embodiment, the ionizing is positive ionization (e.g. using an acidic buffer in the mobile phase). In another embodiment, the ionizing is negative ionization (e.g using a basic buffer in the mobile phase). In an embodiment, ionizing the one or more ionizable products comprises Matrix-assisted laser desorption/ionization (MALDI).

In yet another embodiment, the MS is selected from electrospray ionization tandem MS (ESI-MS/MS) and MALDI-time of flight (MALDI-TOF) MS.

In another embodiment, the selected signal to noise ratio is at least 4, at least 5, at least 6, at least 10.

In a further embodiment, detection using MS comprises recording product ion intensity by single ion monitoring (SIM) and/or product ion parent to fragment transition by single reagent monitoring (SRM). In an embodiment, the product ion is assayed by SIM and/or SRM using an optimized fragmentation energy and m/z range.

In an embodiment, the reporter enzyme detection probe comprises a primary target binding moiety (e.g. for direct target substance binding) or a secondary target binding moiety (e.g. for indirect target substance binding) and a reporter enzyme comprising enzymatic activity, wherein the target binding moiety is covalently bound to the reporter enzyme.

In another embodiment, the reporter enzyme comprises lyase, hydrolase, synthase, synthetase, oxidoreductase, dehydrogenase, oxidase, transferease, isomerase, ligase, protease, such as trypsin, proteinase, peroxidase, glucose oxidase, myeloperoxidase, oxidase, monooxygenase, cytochrome, alkaline phosphatase, decarboxylase, lipase, caspase, amylase, peptidase, transaminase, and/or kinase activity. In another embodiment, the reporter enyme is selected from DNA or RNA polymerase, TAQ, restriction enzymes, klenow fragment and DNA ligase.

In an embodiment, the primary target binding moiety that binds specifically to the target substance is an antibody or a binding fragment thereof. In another embodiment, the secondary target binding moiety that binds specifically to the primary detection agent comprises avidin or streptavidin or is an antibody or binding fragment thereof specific for a primary detection agent specific for the immobilized target substance.

In some embodiments, the primary detection agent comprises biotin conjugated to an antibody or binding fragments thereof specific for the immobilized target substance.

In an embodiment, any of the antibodies described may be a monoclonal antibody, polyclonal antibody, chimeric antibody, and/or monospecific antibody.

In an embodiment, the reporter enzyme is horseradish peroxidase or alkaline phosphatase.

In another embodiment is provided a method wherein the substrate is readily ionizable under ESI-MS/MS or MALDI-TOF and generates a product ion characterized by a high signal to noise ratio, and the substrate is optionally selected from:

a. a compound selected from phenols, amines, optionally phenolic amines, amides, aromatic compounds, olefin halogenations, luminol, pyrogallol, ABTS, Amplex® Red when the reporter enzyme is HRP, b. a phosphorylated nucleotide, phosphorylated alkaloid, phosphorylated amino acid, phosphorylated amino acid polymer, and phosphorylated metabolite when the enzyme is AP; or c. opiates, detergents, dye precursor, alcohols, matrix, when the substrate is HRP or AP.

$H_2O_2$ or other oxidizer is added with the substrate when HRP is employed.

In an embodiment the substrate is selected from pyridoxamine-5-phosphate (PA5P), p-nitrophenyl phosphate (PNPP), Amplex® Red (AR), naphthol ASMX phosphate, luminol, Lumigen® TMA3, Lumigen® TMA6, sphingosine, 4MUP (4-Methylumbelliferyl phosphate), L-(+)-2-amino-6-phosphonohexanoic acid, BCIP (5-bromo-4-chloro-3-indolyl phosphate) (e.g. BluePhos®), and/or phenylbenzene ω phosphono-α-amino O-phospho-DL-threonine. In another embodiment, the substrate is selected from a nucleoside monophosphate such as AMP, CMP, GMP, TMP, UMP; a nucleoside diphosphate such as ADP, CDP, GMP, TDP, UDP; a nucleoside triphosphate, such as ATP, CTP, GTP, TTP, UTP; a phospho-ribose; and an anhydride, such as nucelotide diphosphates or triphosphates.

In another embodiment, the substrate is selected from:

a. AR, luminol, Lumigen® TMA3, Lumigen® TMA6 when the reporter enzyme detection probe comprises HRP; or b. PA5P, AMP, CMP, ATP, CTP, naphthol ASMX phosphate, 4MUP, phosphosphingosine, Phenylbenzene ω phosphono-α-amino acid or PNPP when the reporter enzyme detection probe comprises AP.

In an embodiment the substrate is selected from AMP, CMP, PA5P, naphthol ASMX phosphate, and PNPP when the reporter enzyme detection probe comprises AP.

In another embodiment, the substrate is selected from AR and Lumigen® TMA3.

In a further embodiment, the substrate reaction solution comprises Tris buffer, having a pH optionally of about 7 to about 10, optionally about 8.8.

In another embodiment, the substrate reaction solution comprises a detergent, optionally deoxycholate. All washes after sample incubation, the detection probe incubation solution and the reporter enzyme incubation solution can include deoxycholate. Typically the substrate reaction solution does not include deoxycholate.

In an embodiment, the substrate reaction solution further comprises 4-iodophenylboronic acid when the substrate reaction product is luminescent e.g. comprises luminol or other enhanced chemiluminescent (ECL) substrate. For example, HRP catalyses the oxidation of luminol to 3-aminophthalate via several intermediates. In an embodiment, the substrate reaction solution comprises $H_2O_2$ when the reporter enzyme detection probe comprises HRP.

In an embodiment, the step of immobilizing the test substance comprises: coupling a capture molecule to the solid phase by incubating the solid phase with the capture molecule in coating solution, blocking the solid phase with blocking solution, adding the target substance to the solid phase in antigen incubation solution and removing any unbound target substance.

In another embodiment, the step of incubating the immobilized target substance with a reporter enzyme detection probe in solution under conditions for forming target: enzyme detection probe complexes comprises: incubating the immobilized target substance with primary detection agent and/or reporter enzyme detection probe in detection probe incubation solution. In an embodiment, he detection probe incubation solution, which can be used with the primary detection agent (e.g. the capture antibody) and/or the reporter enzyme detection probe comprises (e.g. SA-AP or SA-HRP), comprises 1×PBS+0.05% Na-deoxycholate.

In an embodiment, the capture molecule is coupled to the solid phase in a coating solution optionally comprising a carbonate, Tris, tricine, or methylamine buffer, optionally $Na_2CO_3/NaCHO_3$ buffer.

In another embodiment, the target: enzyme detection probe complex is incubated with a reporter enzyme detection probe substrate in substrate reaction solution to generate one or more ionizable products for a period of time less than 60 minutes, less than 50 minutes, less than 40 minutes, less than 30 minutes, less than 20 minutes, less than 15 minutes, less than 10 minutes, less than 5 minutes, less than 2 minutes, or less than 1 minute.

In one embodiment, the substrate is AR and one of the one or more ionizable products generated comprises resorufin, the product ion of which is assayed by SIM at 214 m/z and SRM using the major intense fragment at 214-186 m/z.

In another embodiment, the substrate is naphthol ASMX phosphate and one of the one or more ionizable products generated comprises dephosphorylated naphthol ASMX, the product ion of which is assayed by SIM at 292 m/z and SRM using the major intense fragment at 292-171 m/z.

In an embodiment, the ionizable products are ionized to product ions in ionization solution.

Another aspect provides a method of quantifying the amount of a target substance in a sample comprising the steps:

a. detecting a target substance according to the method of claim 1; and b. quantifying the amount of target substance in the sample based on the intensity of the signal for one or more of the products detected by mass spectrometry.

In one embodiment, the quantification comprises comparing the intensity of the signal for one or more products against signal intensities generated using a known quantity (e.g. standard) and/or quantities (e.g. standard curve) of target substance, under similar conditions.

In an embodiment, the intensity of the signal for one or more product is compared to an internal standard. In an embodiment, the intensity of the signal for one or more product is compared to an external standard.

In an embodiment, the internal standard comprises an isotope dilution curve or an internal one point calibration. In an embodiment, the external standard is a target substance standard curve.

In an embodiment, the quantification comprises log transforming the standard curve signal intensities.

In another embodiment, the target substance is present in the sample in at least a pico mol, femto mol, atto mol, zepto mol or yocto mol range.

In a further embodiment, the sample is a biological sample, industrial product or environmental sample. In yet another embodiment, the biological sample is a blood sample, urine sample, fecal sample, effusate or tissue sample.

In an embodiment, the target substance is a polypeptide selected from a tumour marker, autoantigen, hormone, chemokine, cytokine, cardiac protein. In another embodiment, the target substance is a microorganism, optionally a bacteria, optionally an *E. Coli* species, *Salmonella* species, *Pseudomonas* species, or *anthrax* species.

In an embodiment, the tumour marker is prostate specific antigen (PSA). In another embodiment, the cardiac protein is Troponin T.

In another aspect, the disclosure provides a method for detecting and/or quantifying a target substance in sample comprising:

a. contacting a sample comprising the target substance with an immobilized antibody specific for target substance;

b. contacting the immobilized target substance with a reporter enzyme detection probe, wherein the reporter enzyme detection probe has enzyme activity and wherein the reporter enzyme detection probe is able to bind specifically to the immobilized target substance or a primary detection agent specifically bound to the target substance;

c. contacting the immobilized reporter enzyme detection probe with a substrate which reacts with the enzymatic activity of the reporter enzyme detection probe to generate one or more ionizable products for a period of time; and d. detecting one or more of the products using mass spectrometry (MS).

In yet another aspect, the disclosure provides a method of screening a substrate that will generate one or more products after reaction with a reporter enzyme, wherein one or more of the products have a low limit of detection (LOD) and low limit of quantification (LOQ) when detected using mass spectrometry, comprising the steps:

a. contacting substrate with known quantities of a reporter enzyme to generate one or more products;

b. separating the products; and c. analyzing the products using mass spectrometry to measure the LOD and the LOQ.

Yet another aspect relates to a kit comprising a reporter enzyme detection probe comprising an enzyme and a target binding moiety and one or more of: a substrate, solid phase, a standard, optionally a product ion standard, optionally for preparing a standard curve or tuning, coating solution, blocking solution, antigen incubation solution, detection probe incubation solution, substrate reaction solution, quenching solution, ionization solution.

In an embodiment, the quenching solution comprises acetonitrile, methanol, ethanol, isopropanol, acetic acid, formic acid, tri-fluoroacetic acid for positive ionization or ammonium hydroxide, methylamine, ethylamine for negative ionization. In an embodiment, the quenching solution comprises 50% Acetonitrile, 0.1% Acetic acid or 0.1% formic acid or 0.1% trifluoroacetic acid for positive ionization or 0.1% ammonium hydroxide for negative ionization.

In an embodiment, the target substance is a biopolymer, optionally a polypeptide, for example a polypeptide from a body fluid, tissue or cell, optionally a diagnostic polypeptide, selected from a tumour marker, autoantigen, hormone, chemokine, cytokine, cardiac protein. The biopolymer can alternatively be a nucleic acid molecule, lipid, or carbohydrate.

In another embodiment, the target substance is a microorganism, optionally a bacteria, optionally an *E. Coli* species, *Salmonella* species, *Pseudomonas* species, or *anthrax* species.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which:

FIG. 3.2.5: The MS spectra for TMA-3 product represented by the m/z 286.21 at ~18.60 min. The MS was generated by scanning from 200.00-550.00 m/z. This 286.21 m/z peak had an ion intensity of 4.50×104.

Figure 29:
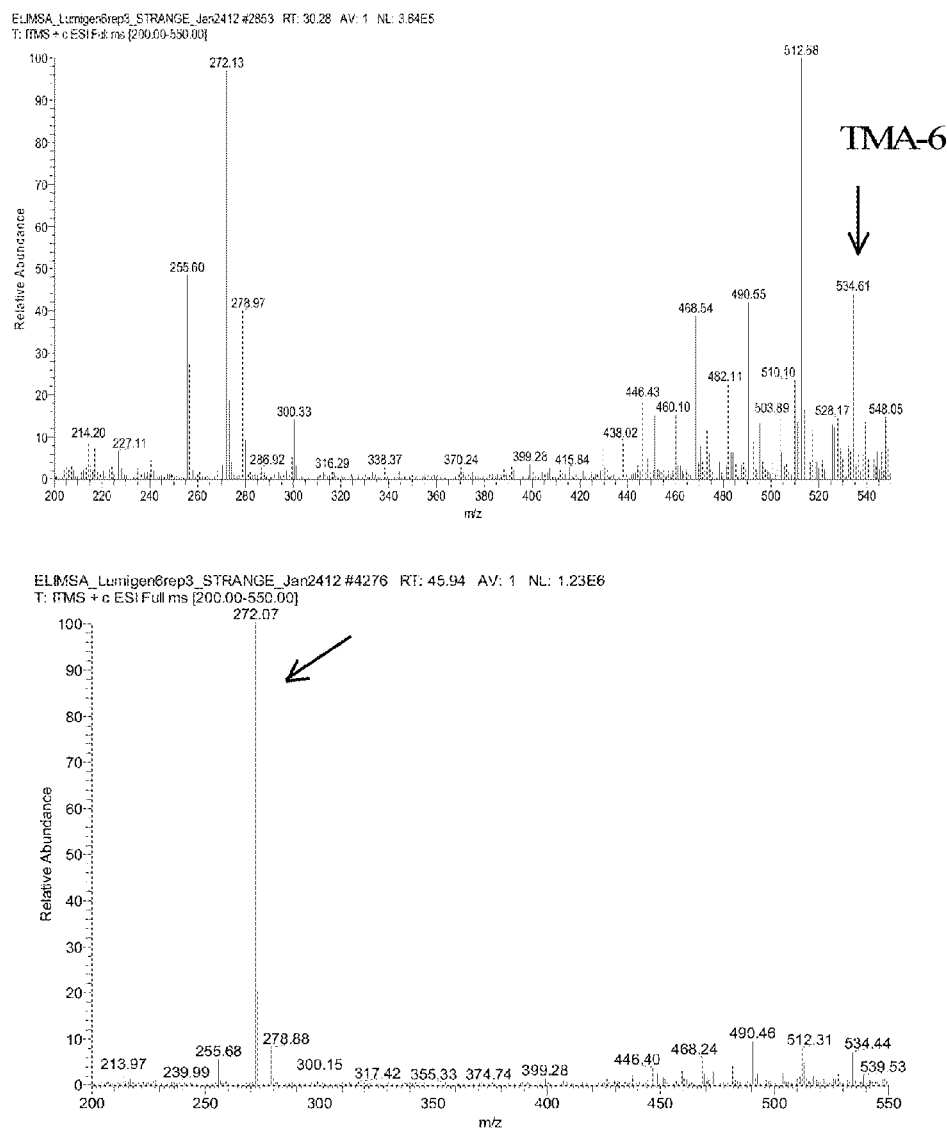

FIG. 29: The MS spectra for TMA-6 (m/z 534.61) scanned in the range 200-550 m/z. The ion intensity of the 534.61 m/z peak was 1.60×105. The MS spectra for TMA-6 product represented by the m/z 272.21 at ~14.37 min. z peak had an ion intensity of 3.86×E5.

Figure 30:
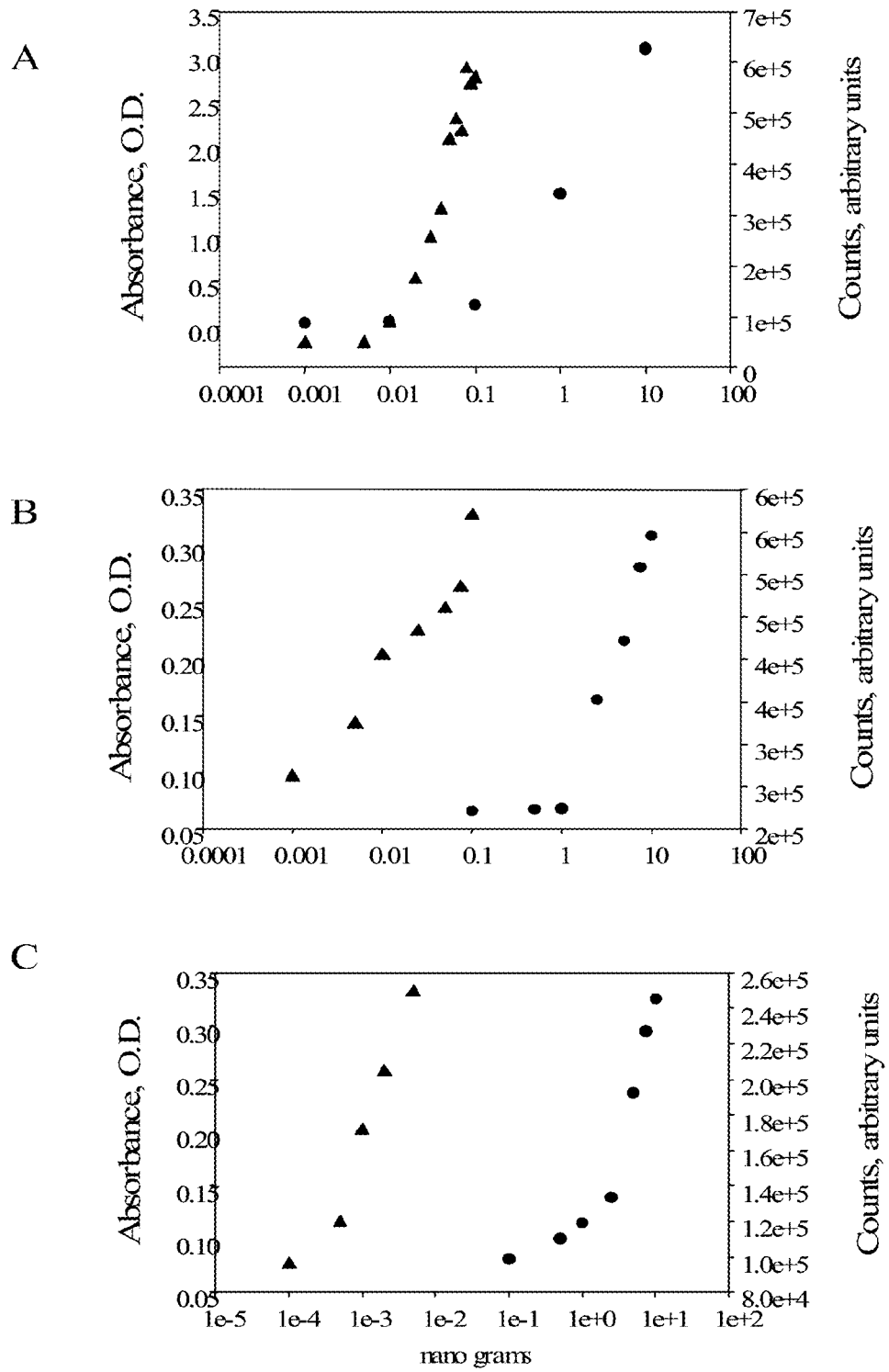

FIG. 30: The log protein comparison of the sensitivity of PSA ELIMSA (▲) verses colorimetric ELISA (●). Panels: A, Amplex® Red substrate; B, Blue Phos substrate verses Naphthol ASMX phosphate; C, PNPP (para nitrophenol phosphate).

Figure 31A:
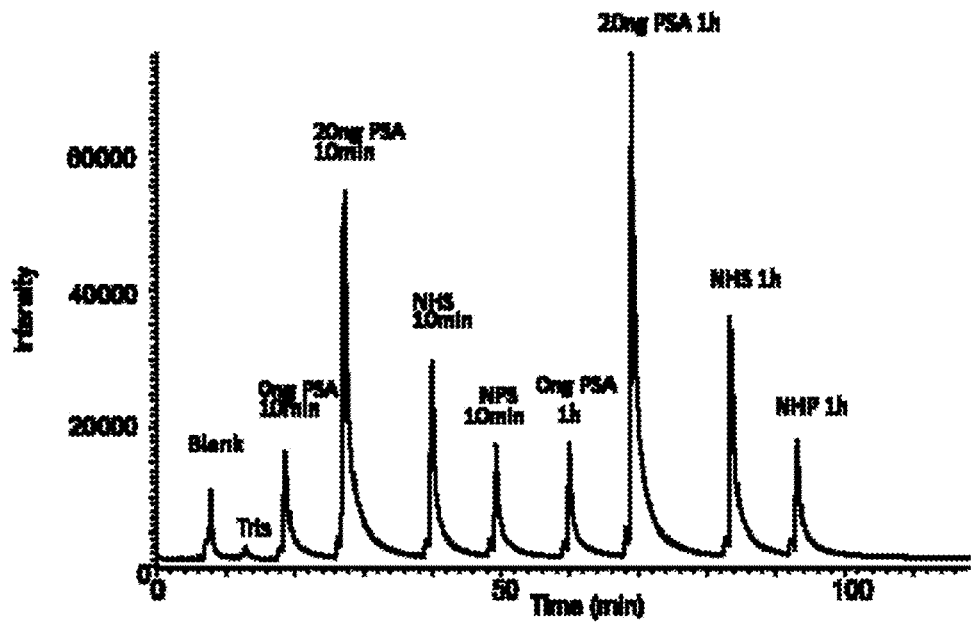

FIG. 31A: Lumigen® ELIMSA using Lumigen® TMA3 as the substrate. Two PSA standards (0 and 20 ng) and two samples (serum and plasma from human male blood) were incubated with Lumigen® TMA3 for 10 minutes and 1 hour and quenched in 0.1% Formic acid and diluted 20 fold. 20 ul of the diluted samples was injected at 20 ul/min onto a normal phase column isocratically in 70% Acetonitrile with 0.1% Acetic acid with SIM286.

Figure 31B:
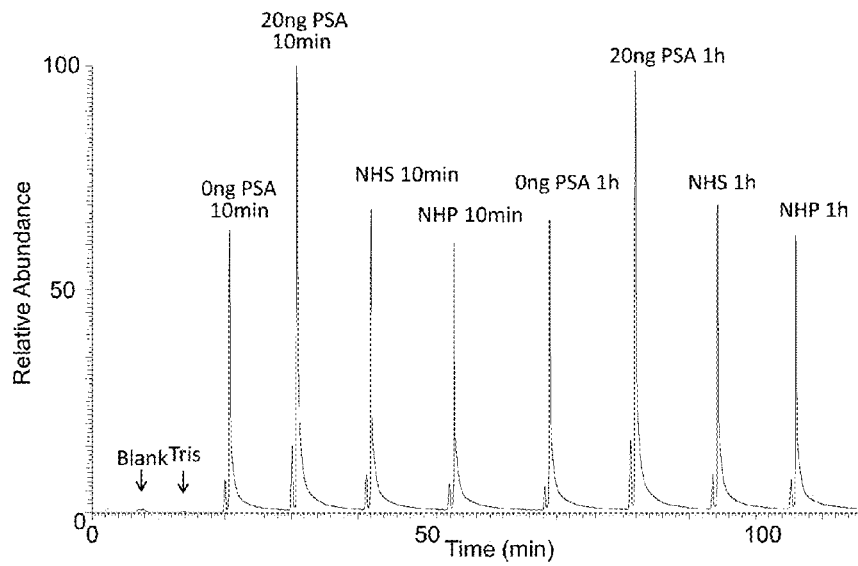

FIG. 31B: Lumigen® ELIMSA using Lumigen® TMA6 as the substrate. Two PSA standards (0 and 20 ng) and two samples (serum and plasma from human male blood) were incubated with Lumigen® TMA6 for 10 minutes and 1 hour and quenched in 0.1% Formic acid and diluted 20 fold. 20 ul of the diluted samples was injected at 20 ul/min onto a normal phase column isocratically in 70% Acetonitrile with 0.1% Acetic acid with SIM272.

Figure 32A:
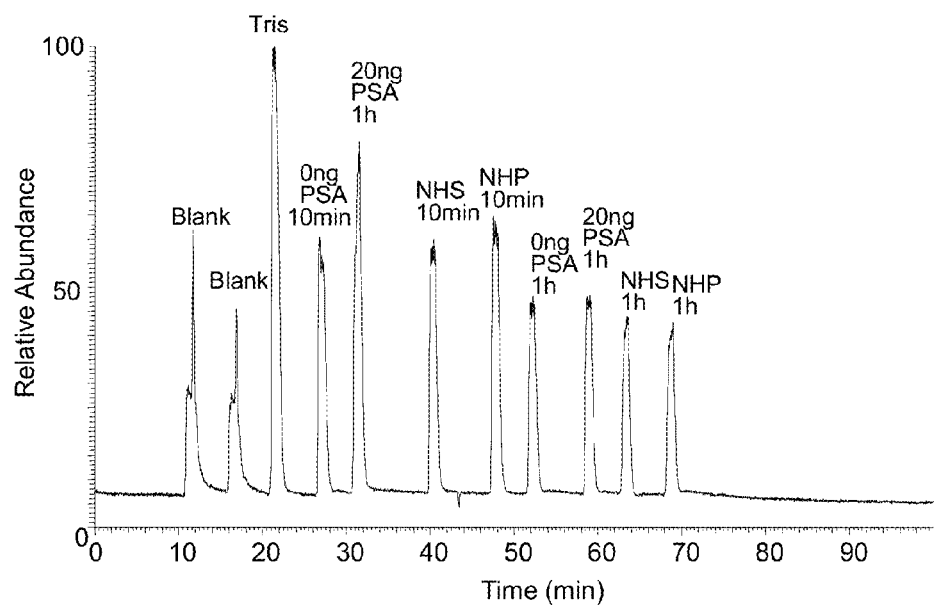

FIG. 32A: ELIMSA using Sphingosine-1-phosphate as the substrate. Two PSA standards (0 and 20 ng) and two samples (serum and plasma from human male blood) were incubated with Sphingosine-1-phosphate for 10 minutes and 1 hour and quenched in 0.1% Formic acid and diluted 20 fold. 20 ul of the diluted samples was injected at 20 ul/min onto a normal phase column isocratically in 70% Acetonitrile with 0.1% Acetic acid with SIM298.

Figure 32B:
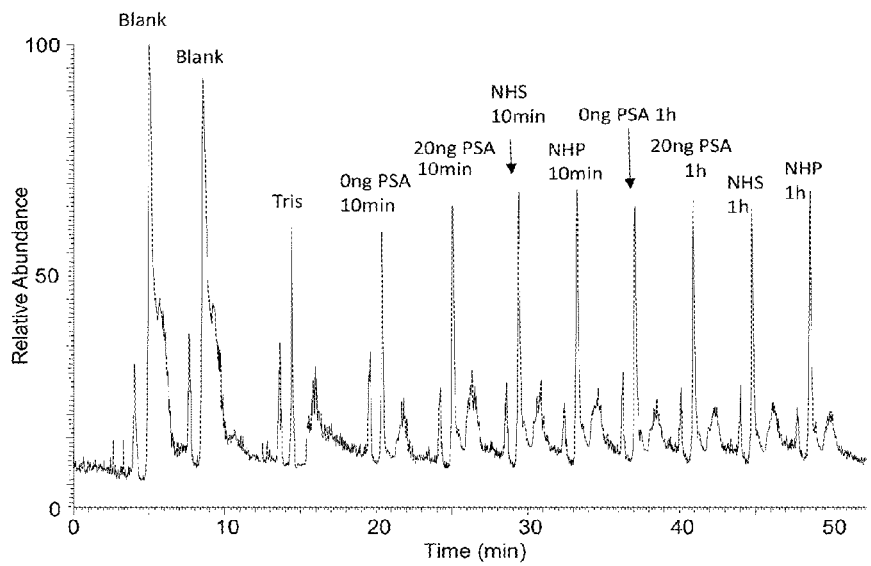

FIG. 32B: ELIMSA using Sphingosine-1-phosphate as the substrate. Two PSA standards (0 and 20 ng) and two samples (serum and plasma from human male blood) were incubated with Sphingosine-1-phosphate for 10 minutes and 1 hour and quenched in 0.1% Formic acid and diluted 20 fold. 20 ul of the diluted samples was injected at 20 ul/min onto a normal phase column isocratically in 70% Acetonitrile with 0.1% Acetic acid with SIM200

Figure 32C:
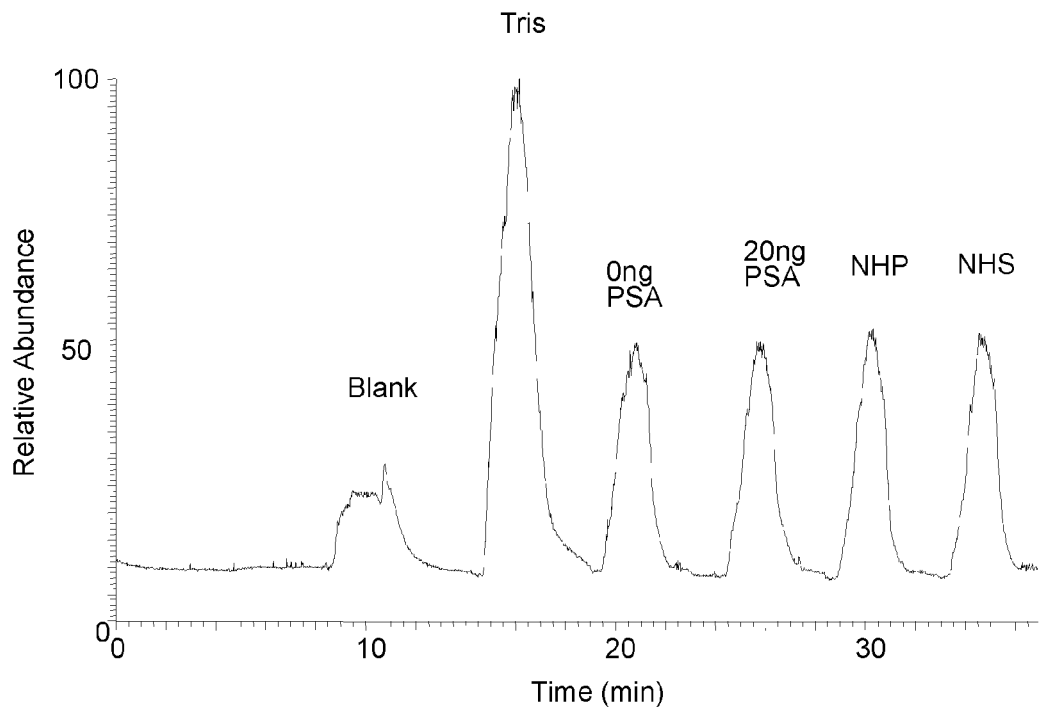

FIG. 32C: ELIMSA using Sphingosine-1-phosphate as the substrate. Two PSA standards (0 and 20 ng) and two samples (serum and plasma from human male blood) were incubated with Sphingosine-1-phosphate for 10 minutes and 1 hour and quenched in 0.1% Formic acid and diluted 20 fold. 20 ul of the diluted samples was injected at 20 ul/min onto a normal phase column isocratically in 50% IPA with 0.1% Acetic acid with SIM298.

Figure 33A:
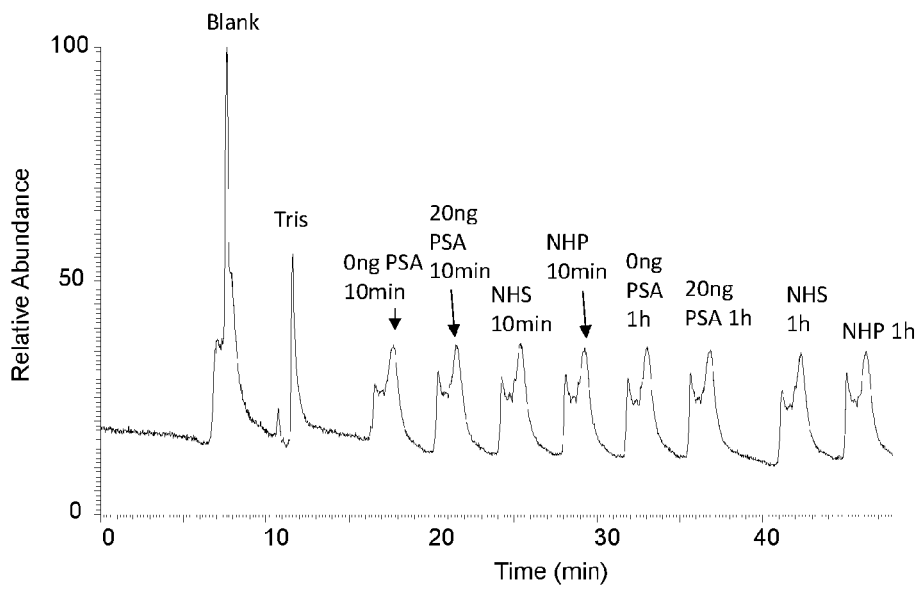

FIG. 33A: ELIMSA using 4MUP as the substrate. Two PSA standards (0 and 20 ng) and two samples (serum and plasma from human male blood) were incubated with 4MUP for 10 minutes and 1 hour and quenched in 0.1% Formic acid and diluted 20 fold. 20 ul of the diluted samples was injected at 20 ul/min onto a normal phase column isocratically in 70% Acetonitrile with 0.1% Acetic acid with SIM231.

Figure 33B:
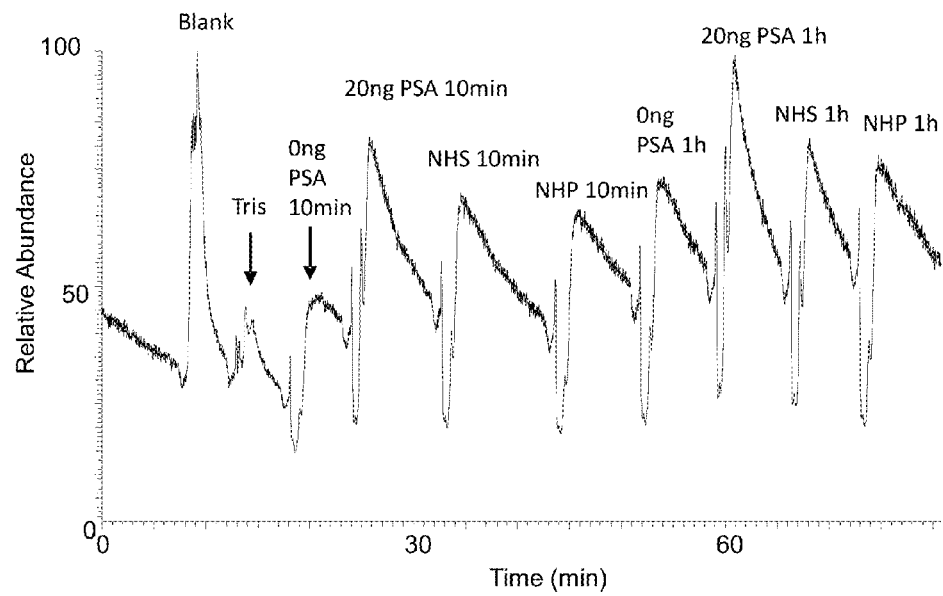

FIG. 33B: ELIMSA using 4MUP as the substrate. Two PSA standards (0 and 20 ng) and two samples (serum and plasma from human male blood) were incubated with 4MUP for 10 minutes and 1 hour and quenched in 0.1% Formic acid and diluted 20 fold. 20 ul of the diluted samples was injected at 20 ul/min onto a normal phase column isocratically in 70% Acetonitrile with 0.1% Acetic acid with SIM176.

Figure 33C:
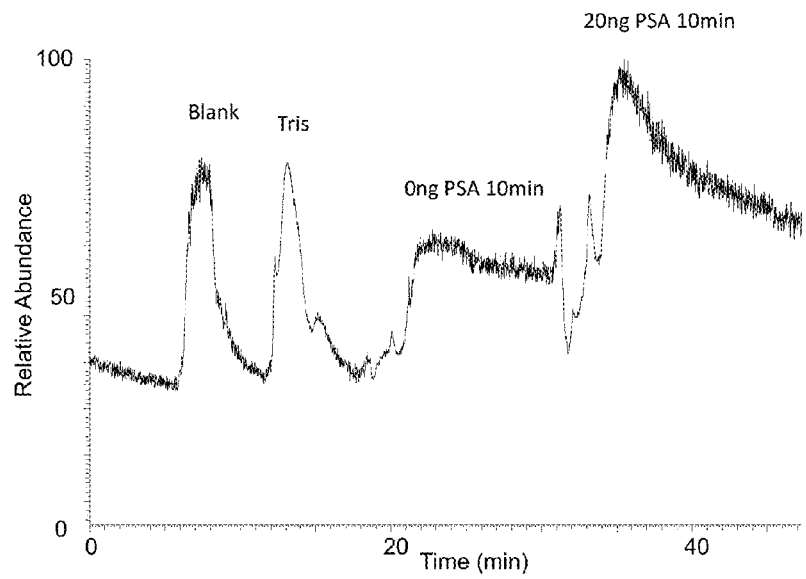

FIG. 33C: ELIMSA using 4MUP as the substrate. Two PSA standards (0 and 20 ng) and two samples (serum and plasma from human male blood) were incubated with 4MUP for 10 minutes and quenched in 0.1% Formic acid and diluted 20 fold. 20 ul of the diluted samples was injected at 20 ul/min onto a normal phase column isocratically in 50% IPA with 0.1% Acetic acid with SIM177.

Figure 34:
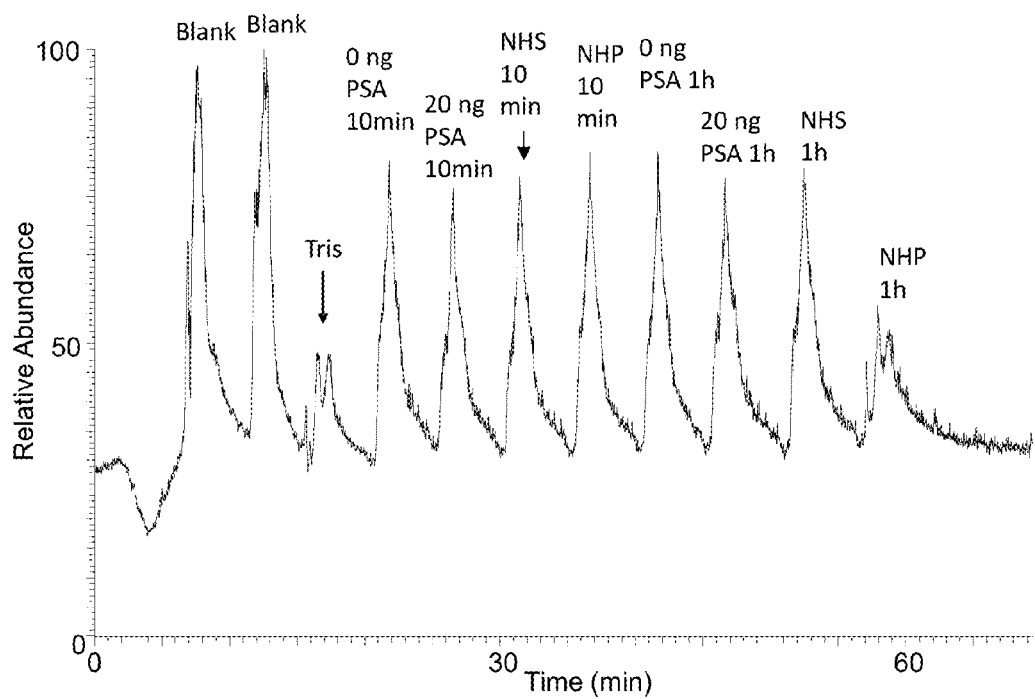

FIG. 34: L-(+)-2-amino-6-phosphonohexanoic acid SIM132 1 in 20 in 0.1% FA 20 ul at 20 ul/min at 70% AcN Blank, Tris, 0 ng PSA, 20 ng PSA, NHS, NHP at 10 min and 1 h. ELIMSA using L-(+)-2-amino-6-phosphonohexanoic acid as the substrate. Two PSA standards (0 and 20 ng) and two samples (serum and plasma from human male blood) were incubated with L-(+)-2-amino-6-phosphonohexanoic acid for 10 minutes and 1 hour and quenched in 0.1% Formic acid and diluted 20 fold. 20 ul of the diluted samples was injected at 20 ul/min onto a normal phase column isocratically in 70% Acetonitrile with 0.1% Acetic acid with SIM132.

Figure 35:
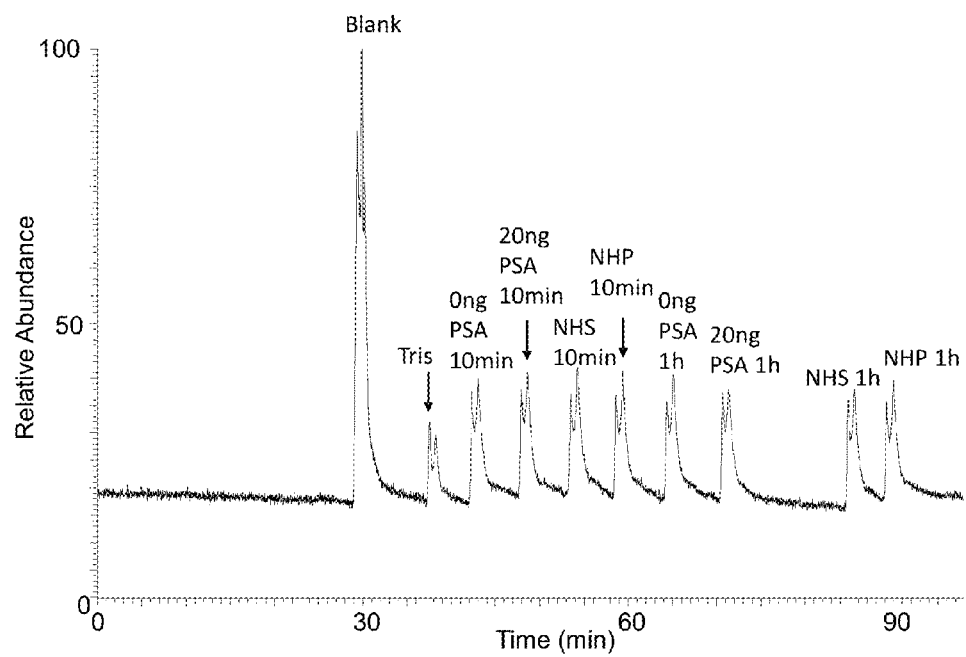

FIG. 35: ELIMSA using BCIP as the substrate. Two PSA standards (0 and 20 ng) and two samples (serum and plasma from human male blood) were incubated with BCIP for 10 minutes and 1 hour and quenched in 0.1% Formic acid and diluted 20 fold. 20 ul of the diluted samples was injected at 20 ul/min onto a normal phase column isocratically in 70% Acetonitrile with 0.1% Acetic acid with SIM244.

Figure 36:
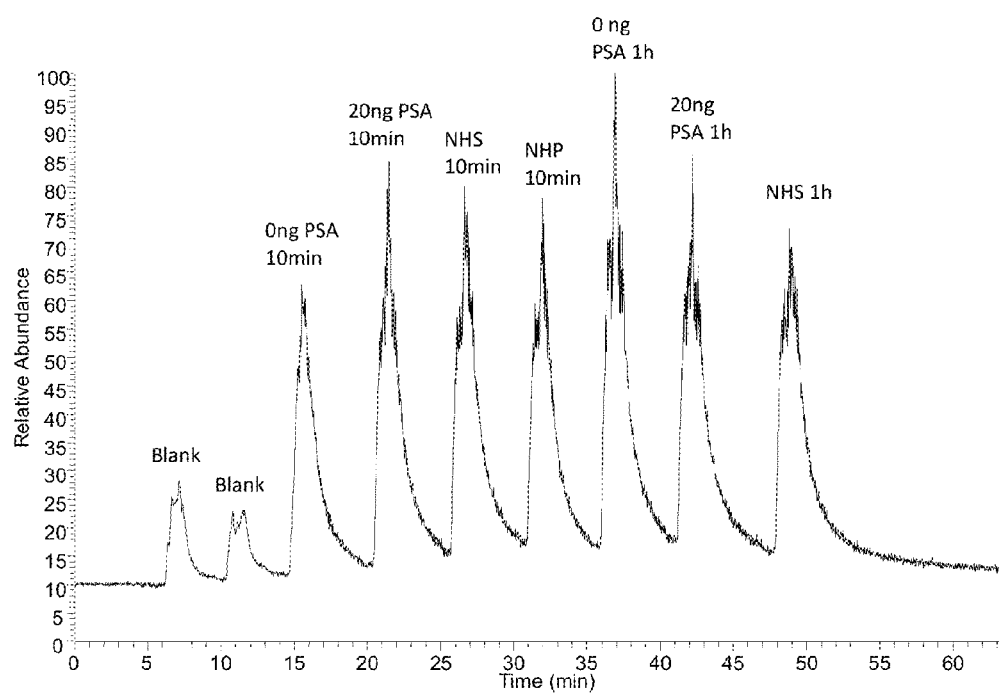

FIG. 36: Phenylbenzene ω phosphono-α-amino acid SIM255 1 in 20 in 0.1% FA 20 ul at 20 ul/min at 70% AcN Blank, Tris, 0 ng PSA, 20 ng PSA, NHS, NHP at 10 min and 1 h. ELIMSA using phenylbenzene ω phosphono-α-amino acid as the substrate. Two PSA standards (0 and 20 ng) and two samples (serum and plasma from human male blood) were incubated with P phenylbenzene ω phosphono-α-amino for 10 minutes and 1 hour and quenched in 0.1% Formic acid and diluted 20 fold. 20 ul of the diluted samples was injected at 20 ul/min onto a normal phase column isocratically in 70% Acetonitrile with 0.1% Acetic acid with SIM255.

Figure 37A:
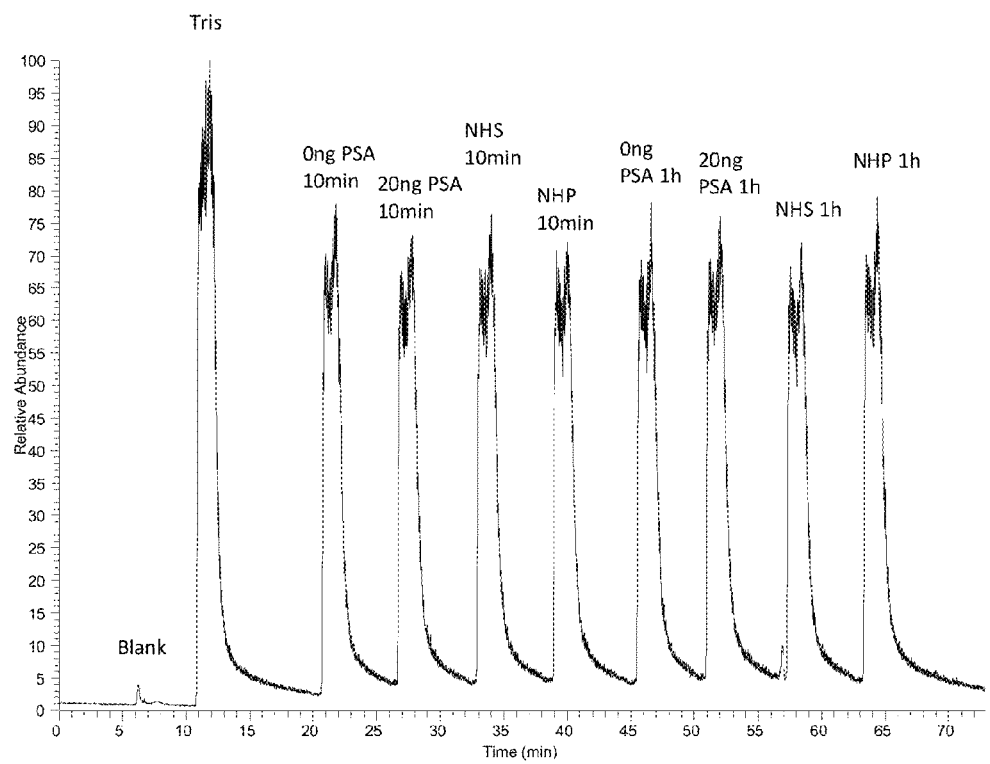

FIG. 37A: O-phospho-DL-Threonine SIM122, 1 in 20 in 0.1% FA 20 ul at 20 ul/min at 70% AcN Blank, Tris, 0 ng PSA, 20 ng PSA, NHS, NHP at 10 min and 1 h. ELIMSA using O-phospho-DL-Threonine as the substrate. Two PSA standards (0 and 20 ng) and two samples (serum and plasma from human male blood) were incubated O-phospho-DL-Threonine for 10 minutes and 1 hour and quenched in 0.1% Formic acid and diluted 20 fold. 20 ul of the diluted samples was injected at 20 ul/min onto a normal phase column isocratically in 70% Acetonitrile with 0.1% Acetic acid with SIM122.

Figure 37B:
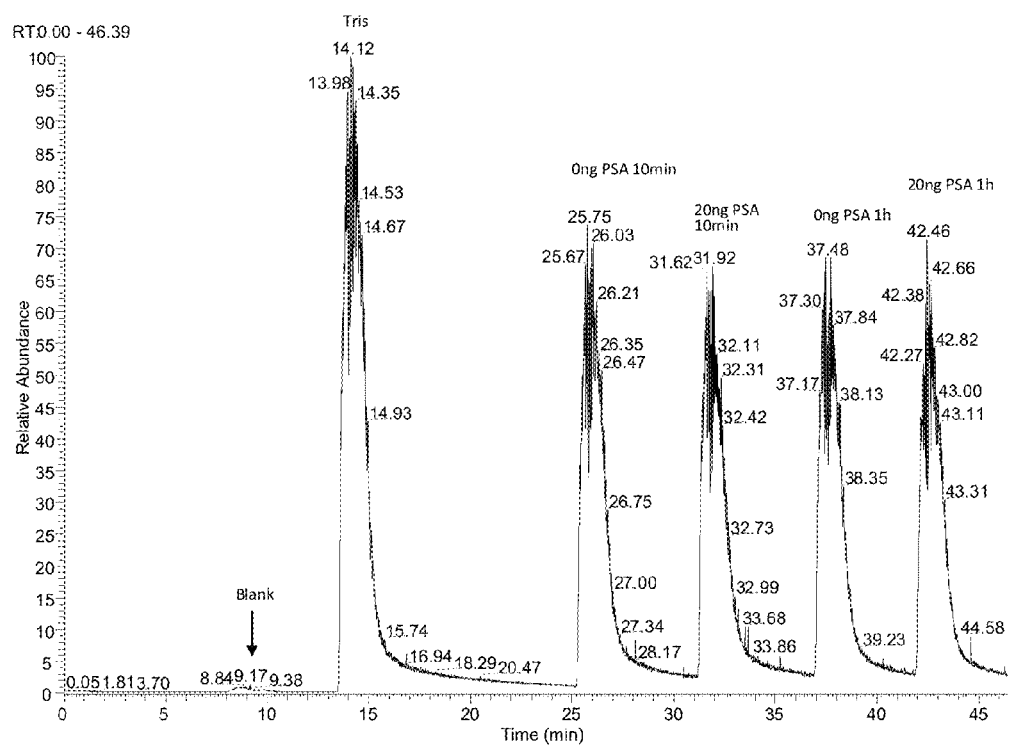

FIG. 37B: O-phospho-DL-Threonine SIM122 in 0.1% Acetic acid 1 in 20 in 0.1% FA 20 ul at 20 ul/min at 70% AcN Blank, Tris, 0 ng PSA, 20 ng PSA at 10 min and 1 h. ELIMSA using 0-phospho-DL-Threonine as the substrate. Two PSA standards (0 and 20 ng) and two samples (serum and plasma from human male blood) were incubated O-phospho-DL-Threonine for 10 minutes and 1 hour and quenched in 0.1% Formic acid and diluted 20 fold. 20 ul of the diluted samples was injected at 20 ul/min onto a normal phase column isocratically in 70% Acetonitrile with 0.1% Acetic acid with SIM122.

Figure 38:
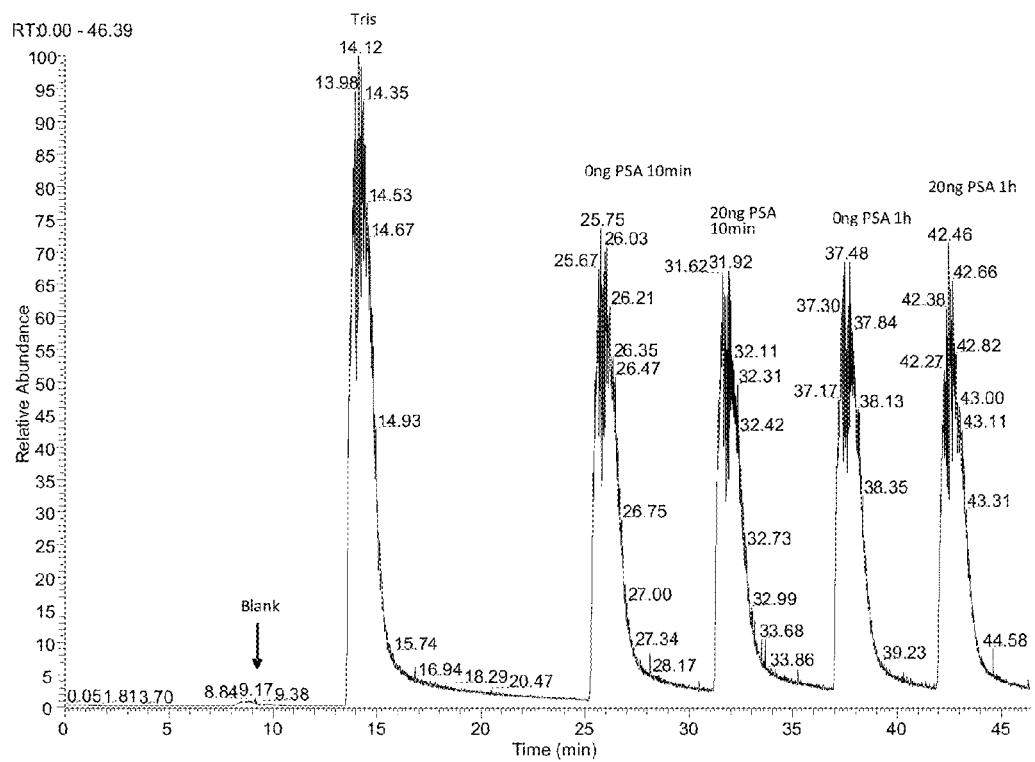

FIG. 38: AMP SIM268, 1 in 20 in 0.1% FA 20 ul at 20 ul/min at 70% AcN Blank, Tris, 0 ng PSA, 20 ng PSA, NHS, NHP at 10 min and 1 h. ELIMSA using AMP as the substrate. Two PSA standards (0 and 20 ng) and two samples (serum and plasma from human male blood) were incubated with AMP for 10 minutes and 1 hour and quenched in 0.1% Formic acid and diluted 20 fold. 20 ul of the diluted samples was injected at 20 ul/min onto a normal phase column isocratically in 70% Acetonitrile with 0.1% Acetic acid with SIM268.

Figure 39:
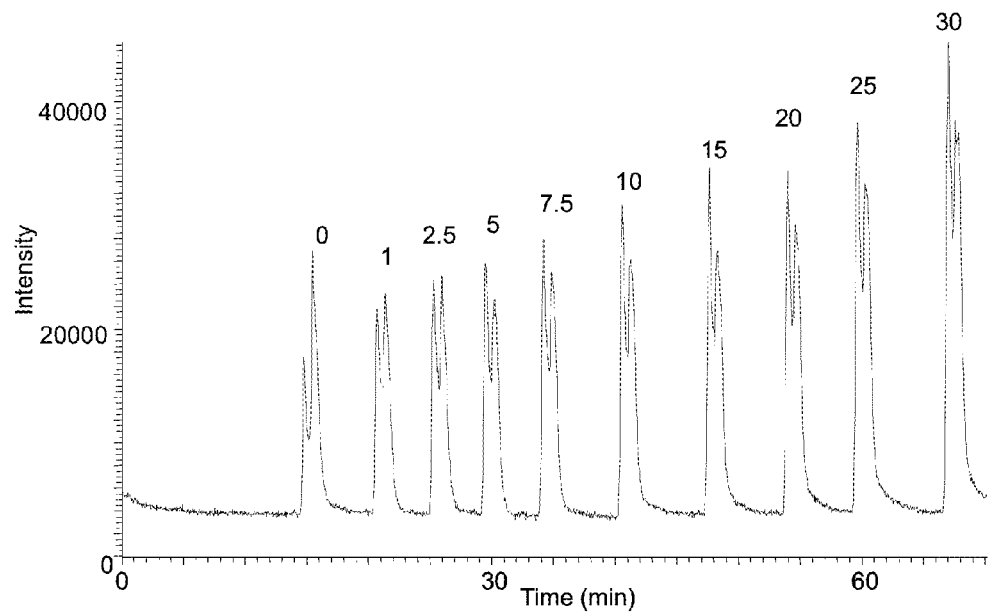
Figure 40A:
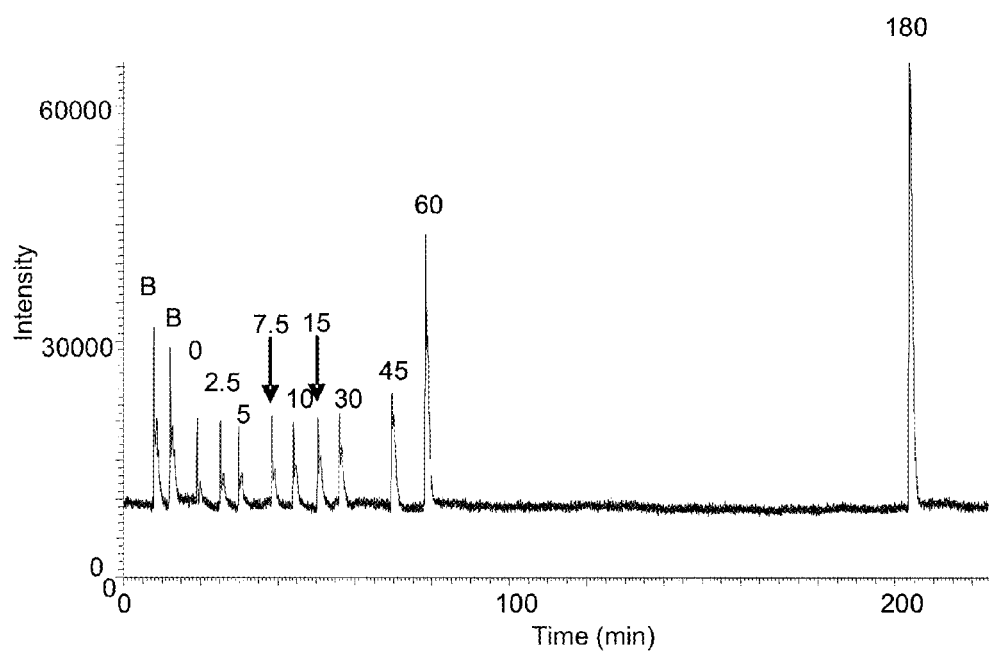
Figure 40B:
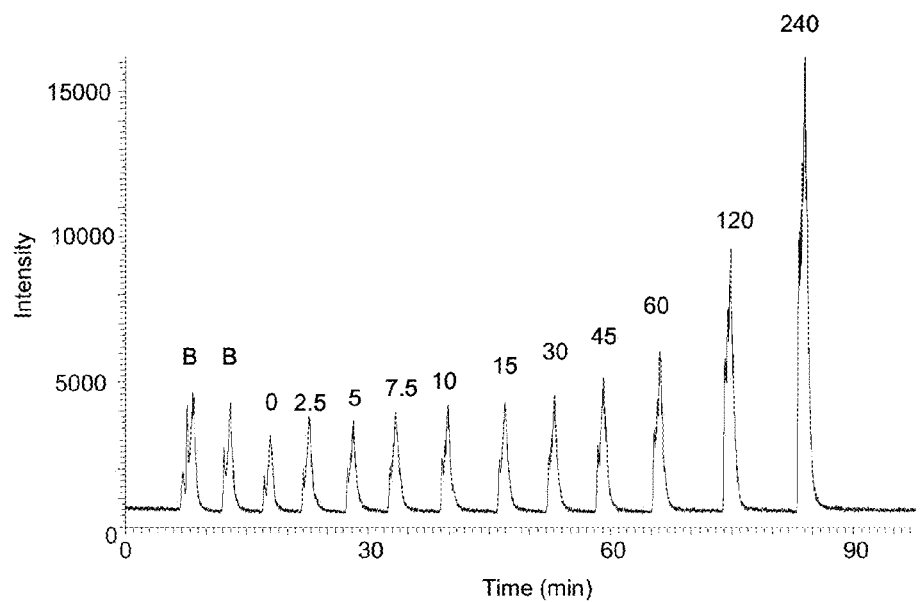
Figure 40C:
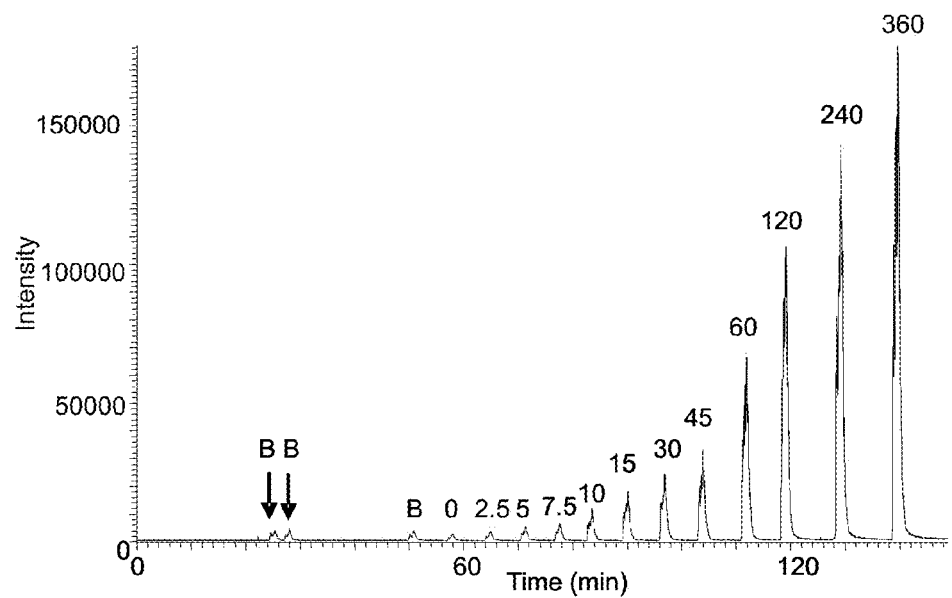
Figure 40D:
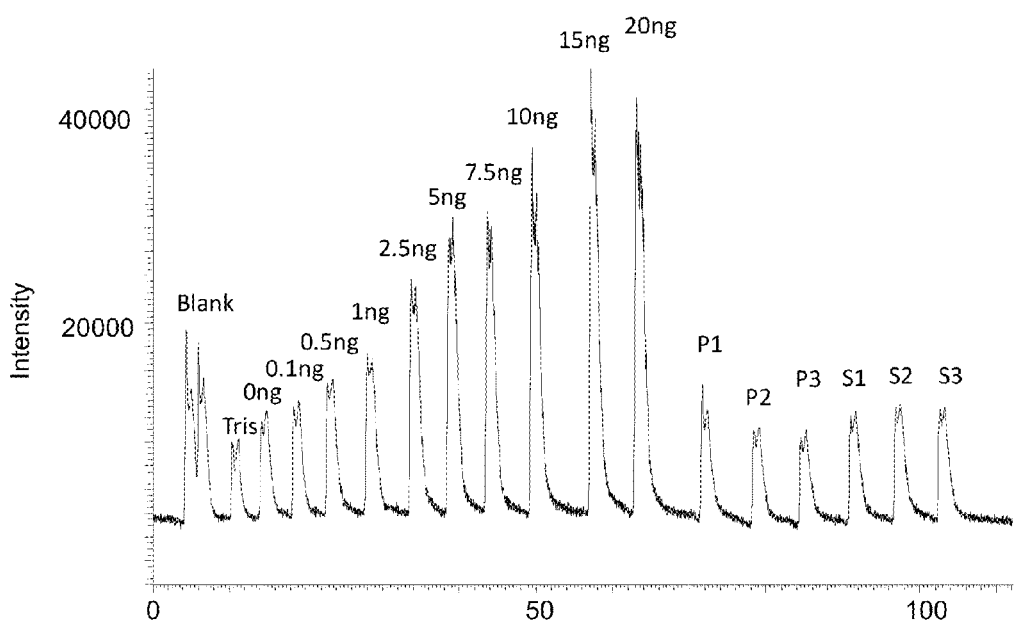

FIG. 39: ATP time course. The response for the production of adenosine after incubation with AP for 0, 1, 2.5, 5, 7.5, 10, 15, 20, 25 and 30 minutes is shown.

FIG. 40A-D: PA5P time course SIM169. PA5P SIM169 ELIMSA PSA standard 0, 0.1, 0.5, 1, 2.5, 5, 7.5, 10, 15 and 20 ng PSA, 3 normal human male plasma samples, 3 normal human male serum samples.

Figure 41:
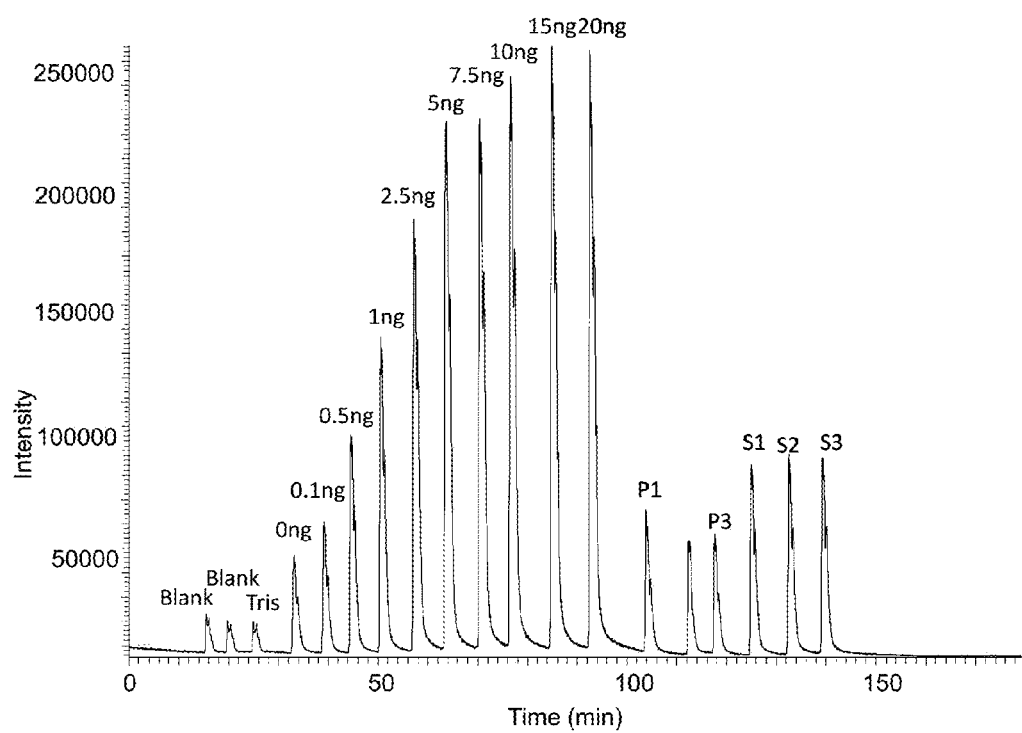

FIG. 41: PA5P SIM169 ELIMSA PSA standard 0, 0.1, 0.5, 1, 2.5, 5, 7.5, 10, 15 and 20 ng PSA, 3 normal human male plasma samples, 3 normal human male serum samples. The relationship between the SIM169 [M+H] and the ng added to the 100 microliter ELIMSA reaction prior to dilution 20 fold and injection of the equivalent of 1 microliter is show alongside the unknown standards.

Figure 42:
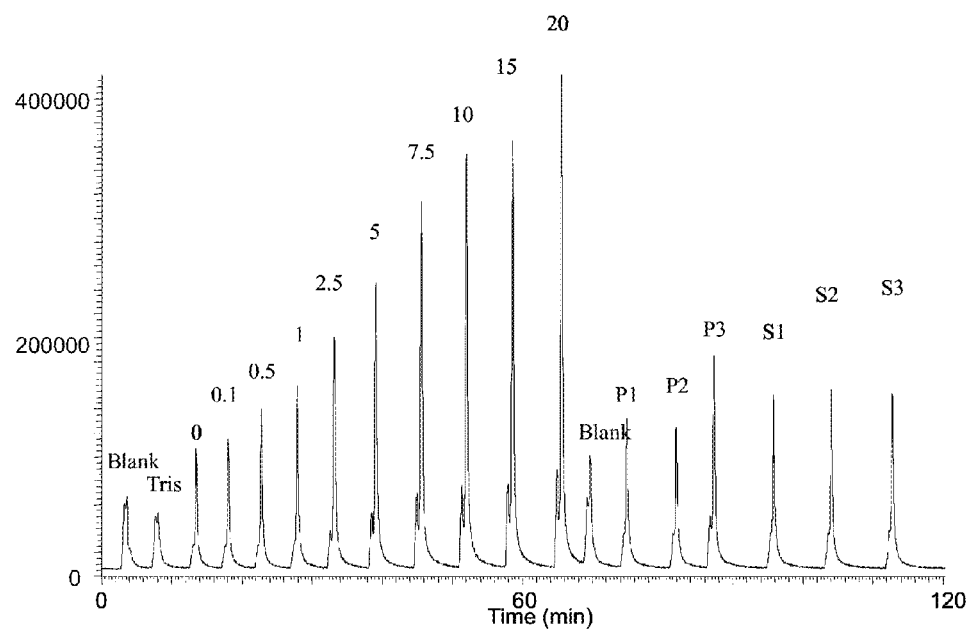

FIG. 42: Amplex® Red SIM214 ELIMSA. An independent replicate of the ELIMSA using HRP and the Amplex® Red substrate monitored by SIM at 214 m/z is shown with standards from 0 to 20 ng per well followed by three unknown plasma and serum samples.

Figure 43:
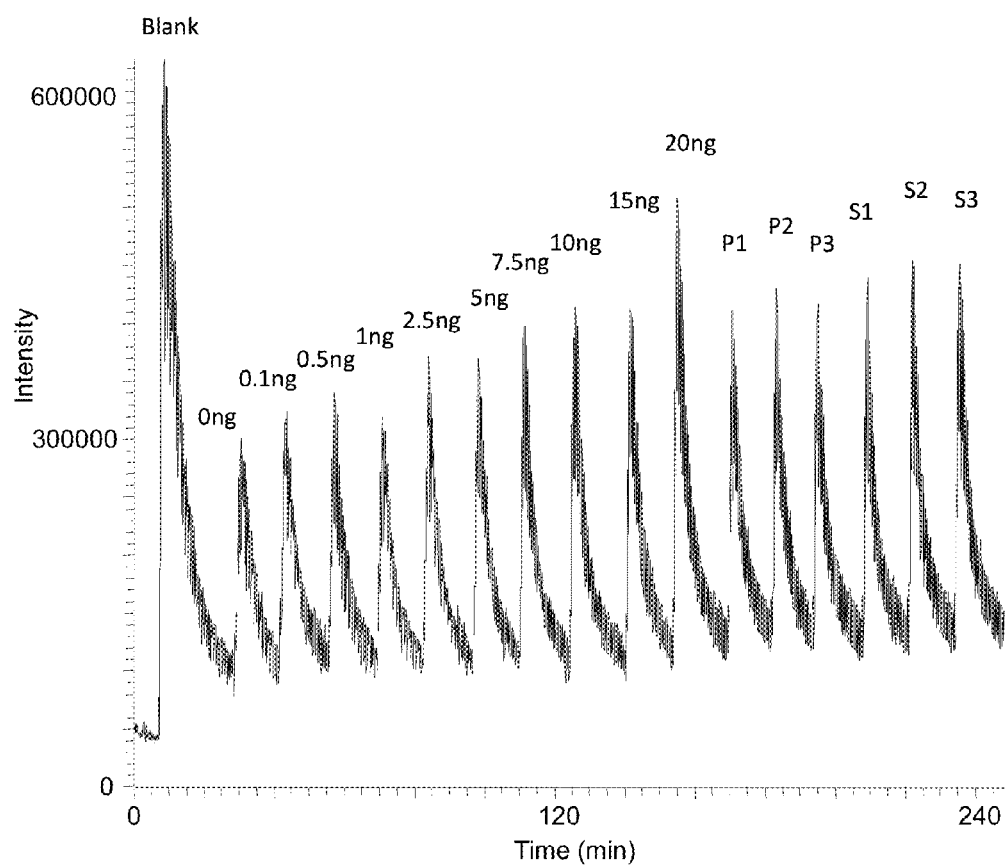

FIG. 43: pNPP ELIMSA PSA standard 0, 0.1, 0.5, 1, 2.5, 5, 7.5, 10, 15 and 20 ng PSA, 3 normal human male plasma samples, 3 normal human male serum samples. The relationship between the SIM138 [M+H] and the ng added to the 100 microliter ELIMSA reaction prior to dilution 20 fold and injection of the equivalent of 1 microliter. ELIMSA reaction was quenched in 50% AcN, 0.1% Na-vanadate FIG. 44: The infusion screen of pNPP by SIM138 in negative mode. The three infusions are: I, buffer alone; II, buffer plus pNPP; III buffer, pNPP plus AP. Reaction was quenched in 50% Acetonitrile, 0.1% Acetic acid FIG. 45A: TIC of multiple detection of Amplex® Red SIM214 and Naphthol ASMX phosphate SIM292 ELIMSA. ELIMSA reactions were quenched, combined and diluted 20 fold. PSA standard in pg per well, samples were diluted 100 fold. ELIMSA reactions were quenched, combined and diluted 20 fold FIG. 45B: MS of multiple detection of Amplex® Red SIM214 and Naphthol ASMX phosphate SIM292 ELIMSA. Multiple detection by SRM would also be possible.

Figure 46A:
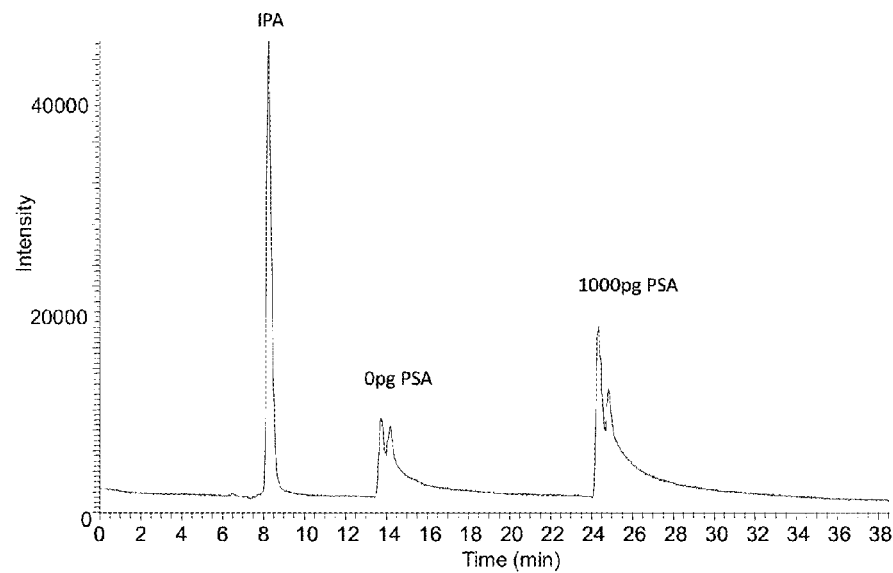
Figure 46B:
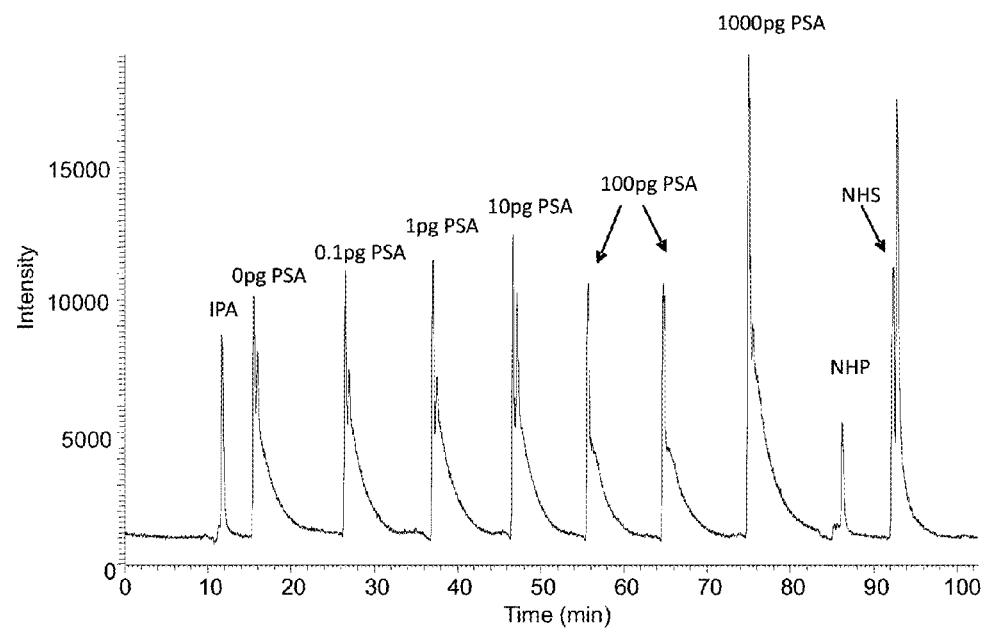

FIGS. 46A-B: ELIMSA using AMP as the substrate. PSA standards and two samples (plasma and serum) were incubated with AMP for 10 minutes prior to quenching the reaction in formic acid. Samples were dried down and extracted in 20 microliter IPA on ice for at least 5 minutes. 2 ul of the extract was injected onto a normal phase column in 70% Acetonitrile with 0.1% Acetic acid with SIM268.

Figure 46C:
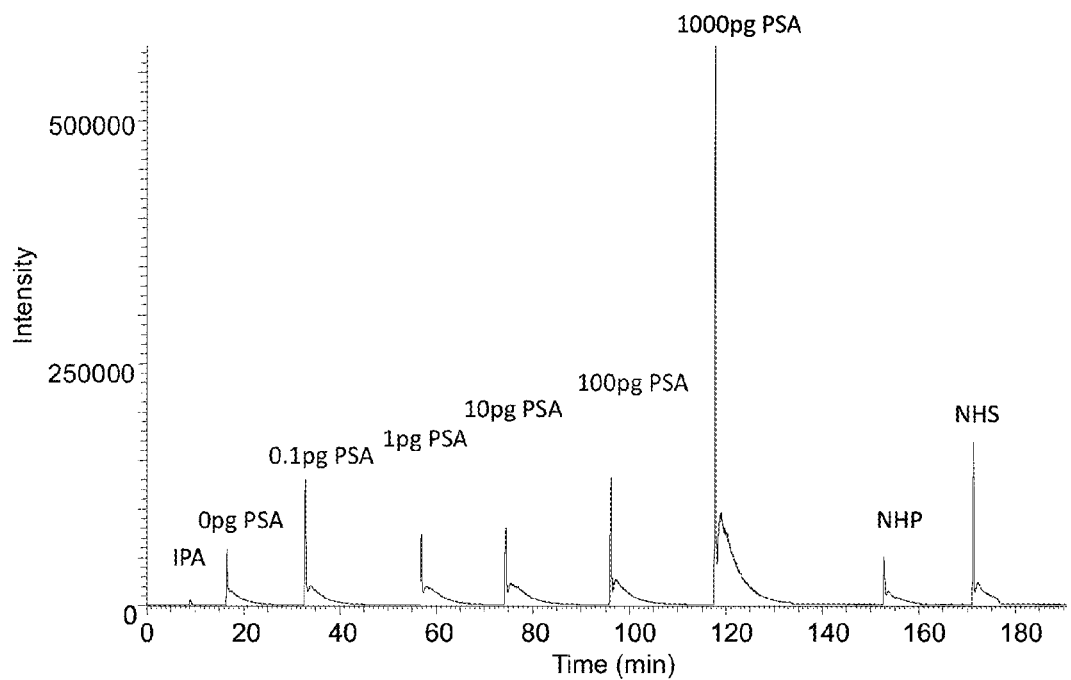

FIG. 46C. A ELIMSA using AMP as the substrate. PSA standards and two samples (plasma and serum) were incubated with AMP overnight prior to quenching the reaction in formic acid. Samples were dried down and extracted in 20 microliter IPA on ice for at least 5 minutes. 2 ul of the extract was injected onto a normal phase column in 70% Acetonitrile with 0.1% Acetic acid with SIM268.

Figure 47A:
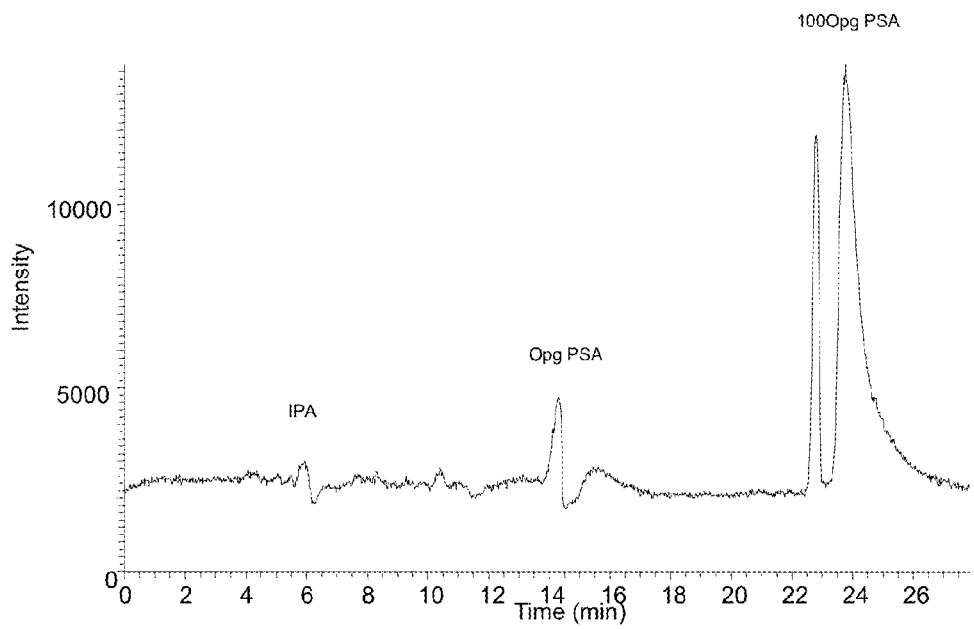

FIG. 47A: ELIMSA using PA5P as the substrate. PSA standards (0 and 1000 ng) were incubated with PA5P for 10 minutes prior to quenching the reaction in formic acid. Samples were dried down and extracted in 20 microliter IPA on ice for at least 5 minutes. 2 ul of the extract was injected onto a normal phase column in 70% Acetonitrile with 0.1% Acetic acid with SIM169.

Figure 47B:
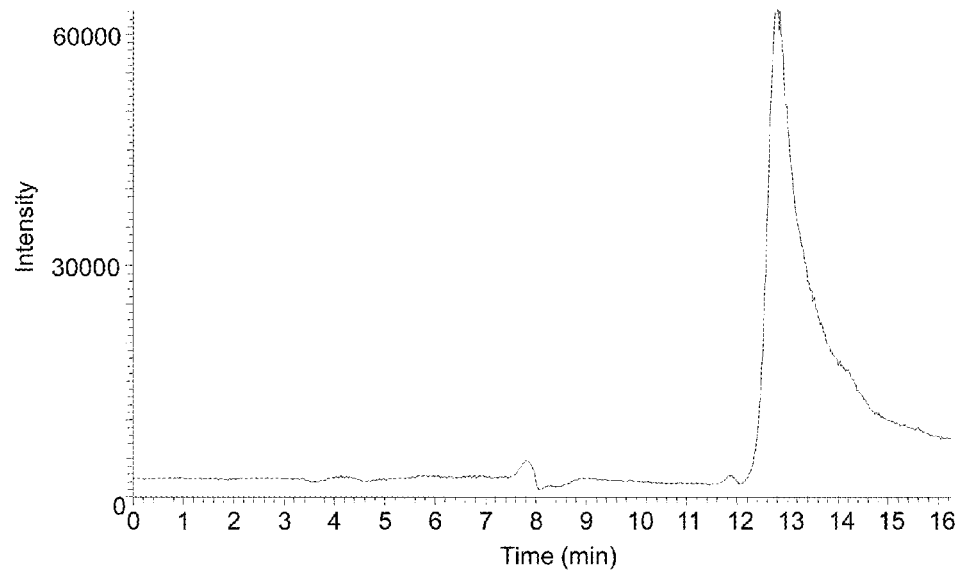

FIG. 47B: ELIMSA using PA5P as the substrate. PSA standards (0 and 1000 ng) were incubated with PA5P for 1 hour prior to quenching the reaction in formic acid. Samples were dried down and extracted in 20 microliter IPA on ice for at least 5 minutes. 2 ul of the extract was injected onto a normal phase column in 70% Acetonitrile with 0.1% Acetic acid with SIM169.

Figure 47C:
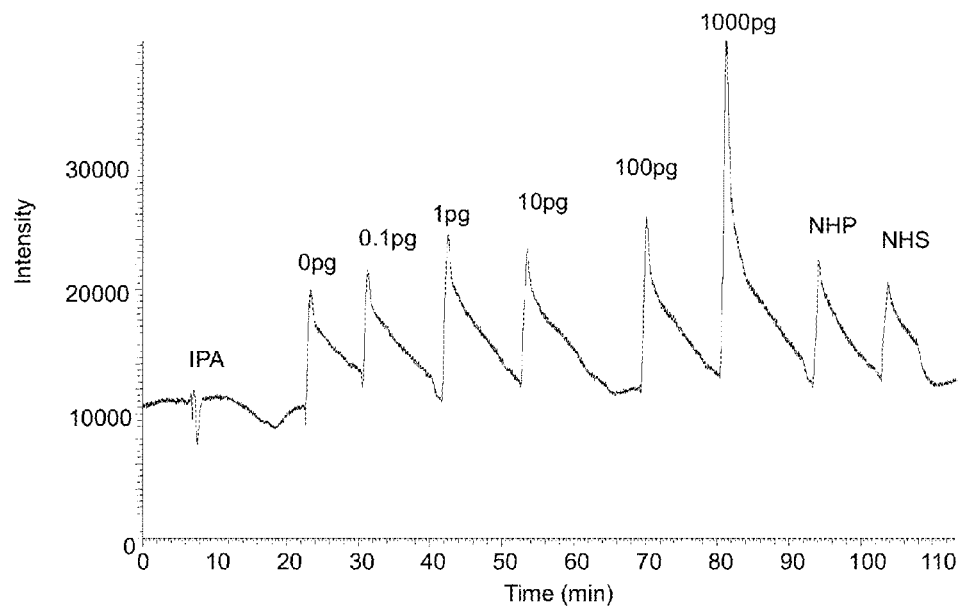

FIG. 47C: ELIMSA using PA5P as the substrate. PSA standards and two samples (plasma and serum from human male blood) were incubated with PA5P for 1 hour prior to quenching the reaction in formic acid. Samples were dried down and extracted in 20 microliter IPA on ice for at least 5 minutes. 2 ul of the extract was injected onto a normal phase column in 70% Acetonitrile with 0.1% Acetic acid with SIM169. A detector response from as little as 2 µl injected from the 20 µl of IPA extract from 0.1 µg of PSA per well prior to drying and extraction was observed (i.e. 330 zepto mol on column).

Figure 48:
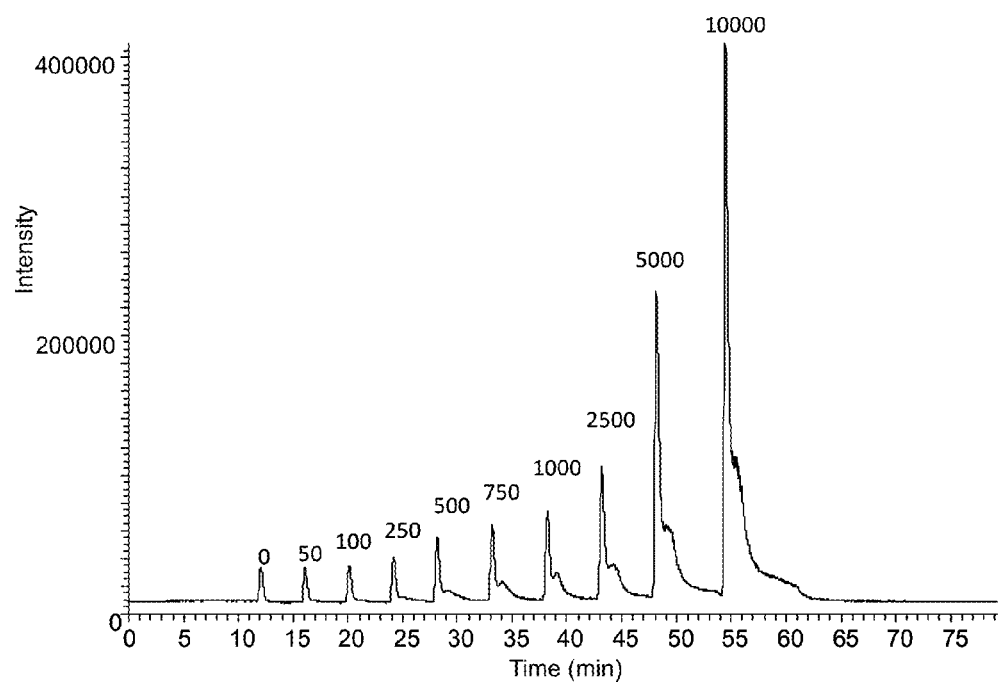

FIG. 48. Pyridoxamine standard curve. Pyridoxamine is the enzyme reaction product of PA5P. Pyridoxamine was obtained from Sigma Aldrich. Standards are in nM and only 2 ul of the standards were injected onto the column. The experiment shows that the LC-ESI-MS system is sensitive to femto mol to pico mol amounts of pyridoxamine on column. Pyridoxamine std curve in nM, only 2 ul was injected on a 10 cm normal phase column in 70% AcN.

Figure 49:
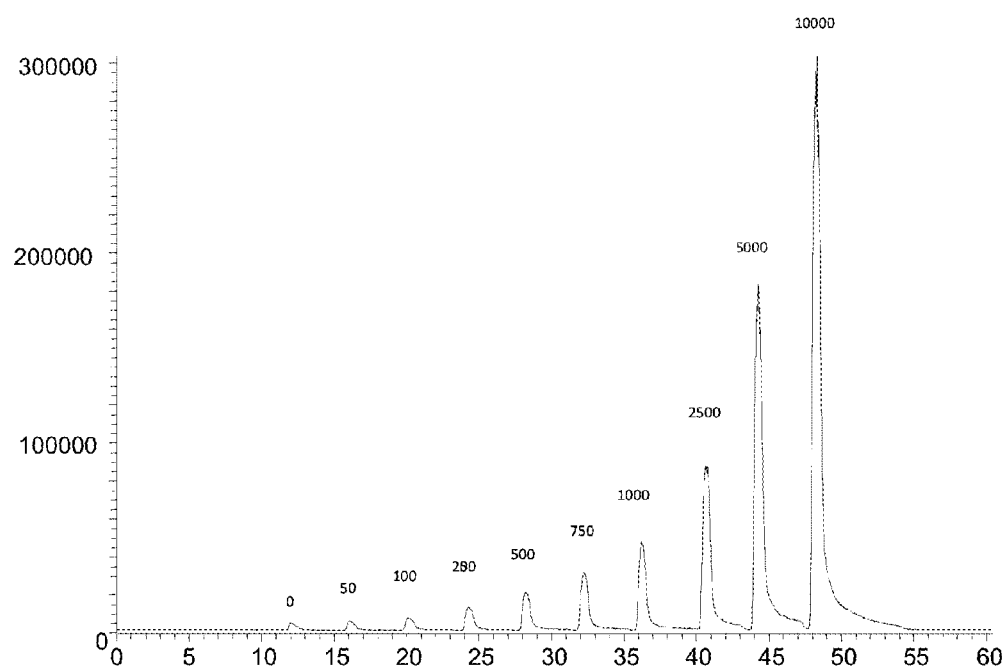

FIG. 49. Adenosine standard curve. Adenosine is the enzyme reaction product of AMP. Adenosine was obtained from Sigma Aldrich. Standards are in nM and only 2 ul of the standards were injected onto the column. The experiment shows that the LC-ESI-MS system is sensitive to femto mol to pico mol amounts of adenosine on column. Adenosine std curve in nM, only 2 ul was injected on a 10 cm normal phase column in 70% AcN.

Figure 50:
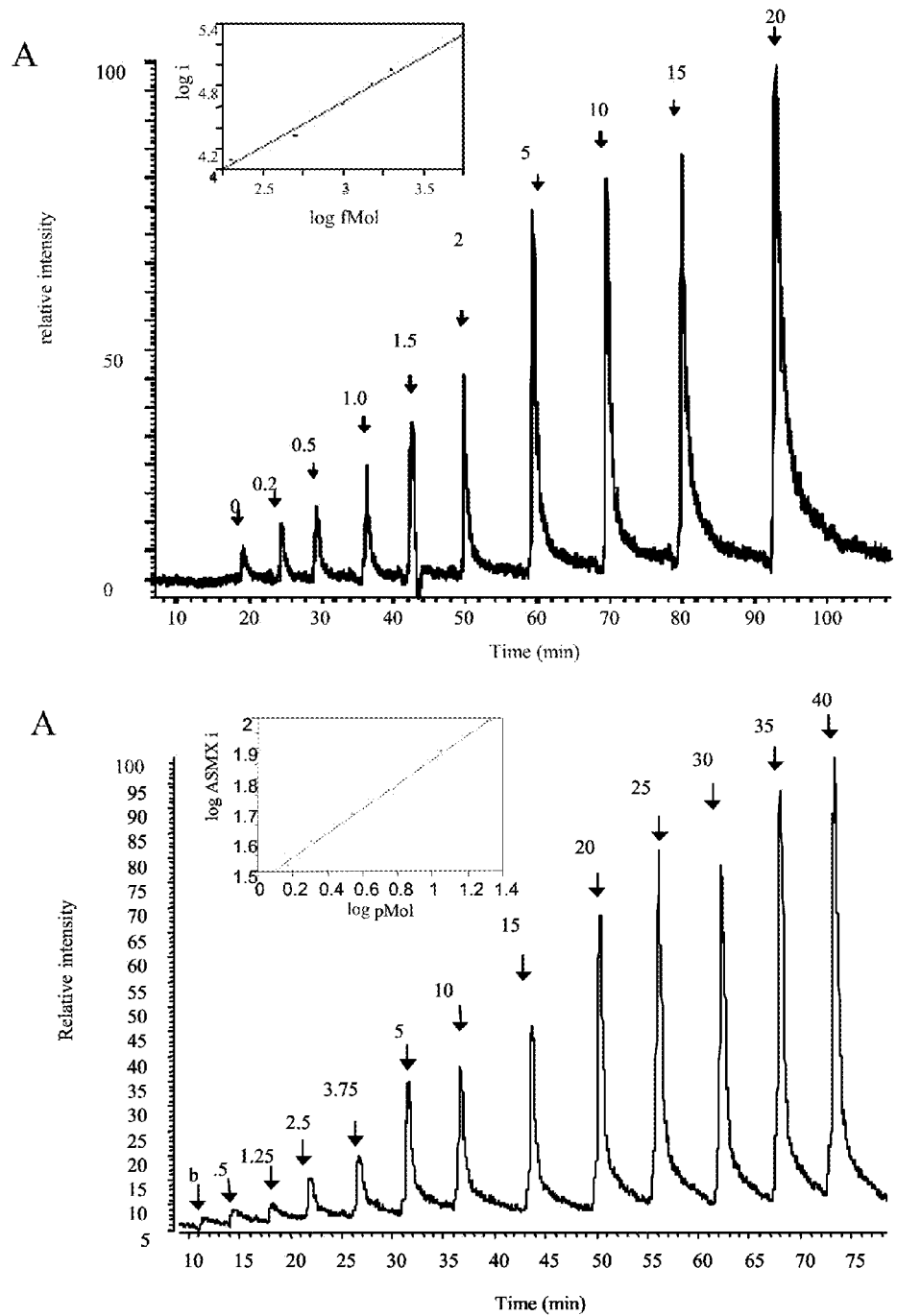

FIG. 50. An isocratic LC-MS chromatogram of the standard dilution curve made from the enzyme products resorufin and ASMX. Panels: A, dilution of resorufin standard; B, dilution of ASMXP enzymatic product. The amount of standard injected in pico mol is indicated by the arrow. The inset shows the log relationship over the range of hundreds of femto mol to pico mol injected.

Figure 51:
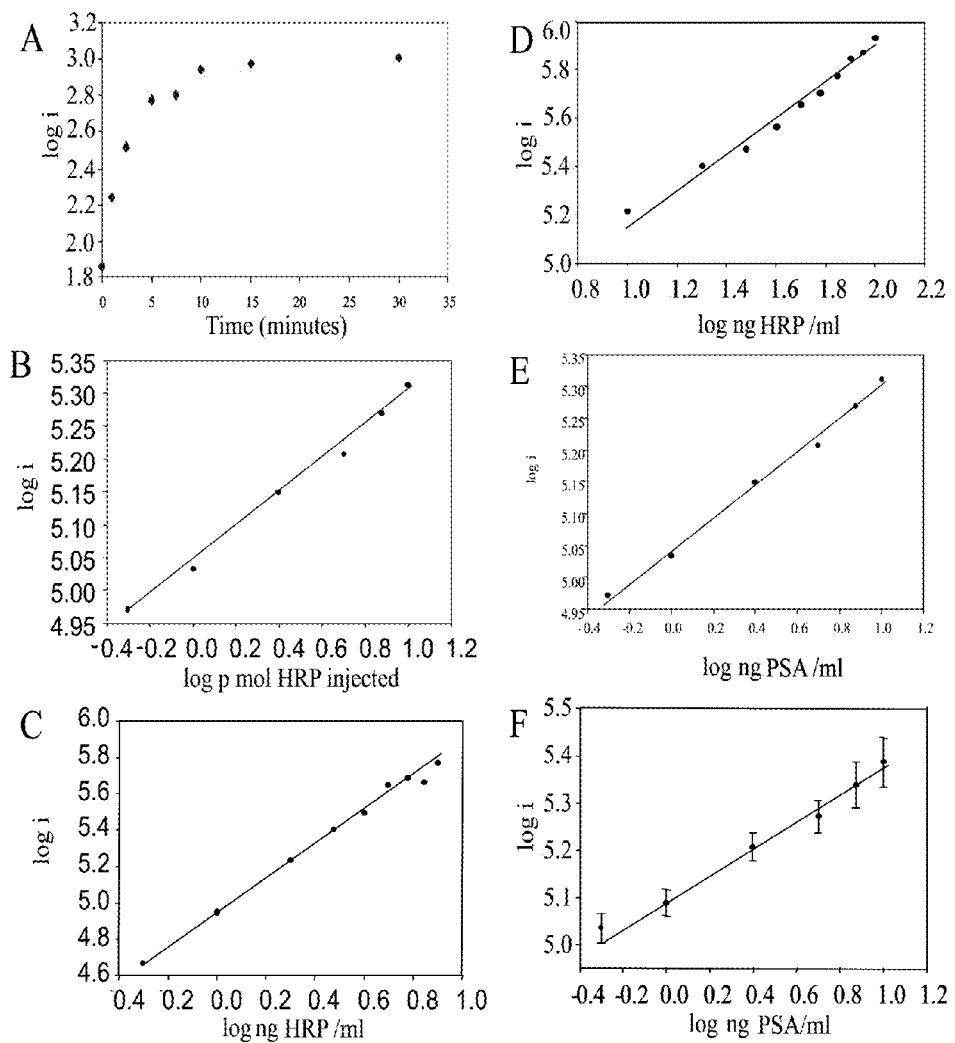

FIG. 51. The development of the Amplex Red ELIMSA by SIM at 214 m/z M+H. Panels: A, the time dependence of the HRP enzymatic product of amplex red; B, the resorufin standard dilution curve measured relating log intensity to log pmol; C, The HRP response curve from 0.5 to 10 ng per ml; D, the HRP response curve from 5 to 100 ng per ml; E, a example of a PSA ELIMSA standard curve from 0.1 ng to 10 ng per well; The average of three consecutive ELIMSA standard curves. Typical R2 values were consistently ~0.99 after log transformation.

Figure 52:
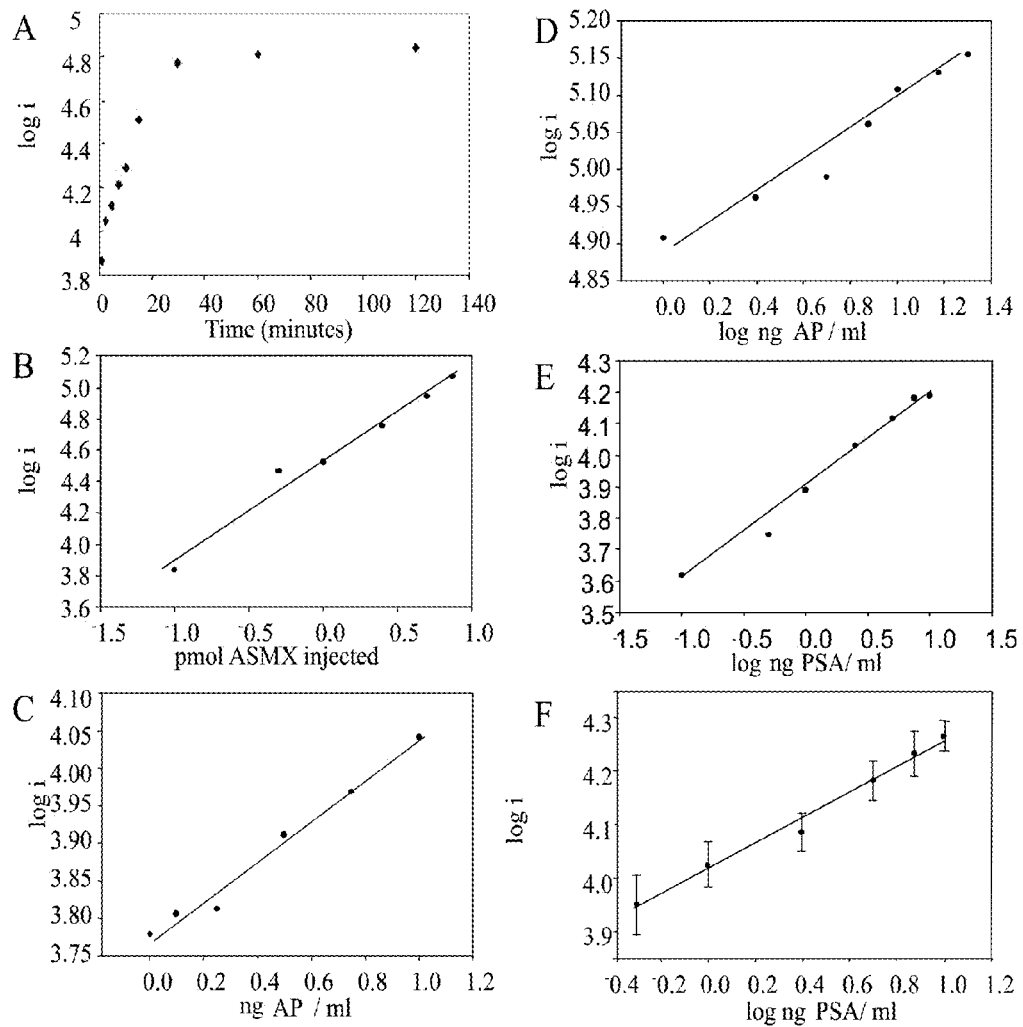

FIG. 52 The development of the ASMX phosphate ELIMSA by SIM 292 m/z M+H. Panels: A, the time dependence of the AP enzymatic product of ASMXP; B, the ASMX enzyme product standard dilution curve relating log intensity to log pmol; C, The AP response curve from 0.1 to 10 ng per ml; D, the AP response curve from log 1 to 20 ng per ml; E, a PSA ELIMSA standard curve from 0.1 to 10 ng per well; F, The average of three consecutive ELIMSA standard curves. Typical R2 values were consistently ~0.99 after log transformation.

Figure 53:
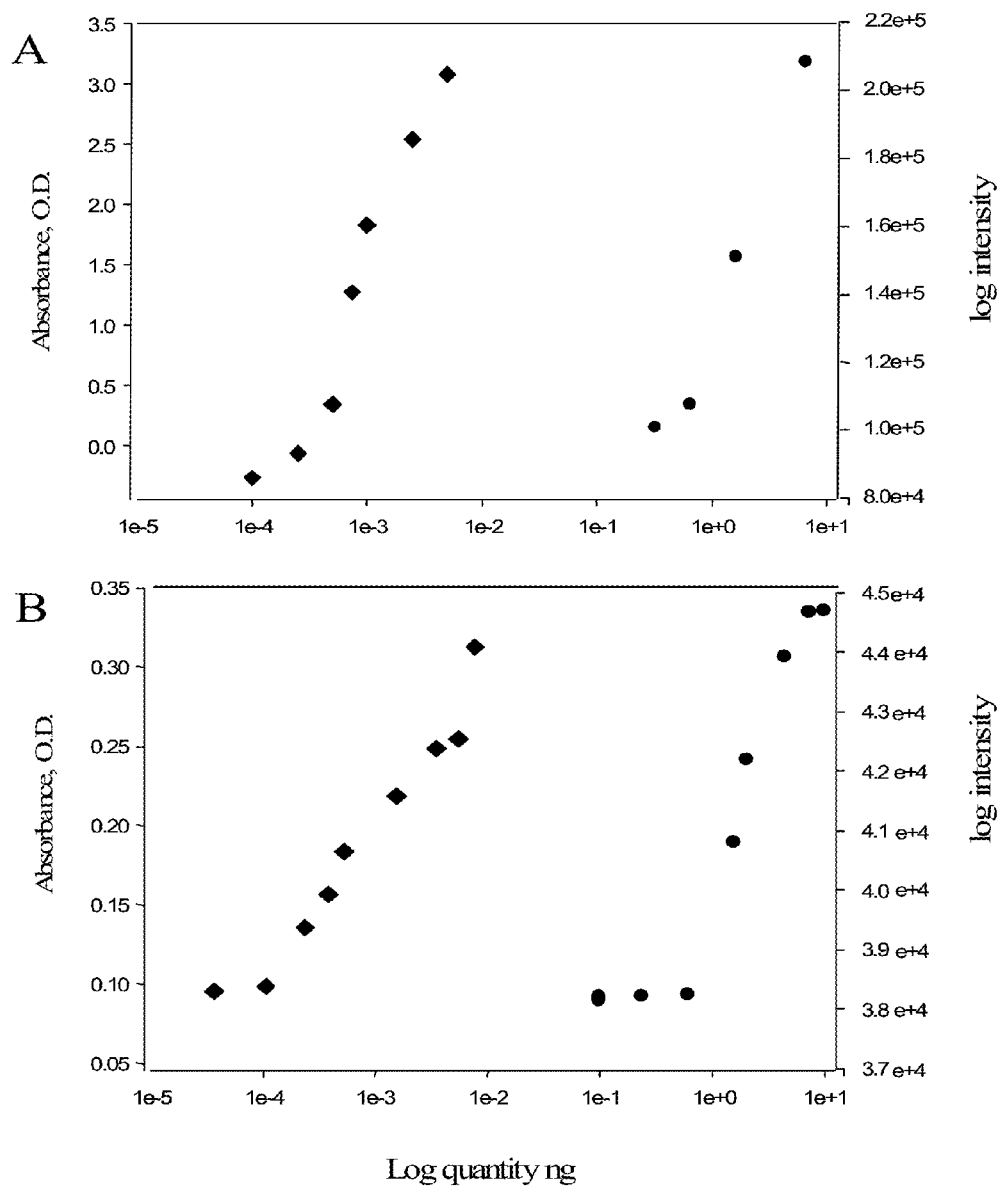

FIG. 53. The log protein comparison of the absolute sensitivity of the PSA ELIMSA (▲) versus colorimetric ELISA in nano grams per detection (●). Panels: A, amplex red substrate; B, Blue Phos substrate versus ASMX Naphthol phosphate.

Figure 54:
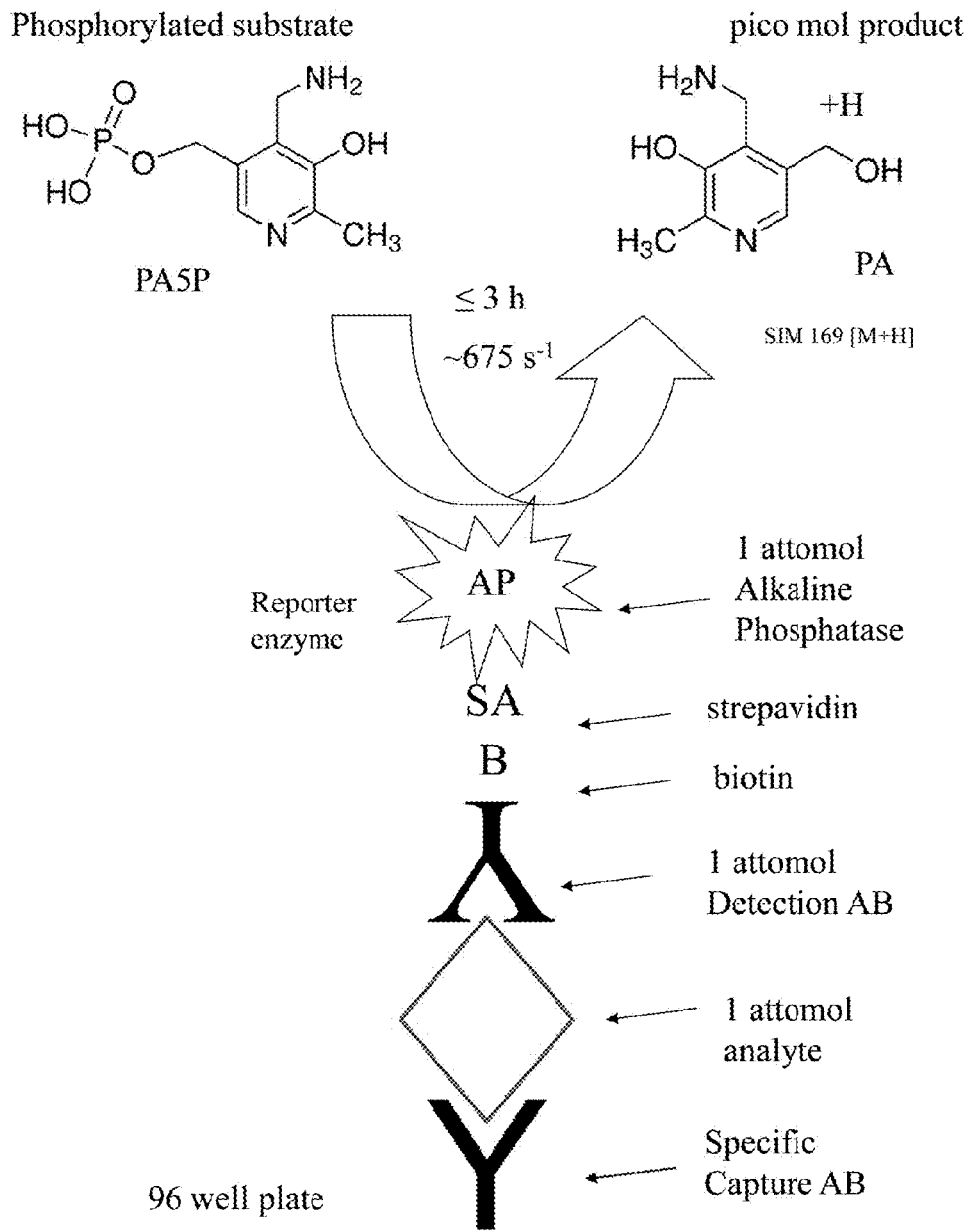

FIG. 54. The scheme for ELIMSA using PA5P as a substrate for enzymatic amplification of the aalyte for detection by LC-ESI-MS.

Figure 55:
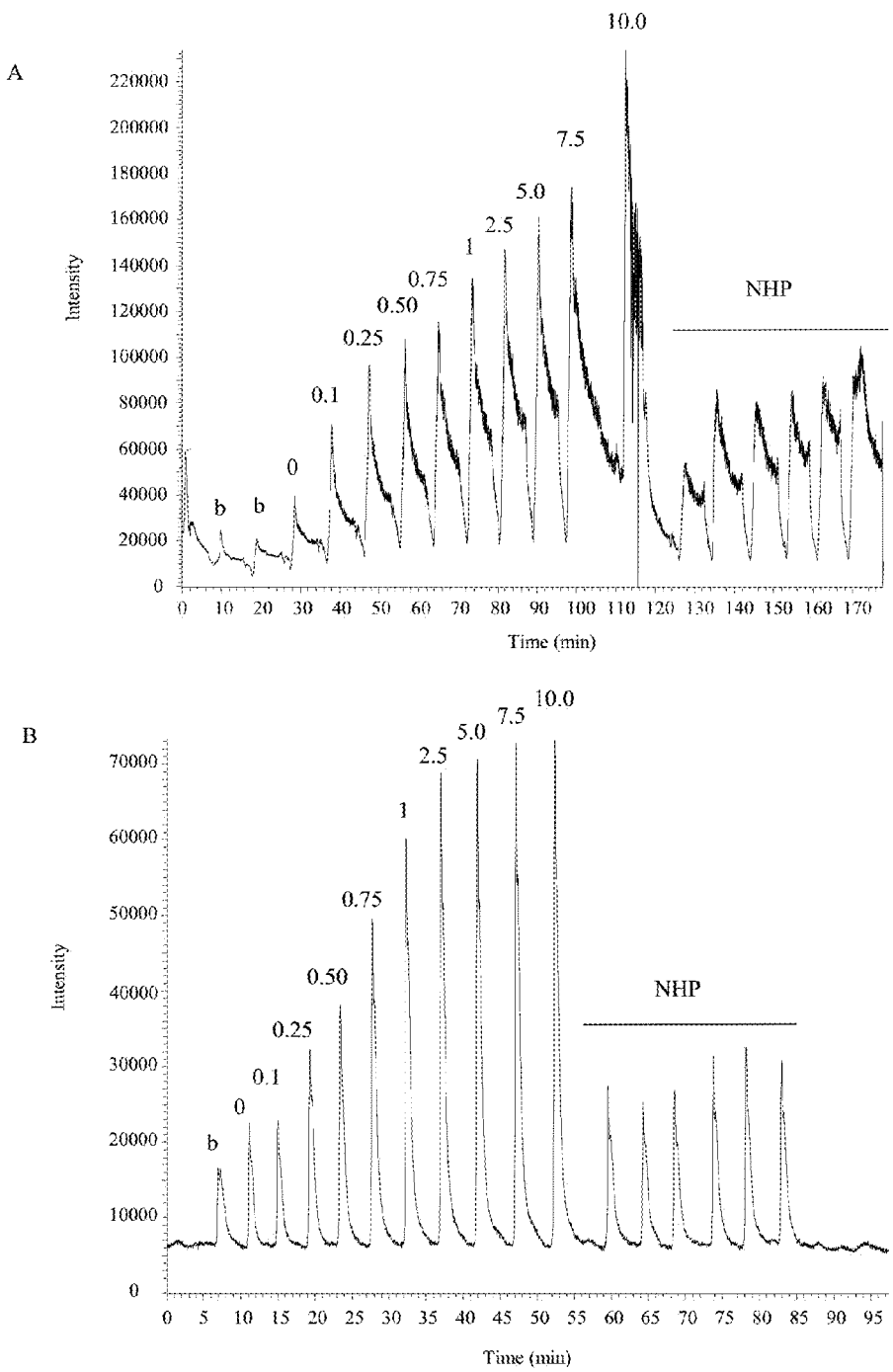

FIG. 55. Comparison of the previously published maphthol AS-MX reported molecule versus pyridoxamine (PA) by LC-ESI-MS. Panels: A, the isocratic chromatograph showing an ELIMSA experiment measured by the production of ASMX monitored at SIM at 292 m/z [M+H] (note the chromatographic failure and severe peak tailing as the injection quantity increases); B, the isocratic chromatograph showing an ELIMSA experiment measured by the production of PA monitored at SIM 169 [M+H] m/z; The isocratic chromatographs show the injection of 2 µl of the standard in nM as indicated by the arrow in 0.1% FA on normal phase in 70% acetonitrile connected to an electrospray source.

Figure 56:
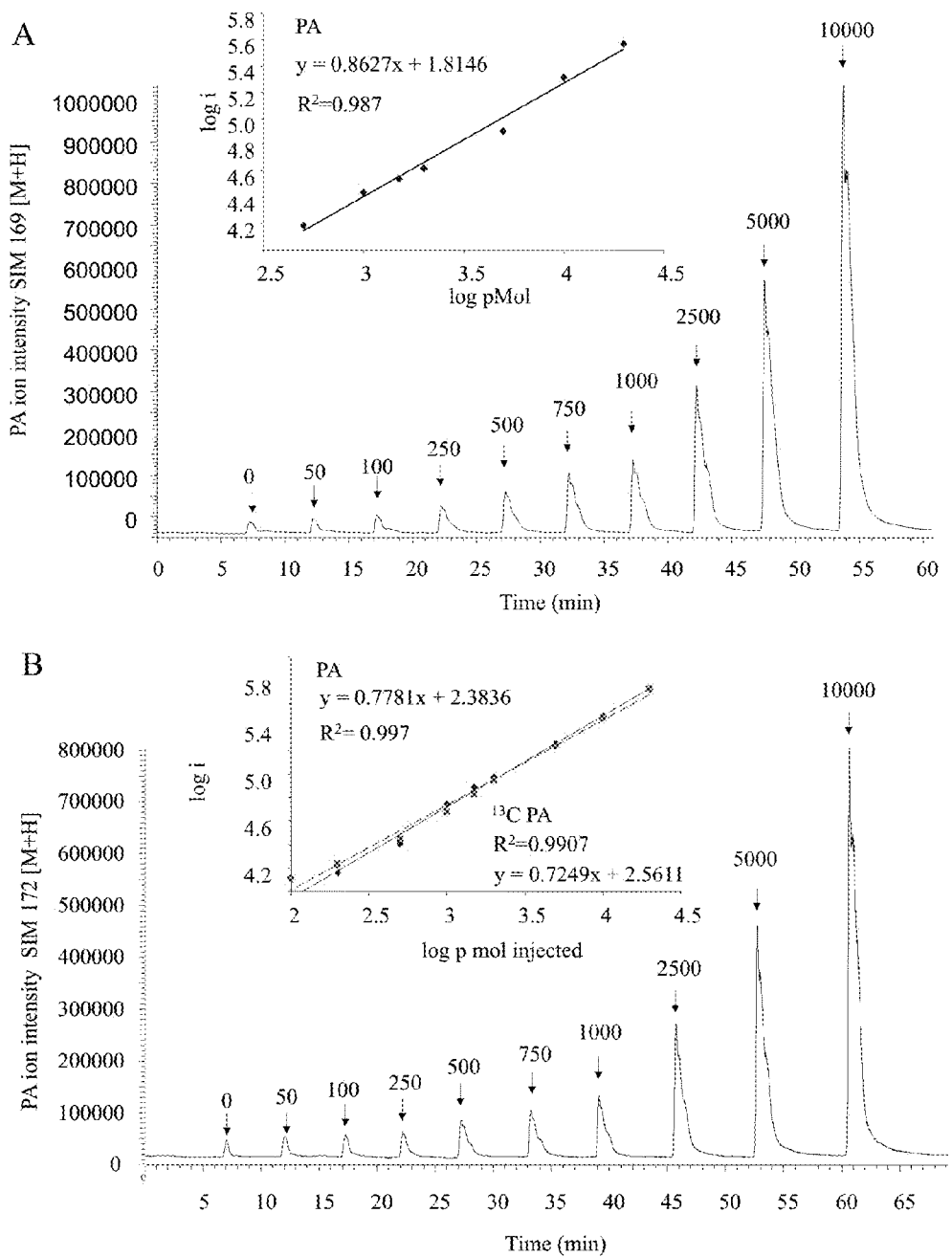

FIG. 56. Comparison of PA and 13C PA external standards by LC-ESI-MS. Panels: A, the isocratic chromatograph showing the dilution series of PA monitored at SIM 169 [M+H] m/z (inset shows linearity after log transformation); B, The isocratic chromatograph showing dilution series of 13C PA monitored at SIM 172 [M+H] m/z (inset shows agreement between natural and isotopically labelled 13C-pyridoxamine). The isocratic chromatographs show the injection of 2 µl of the standard in nM as indicated by the arrow in 0.1% FA on normal phase in 70% acetonitrile connected to an electrospray source. Note the background noise as shown by low error within the width of the baseline compared to the peak heights showing high signal to noise ratio. There is apparently a small amount of substrate that is not phosphorylated as provided by the manufacturer.

Figure 57:
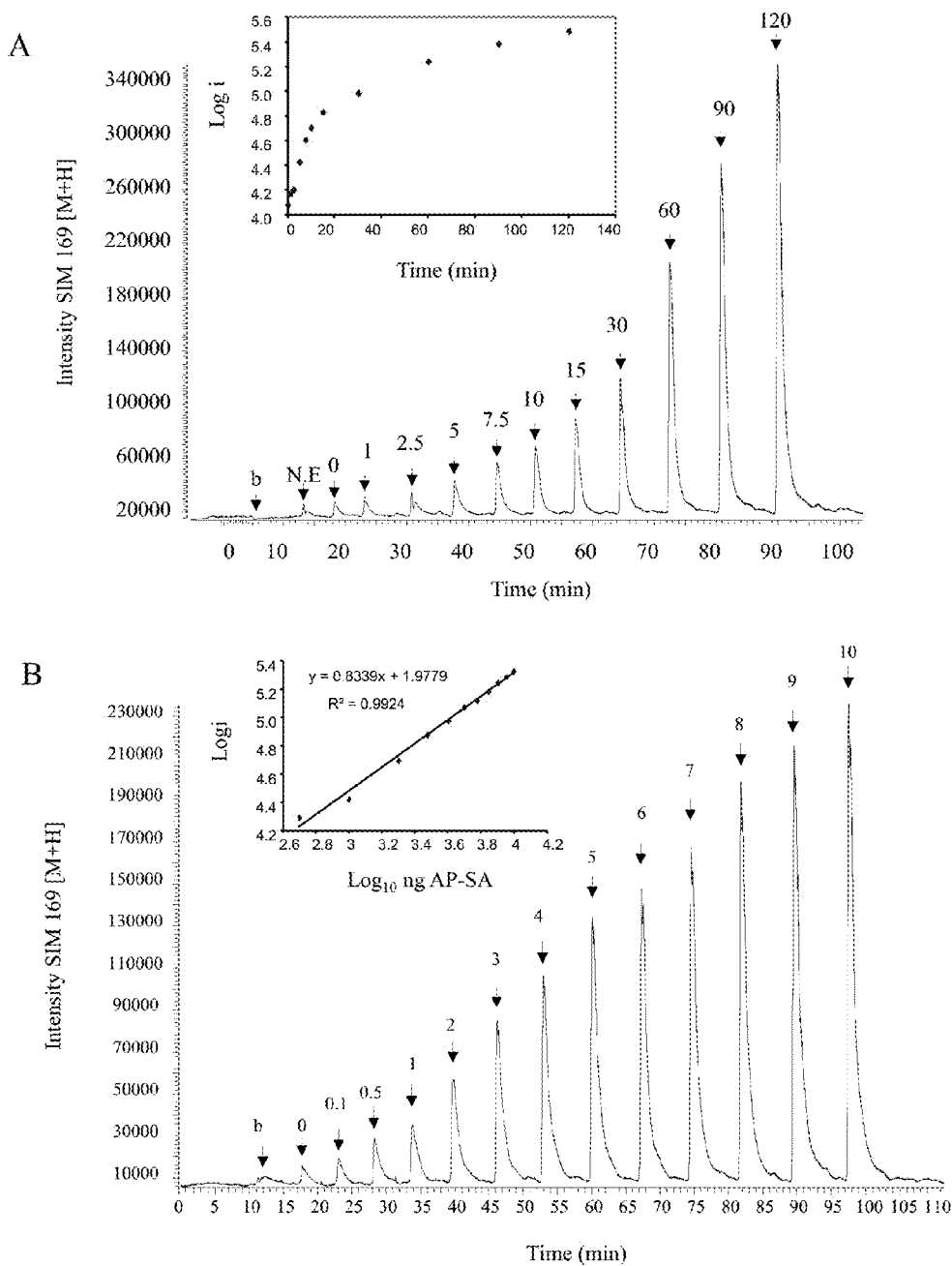

FIG. 57. Isocratic chromatogram showing the enzymatic production of pyridoxamine (PA) from pyridoxamine-5-phosphate (PA5P) by the enzyme alkaline phosphatase conjugated to streptavidin (AP-SA). Panels: A, the time course of PA production by the AP-SA conjugate (5 ng) added to 1 ml of 1 mM PA5P in 20 mM tris pH 8.8 as measured using LC-MS with SIM of pyridoxamine (PA) at 169 m/z [M+H]. The normal-phase isocratic chromatograph of the time course of the AP-SA enzyme reaction to produce PA from PA5P showing blank or the reaction time in minutes (inset shows the plot of log 169 [M+H] intensity versus time); B, the AP-SA conjugate amount shown in ng/ml was added to 1 ml of 1 mM PA5P in 20 mM tris pH 8.8 (inset shows the log linear relationship between log PA ion intensity when the amounts of AP-SA in log ng/ml were added to the reaction). The production of PA was sampled by removing 10 ul of the reaction that was mixed with 90 µl of 0.1% formic acid and 2 µl of the diluted sample was manually injected. Blank injection (b) and no enzyme (N.E.) reaction injections are shown.

Figure 58:
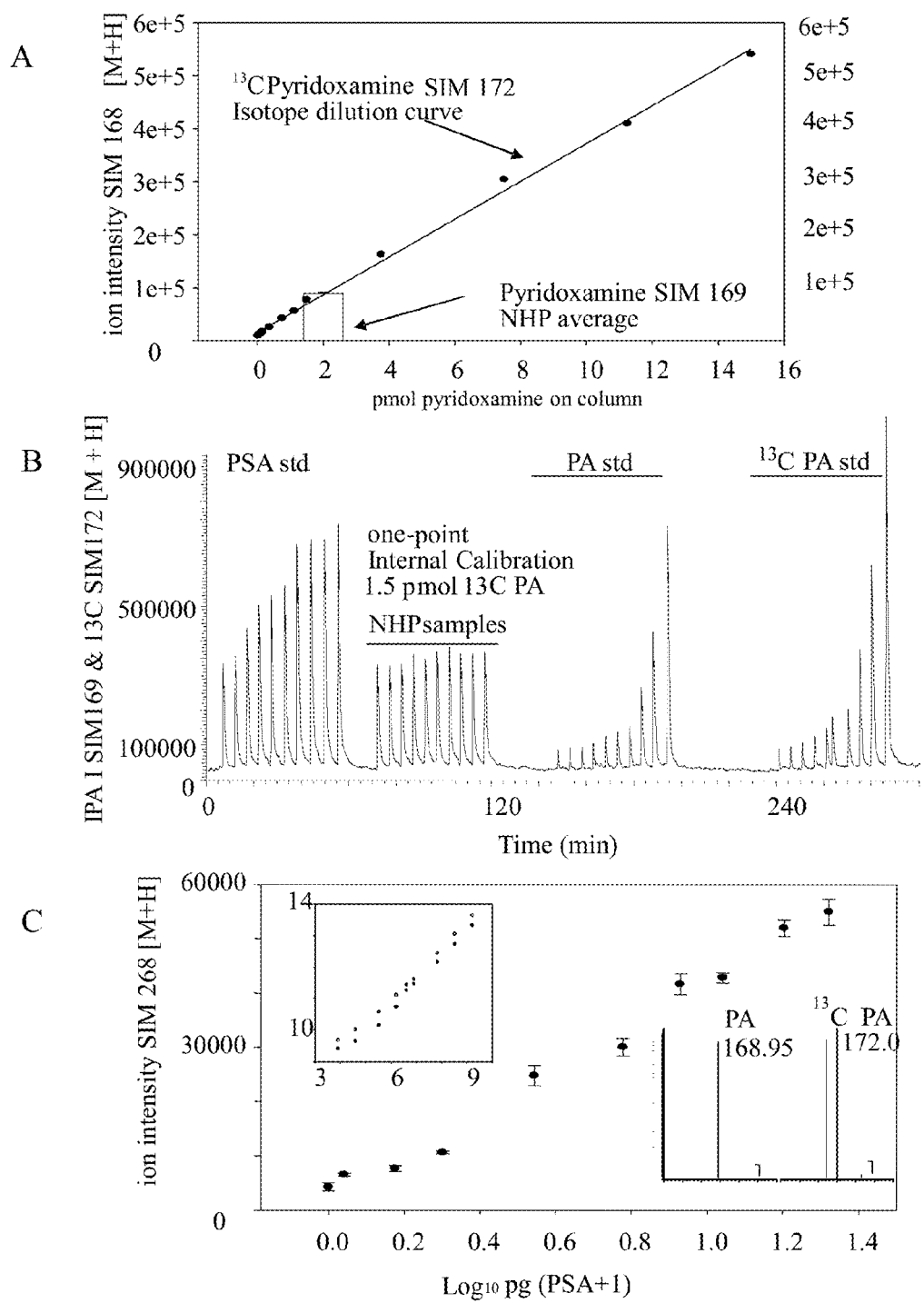

FIG. 58. Measurement of ELIMSA with external PSA standards by PA production alongside to internal isotope dilution, internal one point calibration and external PA and 13C PA curves. Panels: A, The internal 13C isotope dilution curve for 12 NHP samples that showed an average of ~2.01±0.0377 pmo PA injected from each replicate well; B, The isocratic chromatograph showing the AP-SA ELIMSA with an external PSA standard curve linear from 0.1 to 10 ng per well [with 1.5 pmol 13C internal standards], followed by 10 NHP samples (with 1.5 pmol 13C internal standards), and finally PA and 13C PA external standards as shown; C, The average PSA standard intensity values over three separate days showed an R2 of 0.99 [insets: upper left, the external pyridoxamine (PA) standard curve with (SIM 169), and the 13C external PA curve; lower right, the intensity match between the NHP PSA ELIMSA at SIM 169 and 1.5 pmol of the 13C pyridoxamine internal standard that showed nearly equal intensity match between the NHP PSA ELISA at SIM 169 and 1.5 pmol 13C PA internal one point calibration standard].

Figure 59:
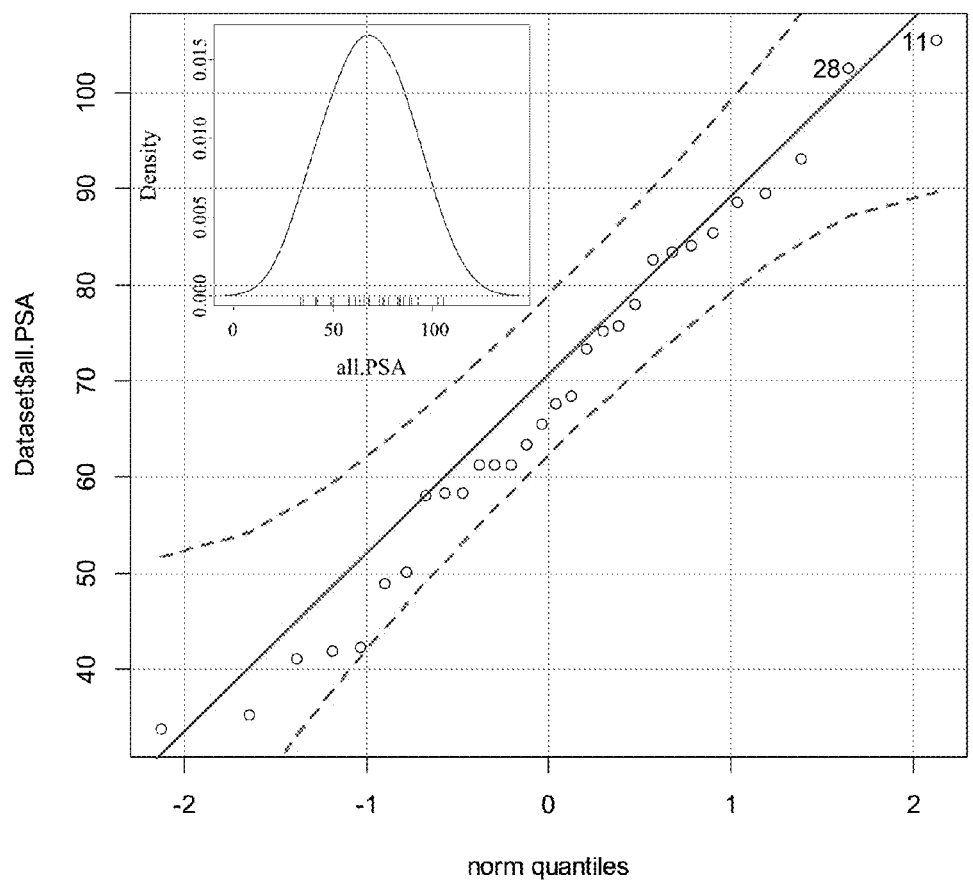

FIG. 59. The normality of PSA levels measured from NHP using ELIMSA. The normal diagnostic QQ plot (inset: fit of the normal distribution). The Shapiro-Wilk test for Goodness of fit to the normal distribution was performed and showed a W 0.968499 and Prob<W 0.3222 W of which indicates that we cannot reject the null hypothesis (Ho) that the data is from the Normal distribution (i.e. small p values—reject Ho). The graphs were created with the R open source statistical analysis system from the population of PSA values shown in Table 5.

Figure 60:
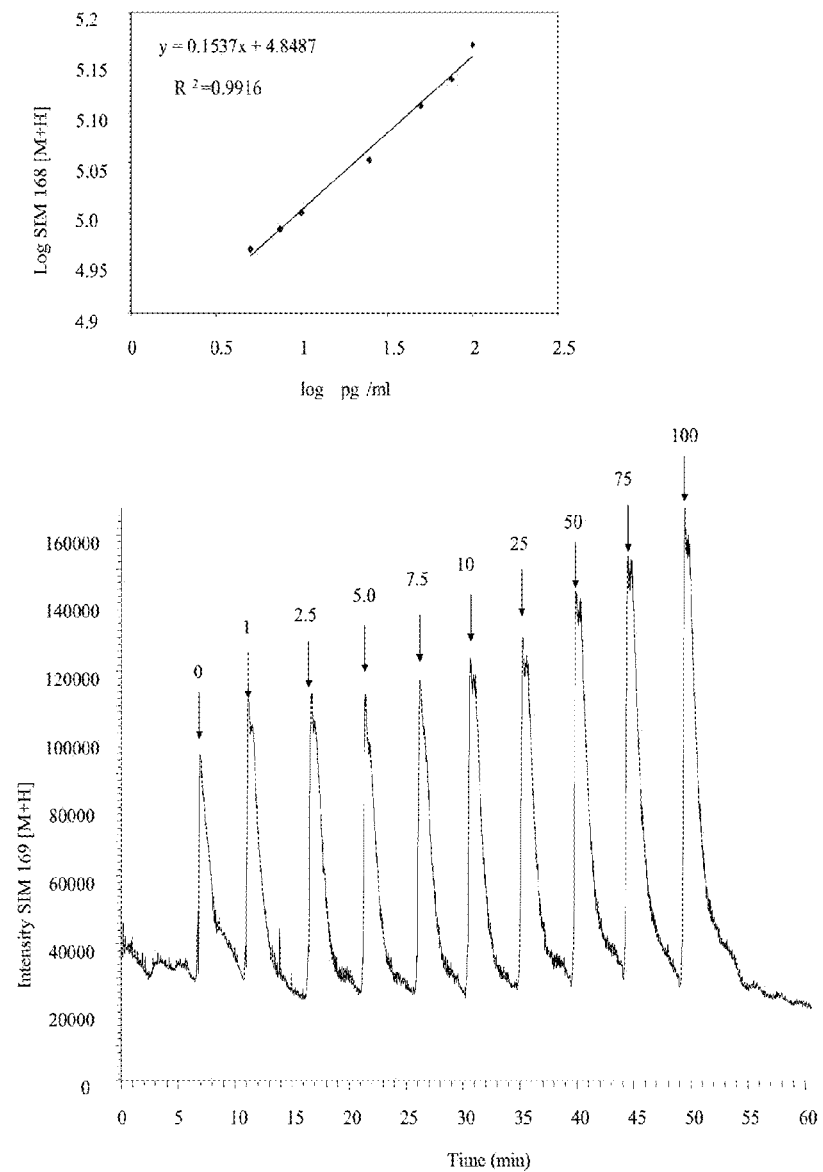

FIG. 60. Detection of AP-SA from 1 to 100 pico gram per ml with analysis of 0.2 micro liters that shows sensitivity on the order of 1.05 E-21 mol. i.e. 1 zepto mol, of AP-SA under analysis. In order to reliable detect such low level the enzyme assay solution contained 1 mg/ml BSA to prevent non-specific adsorption of the PA enzyme product to the experimental apparatus. There is apparently a small amount of substrate that is not phosphorylated as provided by the manufacturer and this is more apparent at lower amounts under analysis.

Figure 61:
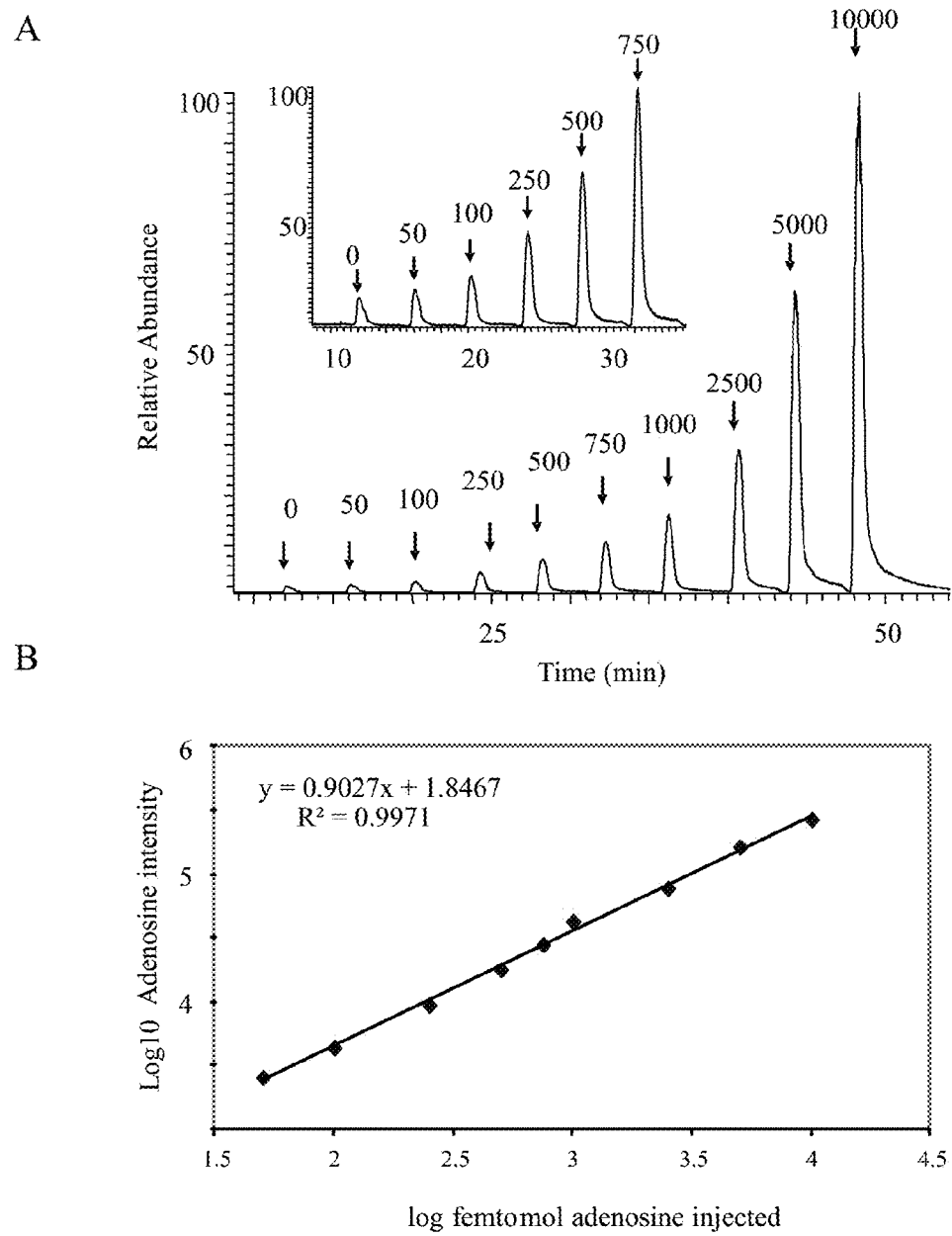

FIG. 61. The relationship between the adenosine injected and ion intensity by SIM at 268 m/z [M+H]. Panels: A, the normal-phase isocratic LC-MS chromatogram of the adenosine dilution series where the amount injected on column in femtomoles is shown (inset shows the signal to noise achieved at low quantity injected); B, the log-linear relationship between intensity and the log amount of adenosine injected on to the column. Hence mass spectrometry is inherently quantitative for the analyte adenosine at least over the range shown.

Figure 62:
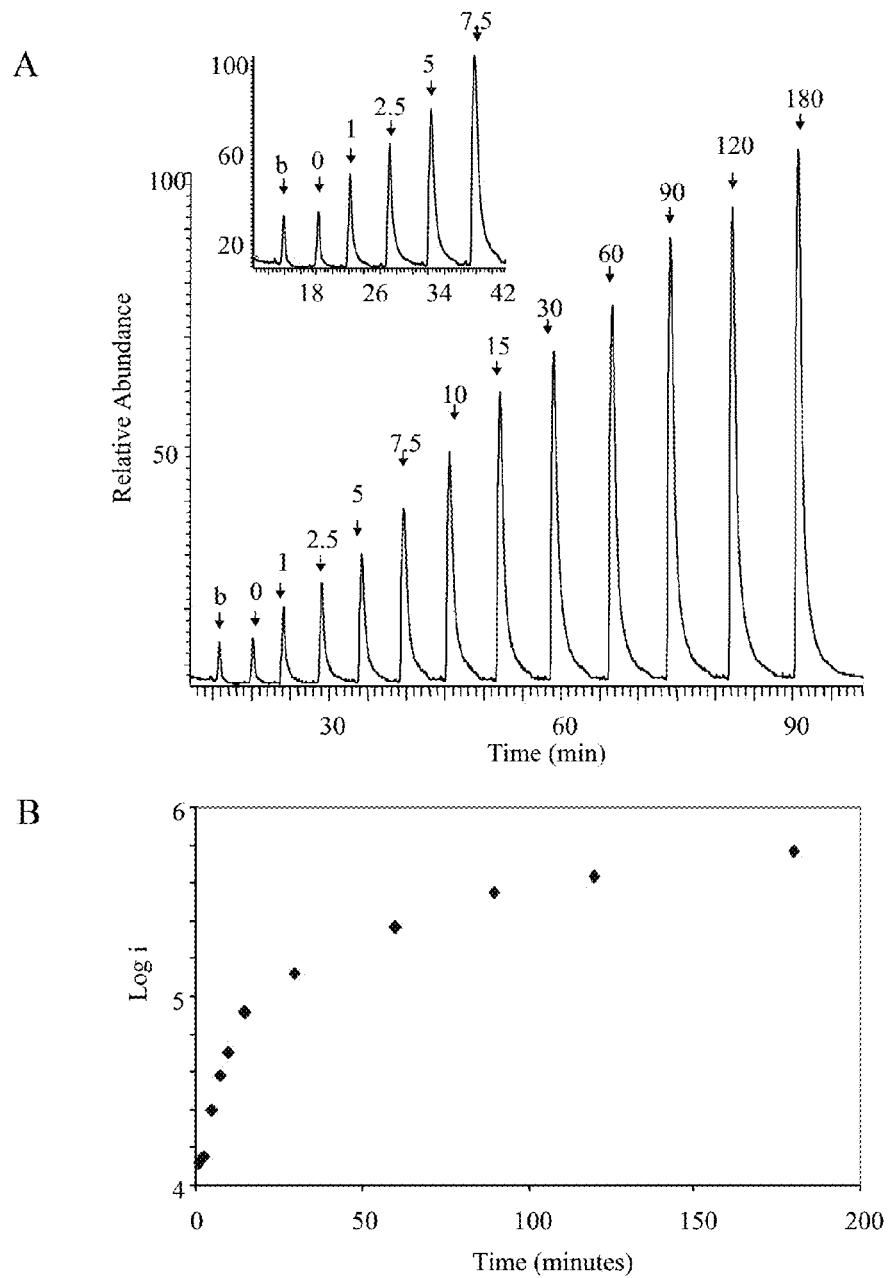

FIG. 62. The time course of adenosine production by AP as measured using LC-MS with SIM of adenosine at 268 m/z [M+H]. Panels: A, The normal-phase isocratic chromatograph of the time course of the AP enzyme reaction to produce adenosine from AMP showing blank (b) or the reaction time in minutes (inset shows first time points); B, The plot log 268 [M+H] intensity versus time.

Figure 63:
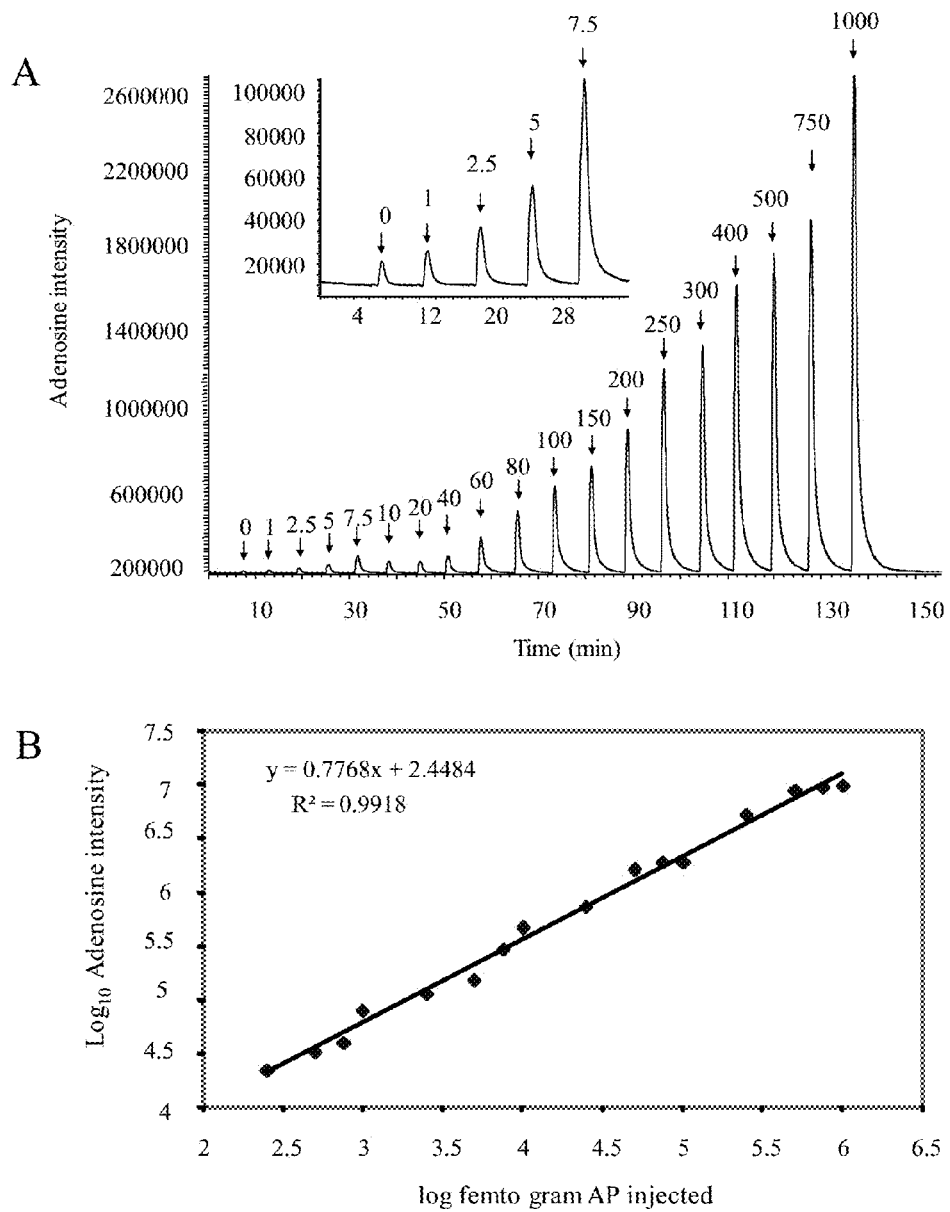

FIG. 63. The linear quantification of femto gram per ml to atto gram absolute amounts of the alkaline phosphatase-streptavidin probe (AP-SA) by LC-MS with single ion monitoring at 268 m/z [M+H]. A total of 2 micro liters of the adenosine product after drying under vacuum and extracting in acetone was injected. Panels: A, the normal-phase isocratic chromatogram, showing the concentration of AP from 1 to 1000 pico grams per ml (inset shows detection of as little as 1 pico gram per ml with injection of 0.2 micro liters ~1.0 E-21 mol on column); B, the log-linear relationship between AP injected and adenosine intensity. The smallest standard is 200 atto grams which is about 105 yoctomols on column.

Figure 64:
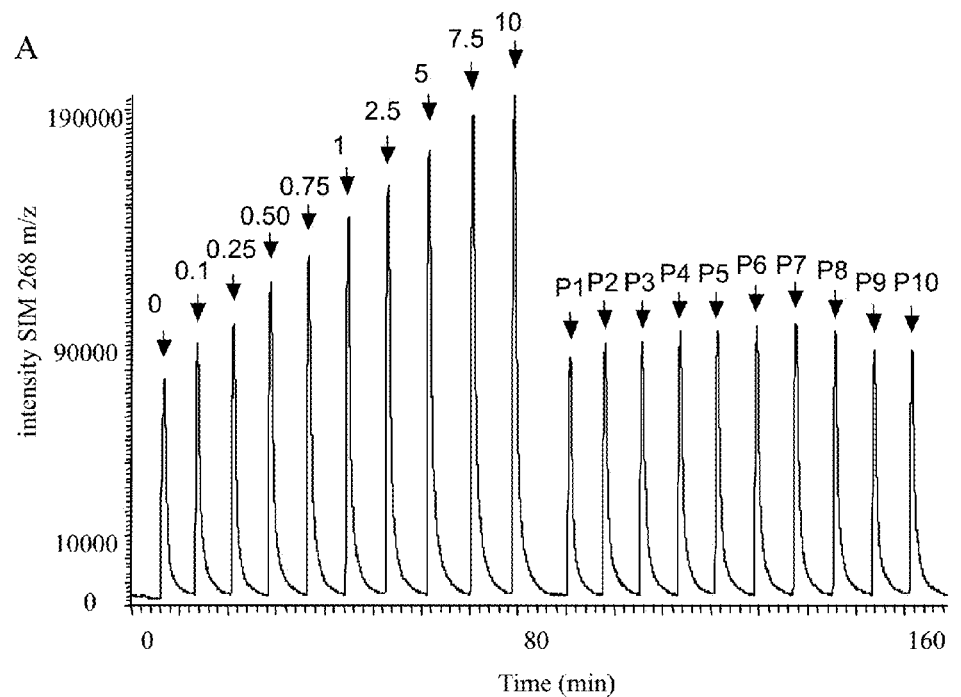
Figure 64:
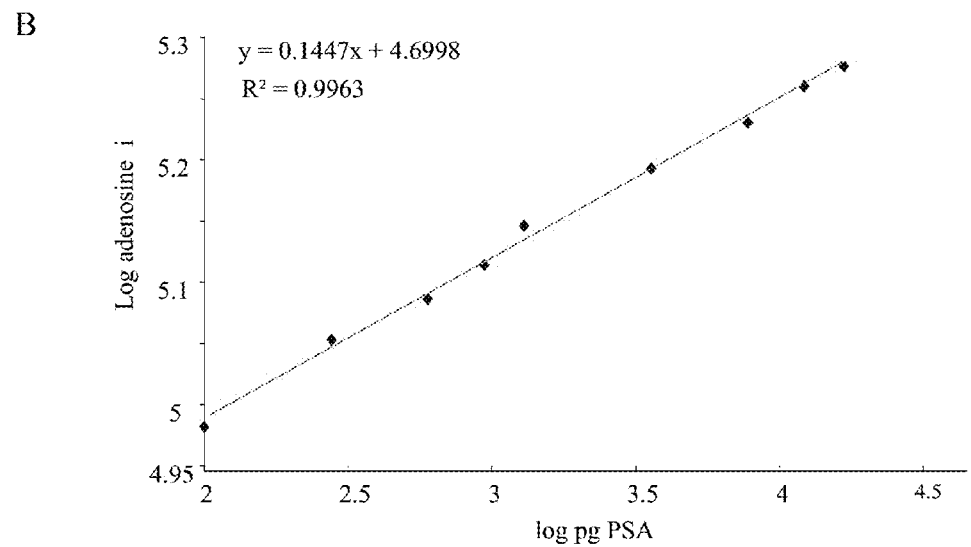

FIG. 64. The ELIMSA assay for PSA from NHP samples. Panels: A, a typical ELIMSA isocratic LC-ESI-MS experiment showing a standard curve of known PSA amounts as shown by arrows in ng per well.

Figure 65:
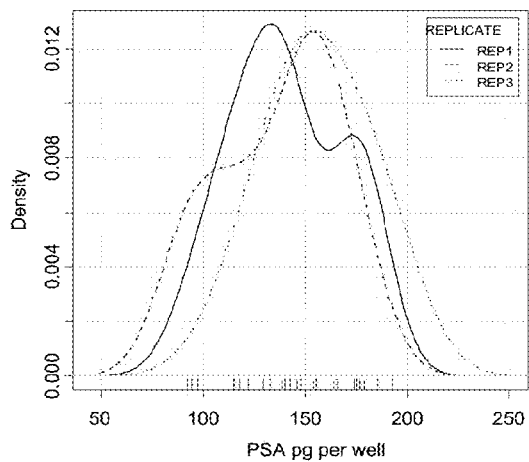
Figure 65:
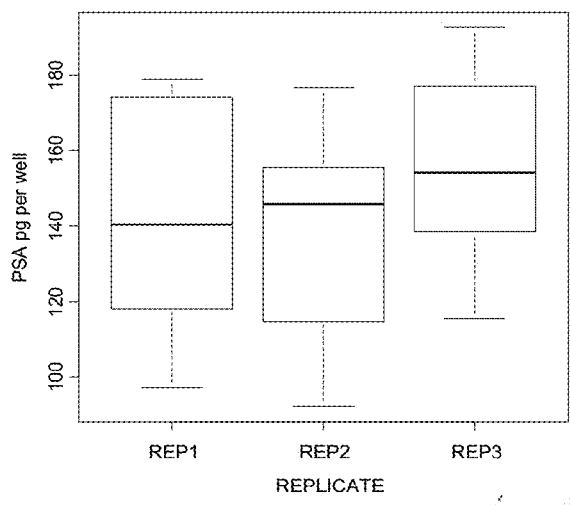
Figure 65:
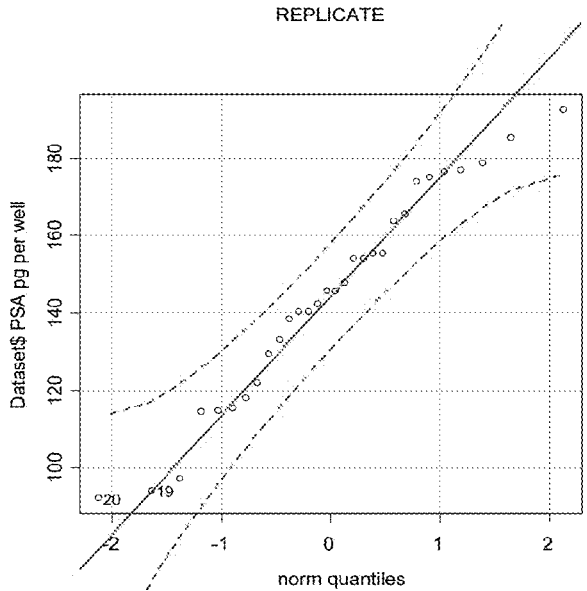

FIG. 65. The homogeneity and normality of the same normal human plasma (NHP) prostate specific antigen (PSA) distributions measured on three independent experiments. Panels: A, the density plot of the three replicate days; B, the box plot showing the mean and 95% confidence internal for the PSA estimates (mean, SE: REP1 141.01, 8.81; REP2 136.73,9.31; REP3 156.18,7.65); C, the quantile plot showing the normality of the combined results of the three test days. The distributions of the data were calculated and plotted with the R statistical analysis system. There was no statistically significant difference between the three replicates by ANOVA.

Figure 66:
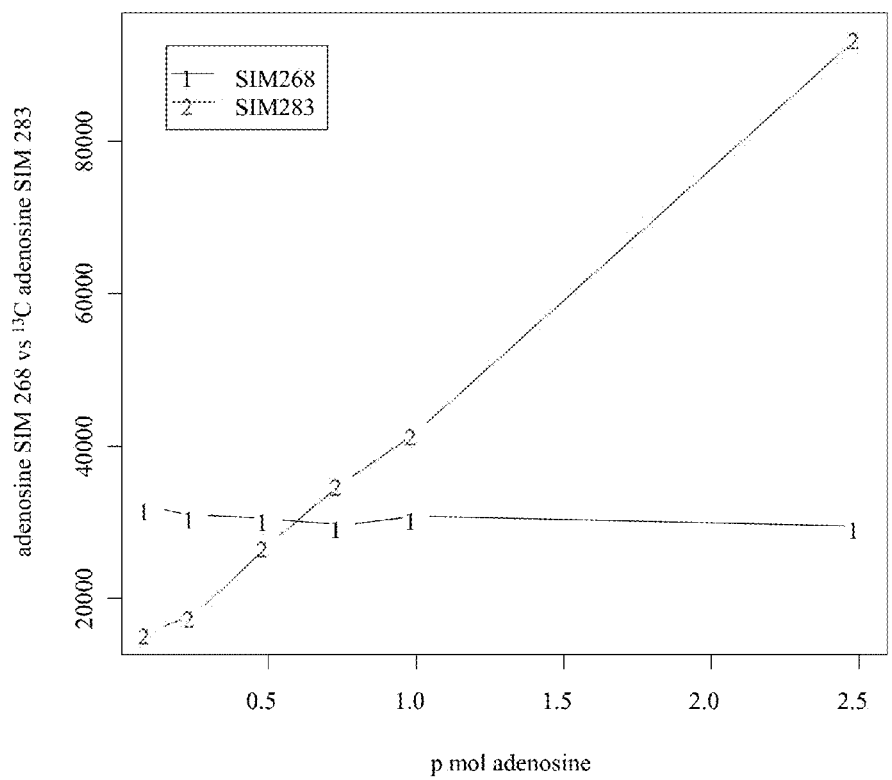

FIG. 66. Estimation of the production of adenosine (A) at SIM 268 by the ELIMSA assay of PSA from a normal human plasma sample by the serial dilution of an internal 13C adenosine (13C A) SIM 283. Reading the average value of SIM268 off the SIM283 standard curve yields and estimate of 0.59 pmol A produced by the ELIMSA reaction [See Table 7].

Figure 67:
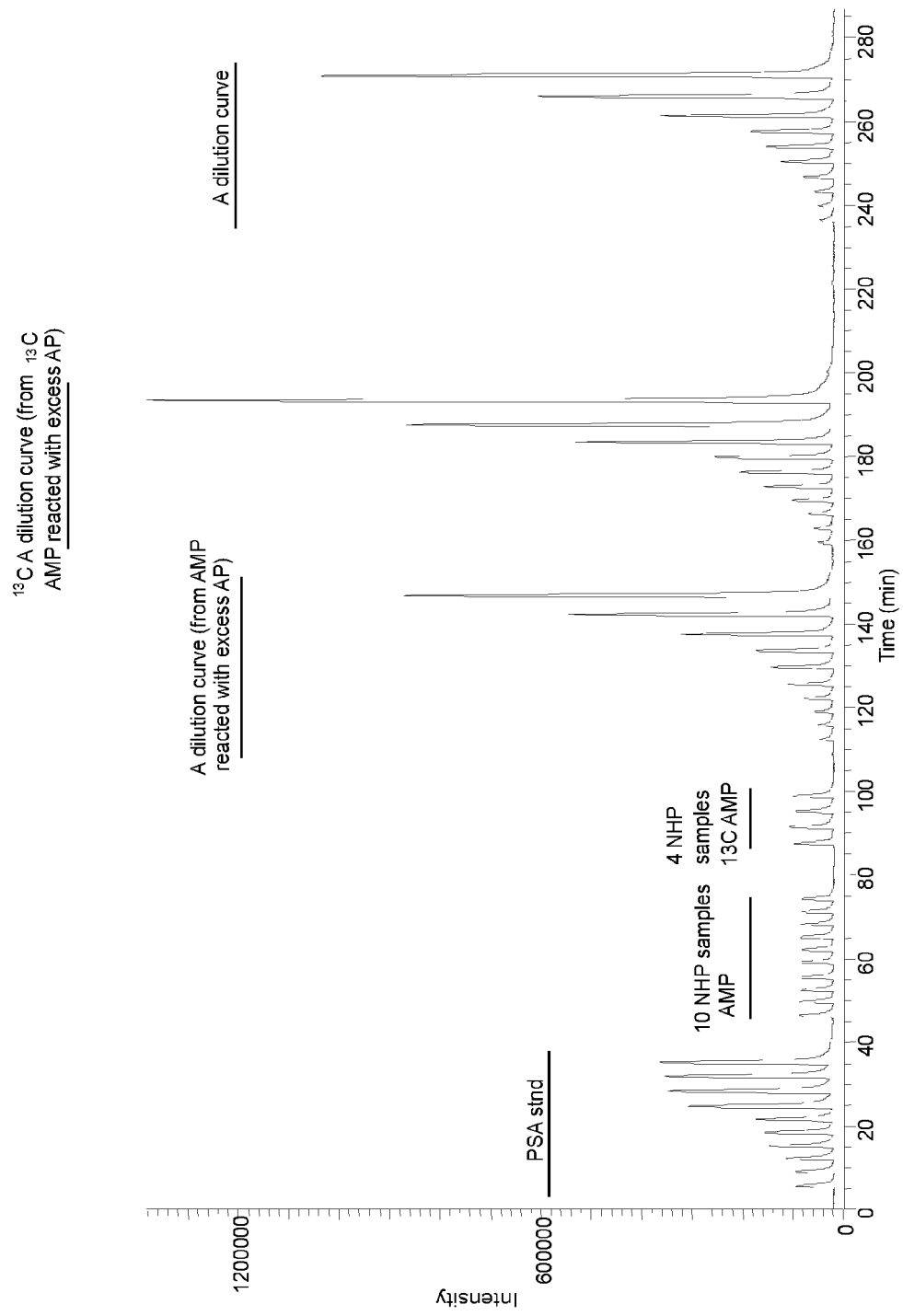

FIG. 67. Experimental set up for the comparison of Adenosine (A, SIM268) produced from the PSA ELIMSA to internal 13C adenosine (13C A, SIM283) or external standard(s). TIC trace left to right: PSA standard curve from ELIMSA from 0.1 to 1 ng per well; 10 normal human plasma samples (NHP) to measure against external standards; 10 NHP samples with internal 13C A standards (50 pmol 13C A SIM 283); External A standard from reaction of substrate stock with excess AP-SA monitored at SIM 268; External standard from 13C A monitored at SIM 283; External standard from adenosine from a second stock. [The results of the internal and external standard experiments are in Table 4].

Figure 68:
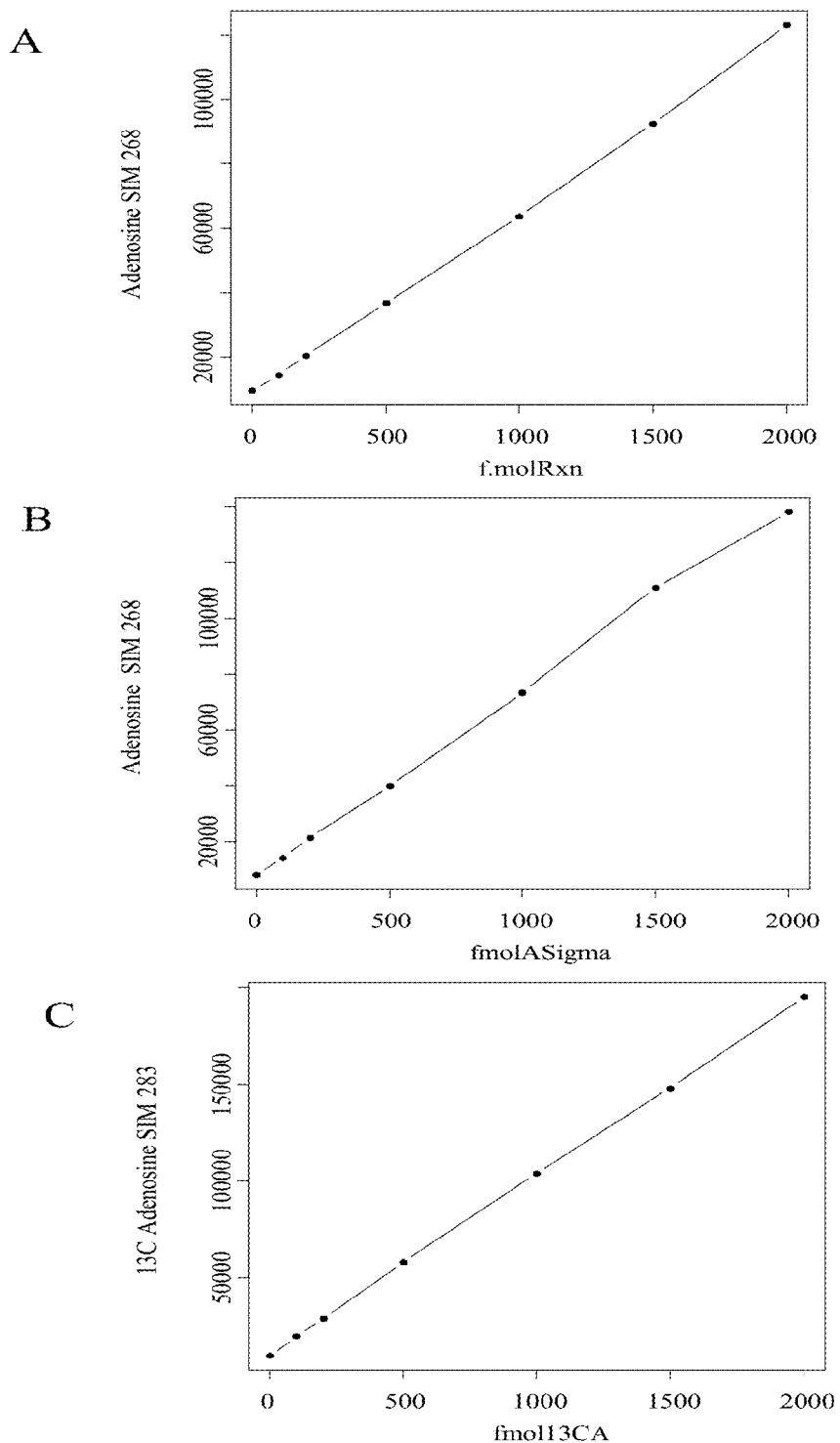

FIG. 68. The linearity of adenosine (A) or 13C adenosine external standard curves. Panels: Top, the adenosine monophosphate (AMP) substrate stock completely reacted with excess AP-SA for SIM268; Middle, external adenosine standard curve from a purchased dry powder stock for SIM 268; Bottom, external curve from 13C adenosine stock for SIM 283.

Figure 69:
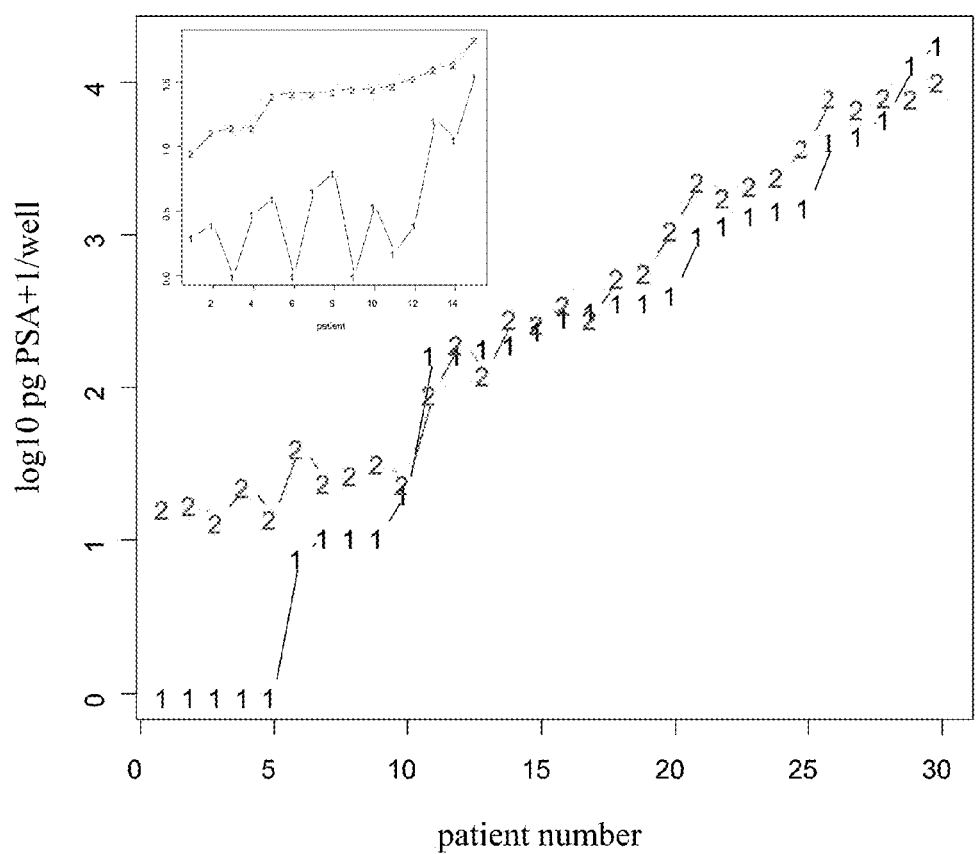

FIG. 69. The ELIMSA assay of human plasma samples and comparison to traditional ELISA methods for the quantification of PSA. The comparison of the automated ECL for total PSA (1) versus the ELIMSA assay of the same reagents (2) over 30 patient samples ranked by the ECL results. The ELISA results dropped precipitously below 100 pico grams per well and was not able to differentiate many samples from zero. In contrast ELIMSA could quantify all samples. [Inset: Manual ECL assay (1) versus ELIMSA (2) with the same reagents. In both instances some samples that could not be separated by the background in ECL could be quantified by ELIMSA. ANOVA analysis of the results from ELIMSA verses ECL for samples of less than 100 picograms showed a statistically significant difference between ELIMSA versus ECL.

Figure 70:
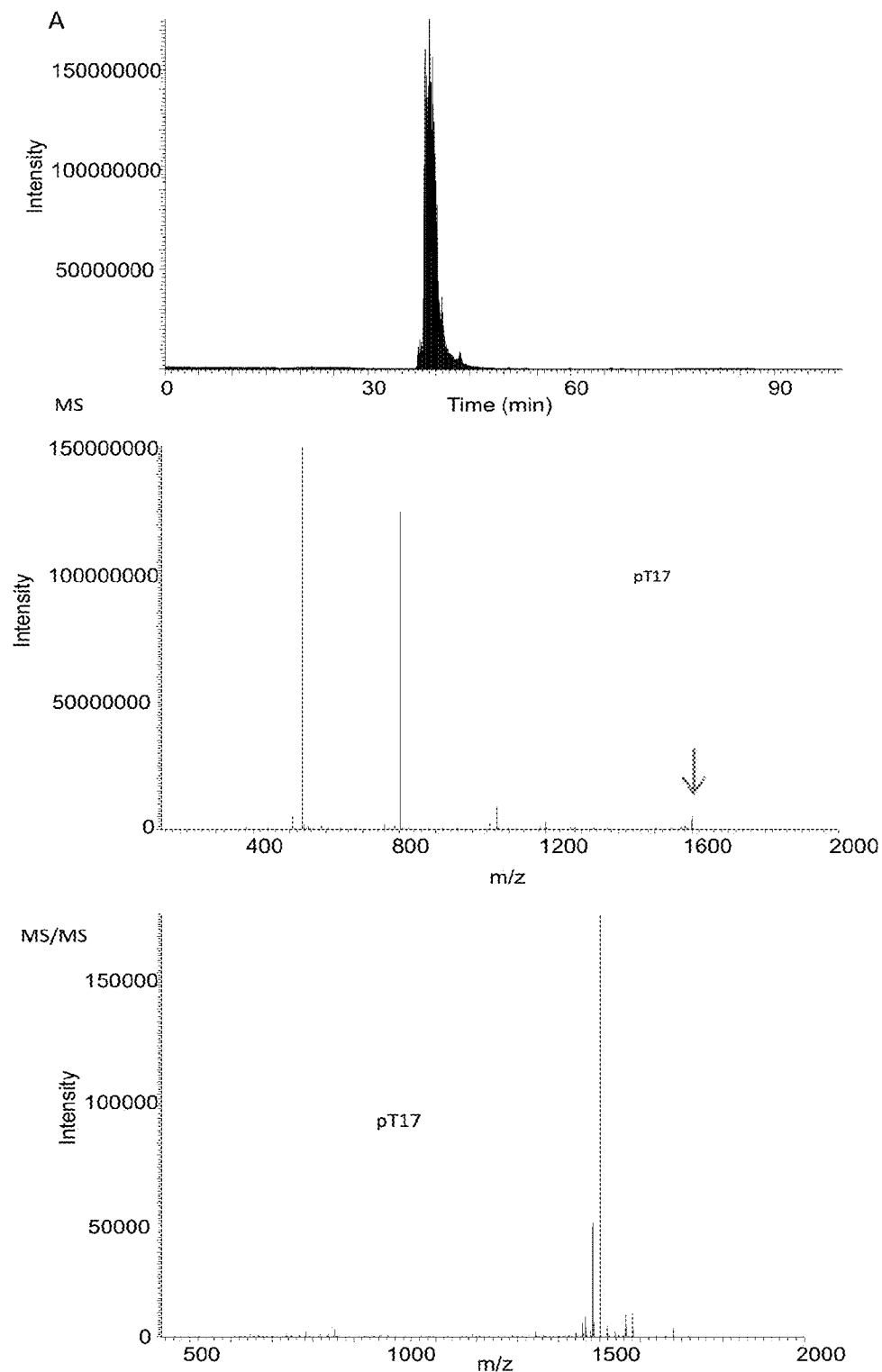
Figure 70:
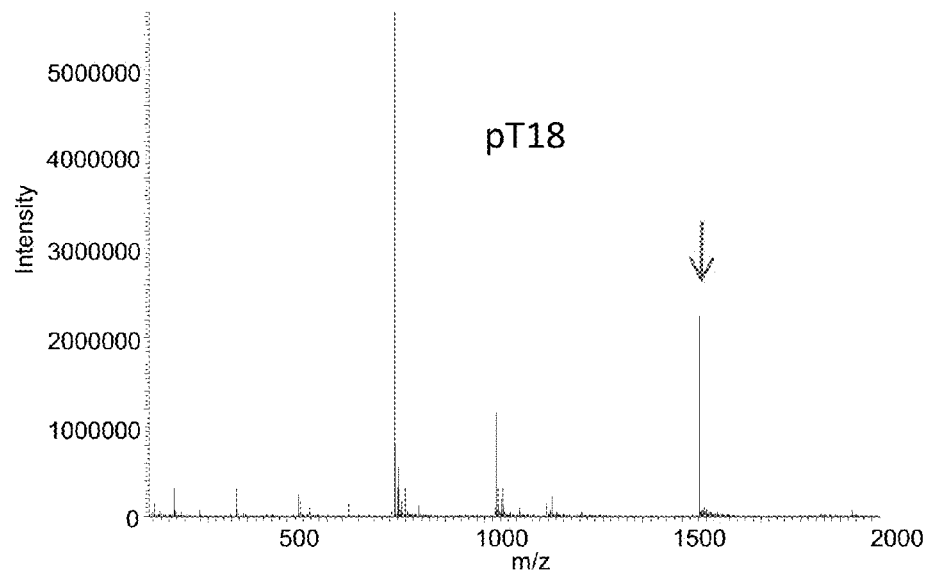
Figure 70:
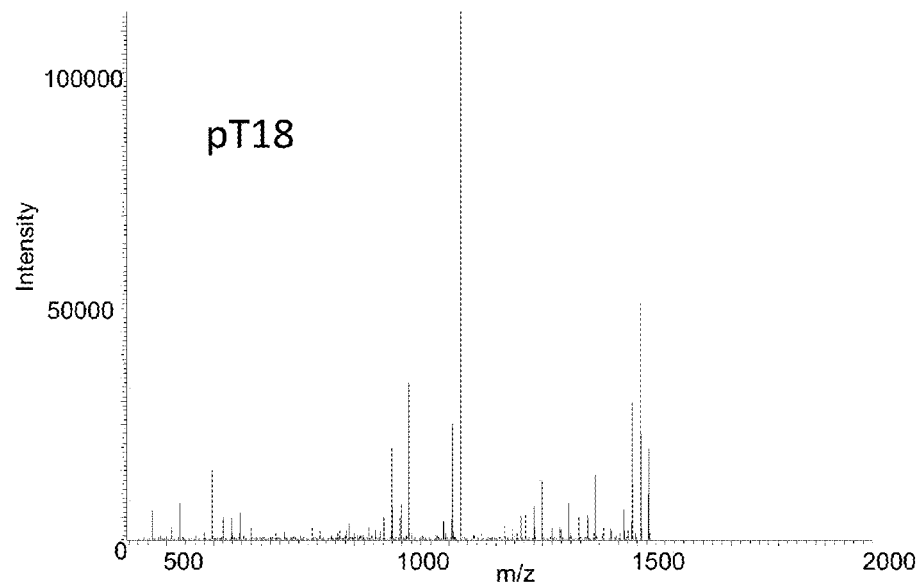
Figure 70:
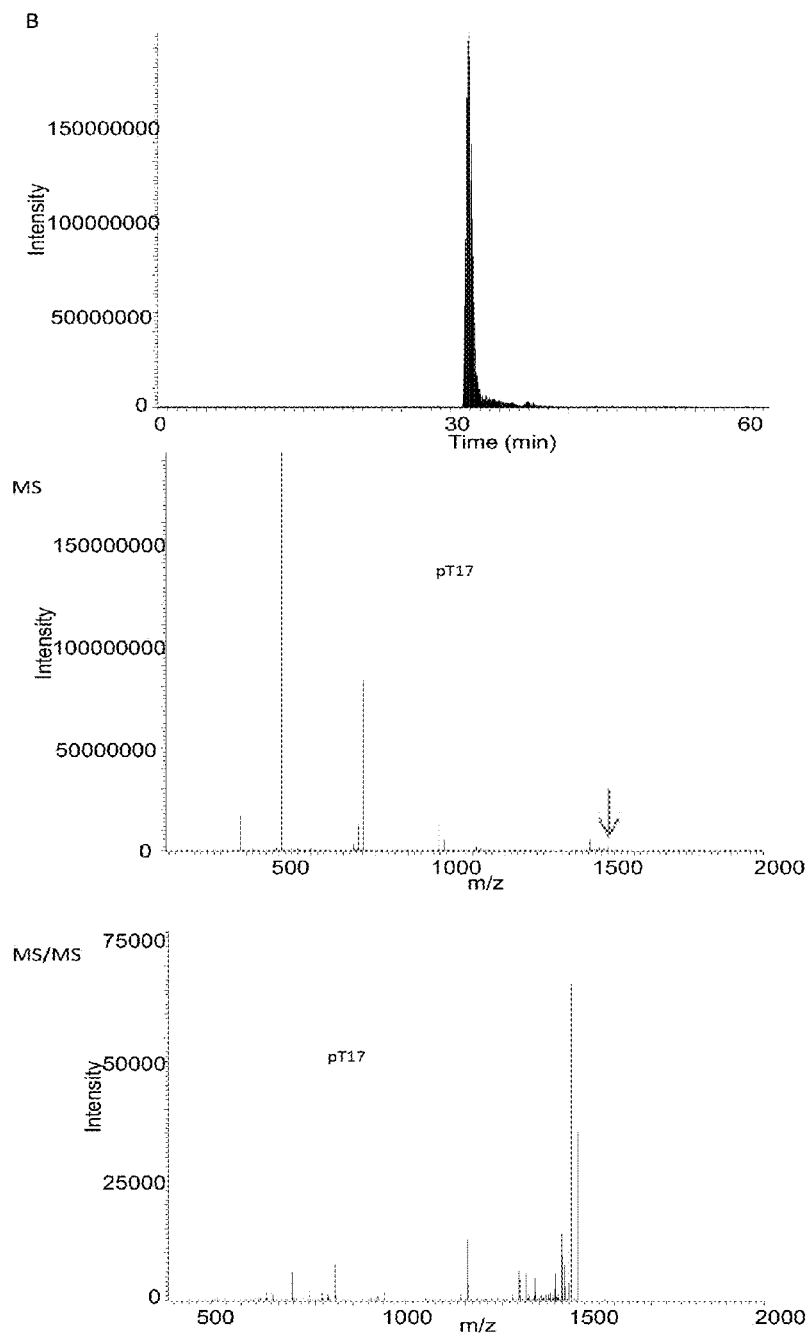
Figure 70:
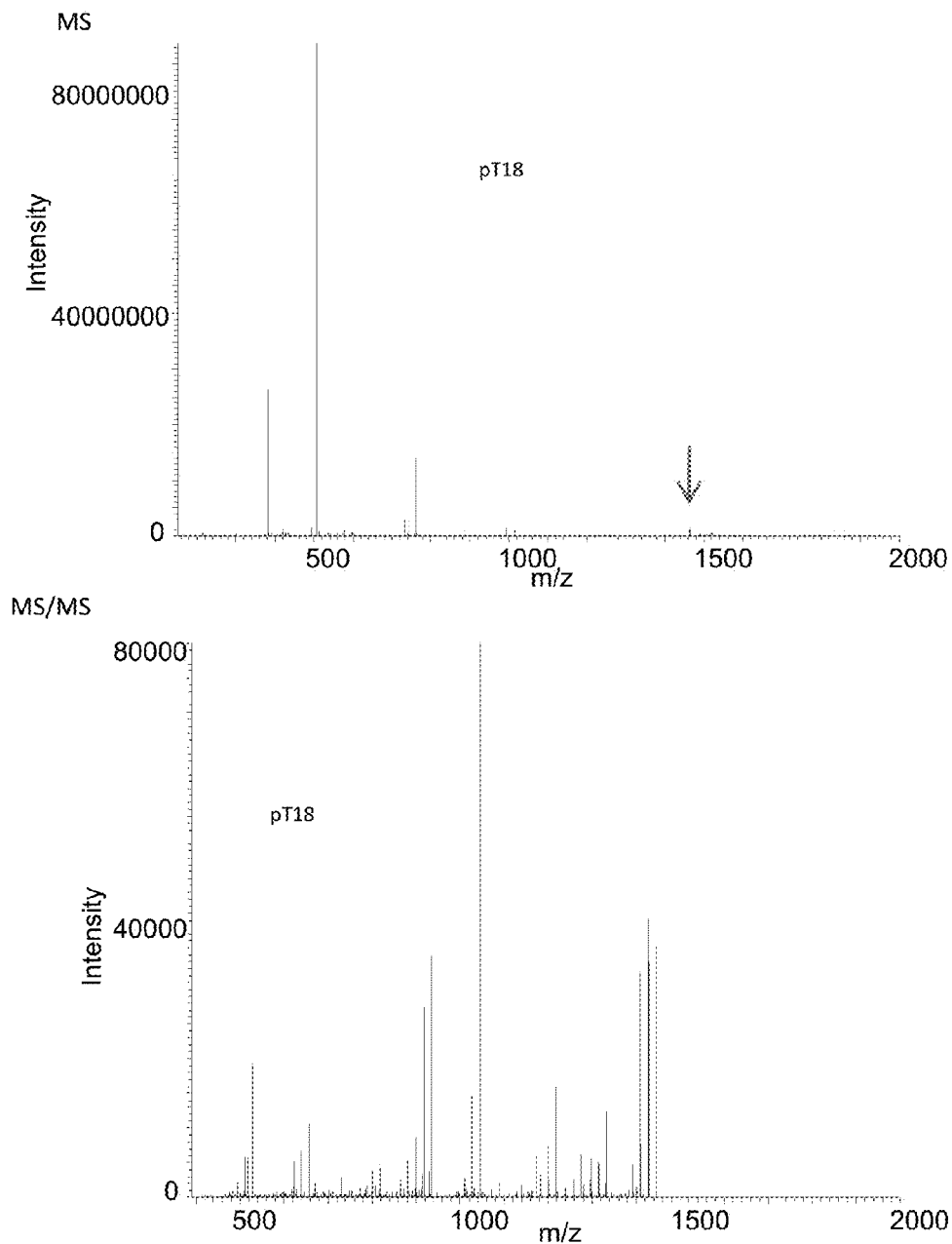

FIG. 70. Panel A the phosphopeptide substrates pT17 and pT18 analyzed, indentified and quantified in the same liquid chromatography and tandem and mass spectrometry analysis. Panels: Top, liquid chromatography, electrospray ionization and intensity trace trace from tandem mass spectrometry (arrow shows product ion m/z); Bottom, MS and MS/MS identification and quantification of substrate peptide ion intensity; Panel B the dephosphorylated peptide products of substrates pT17 and pT18 analyzed, indentified and quantified in the same liquid chromatography and tandem and mass spectrometry analysis. Top: liquid chromatography, electrospray ionization and intensity trace from tandem mass spectrometry (arrow shows product ion m/z); Bottom, MS and MS/MS identification and quantification of product peptide ion intensity.

Figure 71:
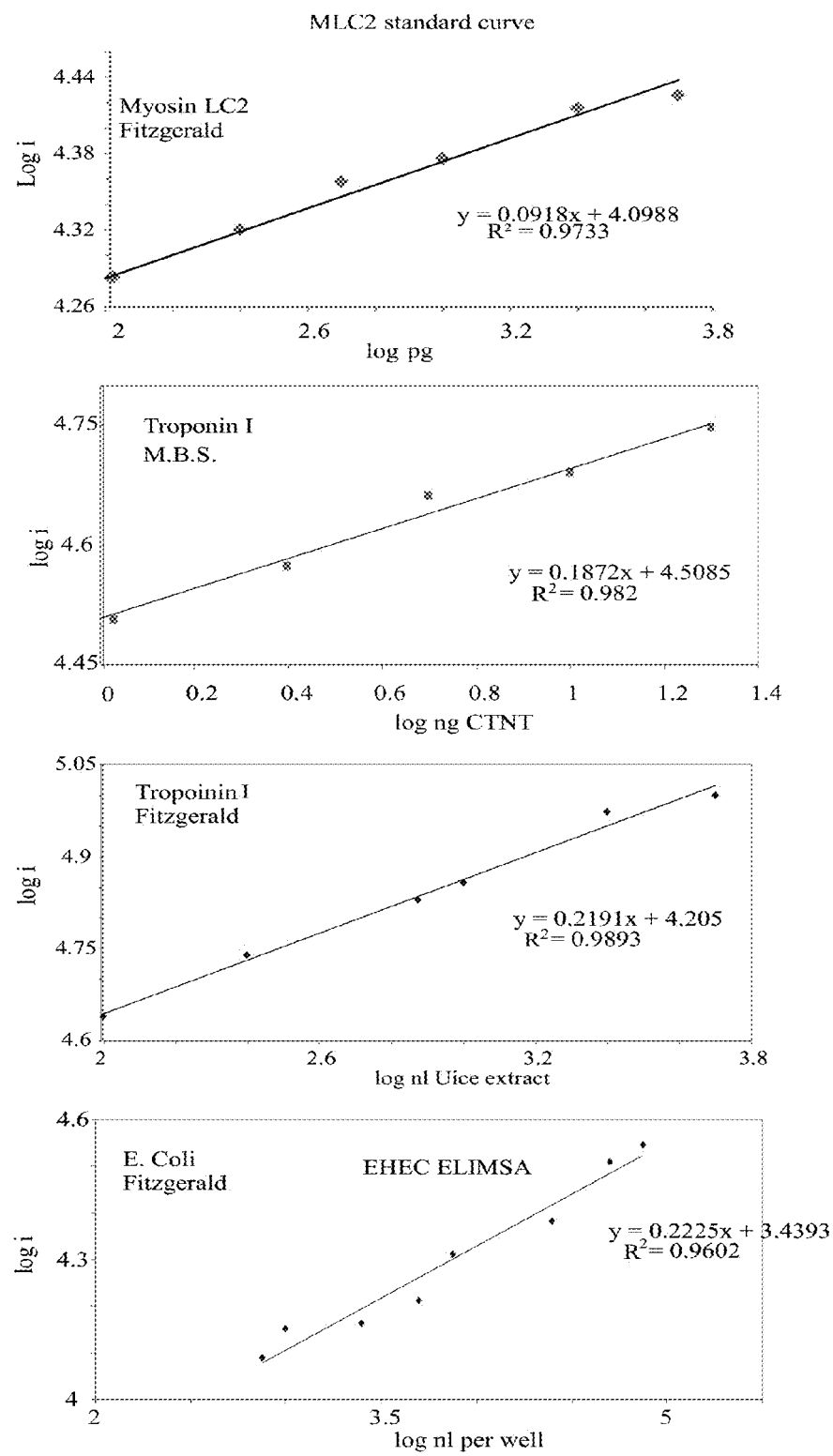

FIG. 71. ELIMSA assays for: myosin Light chain 2 (MLC2); Troponin I; Troponin I different antibodies; E. coli 0157.

DETAILED DESCRIPTION OF THE DISCLOSURE

I. Definitions

The term "adenosine monophosphate" or "AMP" as used herein means a compound having the structure:

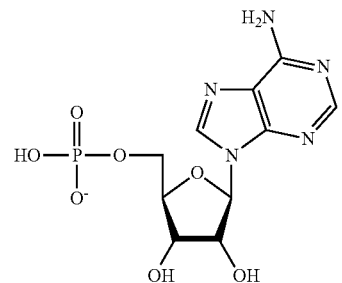

or pharmaceutically acceptable salts or solvates thereof as well as mixtures thereof. AMP can be obtained for example from Sigma Aldrich.

The term "Amplex® Red" or "AR" as used herein means:

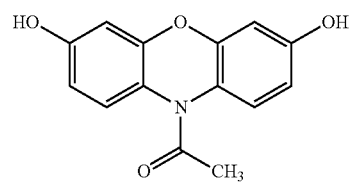 [SMILES: CC(=O)N1c2ccc(O)cc2Oc2cc(O)ccc21]

or pharmaceutically acceptable salts or solvates thereof as well as mixtures thereof. Amplex® Red can be obtained for example from Resazurin which is structurally related and has the formula 7-Hydroxy-3H-phenoxazin-3-one 10-oxide is also referred to as Amplex® Red. Accordingly, Amplex® Red as used herein includes both AR and Resazurin.

The term "antibody" and/or "immunoglobulin" as used herein is intended to include monoclonal antibodies including chimeric and humanized monoclonal antibodies, polyclonal antibodies, humanized antibodies, human antibodies, and chimeric antibodies. The antibody may be from recombinant sources and/or produced in transgenic animals. The term "antibody fragment" as used herein is intended to include Fab, Fab', F(ab')$_2$, scFv, dsFv, ds-scFv, dimers, minibodies, diabodies, and multimers thereof and bispecific antibody fragments. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, dsFv, ds-scFv, dimers, minibodies, diabodies, bispecific antibody fragments and other fragments can also be synthesized by recombinant techniques. The antibodies are optionally in any useful isotype, including IgM and IgG, such as IgG1, IgG2, IgG3 and IgG4.

Immunoglobulins are a superfamily of shape recognition molecules with the exquisite capacity to specifically bind to at least trillions of different molecules or surface antigens[1]. Mono specific antibodies may be raised in animals and purified by affinity chromatography [4]. Monoclonal antibodies may be raised in mice, secreted from hybridoma cell lines and applied to an unlimited number of target analytes [5].

To produce monoclonal antibodies, antibody producing cells (lymphocytes) can be harvested from a subject immunized with a target substance, and fused with myeloma cells by standard somatic cell fusion procedures thus immortalizing these cells and yielding hybridoma cells. Such techniques are well known in the art, (e.g. the hybridoma technique originally developed by Kohler and Milstein as well as other techniques such as the human B-cell hybridoma technique, the EBV-hybridoma technique to produce human monoclonal antibodies, and screening of combinatorial antibody libraries.

The term "biopolymer" as used herein means any polypeptide, polynucleotide, lipid, carbohydrate or combination thereof.

The term "5-Bromo-4-chloro-3-indolyl phosphate" or "BCIP" means as used herein a compound having the structure:

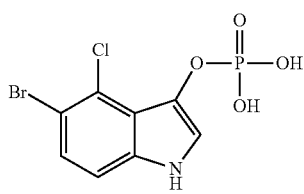 [SMILES: O=P(O)(O)Oc1c[nH]c2ccc(Br)c(Cl)c12]

or pharmaceutically acceptable salts or solvates thereof as well as mixtures thereof. BCIP can be obtained for example from Sigma Aldrich.

The term "ionizable product", as used herein means a product generated by a reporter enzyme, that comprises one or more ionizable groups. For example, an ionizable product may have one or more basic or amine groups for positive ionization and one or more acidic or hydroxyl groups for negative ionization. Ionizable groups may include =NH, —NH2, guanidinium, methyl, ethyl, alky, phenyl, ribose, inositiol, phospholipid, carbohydrate, nucleic acid, carbonyl, aldehyde, ketone, carboxyl, hydroxyl, enol, guanidium, imidazole, sulfhydryl, disulfide, sulfate, phosphate, sulfonyl, nitrate, nitric oxide, thioester, ester, ether, anhydride, phosphoryl, mixed anhydride, and/or other ionizable groups known in the art. An ionizable product assessed, optionally efficiently enters the gas phase by electrospray ionization.

The term "L-(+)-2-amino-6-phosphonohexanoic acid" as used herein means:

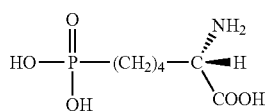

or pharmaceutically acceptable salts or solvates thereof as well as mixtures thereof. L-(+)-2-amino-6-phosphonohexanoic acid can be obtained for example from Sigma Aldrich.

The term "Lumigen® TMA-3" or "TMA-3" as used herein means

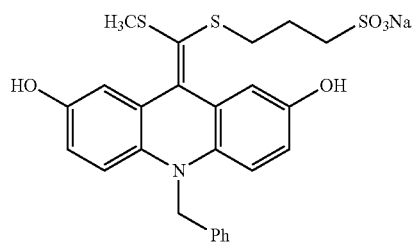

or pharmaceutically acceptable salts or solvates thereof as well as mixtures thereof. TMA-3 can be obtained for example from Beckman Coulter Company.

The term "Lumigen® TMA-6" or "TMA-6" as used herein means

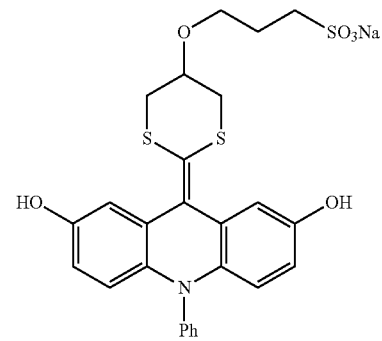

or pharmaceutically acceptable salts or solvates thereof as well as mixtures thereof. TMA-6 can be obtained for example from Beckmann Coulter Company.

The term "4-Methylumbelliferyl phosphate" or "4-MUP" as used herein means a compound having the structure:

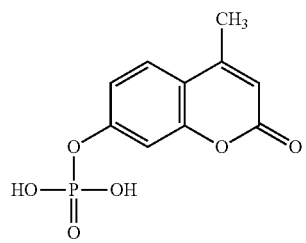 [SMILES: Cc1cc(=O)oc2cc(OP(=O)(O)O)ccc12]

or pharmaceutically acceptable salts or solvates thereof as well as mixtures thereof. 4-MUP can be obtained for example from Sigma Aldrich.

The term "Naphthol ASMX phosphate" as used herein means a compound having the structure:

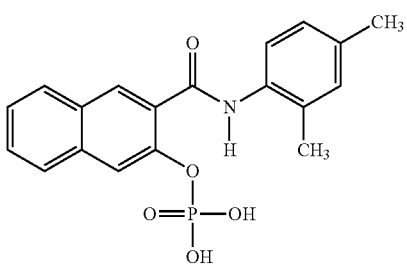 [SMILES: Cc1ccc(NC(=O)c2cc3ccccc3cc2OP(=O)(O)O)c(C)c1]

or pharmaceutically acceptable salts or solvates thereof as well as mixtures thereof. Naphthol ASMX phosphate can be obtained for example from Sigma Aldrich.

The term "O-phospho-DL-Threonine" as used herein means a compound having the structure:

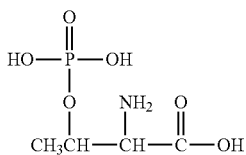

or pharmaceutically acceptable salts or solvates thereof as well as mixtures thereof. O-phospho-DL-Threonine can be obtained for example from Sigma Aldrich.

The term "Para nitrophenol phosphate" or "PNPP" as used herein means a compound having the structure:

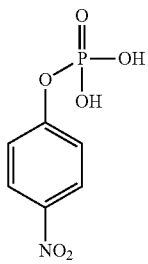 [SMILES: O=[N+]([O-])c1ccc(OP(=O)(O)O)cc1]

or pharmaceutically acceptable salts or solvates thereof as well as mixtures thereof. Para nitrophenol phosphate can be obtained for example from Sigma Aldrich.

The term "phenylbenzene ω phosphono-α-amino acid" as used herein means compound having the structure:

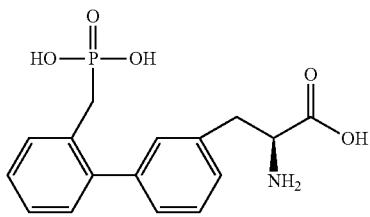 [SMILES: N[C@@H](Cc1cccc(-c2ccccc2CP(=O)(O)O)c1)C(=O)O]

or pharmaceutically acceptable salts or solvates thereof as well as mixtures thereof. Phenylbenzene ω phosphono-α-amino acid can be obtained for example from Sigma Aldrich.

The term "pyridoxamine 5-phosphate" or "PA5P" as used herein means compound having the structure:

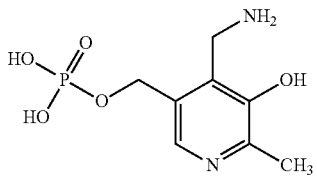 [SMILES: Cc1ncc(COP(=O)(O)O)c(CN)c1O]

or pharmaceutically acceptable salts or solvates thereof as well as mixtures thereof. PA5P can be obtained for example from Sigma Aldrich.

The term "primary detection agent" as used herein means an agent that selectively binds to a target substance, for example an antibody or antibody binding fragment. The primary detection agent is optionally coupled to a detectable label such as biotin. In addition to antibodies and antibody binding fragments, other primary detection agents that bind specifically to target substances are also provided, including for example antibody mimetics, binding polypeptides, such as receptors, binding polypeptide mimetics, nucleic and peptide aptamers, affibodies and anticalins.

The term "reporter enzyme detection probe" as used herein comprises a reporter enzyme component comprising an enzymatic activity, coupled to a detection probe component comprising a target binding moiety. The reporter enzyme is optionally a peroxidase such as horseradish peroxidase or a phosphatase such as alkaline phosphatase although any stable enzyme that can produce ionizable products can be used including for example a lyase, hydrolase, synthase, synthetase, oxidoreductase, dehydrogenase, oxidase, transferease, isomerase, ligase, protease, such as trypsin, proteinase, peroxidase, glucose oxidase, myeloperoxidase, oxidase, monooxygenase, cytochrome, phosphatase such as alkaline phosphatase, decarboxylase, lipase, caspase, amylase, peptidase, transaminase, and kinase. Additional enymes can include DNA or RNA polymerase, TAQ, restriction enzymes, klenow fragment, DNA ligase. The target binding moiety can either be a primary target binding moiety (e.g. a biopolymer such as an antibody) that selectively bind a target substance, or be a secondary target binding moiety that selectively binds a primary detection agent. For example the secondary target binding moiety can comprise a biopolymer such as an antibody that binds an antibody primary detection agent. Alternatively, the secondary target binding moiety comprises avidin or streptavidin that selectively binds a biotyinylated primary detection agent, for example a biotinylated primary detection agent. In addition to antibodies and antibody binding fragments, other biopolymer target binding moieties that bind specifically to target substances or primary detection agents are also provided, including for example antibody mimetics, aptamers, binding polypeptides such as receptors as well as binding polypeptide mimetics, nucleic acids, carbohydrates and/or lipids. Examples include nucleic and/or peptide aptamers, affibodies and anticalins.

The term "selective" as used herein in reference to a probe, optionally an antibody, is used contextually, to characterize the binding properties of the probe, optionally an antibody. For example, an antibody that binds selectively to a given target substance will bind to that target substance either with greater avidity or with more specificity, relative to another, different target substance. In an embodiment, the probe, optionally an antibody, binds at least 2 fold, 3 fold, or 5 fold more efficiently, optionally 3-5 fold, 5-7 fold, 7-10, 10-15, 5-15, or 5-30 fold more efficiently.

The term "sphingosine-1 phosphate" as used herein means a compound having the structure:

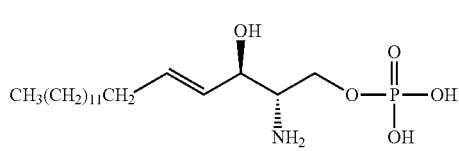

or pharmaceutically acceptable salts or solvates thereof as well as mixtures thereof. Sphingosine-1 phosphate can be obtained for example from Sigma Aldrich.

The term "subject" as used herein includes all members of the animal kingdom including mammals, preferably humans.

The term "target substance" as used herein means any biopolymer, organism or part thereof that is antigenic and/or can act as a ligand for a target substance detection probe.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed ended terms that specify the presence of stated features, elements, components, groups, integers, and/or steps, and also exclude the presence of other unstated features, elements, components, groups, integers and/or steps.

Further, terms of degree such as "substantially", "about"; and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

More specifically, the term "about" means plus or minus 0.1 to 50%, 5-50%, or 10-40%, 10-20%, 10%-15%, preferably 5-10%, most preferably about 5% of the number to which reference is being made As used in this specification and the appended claims, the singular forms "a", and "the" include plural references unless the content clearly dictates otherwise. Thus for example, a composition containing "a compound" includes a mixture of two or more compounds. It should also be noted that the term "or" is generally employed in its sense including "and/or" unless the content clearly dictates otherwise.

The definitions and embodiments described in particular sections are intended to be applicable to other embodiments herein described for which they are suitable as would be understood by a person skilled in the art.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about".

Further, the definitions and embodiments described are intended to be applicable to other embodiments herein described for which they are suitable as would be understood by a person skilled in the art. For example, in the passages herein, different aspects of the invention are defined in more detail. Each aspect so defined can be combined with any other aspect or aspects unless clearly indicated to the contrary. In particular, any feature indicated as being preferred or advantageous can be combined with any other feature or features indicated as being preferred or advantageous.

II. Methods and Products

Described herein is a transformative technology that permits detection of substances in the femto mol to pico mol ranges and/or lower. It is demonstrated herein that dection in the zepto mol to atto mol range can be achieved.

Enzyme linked immuno sorbent assays (ELISA) are the preferred analytical method for the repetitive quantitative analysis of polypeptides molecules of biomedical importance: ELISA may use reporter enzymes such as Horseradish peroxidase (HRP) and or alkaline phosphatase (AP) coupled to specific detection antibodies that capture and bind to each analyte of importance [2, 3].

At present substrates for the reporter enzymes horseradish peroxidase (HRP) or alkaline phosphatase (AP) yield colored, fluorescent or luminescent products. The present disclosure provides a method for detecting the enzymatic products of reporter enzymes that ionize efficiently with a high signal to noise ratio measured by mass spectrometry. Mass spectrometry is sensitive enough to permit detections at amounts far below ECL, fluorescence or colorimetric methods, but also permits monitoring of multiple substrates and products at discrete m/z values. It is possible using the methods described herein to measure the products of common industrial reporter enzymes to zepto mol amounts or lower with limits of quantification to atto mol amounts or lower.

The use of mass spectrometry to measure small molecules may commonly reach the femto to pico mol levels with high signal to noise. The industrial enzymes HRP or AP for example are rugged and durable and have a high catalysis rate for the creation of new small molecule products. The AP or HRP enzymes are for example covalently attached to a specific detection probe such as a polypeptide or antibody that may bind their target and then catalyze many different product reactions over the course of a brief incubation. Thus, the binding of atto mol, or even sub atto mol, amounts of enzyme-probe will yield amounts of small molecule products that accumulate in the femto mol to pico mol range well within the detectable range of by LC-ESI-MS/MS.

Liquid chromatography electrospray ionization and tandem mass spectrometry (LC-ESI-MS/MS) is more sensitive than colorimetric, fluorescent or ECL detection. The combination of the enzymatic production of reported molecules coupled with sensitive mass spectrometry for highly ionizable substrates should provide sensitivity in excess of RIA but without the requirement for standards labelled with isotope or probes labeled with isotope.

Quantification of HRP and AP is demonstrated using LC-ESI-MS/MS to detect the products of the AP and HRP reporter enzyme reactions. It is demonstrated herein that a mass spectrometer can also detect the small molecule products of reporter enzyme activity bound to a specific molecular probe such as an antibody. One atto mol or less of a reporter enzyme such as AP or HRP bound to a specific molecular probe such as a detection antibody will rapidly form femto mol to pico mol amounts of reporter enzyme reaction products well within the reliable detection and quantification limits of LC-ESI-MS/MS. Hence in ELIMSA and related DNA methods the reporter enzymes such as HRP or AP may produce a range of products that can be easily distinguished and detected by mass spectrometry. Antibodies coupled to reporter enzymes that are widely used in biomedical and environmental applications can now be detected and quantified using very sensitive mass spectrometry to create a sensitive and flexible system. Since mass spectrometers can separate and analyze many analytes simultaneously using the methods described herein can allow identification and quantification of many different antigens at the same time to levels far below that which is possible by direct mass spectrometric analysis.

Accordingly an aspect of the disclosure includes a method of detecting a target substance comprising the steps:

a. immobilizing the target substance to a solid phase;

b. incubating the immobilized target substance with a reporter enzyme detection probe in solution under conditions for forming target: enzyme detection probe complexes;

c. washing the solid phase to remove any unbound reporter enzyme detection probe;

d. incubating the target: enzyme detection probe complex with a reporter enzyme detection probe substrate in substrate reaction solution to generate one or more ionizable products; and e. detecting one or more of the one or more ionizable products using mass spectrometry (MS).

The target substance can be any antigenic substance, or any substance that can be selectively bound by a primary detection agent. Examples of target substances are provided below and in the Examples.

In an embodiment, the target substance is immobilized by directly binding the solid phase, optionally by adsorption to the solid phase. For example, a solution, optionally a test sample, comprising the test substance is incubated with a solid phase, optionally a microtiter plate such that the antigen adheres to the plastic for example through charge interactions. This method is for example used in indirect ELISAs.

In another embodiment, the target substance is immobilized to the solid phase indirectly by a capture molecule, optionally a capture antibody or fragment thereof, coupled to the solid phase that binds the target substance. For example as described in the Examples, a known amount of capture molecule such as an antibody or binding fragment thereof prepared in a coating solution, optionally 0.1M Na2CO3/NaCHO3 pH9.6 or other coating solution described herein, is incubated with a solid phase, optionally a microtiter plate. This method is for example used in sandwich ELISAs and competitive ELISAs.

In an embodiment, the immobilized target substance retains one or more accessible epitopes or binding sites capable of binding to a detection agent and/or reporter enzyme detection probe.

In an embodiment, the step of immobilizing the test substance comprises: coupling a capture molecule to the solid phase by incubating the solid phase with the capture molecule in coating solution, blocking the solid phase with blocking solution, adding the target substance to the solid phase in antigen incubation solution and removing any unbound target substance.

In another embodiment, the step of incubating the immobilized target substance with a reporter enzyme detection probe in solution under conditions for forming target: enzyme detection probe complexes comprises: incubating the immobilized target substance with primary detection agent and/or reporter enzyme detection probe in detection probe incubation solution.

In an embodiment, the detection probe incubation solution, which can be used with the primary detection agent (e.g. the capture antibody) and/or the reporter enzyme detection probe (e.g. SA-AP or SA-HRP or biotinylated nucleic acid probe), comprises a non-ionic non-polymeric detergent or a biosalt cholesterol detergent, optionally Na-deoxycholate. In an embodiment, the detection probe incubation solution comprises a buffer such as PBS. Suitable buffers include Tris, BIS, PBS, tricine, citrate, MES, MOPS, HEPES, and/or Bicine. Other suitable buffers include MES, Bis-Tris, ADA, aces, PIPES, MOPSO, Bis-Tris Propane, BES, MOPS, TES, HEPES, DIPSO, MOBS, TAPSO, Trizma, HEPPSO, POPSO, TEA, EPPS, Tricine, Gly-Gly, Bicine, HEPBS, TAPS, AMPD, TABS, AMPSO, CHES, CAPSO, AMP, CAPS, and/or CABS.

In an embodiment, when the probe is a nucleic acid probe, the probe incubation solution can be a sodium chloride buffer such as PBS or SSC hybridization solution.

In an embodiment, the detection probe incubation solution is essentially salt free and/or polymeric detergent free.

In an embodiment, one or more of the coating solution, blocking solution, detection probe solution and/or incubation solution comprises urea. In an embodiment, ureas is added to a sample optionally a biological sample such as blood.

The same incubation solution may be used for both the binding of the primary probes and subsequent binding of the Reporter Enzyme conjugated to a moitie that has an affinity to the primary probe In an embodiment, the capture molecule is coupled to the solid phase in a coating solution optionally comprising a carbonate buffer, optionally $Na_2CO_3/NaCHO_3$. In an embodiment, the coating solution comprises a basic buffer solution, optionally a Tris, tricine or methylamine buffer solution.

The solid phase can be any reaction vessel, optionally a bead, rod or plate, such as a microtitre plate, for example having a polystyrene surface. The solid phase may be any surface, including metal, gold, stainless steel, plastic, glass, silica, normal phase, reverse phase, polycarbonate, polyester, PVDF, nitrocellulose, cellulose, poly styrene, polymer, iron, magnetic, coated magnetic, microbeads, nanobeads, or fullerene. An immunosorbent polystyrene rod with eight to 12 protruding cylinders has been described for example in U.S. Pat. No. 7,510,687.

Nonspecific binding of the test substance to the capture molecule can be reduced by using a blocking solution, optionally comprising BSA and/or serum in buffered solution. Suitable buffers include Tris, BIS, PBS, tricine, citrate, MES, MOPS, HEPES, and/or Bicine. Other suitable buffers include MES, Bis-Tris, ADA, aces, PIPES, MOPSO, Bis-Tris Propane, BES, MOPS, TES, HEPES, DIPSO, MOBS, TAPSO, Trizma, HEPPSO, POPSO, TEA, EPPS, Tricine, Gly-Gly, Bicine, HEPBS, TAPS, AMPD, TABS, AMPSO, CHES, CAPSO, AMP, CAPS, and/or CABS. Buffers that hold the pH of the solution near the optimal for the maximal activity of the reporter enzyme are preferred. These same buffers might be used for the binding of the test substance or the reaction buffer.

The reporter enzyme detection probe comprises a reporter enzyme component and a detection probe component that are coupled together, optionally covalently. In an embodiment, the reporter enzyme comprises peroxidase activity, monooxygenase activity, phosphatase activity, glucose oxidase, protease or caspase activity, for example the reporter enzyme is a peroxidase, monooxygenase, phosphatase, glucose oxidase, protease, endoproteinase, exopeptidase or a caspase. In another embodiment, the reporter enzyme is selected from a lyase, hydrolase, synthase, synthetase, oxidoreductase, dehydrogenase, oxidase, transferease, isomerase, ligase, protease, such as trypsin, endoproteinase, exopeptidase, proteinase, peroxidase, glucose oxidase, myeloperoxidase, oxidase, monooxygenase, cytochrome, phosphatase sicj as alkaline phosphatase, decarboxylase, lipase, caspase, amylase, peptidase, transaminase, and kinase. Additional enymes can include DNA or RNA polymerase, TAQ, restriction enzymes, klenow fragment, DNA ligase. In yet another embodiment, the reporter enzyme is selected from HRP, AP, ligase, DNA Polymerase (for example klenow or TAQ), restriction enzymes, and proteases, cytochrome monooxygenases, glucose oxidase, GAPDH, and other glycolysis and TCA cycle enzymes.

In an embodiment, the reporter enzyme is a peroxidase optionally horseradish peroxidase or myeloperoxidase. In another embodiment, the reporter enzyme is a phosphatase optionally alkaline phosphatase. In an embodiment, the monooxygenase is cytochrome C monoxygenase. In another embodiment, the protease is trypsin, chymotrypsin, elastase, pepsin, cathepsin, renin or papain, ASP-N or ARG-C. In yet another embodiment, the trypsin is modified trypsin In an embodiment, the reporter enzyme detection probe comprises a primary target binding moiety and an enzyme comprising enzymatic activity, wherein the primary target binding moiety is covalently bound to the reporter enzyme and binds specifically to the target substance.

In another embodiment, the reporter enzyme detection probe comprises a secondary target binding moiety and an enzyme comprising enzymatic activity, wherein the secondary target binding moiety is covalently bound to the reporter enzyme and binds specifically to a primary detection agent specific for the target substance. For example the secondary target binding moiety can comprise an antibody that binds an antibody primary detection agent. Alternatively, the secondary target binding moiety comprises a high affinity binging molecule such as avidin or streptavidin that selectively binds a biotiynylated primary detection agent, for example a biotinylated primary antibody.

In another embodiment, the step of incubating the immobilized target substance with a reporter enzyme detection probe comprises incubating the immobilized target substance with a primary detection agent specific for the immobilized target substance prior to and/or simultaneously with incubating with the reporter enzyme detection probe to form the target: enzyme detection probe complex.

In an embodiment, the target binding moiety and/or the primary detection agent comprises an antibody or an antibody binding fragment. In another embodiment, the secondary target binding moiety that binds specifically to the primary detection agent comprises avidin or streptavidin or is a secondary antibody.

In a further embodiment, the primary detection agent comprises biotin conjugated to an antibody or antibody fragment specific for the target substance.

In an embodiment, any of the antibodies described may be a monoclonal antibody, polyclonal antibody, chimeric antibody, monospecific antibody.

In addition, the target binding moiety and/or the primary detection agent can comprise a biopolymer such as an aptamer, polypeptide, nucleic acid, carbohydrate, lipid or other biochemical detection molecule that selectively binds its "target" with similar affinity to an antibody: antigen reaction.

For example, enzyme-linked detection methods using industrial reporter enzymes have been adapted in the art to utilize a variety of biopolymers including glycans, aptamers, polynucleotides, lectins, and proteins as detection probes and/or targets.

Wuhrer et al. (2010) describes the use of biotinamidocaproyl hydrazide (BACH) labelled glycans and alkaline phosphatase-conjugated streptavidin as probes to detect carbohydrate binding proteins immobilized to a plate.

Zhang et al. (2012) describe an enzyme linked aptamer assay, involving functional cocaine-detecting aptamers which are divided into two fragments. One fragment is immobilized to a surface and the other fragment is biotinylated. Detection of cocaine is accomplished through streptavidin conjugated HRP.

Mallet et al. (1993) describe an enzyme-linked oligosorbent assay (ELOSA) for detection of polymerase chain reaction-amplified human immunodeficiency virus type 1. Denatured PCR product was hybridized with a passively adsorbed oligonucleotide capture probe and a horseradish peroxidase-labeled oligonucleotide detection probe. The ELOSA assay has also been extended to detecting the products of RT-PCR.

Kumada et al. (2012) describes an ELISA assay using immobilized scFV, prepared in E. Coli, as the capture antibody and HRP-labelled lectins for detecting the glycochains of glycoproteins, including glyco-biomarkers. HRP-labelled lectins have also been used as probes to estimate the degree of glycosylation of immunoglobulins (Petrosian et al., 2006).

Darwish et al., (2009) describes a competitive ELISA in which FLV in a sample competes for binding to limited quantities of anti-FLV detection antibody with plate bound BSA-FLV. A primary anti-FLV rabbit antibody and a secondary HRP-conjugated anti-rabbit antibody are used to detect the binding.

The reaction is reporter enzyme dependent. For example, it is demonstrated herein that incubating a substrate that can be acted upon by the reporter enzyme detection probe in an appropriate substrate reaction solution produces little or no signal in the absence of the reporter enzyme detection probe. In contrast the addition of reporter enzyme detection probe comprising HRP or AP enzyme resulted in strong detection of an ELIMSA product ion. The product ion was shown to be dependent on the presence of the enzyme, and to be both time and concentration dependent. Thus the ELIMSA product ions show all the hallmarks of an enzyme dependent assay.

The method disclosed herein can also be performed in solution in the absence of a solid phase, wherein the target substance is not immobilized but suspended on microbeads or magnetic microbeads or in a colloidal suspension or otherwise not entirely immobilized but free to move in a solution Substrates that produce ionizable products that provide a high signal to noise ratio are desired. For example the selected signal to noise ratio is at least 3, at least 4, at least 5, at least 6, at least 10. In an embodiment the signal to noise ratio is greater than or equal to 5. The signal to noise ratio is the ratio of the mass signal (peak height) to noise (amplitude of base level fluctuation). The signal to noise ratio can be determined for example, by measuring the ratio of signal intensity from a blank sample or base line compared to that of a known quantity of analyte or a sample using MS. [An example of a substrate that produces an ionizable product that when ionized to a product ion has a high signal to noise ratio is naphthol ASMX phosphate which is dephosphorylated. A high signal to noise ratio, as used herein, is a signal to noise ratio greater than at least 5, at least 6, at least 10.

The substrate requires at least one ionizable group for example comprising at least one of $NO_2$, $SO_4$, $PO_3$, $NH_2$, =NH—, COOH, NH—NHR—, NH2-NR—NH2, ionizable for example by electrospray or MALDI, and is a substrate for a selected reporter enzyme. In the case of HRP for example, a suitable substrate is one that is able to donate an electron to $H_2O_2$. As another example, in the case of phosphatases such as AP the substrate has at least one phosphate group that may be cleaved by the enzyme.

In an embodiment, the substrate is selected from:
a. a compound selected from phenols, amines, optionally phenolic amines, amides, aromatic compounds, olefin halogenations, luminol, pyrogallol, ABTS, Amplex® Red when the reporter enzyme is HRP,
b. a phosphorylated molecule optionally a phosphorylated nucleotide, phosphorylated alkaloid, phosphorylated amino acid, phosphorylated amino acid polymer, and phosphorylated metabolite when the enzyme is AP; or
c. opiates, detergents, dye precursor, alcohols, matrix, when the substrate is HRP or AP.

In an embodiment, the amino acid polymer as N amino acids where N is any number between 2 and 20 amino acids, optionally any number between 2 and 15 amino acids or less than 12 amino acids.

In an embodiment, the amino acid is selected from—or the amino acid polymer comprises—one or more of amino acids listed in Table A wherein at least one of the amino acids is phosphorylated.

TABLE A

| Amino acids | | |
|---|---|---|
| Amino acid | Three letter code | One letter code |
| Alanine | ala | A |
| Arginine | arg | R |
| Asparagine | asn | N |
| aspartic acid | asp | D |
| asparagine or aspartic acid | asx | B |
| Cysteine | cys | C |
| glutamic acid | glu | E |
| Glutamine | gln | Q |
| glutamine or glutamic acid | glx | Z |
| Glycine | gly | G |
| Histidine | his | H |
| Isoleucine | ile | I |
| Leucine | leu | L |
| Lysine | lys | K |
| Methionine | met | M |
| Phenylalanine | phe | F |
| Proline | pro | P |
| Serine | ser | S |
| Threonine | thr | T |
| Tryptophan | trp | W |
| Tyrosine | tyr | Y |
| Valine | val | V |

The amino acids and/or amino acid polymers can be modified

In applications using HRP, $H_2O_2$ or other oxidizing source is added with the substrate.

In an embodiment the substrate is selected from pyridoxamine-5-phosphate (PA5P), p-nitrophenyl phosphate (PNPP), Amplex® Red (AR), naphthol ASMX phosphate, luminol, Lumigen® TMA3, Lumigen® TMA6, sphingosine, 4MUP, L-(+)-2-amino-6-phosphonohexanoic acid, BCIP (5-bromo-4-chloro-3-indolyl phosphate) (e.g. Blue-Phos®), phenylbenzene ω phosphono-α-amino acid, O-phospho-DL-threonine and/or a nucleoside monophosphate such as AMP or CMP. Table I for example provides results obtained using these substrates. Substrates can also include known AP and/or HRP substrates for example AR, 3-amino-9-ethylcarbazole, 4-CN (4-Chloro-1-Naphtol, DAB (3,3'-DiAminoBenzimidine, OPD (o-Phenylene Diamine, TMB (3,3",5,5"-tetramethylbenzidine, pNPP (p-Nitrophenyl Phosphate), BCIP (5-bromo-4-chloro-3-indolylphosphate), NBT (nitroblue tetrazolium), INT (p-iodonitrotetrazolium), MUP (4-Methylumbelliferyl Phosphate), FDP Fluorescein DiPhosphate), Naphthol ASMX phosphate, phosphorylated amines, phosphorylated amides, phosphorylated nucleotides and nucleic acid bases, phosphorylated or oligonucleotide polymers.

In another embodiment, the substrate is selected from a nucleoside monophosphate such as AMP, CMP, GMP, TMP, UMP; a nucleoside diphosphate such as ADP, CDP, GMP, TDP, UDP; a nucleoside triphosphate, such as ATP, CTP, GTP, TTP, UTP; a phospho-ribose; and an anhydride, such as nucelotide diphosphates or triphosphates.

In an embodiment, the substrate is selected from nucleotide A, C, G, T, or U where the nucleotide may have 3 or 2 or 1 phosphates that are removed by the enzyme alkaline phosphatase.

In an embodiment, AMP is used as the substrate. In another embodiment, CMP is used as the substrate. In yet another embodiment, UMP is used as a substrate. As demonstrated in the Examples, AMP, ADP, ATP, CMP, CDP, CTP, UMP, UDP and UTP substrates produced reaction products with a measurable peak intensity at the indicated m/z which increased (positive ionization) with AP incubation.

In another embodiment, the substrate is selected from:
a. AR, luminol, Lumigen® TMA3, Lumigen® TMA6 Amplex® Red [when the reporter enzyme detection probe comprises HRP; or
b. PA5P, AMP, nucleotide mono phosphate, naphthol ASMX phosphate, 4MUP, sphingosine phosphate or PNPP when the reporter enzyme detection probe comprises AP.

In a further embodiment, the substrate is selected from PA5P, AMP, Amplex® Red (e.g. AR and Resazurin), Lumigen® TMA3 and/or TMA6, naphthol ASMX phosphate and PNPP.

The substrate can be isotopic, isobaric or affinity tagged, to permit the purification of the substrate.

In another embodiment, the target: enzyme detection probe complex is incubated with a reporter enzyme detection probe substrate (e.g. substrate) in substrate reaction solution to generate one or more ionizable products for a period of time less than 72 hours, less than 24 hours, less than 12 hours, less than 60 minutes, less than 50 minutes, less than 40 minutes, less than 30 minutes, less than 20 minutes, less than 15 min, less than 10 min, less than 5 min, less than 2 min, or less than 1 min.

In an embodiment one or more of the substrate reaction products (e.g. ionizable products) is readily ionizable, optionally under ESI-MS/MS and generates a product ion characterized by a high signal to noise ratio.

In an embodiment, the sample and/or one or more ionizable products are separated and/or digested prior to detection using MS. For example complex biological molecule such as a phosoprotein might be dephosphorylated by the ELIMSA enzyme such as AP and the enzyme activity detected directly or the protein digested and/or fractionated by partition chromatography prior to mass spectral analysis of the digested proteins by detection of the peptide parent ions by SIM, or of the fragment ions by SRM.

In an embodiment, the separation is by liquid chromatography. In yet another embodiment, the liquid chromatography is high-performance liquid chromatography (HPLC). In an embodiment, the HPLC is partition chromatography, normal-phase chromatography, displacement chromatography, reversed-phase chromatography (RPC), size-exclusion chromatography, Ion-exchange chromatography, bioaffinity chromatography, aqueous normal-phase chromatography, nanoflow liquid chromatography or ultra high performance liquid chromatography (UPLC). In an embodiment, the HPLC is isocratic normal phase chromatography.

In an embodiment, the step of detecting the one or more ionizable products using MS comprises ionizing the one or more ionizable products, optionally by electrospray ionization (ESI) to produce one or more product ions with a selected signal to noise ratio, and subjecting the one or more product ions to MS optionally tandem MS (MS/MS).

In an embodiment, the ionizable product, comprises one or more amines for ionization in the positive mode. In another embodiment, the ionizable product comprises one or more hydroxyl or acidic groups that will permit ionization in the negative mode.

In another embodiment, the ionizing is positive ionization. In a further embodiment, the ionizing is negative ionization.

Proteins and peptides are typically analysed under positive ionisation conditions whereas saccharides and oligonucleotides are typically analysed under negative ionization conditions. The m/z scale is calibrated by analysing a standard sample (e.g. a sample similar type to the sample being analysed (e.g. a protein calibrant for a protein sample), and then applying a mass correction.

An ionizable product can for example be ionized by subjecting the ionizable product to electrospray ionization (ESI), MALDI, chemical ionization, electron impact, laser desorption, electrical ionization, or heat ionization, In an embodiment, the MS used for detecting the product ion electrospray ionization is tandem MS (ESI-MS/MS). In an embodiment the product ion is detected by Paul ion trap, linear ion trap, quadrupole, single-, double-, or triple-quadrupole, time of flight (TOF), quadrupole-TOF, quadrupole-trap, orbital trap, quadrupole-orbital trap, FTICR (Fourier transform ion cyclotron resonance), ion cyclotron resonance mass spectrometry or drift tube.

The experiments described herein were performed with a linear quadrupole ion trap that is a flexible and sensitive mass spectrometer (Schwartz, 2002) and performed with flow rate of 20 ul per minute flow rate that is a robust chromatography system designed for rapid and easy development of substrates and comparison of enzymes under stable conditions. Using these systems as little as 100 yoctomols of target substance could be detected (corresponding to about 100-1000 molecules) when for example using PA5P and AMP as substrates. There have been developments in mass spectrometry that have increased the sensitivity. Gale and Smith reported a new electrospray ionization source which allows the effective utilization of very small sample volumes at much lower flow rates than previously demonstrated. Xu et al 2003 tested a triple-quadrupole mass spectrometry (MS) system with enhanced resolution capabilities. Both the linearity and the limit of detection were compared in the positive electrospray ionization (ESI) mode with those of a conventional triple-quadrupole instrument. In the unit mass resolution mode, the new mass spectrometer was found to be at least ten-fold more sensitive than the conventional instrument. The sensitivity of the new mass spectrometer under the enhanced mass resolution mode was found to be even better by another factor of two. Other improvements are described by Berger et al 2004, Tang et al 2001, Katta et al 1999, and Schafer et al 2001. Any of these methods can be used. For example reducing the flow rate, the use of a nano spray source, the use of an ion funnel or similar ion capture technology together with triple quadrupole or other modifications of the mass spectrometer may lead to greater sensitivity using the reagents that can be used for ELIMSA and related DNA assays described here.

The assay also permits simultaneous detection of multiple target substrates. Multiple substrates for available for each enzyme and as the enzymes can produce products that may be analyzed by HPLC electrospray mass spectrometry, there exists the capacity of ELIMSA and related hybridization assays to permit the assay of multiple sample assays at the same time as demonstrated herein. For example, in the Examples provided herein, ASMX and Amplex Red (e.g. same LC-ESI-MS run); A, T, C and G (e.g. multiplex); two peptides of AP (LC-ESI-MS/MS (xtra MS i.e. tandem MS for peptides)); and the short oligo nucleotides greater than 1 nucleotide were simultaneously detected.

Furthermore the substrate may be modified with repeating chemical units or polymers, such as the phospho-anhydride of ATP, that permit structurally similar substrates that differ only in the number of repeating additions of a chemical moiety in a polymer that may be analyzed simultaneously.

For example, AP or polynucleotide kinase or DNA ligase or restriction enzyme substrates can include polynucleotide molecules of different lengths and compositions (e.g. sequence composition). This could be useful for example wherein each polynucleotide represents a test subject.

For example, each different length and/or sequence composition of the polynucleotide can be used as a code, processing many possible reactions simultaneously where each patient sample has a different nucleic acid sequence and detecting if each is acted upon by the reporter enzyme, for example for AP determining if each is de-phosphorylated (or Phosphorylated) or for other reporter enzymes, ligated or cleaved by restriction enzyme or modified (e.g. wherein the last nucleotide is removed by a exonuclease or added) or wherein a new polynucleotide is produced by DNA or RNA polymerase.

Similarly different peptides lengths and/or different peptide sequences might be used and phosphorylated or dephosphorylated or cleaved or otherwise post translationally modified by a reporter enzyme used in ELIMSA where each patient receives a different peptide (e.g. a different substrate).

Other repeating units can also be connected to the ionizable molecule or group to make a different code or m/z channel for each patient or sample that could be analyzed in the same infusion of HPLC run. For example ATP can be used with three phosphates or AMP can be used with one phosphate and with different lengths of chemical units attached such as inositol chains of increasing length or carbohydrate oligomers or amino acids, alkyl groups, or nucleosides, or other. For example, Example 6 describes an example of a putative coding system where patient A is assigned an oligo AMP-N (wherein the oligo is of length X), wherein N is any nucleotide, nucleoside or modified base (e.g. ATP, AMP, ADP or comprising a neutral modification for differentiating the molecule(. X can for example any number between and/or including 2-20, optionally from 2 to less than 12.

In an embodiment, the ionizable product which is produced in substrate reaction solution is dried and resuspended for example in water, methanol, ethanol, acetonitrile, hexane, phenol, benzyne, isopropanol (IPA) or other aqueous mixtures of organic solvents modified with organic acids or bases prior to ionizing, for example by MALDI, and prior to separation by chromatography.

It is demonstrated herein, for example in FIGS. 46 and 47 that drying prior to separation and MS analysis permits detection in the zepto mol range.

It is also demonstrated herein that multiple target substrates can be measured simultaneously, for example as shown in FIG. 45.

When multiple target substances are being detected, multiple reporter enzyme detection probes are used.

Whereas the typical ELISA is sensitive to nanogram amounts of PSA the ELIMSA is demonstrated herein to be sensitive to pico gram or femto gram amounts of PSA.

In a further embodiment, detection using MS comprises recording product ion intensity by single ion monitoring (SIM) and/or product ion parent to fragment transition by single reagent monitoring (SRM). In an embodiment, the product ion is assayed by SIM and/or SRM using an optimized fragmentation energy and m/z range. Details are provided in the Examples below. Other fragments or fragmentation methods that may be used include post-source decay, gas collision induced dissociation, chemically induced dissociation, chemically induced ionization, heat, photon or laser dissociation, electron impact dissociation, and/or electrical acceleration dissociation.

The disclosure identifies a number of transitions from ionized reaction product to product fragments including the following. A person skilled in the art would understand that other transitions can also be used.

In an embodiment, the substrate is para nitrophenyl phosphate (PNPP), the product ion of which is assayed by SIM at 138 m/z and/or by SRM using the major intense fragment at 138-108 m/z.

In an embodiment, the substrate is pyridoxamine 5 phosphate (PA5P), the product ion of which is assayed by SIM at 166 m/z and/or by SRM using the major intense fragment at 166-138 m/z.

In an embodiment, the substrate is sphingosine-1-phosphate (SIP), the product ion of which is assayed by SIM at 297 m/z and/or by SRM using the major intense fragment at 297-279 m/z.

In an embodiment, the substrate is L-(+)-2-amino-6-phosphonohexanoic acid, the product ion of which is assayed by SIM at 132 m/z and/or by SRM using the major intense fragment at 132-114 m/z.

In an embodiment, the substrate is O-phospho-DL-threonine, the product ion of which is assayed by SIM at 122 m/z and/or by SRM using the major intense fragment at 122-104 m/z.

In an embodiment, the substrate is 5-bromo-4-chloro-3-indolyl phosphate (BCIP), the product ion of which is assayed by SIM at 242 m/z and/or by SRM using the major intense fragment at 242-198 m/z.

In an embodiment, the substrate is phenylbenzene ω phosphono-α-amino acid, the product ion of which is assayed by SIM at 255 m/z and/or by SRM using the major intense fragment at 255-237 m/z.

In an embodiment, the substrate is naphthol AS-MX phosphate, the product ion of which is assayed by SIM at 292 m/z and/or by SRM using the major intense fragment at 292-171 m/z.

In an embodiment, the substrate is 4-methylumbelliferyl phosphate (4-MUP), the product ion of which is assayed by SIM at 229 m/z and/or by SRM using the major intense fragment at 229-211 m/z.

In an embodiment, the substrate is Amplex® Red (AR), the product ion of which is assayed by SIM at 214 m/z and/or by SRM using the major intense fragment at 214-186 m/z.

In an embodiment, the substrate is 1-(2,3,4-Trimethoxyphenyl)propan-2-amine (TMA-3), the product ion of which is assayed by SIM at 286 m/z.

In an embodiment, the substrate is 1-(2,4,6-Trimethoxyphenyl)propan-2-amine (TMA-6), the product ion of which is assayed by SIM at 272 m/z.

In an embodiment, the substrate is AMP the product ion of which is assayed by SIM at 268 m/z and/or by SRM of the major intense fragment at 268-136 m/z in the positive ionization mode and by SIM at 266 m/z and/or by SRM of the major intense fragment at 266-134 m/z in the negative ionization mode.

A number of different substrate reaction solutions and components can be used, depending for example on the reporter enzyme and substrate. In an embodiment, the substrate reaction solution comprises Tris, tricine, HEPES, methylamine, MES, MOPS, Bicine, buffer, having a pH optionally of about 7 to about 10, optionally about 8.8.

Suitable buffers for the substrate reaction solution include Tris, Tricine, HEPES, methylamine, MES, MOPS or Bicine buffers as well as BIS, PBS, citrate, ADA, aces, PIPES, MOPSO, Bis-Tris Propane, BES, TES, HEPES, DIPSO, MOBS, TAPSO, Trizma, HEPPSO, POPSO, TEA, EPPS, Gly-Gly, HEPBS, TAPS, AMPD, TABS, AMPSO, CHES, CAPSO, AMP, CAPS, and/or CABS.

In an embodiment, the substrate reaction solution comprises 20 mM Tris, pH 8.8.

In another embodiment, the substrate reaction solution comprises a non-ionic, non polymeric detergent, optionally N-octylglucoside, deoxycholate, rapigest, octyl-beta-glucopyranoside, octylglucopyranoside, chaps, big chap, Nonionic Acid Labile Surfactants, Glucosides, n-Octyl-β-D-glucopyranoside, n-Nonyl-β-D-glucopyranosideThioglucosides, n-Octyl-β-D-thioglucopyranoside Maltosides, n-Decyl-β-D-maltopyranoside, n-Dodecyl-β-D-maltopyranoside, n-Undecyl-β-D-maltopyranoside, n-Tridecyl-β-D-maltopyranoside, Cymal-5 or Cymal-6 Thiomaltosides, n-Dodecyl-6-D-thiomaltopyranoside, Alkyl glycosides, Octyl glucose neopentyl glycol, Polyoxyethylene glycols, triton, NP40, Tween™, Tween™ 20, Triton X-100, triton x-45, C8E4, C8E5, C10E5, C12E8, C12E9, Brij, Anapoe-58, or Brij-58.

The substrate reaction solution can comprise one or more components, optionally to enhance the production of ionizable products produced with a substrate. For example, HRP reporter enzyme requires the presence of $H_2O_2$. Accordingly in embodiments using HRP or other peroxidase, $H_2O_2$ is added in conjunction with the substrate. Other molecules can also be used.

Standard ELISA solutions with triton or tween can be used for the coating solution and the antigen incubation solution, used for example to prepare an ELISA plate comprising immobilized antigen but are not optimal due to interference with mass spectrometry.

In an embodiment, the capture antibody is coupled to the plate using a coating solution comprising a carbonate, Tris, tricine or methylamine buffer solution, optionally 0.1M Na2CO3/NaHCO3 pH9.6.

In an embodiment, the detection probe incubation solution, which can be used with the primary detection agent (e.g. the capture antibody) and/or the reporter enzyme detection probe comprises (e.g. SA-AP or SA-HRP), comprises PBS and a non-ionic, non-polymeric detergent, optionally deoxycholate, optionally 0.05% Na-deoxycholate.

In an embodiment, the quenching solution comprises acetonitrile 50% Acetonitrile, 0.1% Acetic acid or 0.1% formic acid or 0.1% trifluoroacetic acid for positive ionization or 0.1% ammonium hydroxide or ammonium acetate for negative ionization In an embodiment, the drying solution comprises water and/or an organic solvent such as methanol, ethanol, propanol, acetonitrile or other solution that may speed drying when used to dilute the aqueous substrate reaction solution.

All solutions are for example HPLC grade or better.

The ionization solution is a buffered solution that is used to enhance or control the formation of ions. Appropriate buffers for the ionization solution would be apparent to those skilled in the art. The ionization buffer can be, for example, isocratic or gradient HPLC buffer. Any acid or base may be used in the ionization solution. In an embodiment, the acid may be formic, acetic or trifluoroacetic acid and the base may be ammonium hydroxide, methylamine, ethylamine, or propylamine.

Another aspect provides a method of quantifying the amount of a target substance in a sample comprising the steps:

a. detecting a target substance according to the method described herein; and b. quantifying the amount of target substance in the sample based on the intensity of the signal for one or more of the product ions detected by mass spectrometry.

In one embodiment, the quantification comprises comparing the intensity of the signal for one or more product ions against signal intensities generated using known quantities of target substance, under similar conditions.

In an embodiment, the intensity of the signal for one or more product is compared to an internal standard optionally an internal standard curve. In an embodiment, the intensity of the signal for one or more product is compared to an external standard optionally an external standard curve.

In an embodiment, the internal standard comprises an isotope standard that is used to provide an isotope dilution curve or internal one point calibration. In an embodiment, the external standard is a standard amount of the target substance which can be diluted to produce a standard curve. The target substance standard can also be radiolabelled.

In an embodiment, the quantification comprises log transforming the standard curve signal intensities to provide a linear standard curve. For example where a wide detection range is desired, log transformation is utilized. Narrow detection ranges may or may not require log transformation.

The standard can for example be a peptide isotope standard for embodiments wherein the molecular probe is a peptide, a radiolabelled metabolite (e.g. 13CPA) or a radiolabelled nucleic acid or nucleotide (e.g. ATP).

In another embodiment, the target substance is present in the sample in at least pico mol, femto mol, atto mol zepto mol, or yoctomol range.

The target substances and sample types that can be assayed are numerous.

For example, the sample can be a biological sample, food sample, industrial product or environmental sample. In yet another embodiment, the biological sample is a blood sample, urine sample, fecal sample, effusate or tissue sample. insulin, gamma globulin, platelets, clotting factors biological drugs.

In an embodiment, the target substance is a disease biomarker, environmental contaminant, food contaminant, quality marker, therapeutic target, biological agent, biological weapon, microbial species, plant, animal, fungus, bacteria, virus, or mycoplasma. In a further embodiment, the target substance is a biopolymer, optionally a polypeptide optionally selected from a tumour marker, autoantigen, hormone, chemokine, cytokine, cardiac protein. For example it is demonstrated herein that myosin light chain and troponin can be readily quantitated using methods described herein.

In an embodiment, the test substance is an insoluble protein optionally a membrane protein. Urea can be used in one or more of the solutions.

In another embodiment, the target substance is a microorganism, optionally a virus or bacteria, optionally an *E. Coli* species, such as *E. coli* 0157, *Salmonella* species, *Pseudomonas* species, or *anthrax* species. In a further embodiment the analyte may be a biopolymer marker of a physiological state including health, disease, drug response, efficacy, safety, injury, trauma, traumatic brain injury, pain, chronic pain, pregnancy, atheroscelrosis, myocardial infraction, diabetes type I or type II, sepsis, cancer, Alzheimer's dementia, multiple sclerosis. In a further embodiment cancer including Bladder, Breast, Colon and Rectal, Endometrial, Kidney (Renal Cell) Cancer, Leukemia, Lung, Melanoma, Non-Hodgkin Lymphoma, Pancreatic, Prostate, Thyroid. In a further embodiment the disease may be emphysema, bronchitis, asthma or chronic obstructive pulmonary disorder.

In an embodiment, the tumour marker is prostate specific antigen (PSA). In another embodiment, the cardiac protein is a Troponin, optionally Troponin T.

In another aspect, the disclosure provides a method for detecting and/or quantifying a target substance in sample comprising:

a. contacting a sample comprising the target substance with an immobilized antibody specific for target substance;

b. contacting the immobilized target substance with a reporter enzyme detection probe, wherein the reporter enzyme detection probe has enzyme activity and wherein the reporter enzyme detection probe is able to bind specifically to the immobilized target substance or a primary detection agent specifically bound to the target substance;

c. contacting the immobilized reporter enzyme detection probe with a substrate which reacts with the enzymatic activity of the reporter enzyme detection probe to generate one or more ionizable products for a period of time; and d. detecting and/or quantifying the one or more ionizable products using mass spectrometry (MS).

In yet another aspect, the disclosure provides a method of screening a substrate that will generate one or more ionizable products after interaction with a reporter enzyme, wherein one or more of the ionizable products have a low limit of detection (LOD) and low limit of quantification (LOQ) when detected using mass spectrometry, the method comprising:

a. contacting substrate with known quantities of a reporter enzyme to generate one or more products;

b. separating the products; and c. analyzing the products using mass spectrometry to measure the LOD and the LOQ.

Yet another aspect relates to a kit comprising;

a. a reporter enzyme detection probe comprising an enzyme and a target binding moiety described herein; and b. one or more of a substrate, solid phase (e.g. plate), a standard coating solution, and target immobilization probe or biopolymer, a known amount of a target standard calibrant, blocking solution, a target detection probe or biopolymer, antigen incubation solution, detection probe incubation solution, substrate reaction solution, at least one substrate, quenching solution, and least one enzyme product standard or calibrant solution and/or ionization solution described herein.

In an embodiment, the standard is a product ion standard, optionally an internal standard, optionally an external standard, optionally an isotopically, affinity tagged or isobarically labelled standard, optionally a recovery standard, optionally a chromatography standard, optionally a mass standard, optionally known amount of an enzyme reaction product standard, optionally for preparing a standard curve or tuning, calibrant.

It is demonstrated herein that AMP, Amplex Red, PA5P and PNPP all have a pure enzyme reaction product standard available to create a standard curve where absolute values are known. Accordingly, in an embodiment the kit comprises an enzyme product standard for AMP, Amplex Red, and/or PNPP.

The kit may contain the calibrant biopolymer standard (e.g the biopolymer to be assayed or quantified such as PSA) one or more solutions (e.g. substrate reaction solution, coating solution, detection probe incubation solution) as described herein. Components such as the detection probe or primary detection agent (e.g. comprising an antibody) are optionally in solution, or may be freeze dried.

Hence adenosine, resorufin, sphingosine, adenosine, phenylbenzene single amino acids and amino acid polymers (peptides), napthol ASMX, nitrophenol, 4-Methylumbelliferone, pyridoxamine or others, including but not limited to any others described here, may be included as absolute enzyme product standards in the kit.

The kit can comprise one or multiple substrates, one or multiple reporter enzymes, conjugated or to be conjugated to detection probe, one or more multiple reporter enzyme detection probes primary detection agents, calibrants, capture biopolymers, substrate reaction solutions, quenching solutions, drying solutions, extraction solvent, ionization solutions, or HPLC buffers.

As examples, the substrates p nitrophenyl phosphate (PNPP), pyridoxamine 5 phosphate (PA5P), nucleotide, adenosine monophosphate (AMP), Naphthol ASMX phosphate (ASMX), para nitrophenol phosphate (PNPP), Amplex® Red (AR) and the Lumigen®s (TMA-3 or TMA-6), 4MUP, Sphingosine phosphate, were all shown to have utility to detect the presence of the HRP or AP labelled probes.

Naphthol ASMX phosphate was sensitive with a sufficient signal to noise ratio. The compound took a long time to return to baseline that may increase the time per sample run and perhaps decrease the number of samples that can be analyzed in a fixed period of time. PNPP had useful chromatography characteristics and showed sensitivity similar to that of ASMX. The Lumigen® compounds are proprietary and so the absolute amounts in the reaction are not know at present. In contrast the Amplex® Red reagent is generically available and the product resorufin is also available permitting the easily estimation of absolute sensitivity. In general the AR had higher backgrounds presumably from a chemical reaction with the reactive oxygen species $H_2O_2$ but showed a wide linear range. The sensitivity of PA5P, AMP, ASMX phosphate makes these substrates attractive for further development of the chromatographic assay. The good sensitivity and chromatography for PNPP make this negative ion mode product an attractive option.

The measurement of free enzyme activity by LC-ESI-MS/MS showed surprising sensitivity in the zepto mol range or less. The absolute amount of enzyme reaction product detectable was in the femto mol range. Hence the absolute detection of the vigorous reporter enzyme AP in an ELIMSA is between 10 and 10,000 times more sensitive depending on the enzyme and substrate combination. The mouse mono clonal antibodies used in this study show a high affinity for the PSA substrate and were capable of forming complexes at concentrations or 1 ng per ml or less. Amplex® Red ELISA hit a sensitivity of about 100 pico grams but the ELIMSA was about 10 to 100 times more sensitive easily reaching 1-10 pico gram of PSA. The AP using the reagent blue phos ELISA reached a limit of about 2 ng but the same reagent system detected by ELIMSA was sensitive to about 0.1 µg or 33 attomol or less. The measurement of the dephosphorylation of PNPP by ELISA was sensitive to about 1 ng but the same reagents measured by ELIMSA apparently reached at least as low as 100 femto gram or about 3 attomols. Hence the sensitivity of the same antibody reagent system measured by ELIMSA was greatly more sensitive than ELISA.

The mouse monoclonal antibodies used herein to detect PSA show a high selectivity for the PSA analyte permitting the specific detection of PSA while the requirement for the binding of both the capture and detection antibody to produce a signal that apparently resulted in good specificity with little signal obtained in the control reaction. The purity of the reagents and solvents were such that there was little difficulty in finding the product ions with a good signal-to-noise in the SIM mode. Since the sample was not complex, the signal was intense and there was little chemical or physical noise obscuring the product there was no need for SRM analysis to achieve specificity.

The ELIMSA technique should extend the application and utility of antibody based detection systems. At present the most potent growth factor and signalling molecules in the cell or body have binding affinities that permit these ligand to bind their receptors in the atto mol concentration range. Thus a quantitative analytical method that can confidently measure analytes to atto mol levels is required for biomedical testing and research. Here for example a 33 attomol quantity of a PSA standard could be detected by ELIMSA using ASMX and even lower amounts apparently in the hundreds of zepto mol range was detected in the negative mode or in the positive mode and after drying and extraction with organic solvents. While the Amplex® Red substrate shows reasonable linearity over a wide range of enzyme concentrations the ASMX system shows one linear range from the pico gram to nano gram range but then another linear range from from 1 to 20 nanograms. The Amplex® Red will be a suitable substrate for analyses in the 0.1 ng range and greater. Analytes at very low levels can be ascertained using naphthol ASMX-phosphate as this system seems more sensitive.

The reporter enzymes such as AP or HRP are versatile and can be coupled to many different molecular probes including aptamers, polypeptides, nucleic acids, carbohydrates, lipid or other biochemical detection molecules. The HRP and AP enzymes have a high catalysis rate and are rugged and durable enzymes that can function in industrial processes reliably. HRP and AP are flexible enzymes that can recognize a variety of substrates to yield product molecules. HRP may catalyze the formation of products resulting from redox reactions that alter the substrates molecular mass. AP may catalyze the release of phosphate from a variety of different substrates changing both the mass and perhaps the charge of the compound. The action of the phosphatase may create reactive groups that permit covalent bonding to create new products. Each HRP or AP enzyme molecule can rapidly yield hundreds or thousands of product molecules over seconds of incubation time. Where the product molecules efficiently enter the gas phase by electrospray ionization, the AP or HRP reporter enzymes might be detected to the zepto mol or less by mass spectrometry.

HRP belongs to the family of peroxidase enzymes common in plants that have a low degree of specificity for electron donors [6]. Peroxidases catalyze the reduction of hydrogen peroxide ($H_2O_2$) a reactive oxygen species ($H_2O_2$): The best studied peroxidases are monomers with molecular weights of 30-40 kDa and contain a single, non-covalently bound heme group; Heme-peroxidases that use $H_2O_2$ as the oxidant are ubiquitous in nature and perform oxidations with the transfer of one-electron; HRP catalyzes many different reactions with various electron donors, such as oxidation of phenols and amines, hydroxylation of aromatic compounds, and olefin halogenations; Horseradish peroxidase (HRP) is one of the least specific enzymes of the peroxidase family [7]. HRP has been reported to hydroxylate aromatic substrates (phenolic compounds, phenylalanine) in the presence of $O_2$ and dihydroxyfumaric acid as a hydrogen donor [8]. HRP can react with luminol in the presence of $H_2O_2$ to produce light that can be measured for chemiluminscent assays using photo multipliers or film for detection [9]. Amplex® Red may be reacted by HRP in the presence of $H_2O_2$ to yield resorufin [10]. The activity of HRP is sometime measured by the oxidation of pyrogallol to form purpurogallin [11] or the oxidation of ABTS (2,2'-azino-bis (3-ethylbenzothiazoline-6-sulphonic acid) [12].

Alkaline Phosphatase (AP) does not require the reactive chemical $H_2O_2$ as an oxidizing agent. Thus AP substrates might have an advantage of lower background and thus perhaps greater signal to noise ratios and better quantification at lower absolute sensitivity. AP is a relatively non-specific enzyme and has been used to dephosphorylate a wide range of substrates including nucleotides, proteins, alkaloids and other metabolites [13]. There are many phosphorylated substrates that might yield products that ionize in an electrospray. The activity of the enzyme is defined with respect to the dephosphorylation of p-Nitrophenyl phosphate (PNPP) [14].

Figure 1:
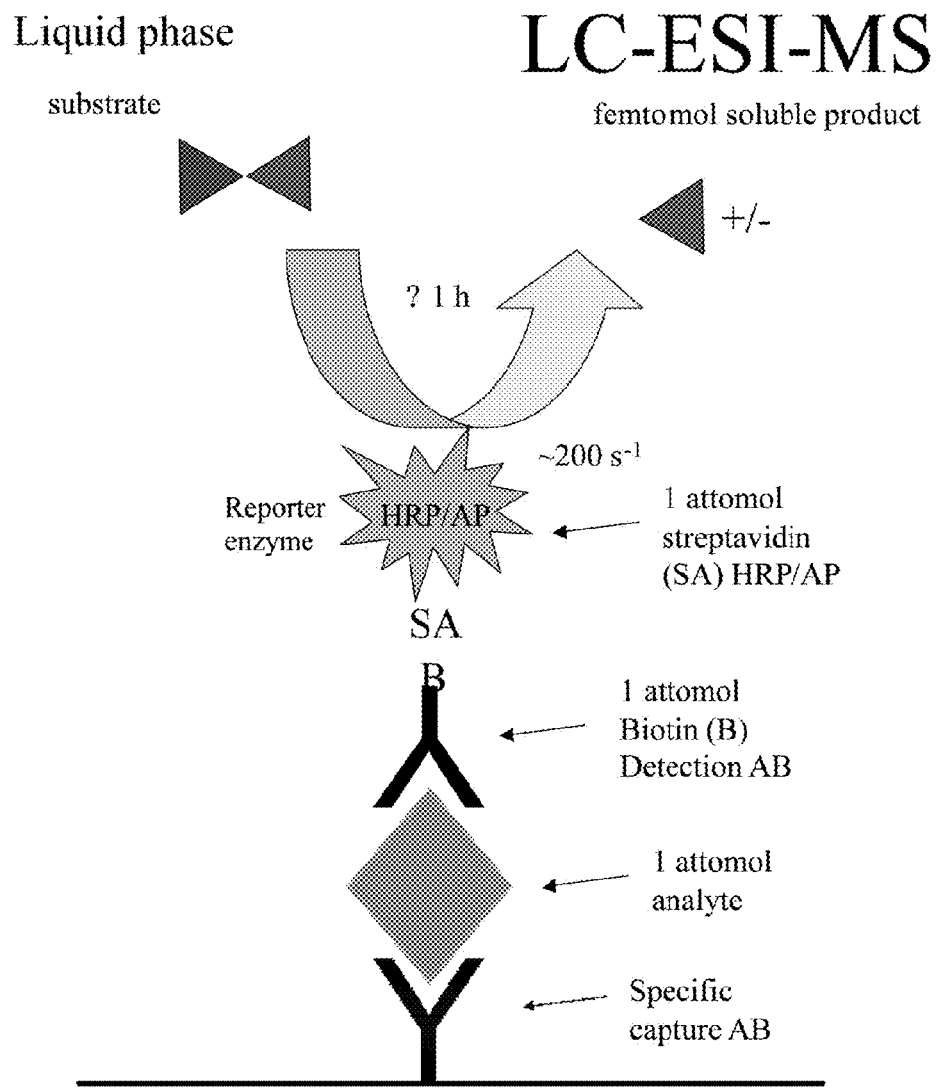
FIG. 1. The scheme for enzyme linked immuno and hybridization mass spectrometric assay.

A method for the quantification of immunological assays is described by applying mass spectrometry to detect the products of reporter assays such as the alkaline phosphatase (AP) and horseradish peroxidase (HRP) enzyme reactions (FIG. 1). There are many molecules from human subjects or microorganisms that are of great importance to medicine, industry, nutrition or the environment that need to be repeatedly analyzed and are often near to, or beyond, the edges of existing analytical technology. The presence of molecules in biological samples, industrial products or the environment may be detected by molecular probes that bind to the target analyte. The molecular probe can be amino acid polymers such as proteins, including antibodies also known as immunoglobulins [1] that may act as probes to detect a variety of target analyte molecules and to quantify their amount. The molecular probes may be coupled to vigorous reporter enzymes. The capacity of reporter enzymes such as alkaline phosphatase (AP) and horseradish peroxidase (HRP) to act on multiple substrates including colorimetric, fluorescent or chemiluminscent substrates has provided increasing sensitivity for Enzyme Linked Immuno Sorbent Assays (ELISA) [2, 3]. The reporter enzymes also are demonstrated herein to act on substrates that yield highly ionizable enzyme reaction products that might be detected and quantified by mass spectrometry (MS). Combining reporter enzymes such as those used from ELISA with for example, sensitive liquid chromatography (LC), electrospray ionization (ESI) and tandem mass spectrometry (MS/MS) permits a sensitive detection and quantification of the molecular probes. Low abundance ligand molecules such as hormones, chemokines, cytokines, and others which exist at atto molar concentrations under physiological conditions may be detected and quantified. The flexibility and sensitivity of mass spectrometry to measure large numbers of compounds simultaneously should permit the quantification of multiple ELIMSA reactions in separate mass-to-charge (m/z) channels. ELIMSA may provide a rapid and relatively simple detection and quantification assay of multiple molecules over a larger range of biologically important concentrations without the use of radiolabels as shown for example in Example 6. Mass spectral analysis of enzyme activity Resorufin is a metabolite produced by cytochrome c monooxygenases in the liver in an enzymatic reaction that may be monitored by mass spectrometry [28]. The commercial colorimetric and fluorescent dye Amplex® Red can be converted to resorufin by the industrial reporter enzyme HRP [10]. It has been previously shown that enzyme activities may be measured by mass spectrometry [29]. The combination of the industrial reporter enzymes HRP or AP coupled to specific antibody probes for ELISA that to date have been measured by colorimetric, fluorescent or chemiluminescent methods are detected and measured by liquid chromatography and mass spectrometry yielding an ultra sensitive analytical system.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

ELIMSA Substrates

Available substrates for the reporter enzymes HRP and AP that will yield products that ionize well and can be resolved sharply and detected sensitively by LC-ESI-MS/MS. The key attribute of the substrates is that they may contain amines for ionization in the positive mode or hydroxyl or acidic groups that will permit ionization in the negative mode. The ionization of candidate compounds of ELIMSA substrates or products has been examined. There are a large number of compounds that are known to be acted on by HRP or AP for fluorescence, colorimetric or ECL detection and a subset of these known molecules have been shown to ionize well. Other compounds, while not known colorimetric or ECL substrates, show structural homology to substrates that yield ionizable enzyme reaction products. Therefore known colorimetric, fluorescence, chemiluminescent or structurally similar molecules were screened to act as substrates with detection tested in water or organic solvent mixtures in both positive mode (e.g. 0.1% acetic acid) and the negative mode (e.g. 0.1% ammonium hydroxide). Several of these substrates produce HRP or AP dependent products of the expected m/z values and with the correct MS/MS spectral elements. The reacted substrates were examined to check for the detection of the predicted products by LC-ESI-MS/MS in aqueous isocratic buffers or binary solvent systems with methanol or acetonitrile. Substrates that have passed the ionization screen are tested for the optimized liquid chromatography conditions in terms of the stationary phase resin (e.g. normal versus reverse phase) and mobile phase solvents (e.g. water, acetontirle, methanol, IPA or a combination) and the use of isocratic verses gradient separation. There is a range of ionizable substrates to compare and choose from for optimizing detection of AP and HRP products by LC-ESI-MS/MS.

ELIMSA Substrate Screening Protocol:
i) tune for the detection of the [M+H] value of the reaction product (e.g. ELIMSA product (also referred to as ELIMSA reaction product or enzyme product));
ii) confirm the major collision induced dissociation fragments of the enzyme reaction product;
iii) create a method to collect ions at the product m/z value (+−5 m/z), fragment the enzymatic products and record the intensity of the major fragment ion;
iii) compare the yield of the product ion from the substrate and reaction buffer alone versus after addition of the enzyme by direct infusion;
v) optimize the HPLC chromatography of the product;
vi) optimize the fragmentation energy for the product ion in single reagent monitoring (SRM) mode to yield an intense fragment ion of the enzyme reaction product;
vii) run an absolute standard curve of the enzymatic product separated by HPLC into micro electrospray as detected by recording parent ion intensity by single ion monitoring (SIM) or parent to fragment transition by SRM;
viii) perform an ELIMSA reaction using the determined conditions and measure the limit of detection (LOD) and limit of quantification (LOQ) for the product ion (SIM) and the intense fragment ion of the enzyme reaction product (SRM).

Example 2

Comparison of ELIMSA to Colorimetric, Chemiluminescence, or Fluorescence

ELIMSA will be compared to ELISA with colorimetric, chemiluminescence, or fluorescence detection. The colorimetric or fluorescent detection of HRP activity with Amplex® Red or ECL detection with luminol will be compared to the sensitivity of ELIMSA with Amplex® Red, TMA-3 and TMA-6. The colorimetric detection of AP with Blue Phos fluorescent or PNPP (p-Nitrophenyl phosphate) detection methods will be compared to ELIMSA with Naphthol AS-MS phosphate and p-Nitrophenyl phosphate.

Direct Comparison of ELIMSA Versus ELISA

The direct comparison of signal verses quantity for ELIMSA and ELISA shows that ELIMSA is for example about 10,000× or more more sensitive than ELISA for the tested substrates (FIG. 30). The ELISA shown is near its limit of sensitivity (signal approaches zero units). In contrast for ELIMSA there is room for further improvement in sensitivity since the signal attained was about 50,000 units and has not yet approached zero.

Example 3

Materials and Methods

Materials

Horseradish peroxidase (HRP) and Alkaliine Phophatase (AP), $H_2O_2$, Amplex® Red, p nitrophenyl phosphate, pyridoxamine 5 phosphate, phospho-Sphingosine, L-(+)-2-amino-6-phosphonohexanoic acid, O-phospho-DL-threonine or other amino acids, 5-Bromo-4-chloro-3-indolyl phosphate disodium salt, Naphthol ASMX phosphate, and 4-Methylumbelliferyl phosphate (4-MUP), deoxycholate, luminol, X-ray film, developer, and fixer were purchased from Sigma-Aldrich. Lumigen® TMA 3 and 6 were purchased from Lumigen® Beckman Coulter. HRP and AP coupled to strepavidin or secondary detection antibodies were obtained from Jackson Laboratories. MaxiSorp 96 well plates were obtained from Nunc (Sigma-Aldrich). Detection antibodies were labelled with biotin using the NHS coupling reagents provided by Pierce. PSA capture and detection antibodies were obtained from Medix Biochemica (Kauniainen, Finland). The PSA calibration antigen was obtained from the Scripps Laboratory (San Diego, Calif.). Formic acid was obtained from FLUKA. HPLC grade water, acetonitrile, methanol acetic acid were obtained from Caledon laboratories. Blue Phos reagent was obtained from Kirkegaard & Perry Laboratories, Gaithersburg, Md. USA.

Substrate Reactions

AP and HRP conjugates with strepavidin (1 mg/ml) were made to 50% glycerol and stored at −20° C. in a frost-free freezer. Amplex® Red (5 mg) was dissolved in 1 ml dimethyl sulfoxide (DMSO) and divided into 50 µl aliquots that were stored in the dark at −20° C. Amplex® Red was diluted with Tris reaction buffer (Tris pH 8.8 20 mM) with a final substrate concentration of 0.1 mM. The HRP amount indicated was added last to Amplex® Red in Tris reaction buffer immediately before the addition of $H_2O_2$ (0.1 mM) to start the reactions. A total of 5 ng of the HRP or AP enzyme per ml was added to reactions for screening. The substrate and enzyme were mixed just prior to the addition of the $H_2O_2$ solution. The TMA-3 and TMA-6 samples were allowed to react for a few minutes until the solution emitted purple fluorescence to confirm the reagents were working well. Luminol was dissolved in dried DMSO and stored in the −20° C. until use. The substrates p-nitrophenyl phosphate (PNPP) and naphthol ASMX phosphate were dissolved in water, aliquoted to 1 mg per tube, lyophyllized and stored at −20° C. in a frost-free freezer until use. The PNPP and ASMX substrates were used at 1 mM final concentration. The HRP substrate luminol was dissolved in DMSO and reacted in the presence of 4-iodophenylboronic acid for greater sensitivity [21].

ELISA Plates

The 96 well plates were coated with 250 ng of capture antibodies in coating buffer (0.1M Na2CO3/NaCHO3 pH9.6) on a rocking platform overnight at 4° C. The wells were blocked with 200 ul of blocking buffer (1% BSA, 1% goat serum in 1×PBS pH7.4) for 30 minutes at room temperature. The wells were briefly washed with 100 ul 1×PBS pH7.4 three times. The standard antigen or biological samples were diluted in 2× Antigen incubation buffer (0.6M NaCl in 2×PBS pH7.4) to a final volume of 100 microliters. To reduce non-specific binding, the wells were then washed three times in washing buffer (1×PBS, 0.05%

Na-Deoxycholate pH7.4). The detection antibody conjugated to biotin was applied in antibody incubation buffer (1×PBS, 0.05% Na-Deoxycholate, 1% BSA, 1% goat serum pH7.4). The wells were washed three times again with washing buffer. The substrate was reacted with the Streptavidin-AP or Strepavidin-HRP in substrate buffer (20 mM Tris pH8.8).

Colorimetric or Fluorescence Detection

The colorimetric or fluorescent signal intensity of the HRP substrate Amplex® Red (AR) and the AP substrates PNPP and Blue Phos (were compared) Amplex® Red is a stable substrate for HRP with selectivity for $H_2O_2$ where the product resorufin is also stable and its longwave spectrum may avoid interference from autofluorescence in some biological samples. Horseradish peroxidase catalyzes de-N-acetylation and oxidation of nonfluorescent Amplex® Red (10-acetyl-3,7-dihydroxyphenoxazine) to the brightly fluorescent resorufin that can be detected colorimetrically at 570 nm or by fluorescence using excitation of 563 nm and emission of 587 nm (75). Oxidation of AR (FW 257.24) consumes stoichiometric amounts of $H_2O_2$ for the production of resorufin (FW 213.19). A possible limitation is interference from other peroxidase substrates present in biological systems. HRP is active over a wide pH range and it may be difficult to quench HRP reactions using acid. The chemilumesncent HRP substrates molecules Lumigen® TMA-3 and TMA-6 were used according the manufactures instructions with the modification that the results of the assay were measured by mass spectometry instead of ECL. The substrates for Alkaline phosphatase (AP) were reacted in 20 mM Tris pH 8.8 buffer. The generically available substrate p-Nitrophenyl phosphate (PNPP) 1 mM was converted by AP to the yellow product 4-nitrophenol that absorbed at 405 nm [14]. The proprietary substrate Blue Phos was converted to a blue color that absorbed at 620 nm [30]. The substrates were tested using from 0.01 ng per well to at least 10 ng per well. The substrate ASMX phosphate may be combined with fast red to yield a fluorescent histological stain [31].

Screening by Direct Infusion

The reaction of AP substrates with a known amount of the free enzymes in solution were screened by diluting the resulting reaction products in a 20 fold dilution of 0.1% acetic acid in water or 70% methanol for positive ionization and 0.1% ammonium hydroxide for negative ionization. The diluted reactions were loaded in to a 500 ul Hamilton syringe for electrospray ionization through a Thermo electrospray source mode. The dephosphorylation of para nitrophenyl phosphate (PNPP) to 4-Nitrophenol was assayed by SIM at 138 [M+H] and SRM at 138-108 [M+H]. The dephopsphorylation of Pyridoxamine 5 phosphate by AP was assayed by SIM at 166, and SRM by 166→138 m/z. The dephosphorylation of Sphingosine 1 phosphate by AP was measured by SIM297 and by SRM 297→279 m/z transition. The dephosphorylation of L-(+)-2-amino-6-phosphonohexanoic acid by AP was assayed by SIM at 132 m/z and SRM by 132→114 transition. The dephosphorylation of O-phospho-DL-Threonine by AP was assayed by SIM122 and by SRM 122→104 m/z transition. The dephosphorylation of BCIP by AP was assayed by SIM at 242 m/z and by SRM at 242→198 m/z transition. The dephosphorylation by phenylbenzene ω phosphono-α-amino acid by AP was assayed by SIM at 255 m/z and by SRM at 255→237 m/z transition. The dephosphorylation of ASMX naphthol phosphate by AP was assayed by SIM at 292 m/z and SRM by 292→171 m/z transition. The dephosphorylation of 4 MUP by AP was assayed by SIM at 229 m/z and by SRM at 229→211 m/z.

The oxidation of Amplex® Red [M+H] 258 yields the product resorufin that was assayed by SIM at 214 [M+H] and was assayed by SRM using the major intense fragment at 214→186 [M+H] consistent with the loss of C—O as a leaving group.

Screening by LC-ESI-MS/MS

The MS spectra data were manually scanned to locate the peaks representing Amplex® Red (258 m/z), resorufin (214 m/z), Lumigen® TMA-3 (504 m/z), Lumigen® TMA-6 (534 m/z) for SIM. The fragmentation energy was optimized and the MS/MS spectra data were manually examined to determine the most intense fragment ion of resorufin (214→186 m/z), Lumigen® TMA-3 (504→286m/z), Lumigen® TMA-6 (534→272 m/z) to sensitively verify and quantify the enzyme reaction products. The dephosphorylation of ASMX naphthol phosphate by AP was assayed by SIM at 292 m/z and SRM by 292→171 m/z transition. The dephosphorylation of para nitrophenyl phosphate (PNPP) to 4-Nitrophenol was assayed by SIM at 138 [M+H] and SRM at 138-108 [M+H].

Method of Quantification

The tuning files, SIM ion and SRM transitions from the infusion experiments were then used to establish the dependence of the LC-ESI-MS/MS signal on the presence of the HRP or AP reporter enzymes. The dependence of the reaction on time was demonstrated by serially sampling over the course of the reaction. Where no product standard was commercially available the optimal reaction time was used to completely react a known amount of substrate to make an estimate of absolute sensitivity. In the case of ECL, the limit of sensitivity for HRP was demonstrated with a known amount of HRP-labelled IgG. The available product standard or enzyme reaction products was then used to characterize the dependence of the LC-ESI-MS/MS assay in terms of the substrate, product or enzyme by existing methods.

ELIMSA

The ELIMSA reactions were performed in the non-ionic detergent 0.05% deoxycholate to limit non-specific binding. The reactions were quenched by diluting the 100 microliter reactions in 20 fold with water, methanol, acetonitrile or mixtures with 0.1% formic acid as indicated. The samples were immediately analyzed by LC-ESI-MS/MS using HPLC and SIM as indicated. Typically the equivalent of only 1 microliter of the 100 microliter ELIMSA reaction was injected. The amount injected may range from 0.1 microliter to 20 microliter. Hence the ELIMSA plot abscisa were labelled ng PSA×100. The equivalent of 1 ul of the ELIMSA reaction was analyzed by injection through a 20 ul loop with a Rheodyne injector. The samples were separated at 10 to 20 microliters per minute through a 15 cm×300 micron ID C18 column (Vydak, Hysperia Calif.). The column buffers used in the experiments were 0.1% acetic acid in water, acetonitrile or methanol buffered with 0.1% acetic acid (positive mode). The HPLC was connected via a metal needle [32] to a micro electropsray source to a Thermo Scientific LTQ XL high performance linear ion trap Mass Spectrometer [33]. The buffers used in the column were 0.1% acetic acid in water and 0.1% acetic acid in acetonitrile or 0.1% acetic acid in methanol.

Results

Traditional ELISA reactions were performed with HRP and AP colorimetric, fluorescent or chemiluminscent substrates to confirm that the immunological reagents in the ELISA were working well. Potential ELIMSA substrates were reacted with free HRP or AP in reaction solution (e.g. reaction buffer) and screened by direct infusion with scan, single ion monitoring (SIM) or single reagent monitoring (SRM). The chromatography required for LC-ESI-MS/MS was developed using the substrate reacted with the free enzymes and separated over C18 in water or aqueous mixtures of methanol, acetonitrile, indole-3 pyruvic acid (IPA), or other mobile phase solvent, in the scan, single ion monitoring (SIM) or single reagent monitoring (SRM). The working immunological reagents were then combined with the substrates that yield good signal to noise ratios to create ELIMSA reactions using the chromatography and MS/MS protocols (LC-ESI-MS/MS).

Detection Limit of ECL

Figure 2:
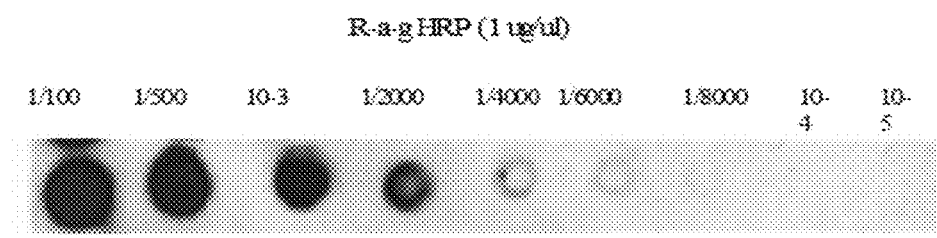
FIG. 2: The detection limit of enhanced chemiluminscence determined with dilution of HRP labelled rabbit anti goat antibody from Jackson Laboratories.

HRP was used directly conjugated to IgG to determine the detection limit of ECL reactions using luminol [26] with sensitive x-ray film as a detection method. The HRP conjugated IgG was shown to have a detection limit of about 125 pico gram where given a molecular mass of IgG at about 150,000 Da represents about 1-10 femto mol absolute detection limit (FIG. 2).

Substrate Screening by Direct Infusion

The ionization of AP products from substrates including adenosine monophosphate (AMP), Amplex® Red, TMA-3, TMA-6, p nitrophenyl phosphate, pyridoxamine 5 phosphate (PA5P), phospho-Sphingosine, L-(+)-2-amino-6-phosphonohexanoic acid, O-phospho-DL-threonine or other amino acids, 5-Bromo-4-chloro-3-indolyl phosphate disodium salt, Naphthol ASMX phosphate, and 4-Methylumbelliferyl phosphate (4-MUP) (AP) were compared in the SIM and SRM mode (Table I). Based on the signal-to-noise ratios produced by the substrate screen, we elected to first focus on the substrates AR, ASMX, TMA-3 and TMA-6 that all ionized in the positive mode as well as PNPP in the negative mode were first selected for further analysis.

Amplex® Red

Figure 3:
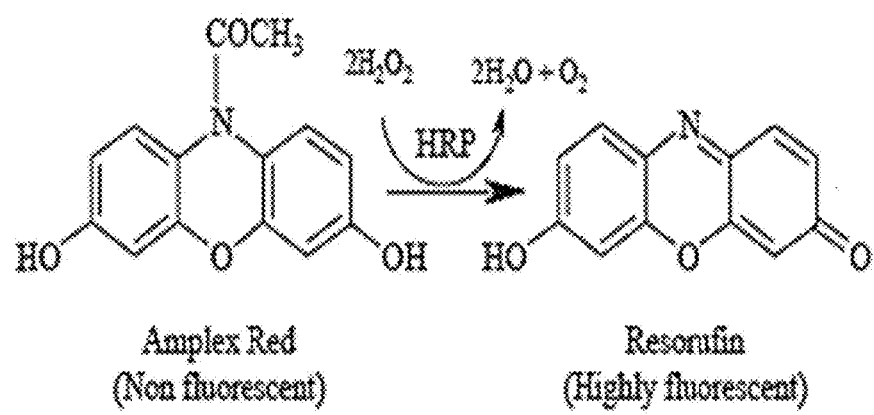
FIG. 3: The conversion of Amplex® Red to resorufin by HRP in the presence of $H_2O_2$.
Figure 4:
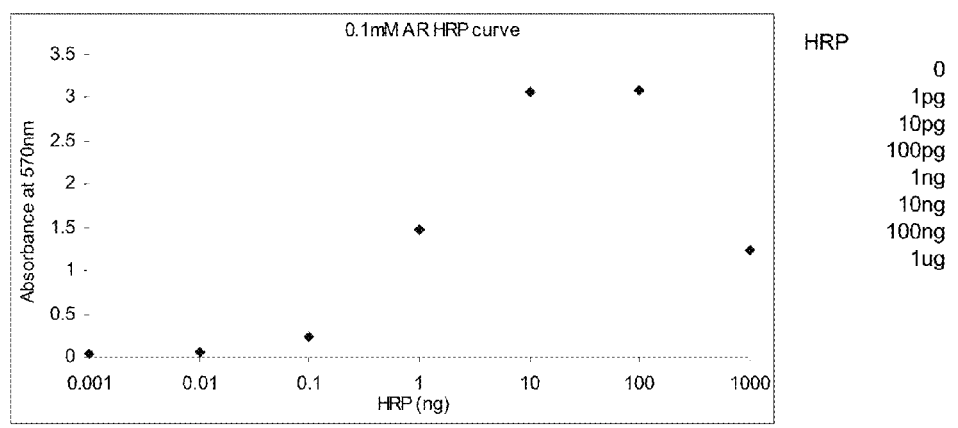
FIG. 4: ELISA of PSA based on the measurement of the oxidation of Amplex® Red to resorufin by absorption at 570 nm.
Figure 5:
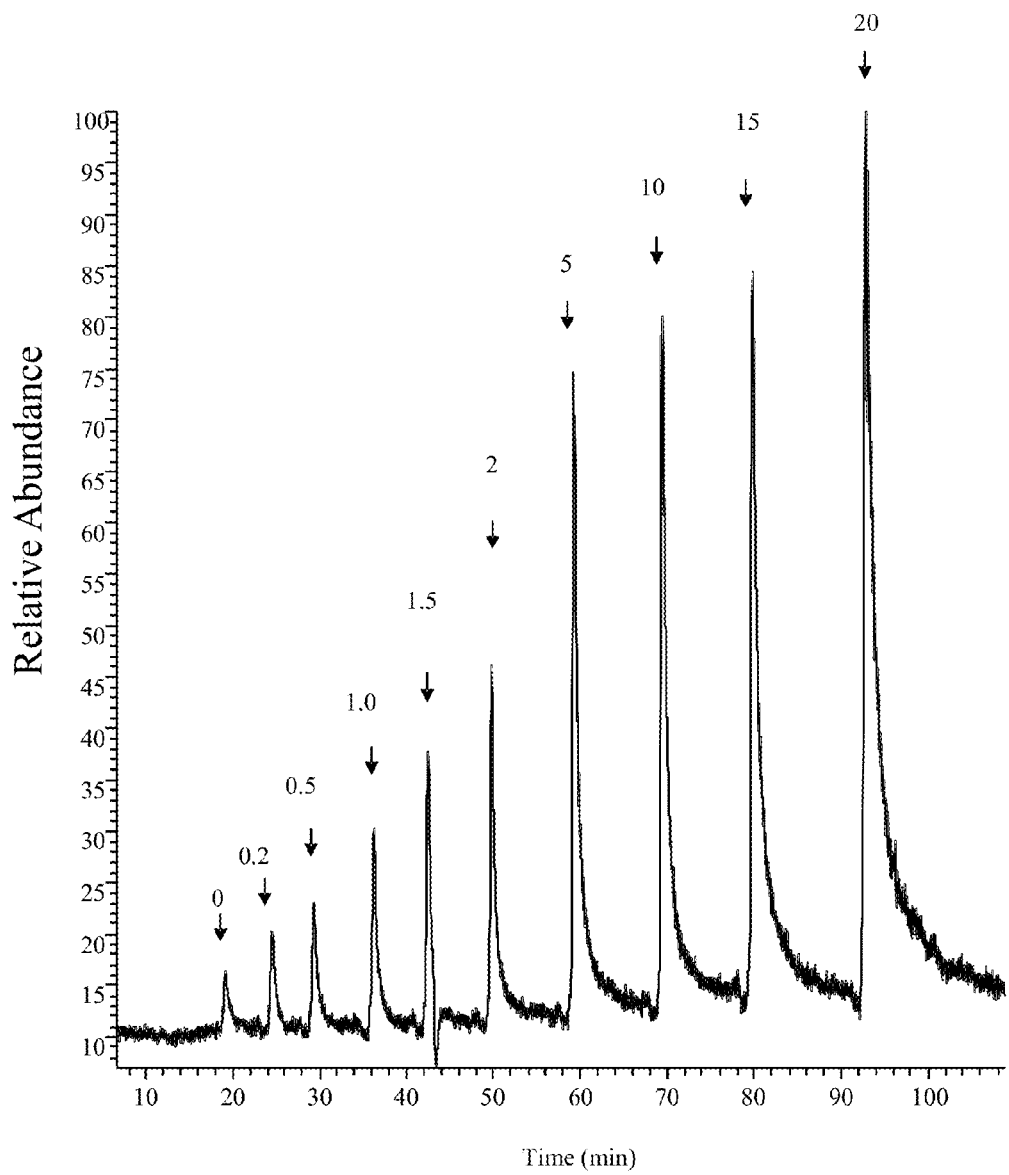
FIG. 5: Resorufin standard dilution curve. The resorufin standard was obtained from Sigma Aldrich. The experiment shows that the LC-ESI-MS system is sensitive to femto mol to pico mol amounts of resorufin on column. The amount injected is shown in pico mols.
Figure 6:
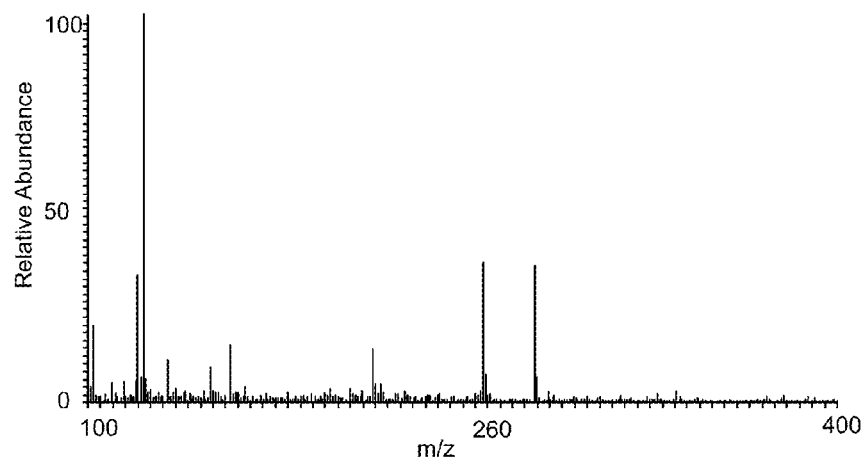
FIG. 6: The biochemical reaction Amplex® Red with $H_2O_2$ by the enzyme HRP to yield the enzyme reaction product resorufin as monitored by LC-ESI-MS. Panels: A, MS spectra of the Amplex® Red [M+H] 258.04 m/z; B, resorufin [M+H] 214 with an intensity of 1.39 E6 arbitrary counts.
Figure 6:
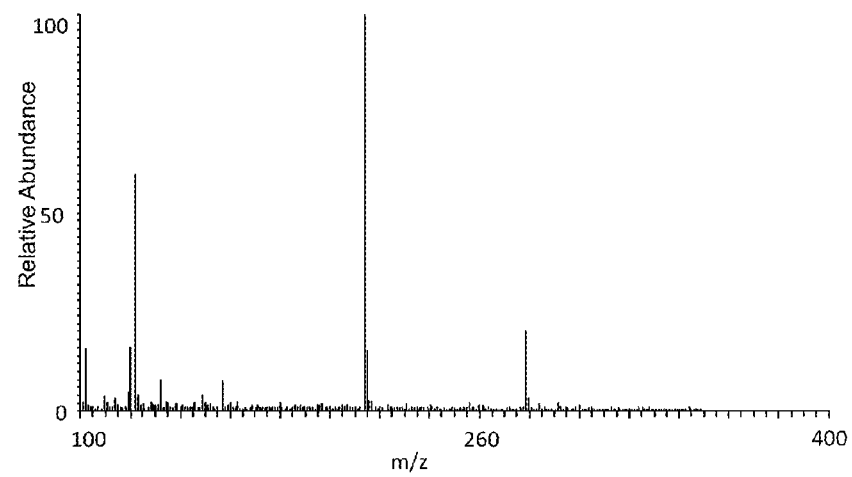
Figure 7:
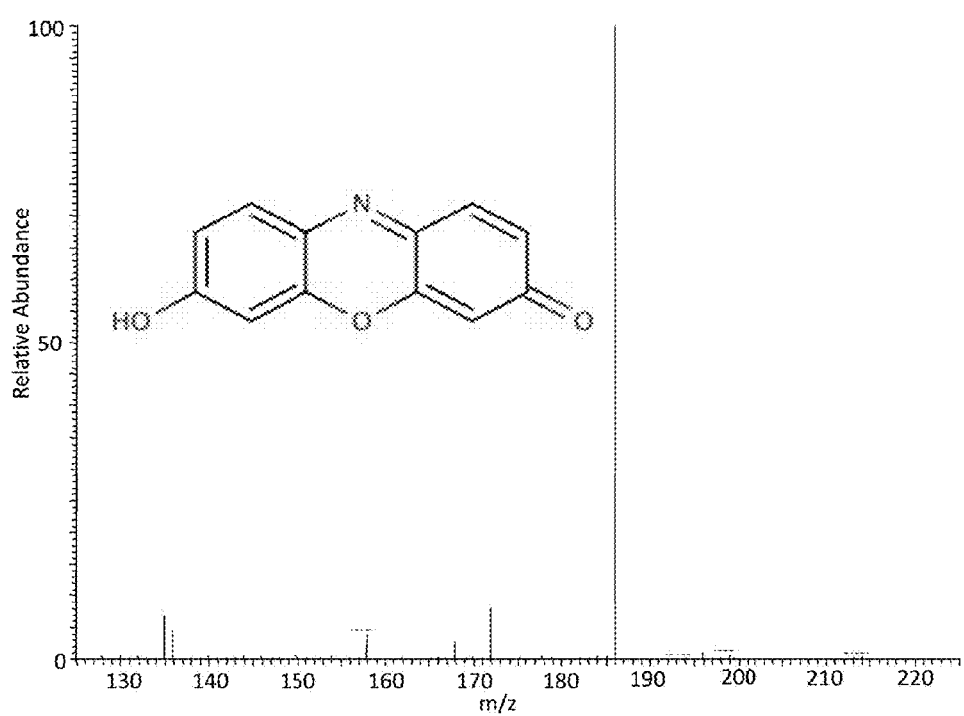
FIG. 7: The MS/MS spectra of resorufin in the reaction condition with HRP and $H_2O_2$ generated by CID fragmentation of peak 213.96 m/z at 38.75 min and scanned for ions 50.00-440.00 m/z. The main fragments of the precursor ion m/z 213.96 were m/z 157.86, 140.94, and 186.01 whose formation from the product is shown.
Figure 8:
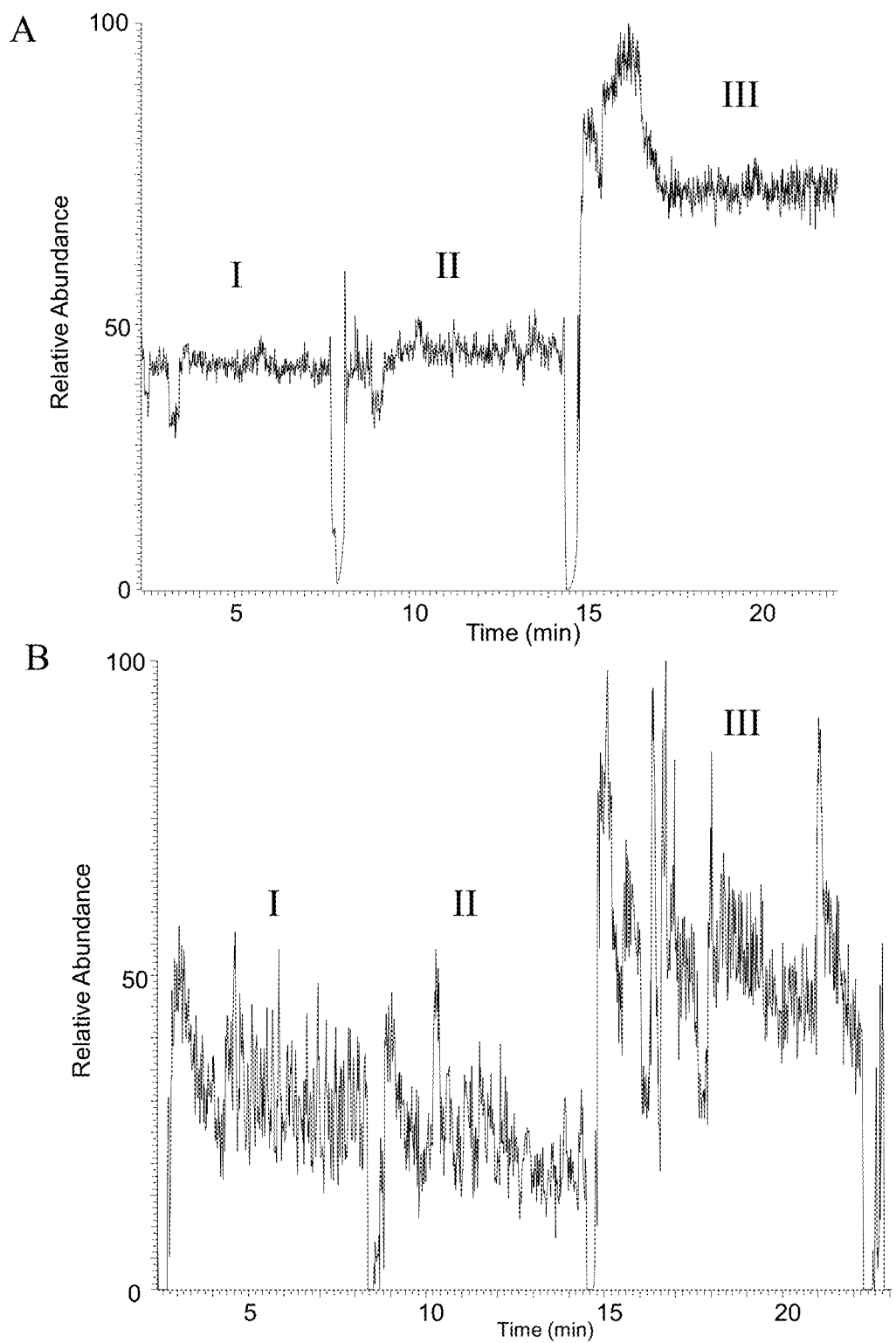
FIG. 8: The INFUSION, screening of Amplex® Red by SIM for resorufin. SIM 214 [M+H]. The three infusions are: I, buffer plus Amplex® Red; II, buffer, Amplex® Red and H2O2; III, buffer, Amplex® Red, H2O2 and HRP.
Figure 9:
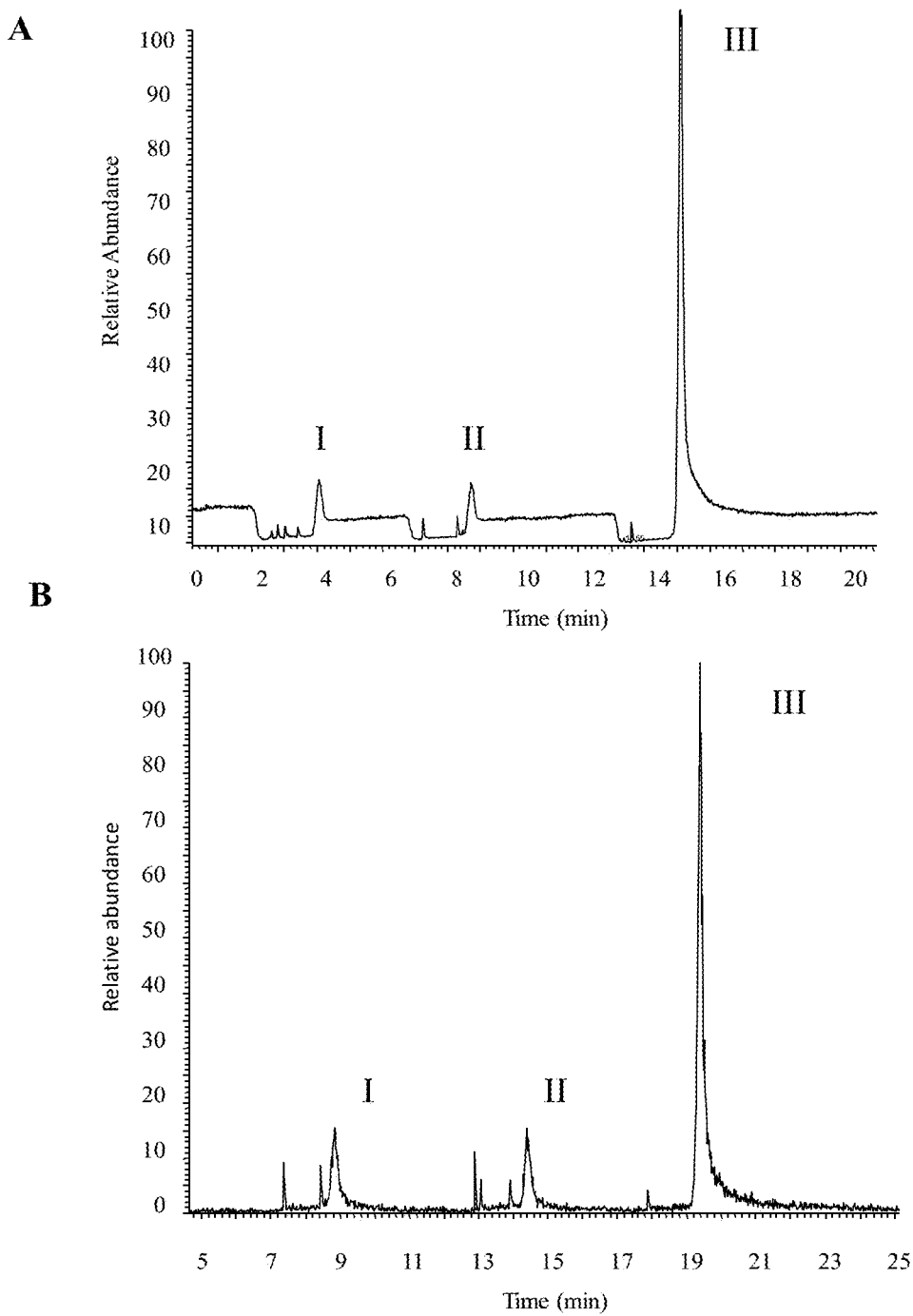
FIG. 9. The isocratic HPLC LC-ESI-MS/MS screening of Amplex® Red by SRM for resorufin. SRM 214→186 [M+H]. The three INJECTIONS are: I, buffer plus Amplex® Red; II, buffer, Amplex® Red and H2O2; Ill, buffer, Amplex® Red, H2O2 and HRP.
Figure 10:
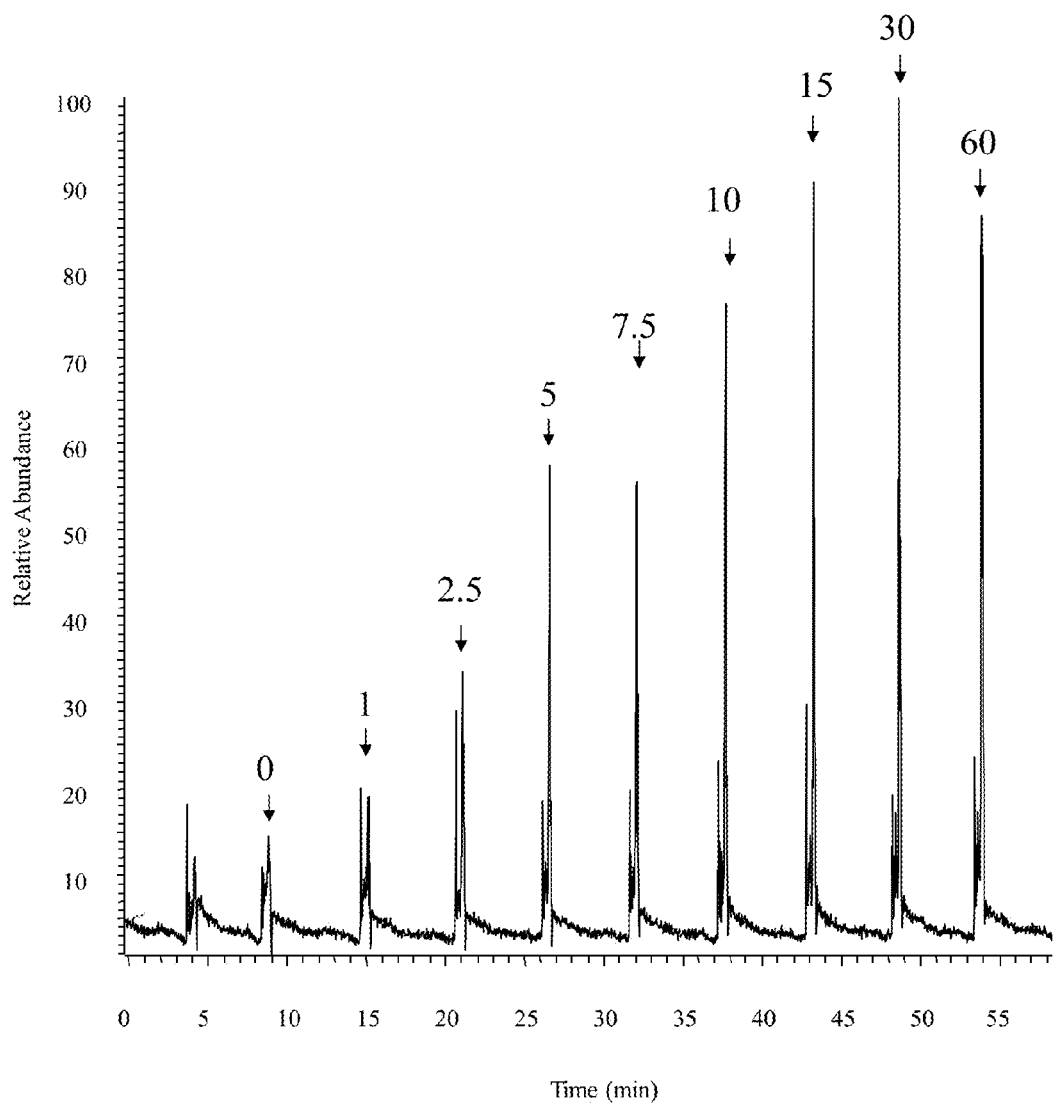
FIG. 10: The time dependence of the HRP enzymatic product of Amplex® Red monitored by SIM at 214 [M+H]. The HRP-SA conjugate (5 ng) was added to 1 ml of 0.1 mM Amplex® Red in 20 mM tris pH8.8. 0.1 mM $H_2O_2$ was added and reactions were stopped by adding 10 ul of the reaction mixture to 190 ul of 0.1% FA at various time points. The equivalent of one microliter of the reaction was analyzed.
Figure 11:
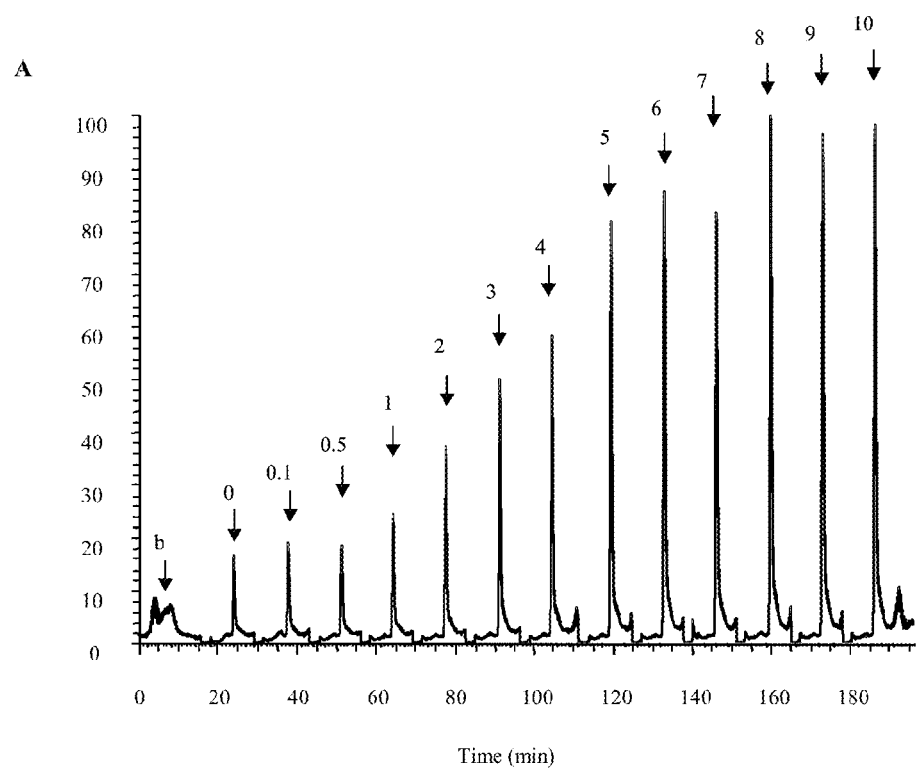
FIG. 11: The linearity of the SIM 214 [M+H] product resorufin product of Amplex® Red by HRP from 0.1 to 10 ng.
Figure 11:
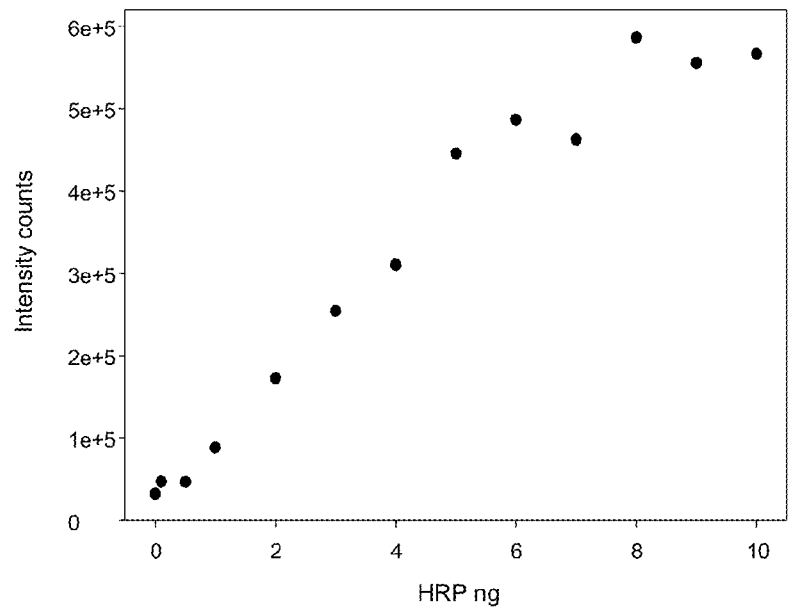
Figure 12:
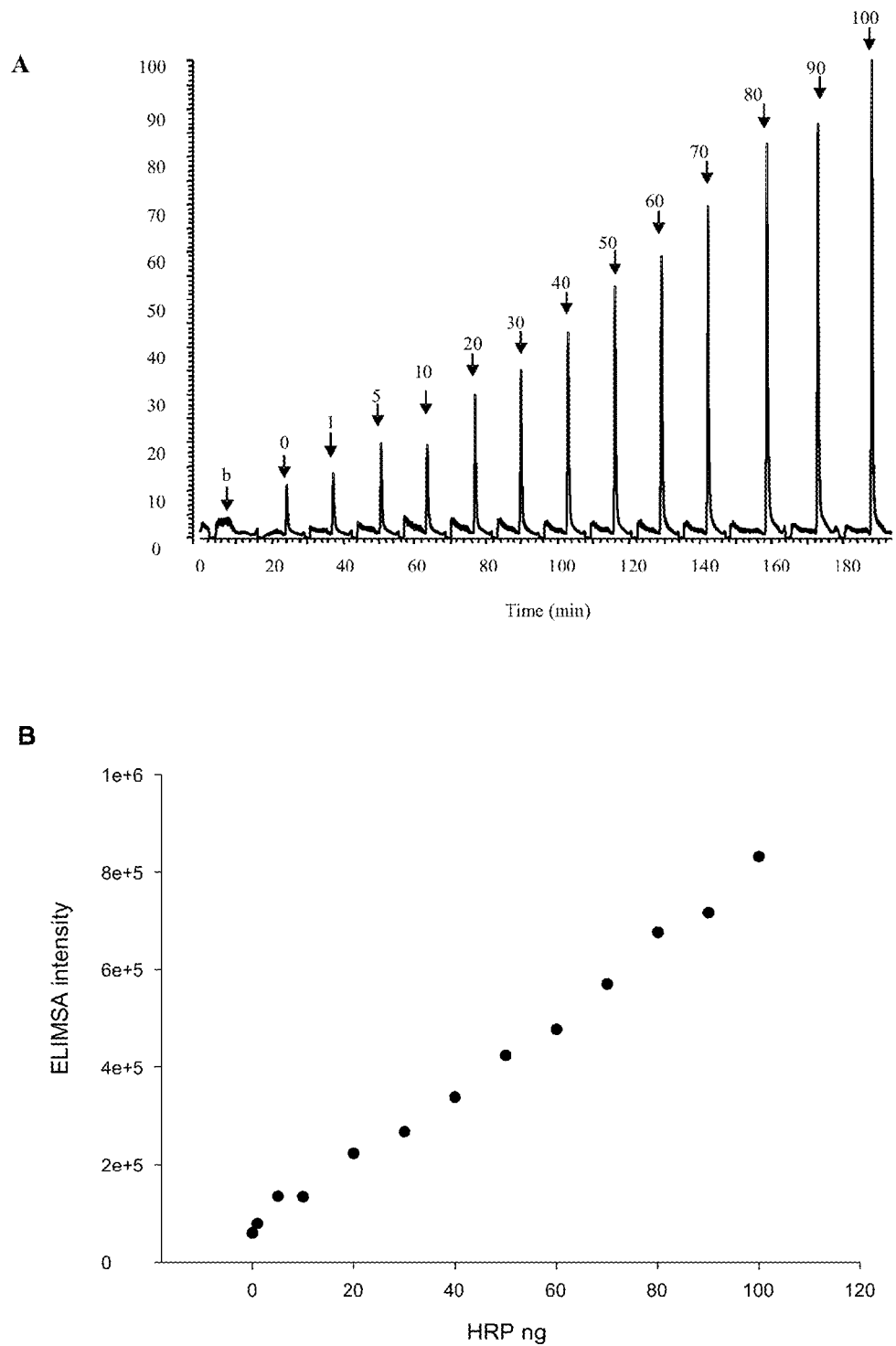
FIG. 12: The linearity of the SIM 214 [M+H] product resorufin product of Amplex® Red by HRP from 5 to 100 ng.
Figure 13:
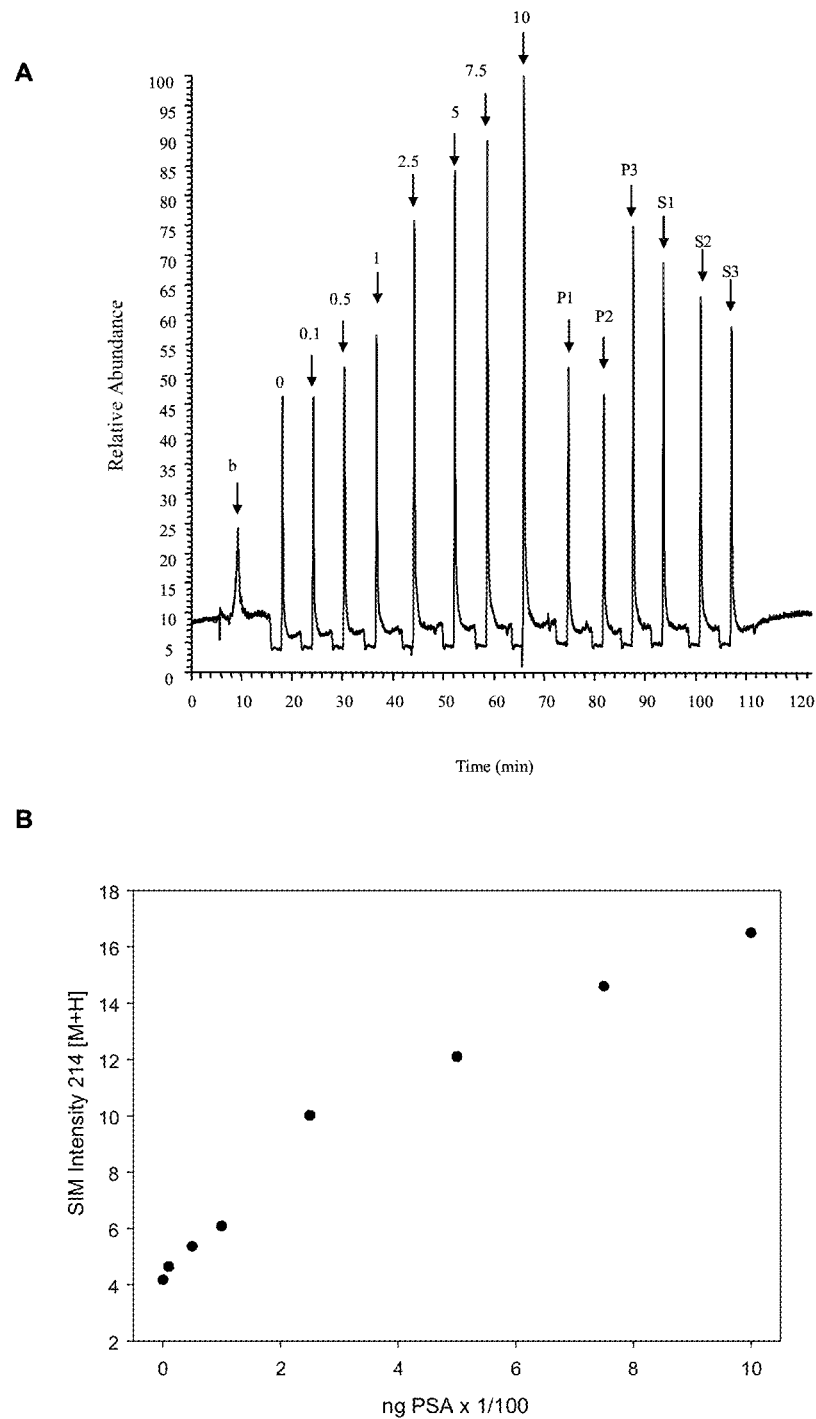
FIG. 13: An ELIMSA assay of the PSA from human serum and plasma using the substrate Amplex Red® and the Enzyme HRP. Panels: A, a series of PSA standards followed by 3 plasma and 3 serum samples from human male blood; B, the relationship between the SIM 214 [M+H] and the ng added to the ELIMSA reaction prior to dilution and injection of the equivalent of 1 microliter.
Figure 14:
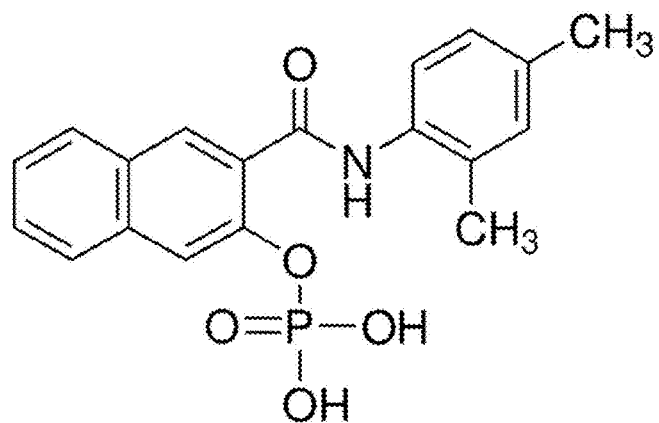
FIG. 14: The dephosphrylation of naphthol ASMX phosphate by Alkaline Phosphatase.
Figure 14:
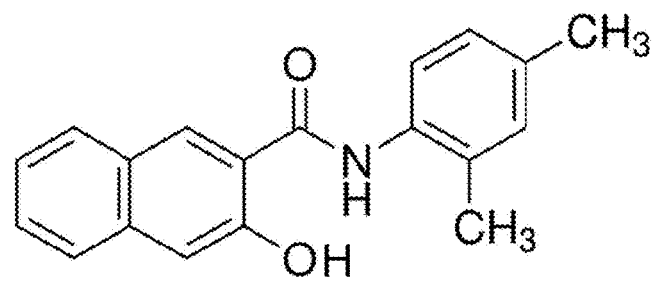
Figure 14:
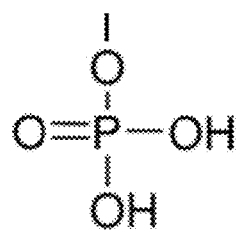

The colorimetric reaction of the HRP substrate Amplex® Red (AR) to resorufin (FIG. 3) in an ELISA format for PSA was found to have a detection limit of about 0.1 ng under the conditions tested and showed linearity to at least 10 ng in good agreement with previous results [10]. The infusion of resorufin in 0.1% acetic acid produced an intense spectral line at 214 [M+H] that was used to tune for the product of Amplex® Red from the HRP reporter enzyme. A dilution series for the resorufin standard showed a clear signal as low as about 200 femto mol (FIG. 5). The AR substrate 258 [M+H] was not found to ionize very efficiently but could be observed separately from its product resorufin over the course of LC-MS in the scan mode (FIG. 6). The Resorufin 214 [M+H] product was characterized by MS/MS and found to yield a major intense fragment of 186 [M+H] (FIG. 7). Infusion showed the production of the SIM 214 [M+H] peak and detection of the SRM 214→186 transition was dependent on the HRP enzyme (FIG. 8). LC-ESI-MS/MS analysis showed the enzyme dependent production of resorufin was detected by SIM and SRM and shown to achieve similar sensitivity but the SIM method showed lower noise levels (FIG. 9). A time course showed that the HRP dependent reaction reaches its maxima by 10 to 15 minutes (FIG. 10). Holding the substrate constant at 0.1 mM in a 200 microliter reaction and varying the free HRP-SA (40+60 kDa) conjugate enzyme showed the enzyme dependent production of resorufin was detectable to 0.1 ng where only 1 microliter was injected corresponding to the equivalent of about 5 atto mol (FIG. 11). The reaction was linear up to 100 nanograms (FIG. 12). In use as an ELIMSA the method showed that capacity to detect about 33 atto mol of PSA and was able to detect PSA in sample below the detection limit of the Amplex® Red colorimetric reaction (FIG. 13). With the use of drying, the detection limit of ELIMSA was reduced to about 330 zepto mol. Drying may be more rapidly achieved by diluting the aqueous sample in organic solvents such as methanol, ethanol, propanol, acetonitrile or other drying solutions.

Naphthol ASMX Phosphate

Figure 15:
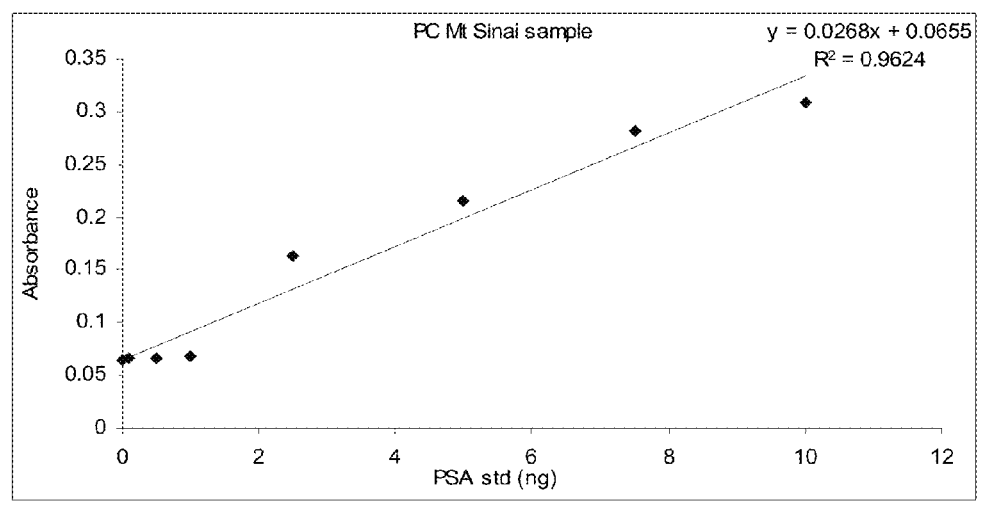
FIG. 15: The ELISA of PSA standard and 30 samples. 50 ul of sample was used per well and incubated for 10 min with 100 ul BluePhos® substrate before measuring at 595 nm. The absorbance at 595 nm is shown.
Figure 16:
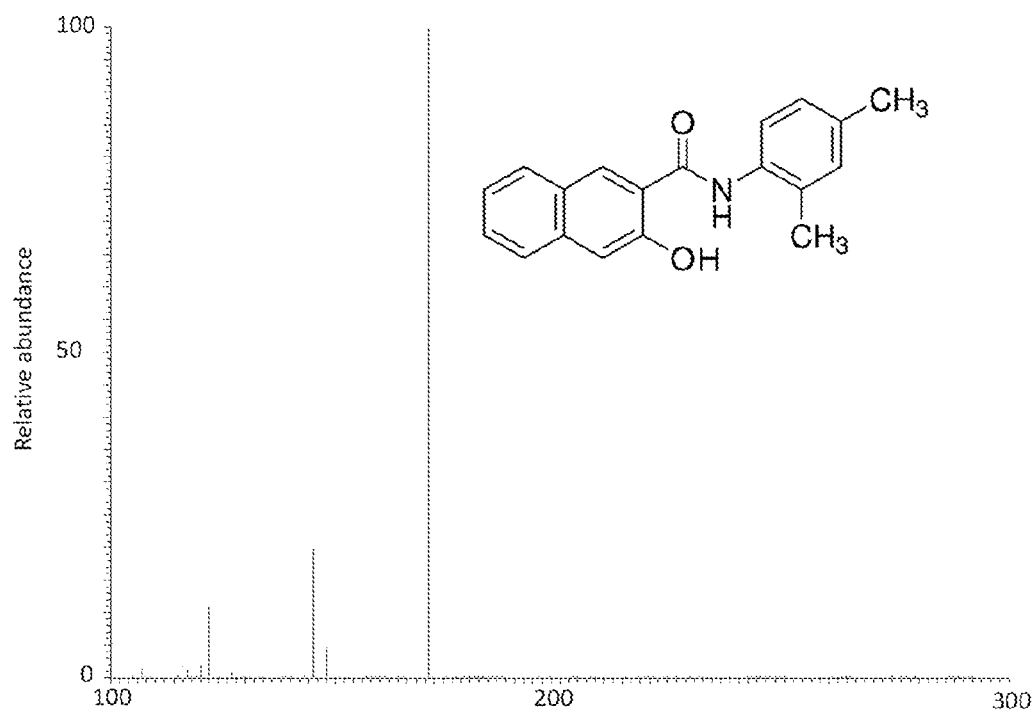
FIG. 16: The MS/MS spectra of reaction of ASMX with AP to generate the 292 [M+H] product that was fragmented by CID to yield a major MS/MS spectral line at 171 [M+H].
Figure 17:
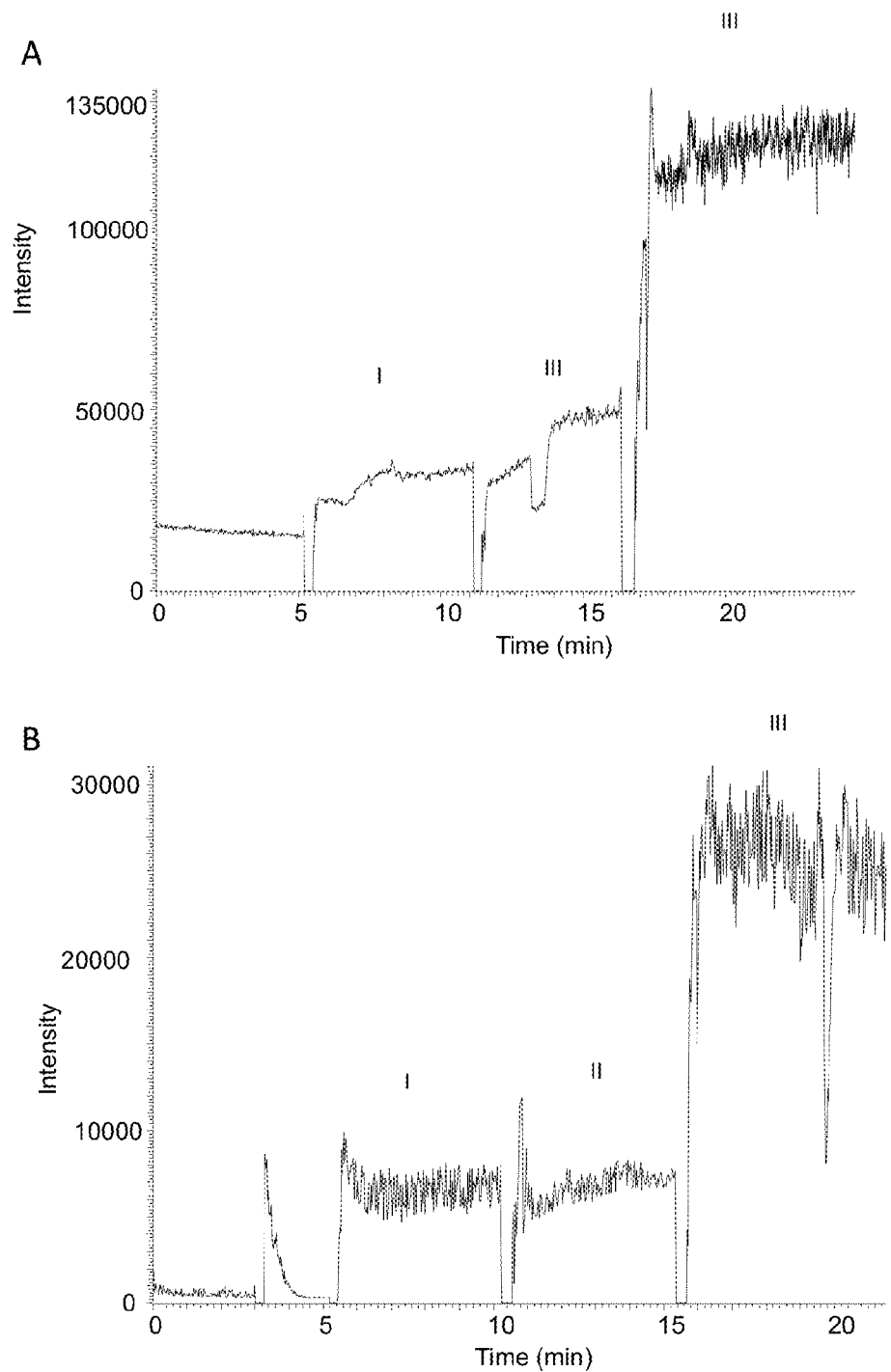
FIG. 17. The infusion screening of ASMX phosphate by SIM and SRM. Panels: A, SIM 214 [M+H]; B, the SRM 214→186 [M+H]. The three infusions are: I, buffer plus II, buffer plus, Napthol ASMX Phosphate; III, buffer, napthol ASMX phosphate and alkaline phosphatase.
Figure 18:
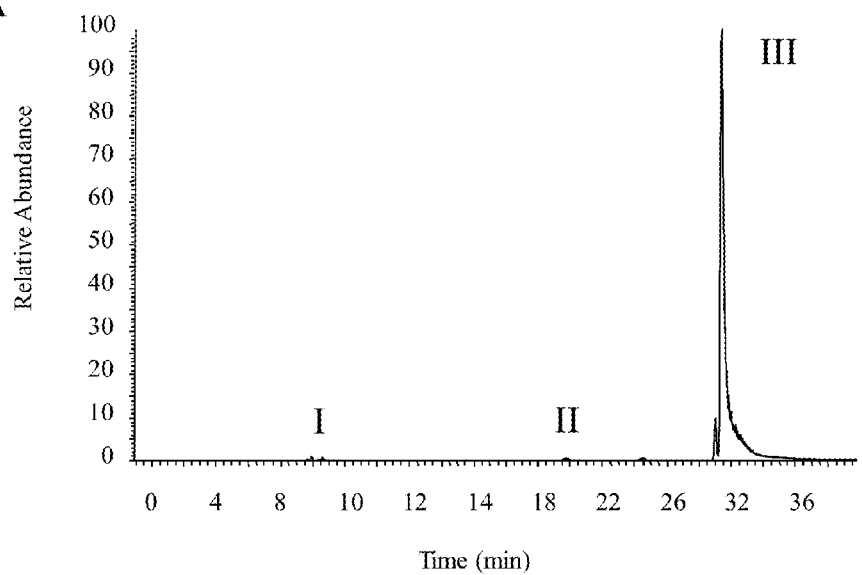
FIG. 18: The isocratic HPLC LC-ESI-MS/MS screening of ASMX phosphate by SIM and SRM. Panels: A, SIM 292 [M+H]; B, the SRM 292-171 [M+H]. The three injections are: I, buffer alone; II, bufferplus ASMX; III, buffer, ASMX and AP.
Figure 18:
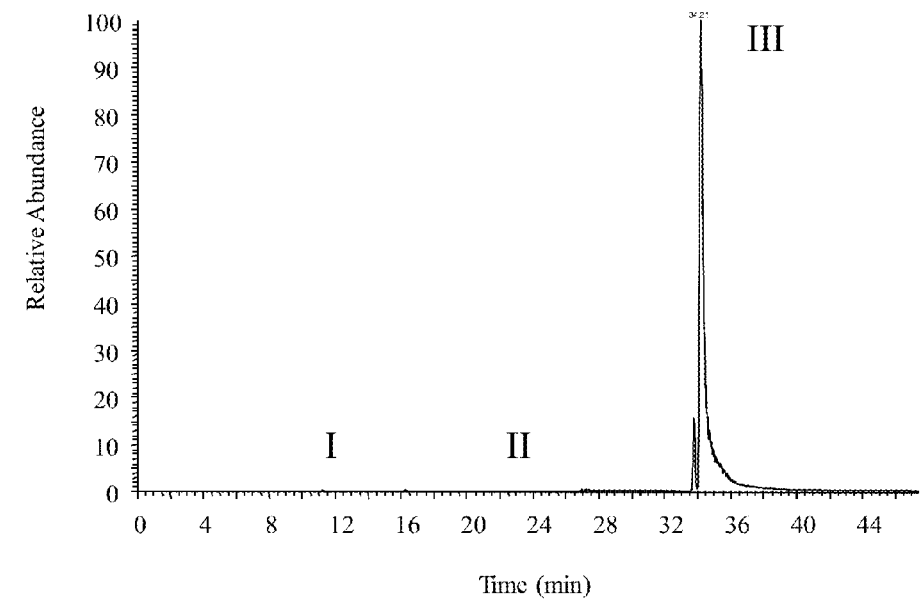
Figure 19:
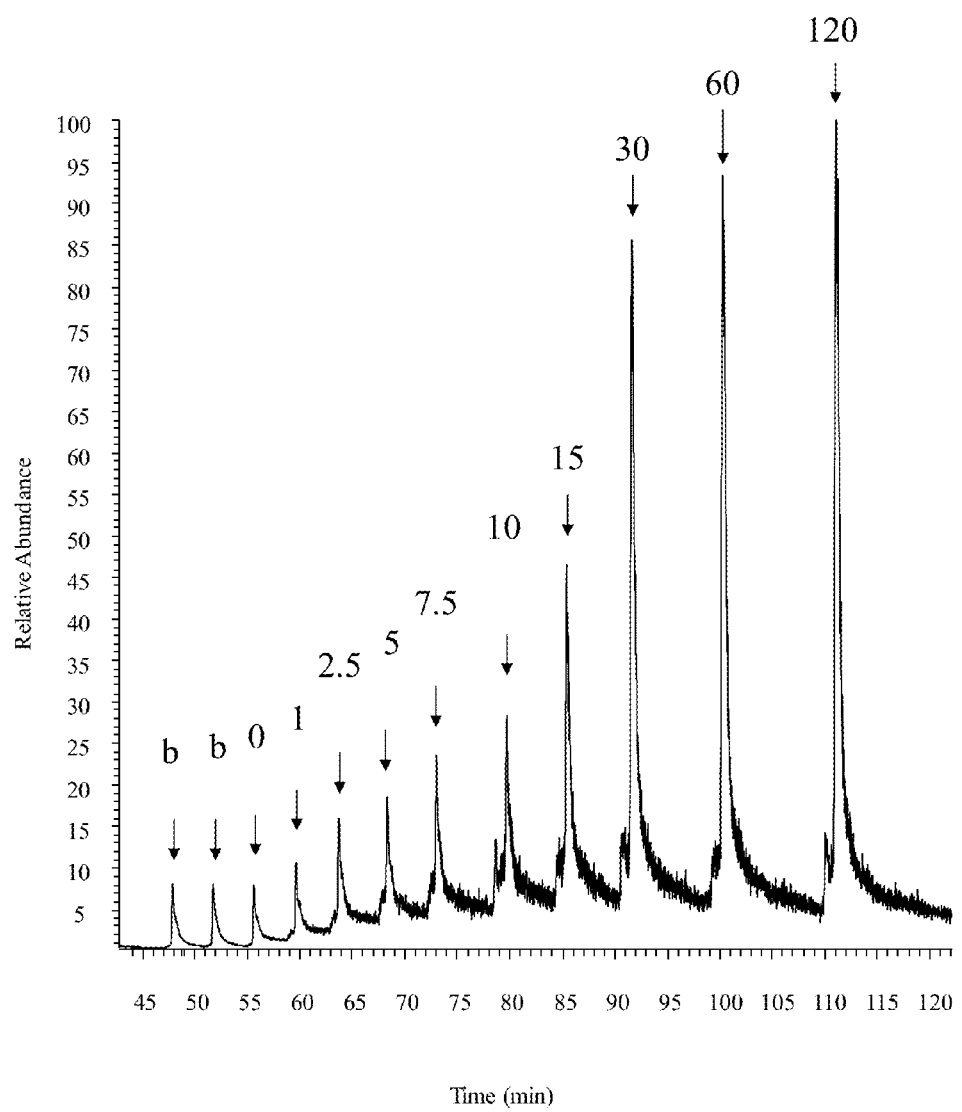
FIG. 19: The time dependence of the AP enzymatic product of ASMX monitored by SIM at 292 [M+H]. The AP-SA conjugate (5 ng) was added to 1 ml of 1 mM ASMX in 20 mM tris pH 8.8 and reactions were stopped after the time indicated by adding 10 ul of the reaction mixture to 190 ul of 0.1% FA at various time points. The equivalent of one microliter of the reaction was analyzed by LC-ESI-MS.
Figure 20:
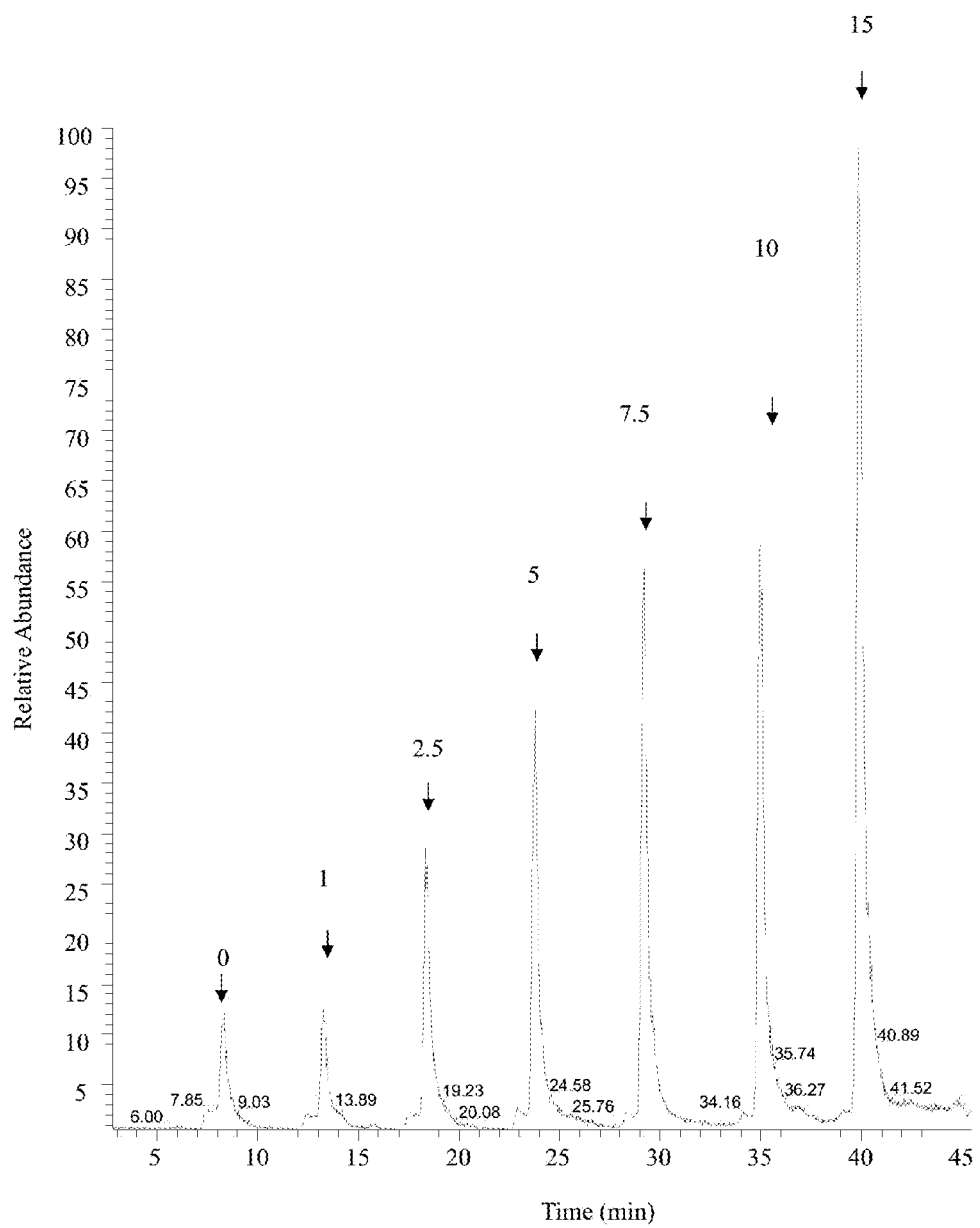
FIG. 20: Naphthol ASMX phosphate enzyme reaction product standard curve. The sensitivity of the mass spec to the enzyme reaction product is shown in pico mols assuming all of the ASMX substrate was quantitatively converted.
Figure 21:
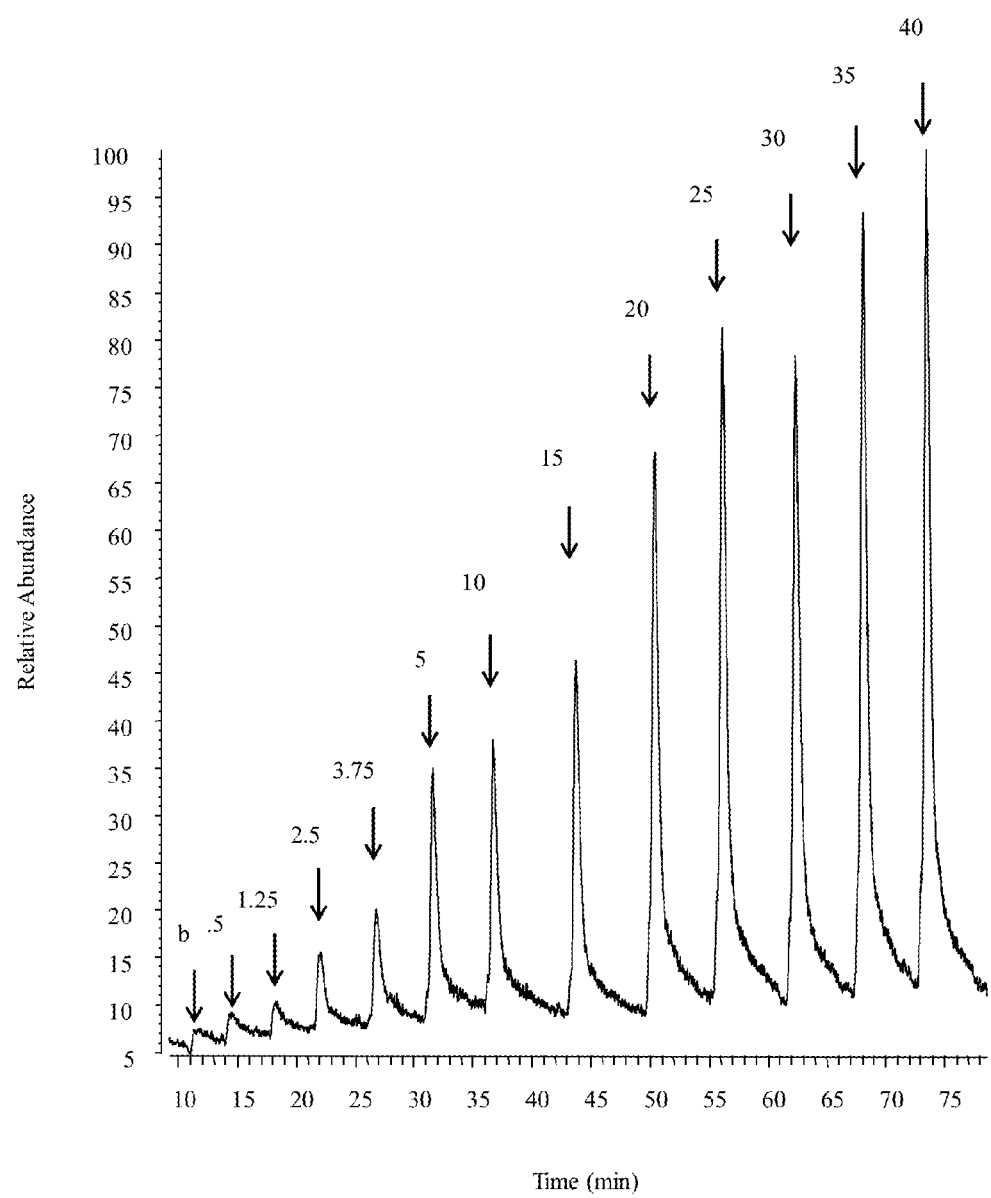
FIG. 21: The free AP-SA conjugate dilution series reacted with ASMX phosphate and detected by LC-ESI-MS/MS. The amount of SA conjugate in nanograms shown by the arrow was added to a 1 ml solution of 1 mM ASMX in 20 mM pH 8.8 tris for 30 minutes. A 10 microliter sample was diluted 100 fold prior to the manual injection of 20 microliters and the enzyme product measured by the SIM 292 m/z.
Figure 22:
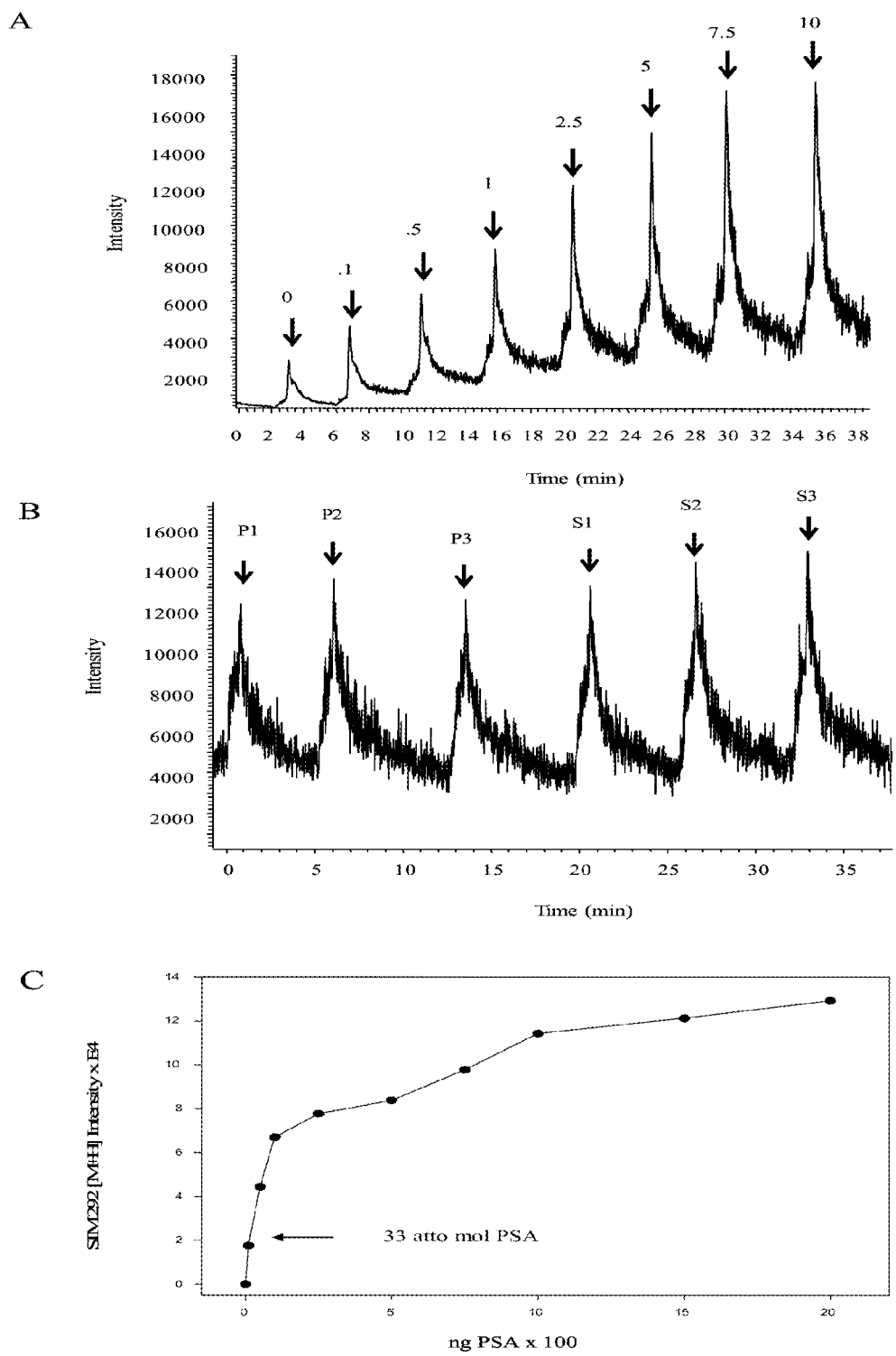
FIG. 22: An ELIMSA assay of the PSA from human serum and plasma using the Naphthol ASMX phosphate substrate detected with AP-SA with SIM of the 292 [M+H] product ion. Panels: A, a series of PSA standards as indicated; B, 3 plasma and 3 serum samples from human male blood; C, the relationship between the SIM 292 [M+H] and the ng added to the 100 microliter ELIMSA reaction prior to dilution 20 fold and injection of the equivalent of 1 microliter.

The AP ELISA system was applied to a set of human serum samples using the Blue Phos method [30] and showed many PSA samples were within the linear range. The colorimetric ELISA using AP substrates such as Blue Phos showed sensitivity to the 0.1 ng range per 100 microliters where the entire 100 ul were used to make the determination (FIG. 15). However, even when 100 microliters of the reaction was analyzed by ELISA some PSA samples were below the range of reliable detection or quantification. In contrast, only 1 microliter of the 100 microliter ELISA reaction with 0.1 ng of PSA (i.e. 0.0001 ng) was required to make a clear detection by the ELIMSA of ASMX by mass spectrometry. The MS/MS analysis of the 292 [M+H] AP product of ASMX had a major intense fragment of 171 [M+H] (FIG. 16). By infusion in SIM mode or SRM mode the ASMX product was dependent on the presence of the AP enzyme (FIG. 17). The LC-ESI-MS by SIM 292 [M+H] or SRM 292→171 [M+H] the ASMX product was dependent on the presence of the AP enzyme (FIG. 18). The time course analysis indicated the that the maximal signal was obtained by about 15 minutes (FIG. 19). The calculated sensitivity to the ASMX enzyme reaction product assuming quantitative conversion was about 1 pico mol as determined by serial dilution (FIG. 20). The absolute sensitivity to the free enzyme probe in solution by SIM 292 [M+H] was 0.01 ng of the AP-SA conjugate (140 kDa+60 kDa) in a 200 ul reaction where 1 micro liter was analyzed (about 50 pico gram or 2.5 atto mol (FIG. 21)). The ELIMSA assay in use for PSA showed that capacity to make quantifications at least as low as 33 atto mol (FIG. 22).

Para Nitrophenol Phosphate (PNPP)

Figure 23:
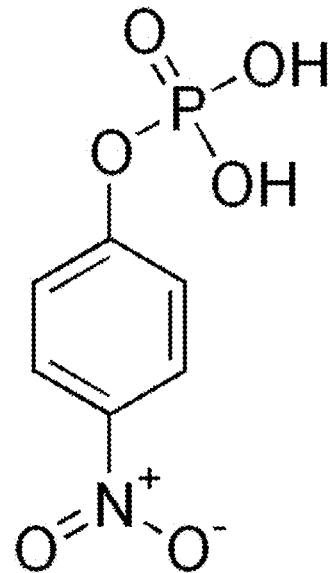
FIG. 23: The dephosphorylation of PNPP by alkaline phosphatase.
Figure 23:
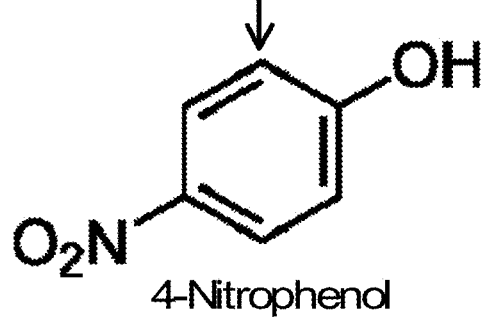
Figure 23:
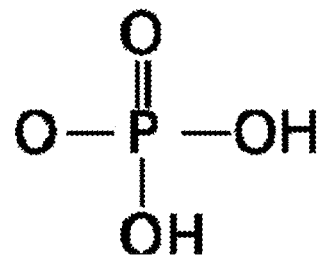
Figure 24:
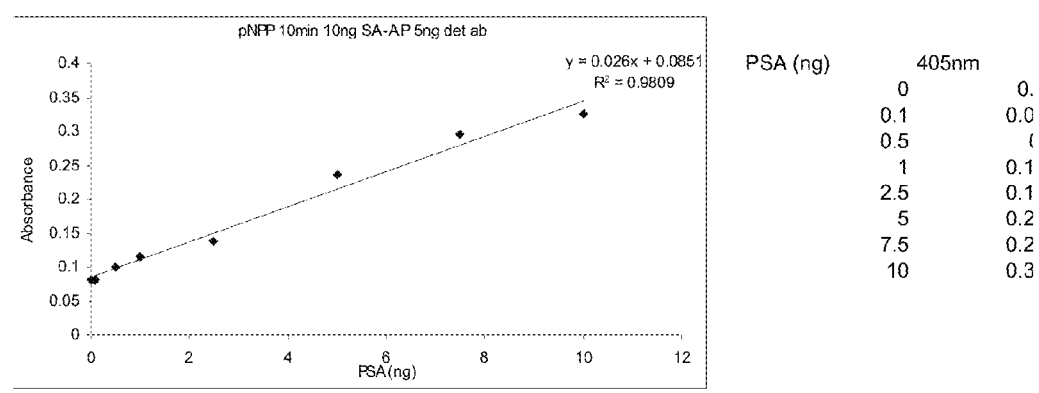
FIG. 24: The ELISA of PSA by the measurement of the dephosphorylation of PNPP to 4 nitrophenol that absorbs at 405 nm from 1 to 10 ng per well.
Figure 25:
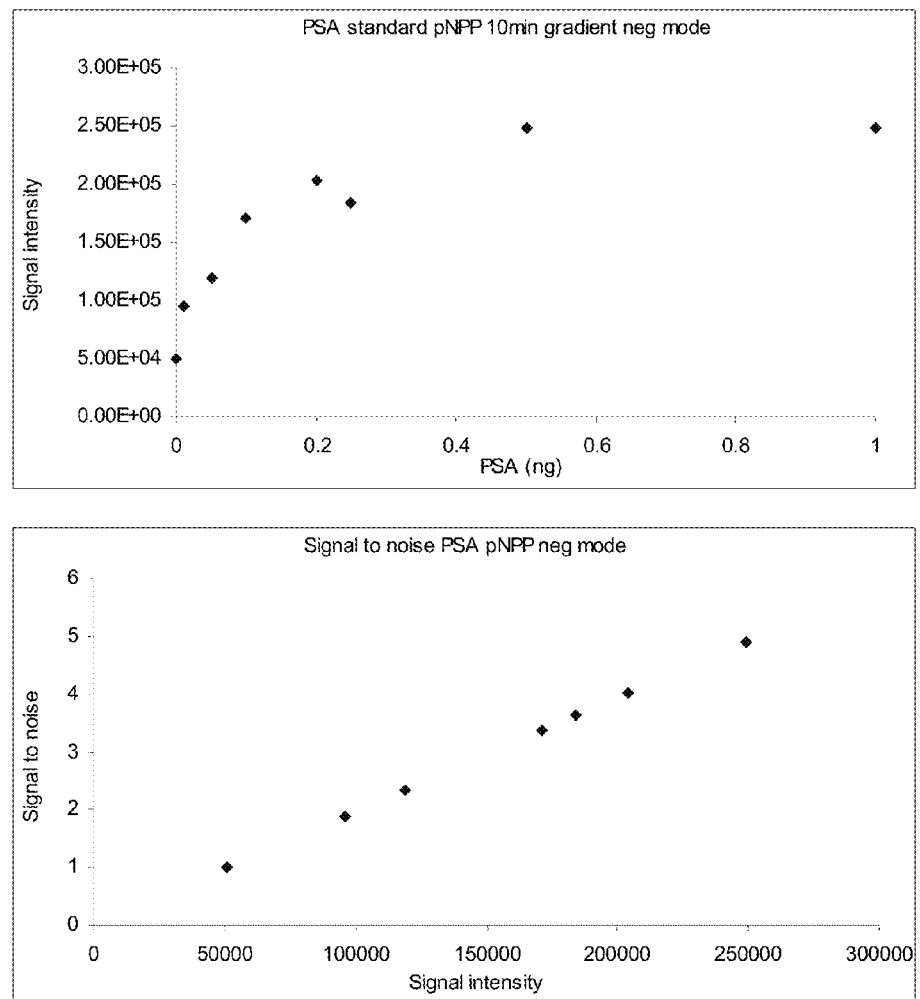
FIG. 25: The ELIMSA of PSA based on detection of nitrophenol from PNPP from 0.01 to 1 ng per well.
Figure 26:
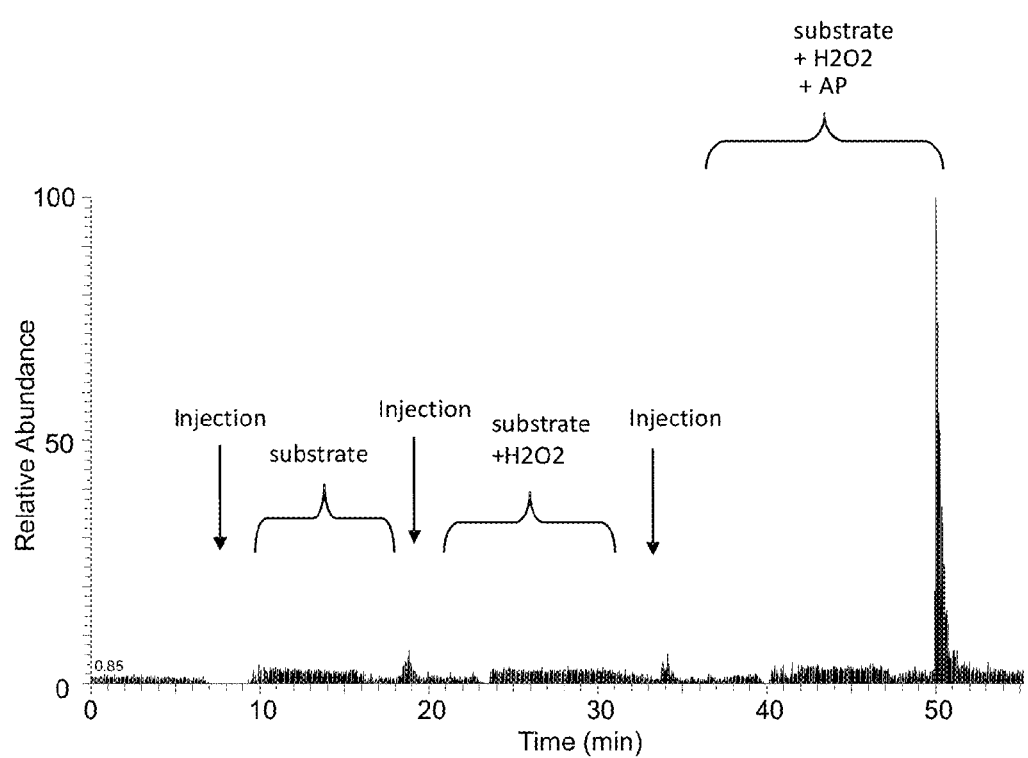
FIG. 26: The chromatogram shows the relative ion abundance specifically for the product ion TMA-3 product (m/z 286) scanned for the m/z range 284.99-287.02. The TMA-3 product ion is less abundant in reaction 1 (TMA-3 only) and reaction 2 (TMA-3 and H2O2) but the ion is significantly higher in abundance in the third reaction condition with HRP as indicated by the abundant peak at time ~50.00-52.00 min in reaction 3.
Figure 27:
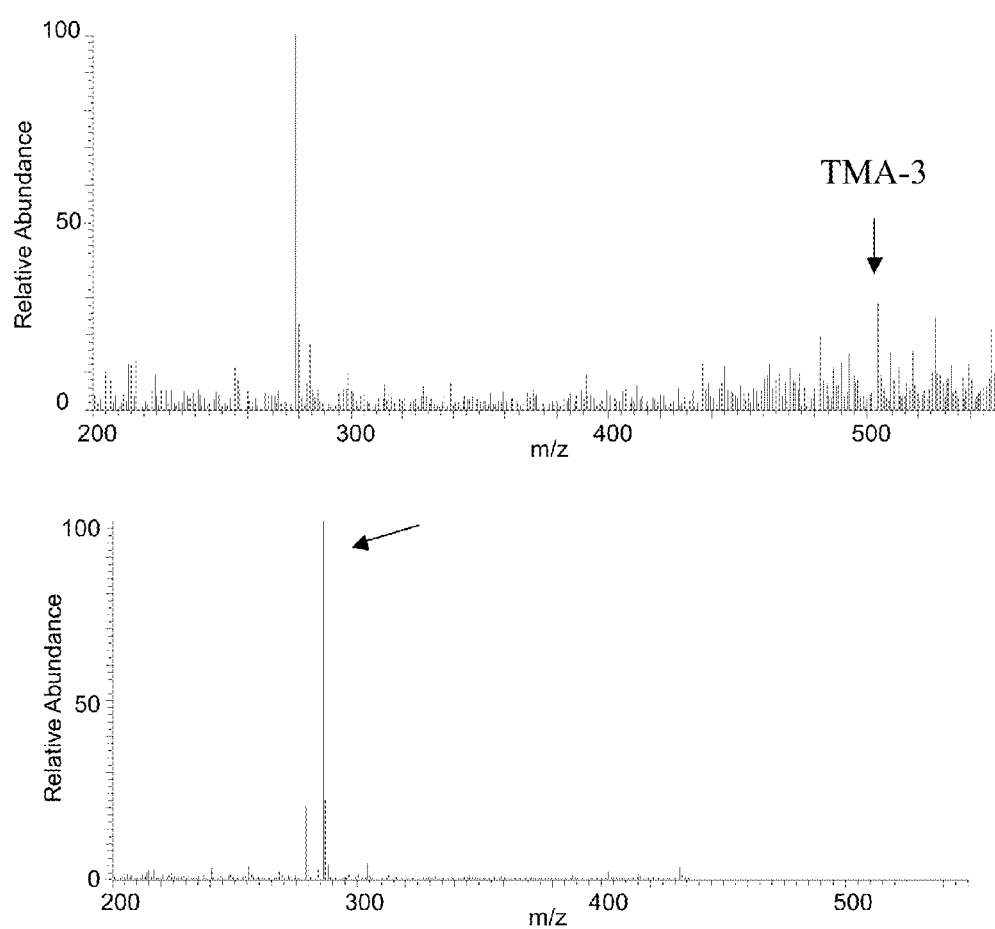
FIG. 27: The MS spectra for TMA-3 (m/z 504.40) in reaction 1 consisting of only TMA-3 was located at 20.38 min scanned for ions in the range of 200-550 m/z. The intensity of the substrate ion is 4.17×104.
Figure 28:
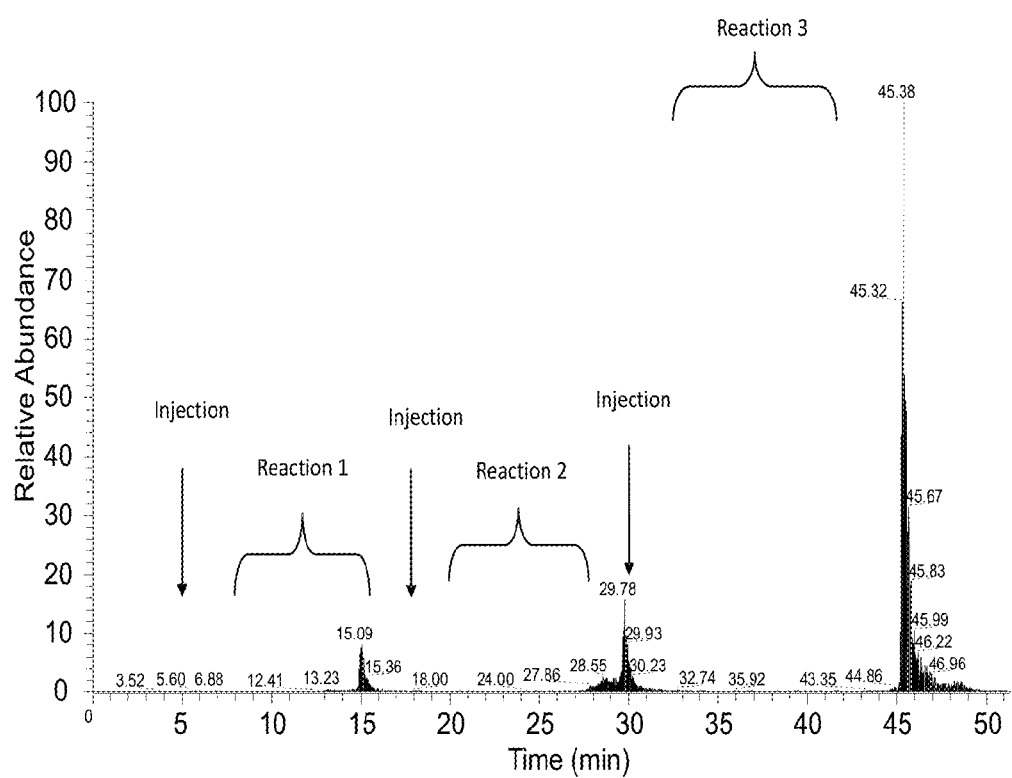
FIG. 28: The chromatogram shows the relative ion abundance specifically for the product ion of TMA-6 (272 m/z) scanned for ions in the m/z range of 271.03-273. 01. The TMA-6 product ion was less abundant in reaction 1 (TMA-6 only) and reaction 2 (TMA-6 and H$_2$O$_2$) but the ion had a significantly high abundance in the third reaction condition with HRP as indicated by the high peak at time 45-46 min in reaction 3.

The colorimetric detection of the PNPP substrate by ELISA (FIG. 23) was in the 0.5 ng range in agreement with previous results [2]. The PNPP substrate yields 4 nitrophenol that has a yellow color and ionizes in the negative mode (FIG. 24). The PNPP substrate was observed to show the production of a product ion by infusion (Table I). The ELIMSA experiment with PNPP showed a detection limit from only 1 microliter of the 0.01 ng reaction (3 atto mol) (FIG. 25).

TMA-3 and TMA-6

The Lumigen® compounds TMA-3 and TM6 were both shown to yield enzyme dependent products by infusion and LC-ESI-MS/MS (FIG. 26-29, Table II & III).

Conclusions

ELIMSA shows the sensitivity to make quantifications in the atto mol to zepto mol range depending on the substrate and reporter enzyme in excess of existing ELISA and RIA techniques. Reliable detection and quantification of atto mol amounts of protein or epitopes based on ELIMSA assays could find broad application in diagnostic, environmental, industrial and basic research. The reporter enzymes such as AP or HRP optionally covalently linked to streptavidin, may also detect nucleic acid, lectin, synthetic or cloned proteins, carbohydrates or other molecular probes permitting for example sub attomol detection of macromolecules and surface antigens.

Example 4

Examples of Substrates and Conditions that can be Used

Lumigen® TMA3 SIM286 1 in 20 ul in 0.1% FA 20 ul at 20 ul/min at 70% AcN Blank, Tris, 0 ng PSA, 20 ng PSA, NHS, NHP at 10 min and 1 h (FIG. 31A).

Lumigen® TMA6 SIM272 1 in 20 in 0.1% FA 20 ul at 20 ul/min at 70% AcN Blank, Tris, 0 ng PSA, 20 ng PSA, NHS, NHP at 10 min and 1 h (FIG. 31B).

Sphingosine-phosphate SIM298 1 in 20 in 0.1% FA 20 ul at 20 ul/min at 70% AcN Blank, Tris, 0 ng PSA, 20 ng PSA, NHS, NHP at 10 min and 1 h (FIG. 32A).

Sphingosine-phosphate SIM200 1 in 20 in 0.1% FA 20 ul at 20 ul/min at 70% AcN Blank, Tris, 0 ng PSA, 20 ng PSA, NHS, NHP at 10 min and 1 h (FIG. 32B).

Sphingosine-phosphate SIM298 1 in 20 in 0.1% FA 20 ul at 10 ul/min at 50% IPA Blank, Tris, 0 ng PSA, 20 ng PSA at 10 min and 1 h (FIG. 32C).

4MUP SIM231 1 in 20 in 0.1% FA 20 ul at 20 ul/min at 70% AcN Blank, Tris, 0 ng PSA, 20 ng PSA, NHS, NHP at 10 min and 1 h (FIG. 33A).

4MUP SIM176 1 in 20 in 0.1% FA 20 ul at 20 ul/min at 70% AcN Blank, Tris, 0 ng PSA, 20 ng PSA, NHS, NHP at 10 min and 1 h (FIG. 33B).

4MUP SIM176 1 in 20 in 0.1% FA 20 ul at 20 ul/min at 50% IPA Blank, Tris, 0 ng PSA, 20 ng at 10 min (FIG. 33C).

L-(+)-2-amino-6-phosphonohexanoic acid SIM132 1 in 20 in 0.1% FA 20 ul at 20 ul/min at 70% AcN Blank, Tris, 0 ng PSA, 20 ng PSA, NHS, NHP at 10 min and 1 h (FIG. 34).

BCIP SIM244 1 in 20 in 0.1% FA 20 ul at 20 ul/min at 70% AcN Blank, Tris, 0 ng PSA, 20 ng PSA, NHS, NHP at 10 min and 1 h (FIG. 35)

Phenylbenzene ω phosphono-α-amino acid SIM255 1 in 20 in 0.1% FA 20 ul at 20 ul/min at 70% AcN Blank, Tris, 0 ng PSA, 20 ng PSA, NHS, NHP at 10 min and 1 h (FIG. 36)

O-phospho-DL-Threonine SIM122, 1 in 20 in 0.1% FA 20 ul at 20 ul/min at 70% AcN Blank, Tris, 0 ng PSA, 20 ng PSA, NHS, NHP at 10 min and 1 h (FIG. 37A)

O-phospho-DL-Threonine SIM122 in 0.1% Acetic acid 1 in 20 in 0.1% FA 20 ul at 20 ul/min at 70% AcN Blank, Tris, 0 ng PSA, 20 ng PSA at 10 min and 1 h (FIG. 37B)

AMP SIM268, 1 in 20 in 0.1% FA 20 ul at 20 ul/min at 70% AcN Blank, Tris, 0 ng PSA, 20 ng PSA, NHS, NHP at 10 min and 1 h (FIG. 38).

FIG. 39 shows an ATP time course.

FIG. 40A-D show PA5P time course using SIM169.

FIG. 41 shows PA5P SIM169 ELIMSA PSA standard 0, 0.1, 0.5, 1, 2.5, 5, 7.5, 10, 15 and 20 ng PSA, 3 normal human male plasma samples, 3 normal human male serum samples. The relationship between the SIM169 [M+H] and the ng added to the 100 microliter ELIMSA reaction prior to dilution 20 fold and injection of the equivalent of 1 microliter.

FIG. 42 shows Amplex® Red using SIM214 ELIMSA.

Figure 44:
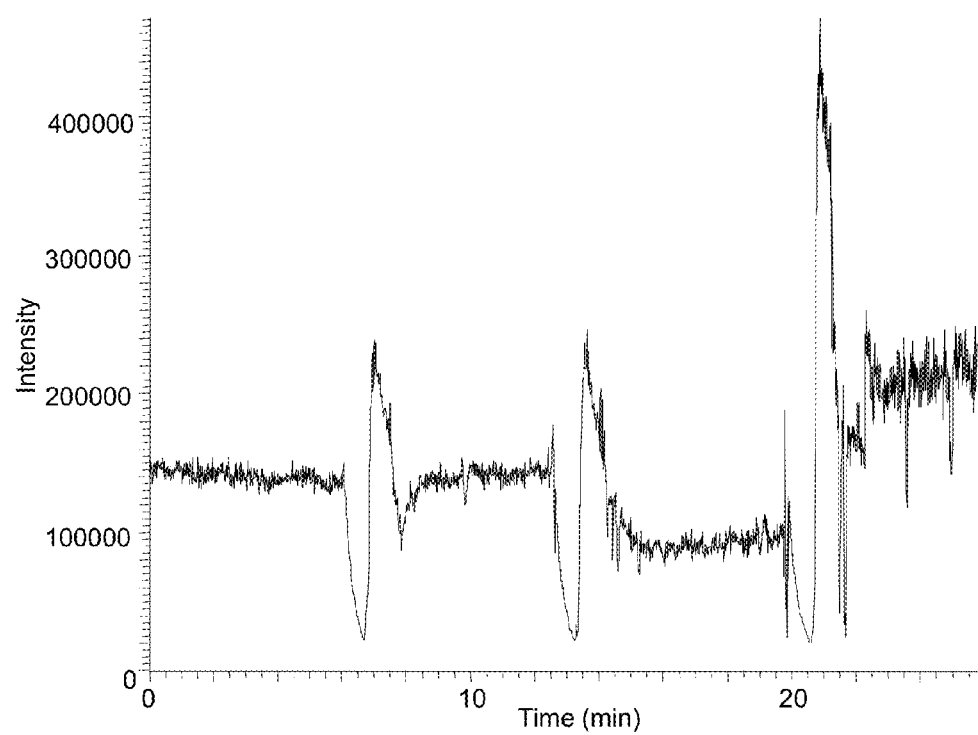
Figure 45A:
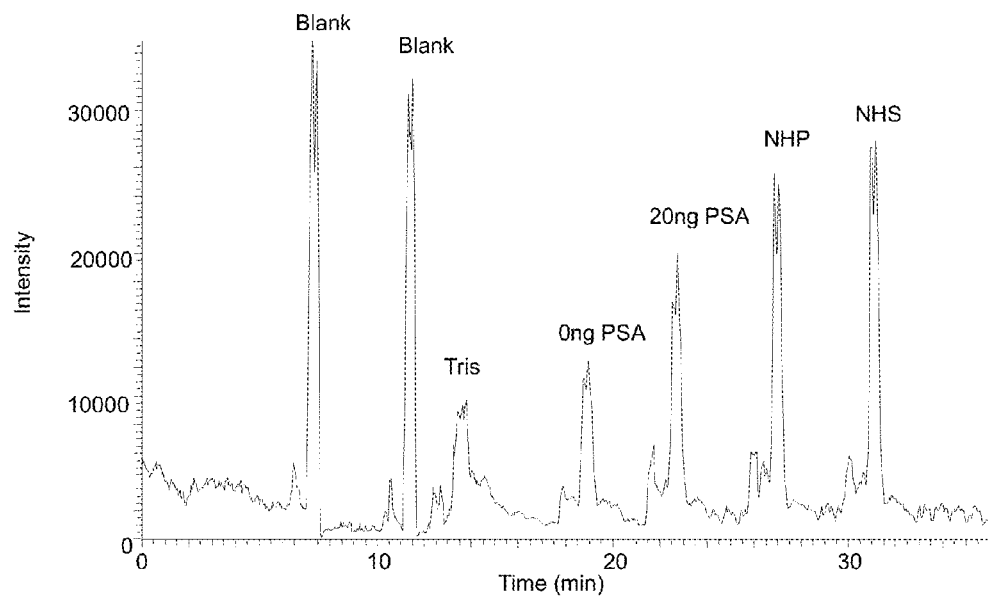

FIG. 43 shows pNPP ELIMSA PSA standard 0, 0.1, 0.5, 1, 2.5, 5, 7.5, 10, 15 and 20 ng PSA, 3 normal human male plasma samples, 3 normal human male serum samples. The relationship between the SIM138 [M+H] and the ng added to the 100 microliter ELIMSA reaction prior to dilution 20 fold and injection of the equivalent of 1 microliter. ELIMSA reaction was quenched in 50% AcN, 0.1% Na-vanadate FIG. 44 shows infusion screens of pNPP by SIM138 in negative mode. The three infusions are: I, buffer alone; II, buffer plus pNPP; III buffer, pNPP plus AP. Reaction was quenched in 50% Acetonitrile, 0.1% Acetic acid FIG. 45A shows Total Ion Current of multiple detection of Amplex® Red SIM214 and Naphthol ASMX phosphate SIM292 ELIMSA. ELIMSA reactions were quenched, combined and diluted 20 fold.

Figure 45B:
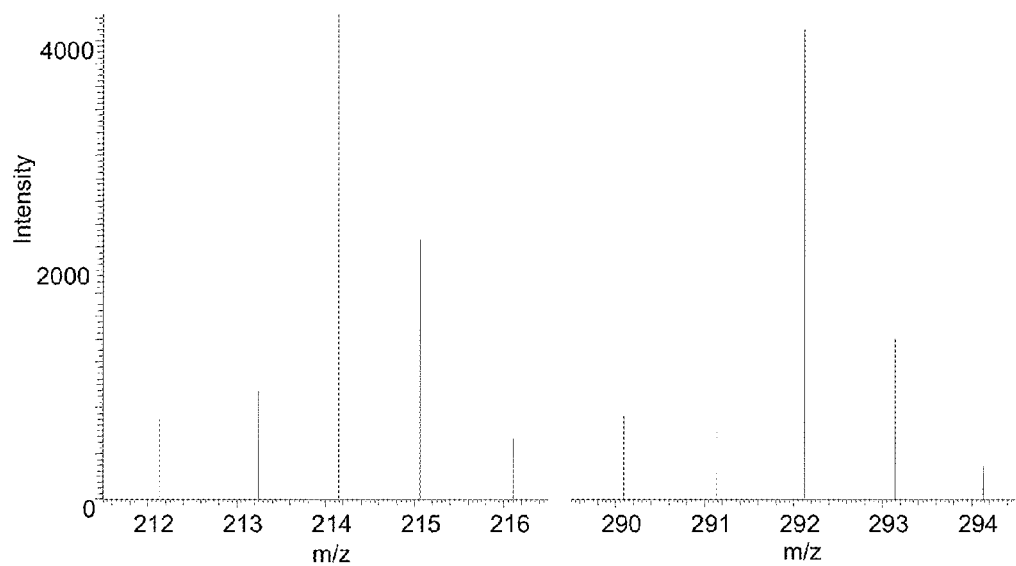

FIG. 45B is a MS trace of multiple detection of Amplex® Red SIM214 and Naphthol ASMX phosphate SIM292 ELIMSA. PSA standard in pg per well, samples were diluted 100 fold. ELIMSA reactions were quenched, combined and diluted 20 fold.

FIG. 46A-B shows ELIMSA using AMP as the substrate. AMP SIM 268 ELIMSA 10 minute reactions were dried down and extracted in 20 microliter IPA on ice for at least 5 minutes. 2 microliter was injected. PSA standards and two samples (plasma and serum) were incubated with AMP for 10 minutes prior to quenching the reaction in formic acid. Samples were dried down and extracted in 20 microliter IPA on ice for at least 5 minutes. 2 ul of the extract was injected onto a normal phase column in 70% Acetonitrile with 0.1% Acetic acid with SIM268.

FIG. 46C shows ELIMSA using AMP as the substrate. AMP SIM 268 ELIMSA 1 hour reactions that were dried down and extracted in 20 microliter IPA on ice for at least 5 minutes. 2 microliter was injected. PSA standards and two samples (plasma and serum) were incubated with AMP overnight prior to quenching the reaction in formic acid. Samples were dried down and extracted in 20 microliter IPA on ice for at least 5 minutes. 2 ul of the extract was injected onto a normal phase column in 70% Acetonitrile with 0.1% Acetic acid with SIM268.

FIG. 47A shows ELIMSA using PA5P as the substrate. PA5P SIM 169 ELIMSA 10 minute reactions that were dried down and extracted in 20 microliter IPA on ice for at least 5 minutes. 2 microliter was injected. PSA standards (0 and 1000 ng) were incubated with PA5P for 10 minutes prior to quenching the reaction in formic acid. Samples were dried down and extracted in 20 microliter IPA on ice for at least 5 minutes. 2 ul of the extract was injected onto a normal phase column in 70% Acetonitrile with 0.1% Acetic acid with SIM169.

FIG. 47B shows ELIMSA using PA5P as the substrate. PA5P SIM 169 ELIMSA 1 hour reactions that were dried down and extracted in 20 microliter IPA on ice for at least 5 minutes. 2 microliter was injected. PSA standards (0 and 1000 ng) were incubated with PA5P for 1 hour prior to quenching the reaction in formic acid. Samples were dried down and extracted in 20 microliter IPA on ice for at least 5 minutes. 2 ul of the extract was injected onto a normal phase column in 70% Acetonitrile with 0.1% Acetic acid with SIM169

FIG. 47C shows ELIMSA using PA5P as the substrate. PA5P SIM 169 ELIMSA 1 hour reactions that were dried down and extracted in 20 microliter IPA on ice for at least 5 minutes. 2 microliter was injected. PSA standards and two samples (plasma and serum from human male blood) were incubated with PA5P for 1 hour prior to quenching the reaction in formic acid. Samples were dried down and extracted in 20 microliter IPA on ice for at least 5 minutes. 2 ul of the extract was injected onto a normal phase column in 70% Acetonitrile with 0.1% Acetic acid with SIM169. A detector response from as little as 2 μl injected from the 20 μl of IPA extract from 0.1 μg of PSA per well prior to drying and extraction was observed (i.e. 330 zepto mol on column).

FIG. 48 shows a pyridoxamine standard curve. Pyridoxamine is the enzyme reaction product of PA5P. Pyridoxamine was obtained from Sigma Aldrich. Standards are in nM and only 2 ul of the standards were injected onto the column. The experiment shows that the LC-ESI-MS system is sensitive to femto mol to pico mol amounts of pyridoxamine on column.

FIG. 49 shows adenosine standard curve. Adenosine is the enzyme reaction product of AMP. Adenosine was obtained from Sigma Aldrich. Standards are in nM and 2 ul of the standards on the column. The experiment shows that the LC-ESI-MS system is sensitive to femto mol to pico mol amounts of adenosine on column.

Example 5

Application to Cancer, Cardiovascular Disease, Water Quality and Infectious Disease Capture and detection monoclonal antibodies, directed against Prostate Specific Antigen (PSA), Troponin T, *E. Coli, salmonella, pseudomonas* and against the recombinant proteins of *Anthrax* or the heat killed virus can be obtained.

The ELIMSA technology can be applied to industrial and biomedical research problems including the analysis of diagnostic proteins such as PSA and Troponin T, food and water contaminants such as *E. coli* and environmental threats such as *Anthrax*.

PSA

In preparation for these experiments, human prostate cancer samples collected under an ethical protocol at Mt Sinai hospital in Toronto will be used to compare ELISA and ELIMSA. The ELISA measurements have already been made on a set of human prostate plasma samples and these results will be compared to that of ELIMSA. A monclonal anti PSA antibody will be directly coupled to HRP or AP using the Pierce biotin labelling kit.

Troponin T

In preparation for these experiments, a set of 20 human heart samples and 30 control samples were collected under an ethical protocol at McMaster University in Hamilton. Capture and detection monoclonal antibodies will be coupled to AP or HRP for the ELISA and ELIMSA direct biotin labelling with the NHS coupling reaction.

E. Coli

In preparation for these experiments pure analytical solvent grade water versus milli Q water, versus tap water and water from clean and contaminated lakes by bacterial plating and trypsin digestion and LC-ESI-MS/MS have been analyzed. However culturing of the same samples on sterile agar plates using aseptic technique showed that all the water samples including the analytical solvent grade water contained at least some bacteria by culture compared to boiled controls. Increasing numbers of peptides from bacterial proteins were detectable by LC-ESI-MS/MS in tap and lake water. However the signal to noise ratios obtained were low and thus it was found that direct mass spectral analysis of tap or lake water would not be amenable to convenient analysis by direct LC-ESI-MS/MS of tryptic digests of the environmental sample. Moreover since many bacterial species and strains show great homology it might be very difficult to separate many strains of bacteria based on only the major conserved proteins of the cell that are easily detectable by mass spectrometry. In contrast, immunological reagents may discern between bacterial strains and serve as a basis for a convenient ELIMSA detection and quantification. A lab culture of *E. coli* could be diluted into sterile water and detected using a monoclonal antibody that is specific for the *E. coli* surface proteins.

Anthrax

A recombinant toxin protein from *Anthrax* or heat killed *anthrax* can serve as the target analyte and a comparison of the corresponding capture and detection antibodies from various suppliers can be undertaken. The detection antibody can be directly labelled with AP or HRP as required for comparative ELISA or ELIMSA reactions.

Example 6

When the substrate is AMP and the reporter enzyme is Alkaline Phosphatase, the products produced include Adenine and phosphate. Different length adenine polymers can be made and/or polymers comprising other bases can be used. For example, when substrate PA-AAAAA (SEQ ID NO:1) is combined alkaline phosphatase the reaction produces A-AAAAA (SEQ ID NO: 2)+P. Different patients can be assigned different substrates. For example:

Patient 1; substrate AMP-AAAAAA (SEQ ID NO: 3) + alkaline phosphatase = A-AAAAAA (SEQ ID NO: 4) + P

Patient 2: substrate AMP-TTTTT (SEQ ID NO: 5) + alklaine phosphatase = A-TTTTTTT (SEQ ID NO: 6) + P

Patient 3 AMP-GGGGGGG (SEQ ID NO: 7)

Patient 4 AMP-CCCCCCCC (SEQ ID NO: 8)

Patient 5 AMP-ATCGATCGATCG (SEQ ID NO: 9)

Patient 6 GMP-AAAAAAAAA (SEQ ID NO: 10)

Patient 7 CTP-AAAAAAAA (SEQ ID NO: 11)

Patient 8 UMP-GCCGTTAA (SEQ ID NO: 12)

. . .

Patient N AMP-N (of length X), wherein N is any nucleotide e.g. AMP-NNNNNNNN (SEQ ID NO: 13). X can for example any number between and/or including 2-15.

Since both the length and the composition of each oligonucleotide substrate can be varied, each patient can get a different known oligo nucleotide substrate that produces a unique mass upon dephosphorylation and there for can be measured by a separate SIM or SRM reading.

A mass spectrometer can perform thousands of SIM and hundreds of SRM at the same time.

The method allows one to measure patient 1 through N simultaneously by knowing the predicted mass of the product of each reaction.

Different enzymes can be used for example the enzyme could also be ligase, or a restriction enzyme or DNA polymerase or any other enzyme that can alter the mass of a substrate.

Multiple wells, for example 2 or more or all 96 wells or 360 wells can be analyzed in the same HPLC run where the different oligo mass represents each patients identity.

Example 7

A new technology termed "ELIMSA" combines the specificity and enzymatic amplification of Enzyme Linked Immuno Sorbent Assay (ELISA) with the sensitivity and flexibility of mass spectrometry (MS). At present, substrates for the reporter enzymes horseradish peroxidase (HRP) or alkaline phosphatase (AP) yield colored, fluorescent or luminescent products. The central concept of ELIMSA is that the reporter enzymes HRP or AP yield products that ionize efficiently with a high signal to noise ratio that can be measured by mass spectrometry. The reporter enzymes HRP or AP may be covalently attached to a specific detection probe such as a protein or antibody to bind their target analyte and then catalyze the rapid production of ionisable, small-molecules. The use of mass spectrometry to measure small molecule products may commonly reach femto to pico mol amounts on column with high signal to noise. Mass spectrometry combined with the enzyme amplification in ELISA provides absolute sensitivity to detect atto mol of PSA and was comparable to, or more sensitive, than radio immune assays and electrochemical detectors. ELIMSA permits monitoring of multiple substrates and products and provides comparison to absolute standards.

Previously, mass spectrometry has been used to quality control the results of ELISA assays in terms of the chemical species created in the biochemical reaction [45] Ion trap mobility spectrometry has been used to examine and quantify the presence of analytes from ELISA reactions using substrates that produced ionisable compounds with detection limits to the nano gram [44]. The use of carbon nanotubes to detect proteins has been reported to reach the pico gram per ml [72] or femto gram range with absolute sensitivity as low a 67 amol [56, 58, 61, 73, 74].

A method for the quantification of low abundance target analytes is performed by applying liquid chromatography with electrospray ionization and tandem mass spectrometry (LC-ESI-MS/MS) to detect the products of the AP and HRP reporter enzyme reactions, yielding a sensitive analytical system. The Enzyme Linked Immuno Mass Spectrometric Assay (ELIMSA) may detect and quantify highly ionizable products from the reporter enzyme reaction of substrates by LC-ESI-MS/MS. The reporter enzymes can be The combination of an ELISA and LC-MS can yield sensitivity to the atto mol range beyond that of traditional ELISA. Similar to colorimetric determinations using UV-VIS spectroscopy, common statistical transformations of the data using log functions are used to attain linear plots [26] and absolute amounts of enzyme products may be recorded as a reference. As a model system to test the concept of ELIMSA circulating protein, prostate specific antigen (PSA) that exists at relatively low levels in blood that are sometimes below detection by traditional ELISA has been selected. One atto mol amounts of PSA, and zepto mol amounts of reporter enzyme such as AP or HRP, bound to a specific molecular probe such as strepavidin rapidly form femto mol to pico mol amounts of enzyme products well within the reliable detection and quantification limits of LC-ESI-MS/MS [26]. Hence ELIMSA may permit the rapid and simple detection and quantification of many molecules over a range of biologically important concentrations without radiolabels but in many cases using existing antibodies, reagents and instruments.

Materials and Methods

Materials

Horseradish peroxidase (HRP) and Alkaline Phosphatase (AP), $H_2O_2$, Amplex Red (10-Acetyl-3,7-dihydroxyphenoxazine), resorufin. naphthol AS-MX phosphate, p-nitrophenyl phosphate, deoxycholate, and luminol were purchased from Sigma-Aldrich. X-ray film, developer, and fixer were purchased from Kodak. HRP and AP coupled to streptavidin or secondary detection antibodies were obtained from Jackson Laboratories. MaxiSorp 96 well plates were obtained from Nunc (Thermo-Fisher Scientific). The NHS-biotin coupling reagent was provided by Pierce. PSA capture and detection antibodies were obtained from Medix Biochemica (Kauniainen, Finland). The PSA calibration antigen was obtained from the Scripps Laboratory (San Diego, Calif.). Formic acid was obtained from FLUKA. HPLC grade water, acetonitrile, methanol acetic acid were obtained from Caledon laboratories. The C18 resin was obtained from Vydak (Hypseria Calif., USA). The normal phase resin was obtained from Sigma Aldrich. Blue Phos reagent was obtained from Kirkegaard & Perry Laboratories, Gaithersburg, Md. USA. PVDF membrane was obtained from Millipore (Billerica, Mass., USA).

Substrate Reactions

AP and HRP conjugates with streptavidin (0.5 mg/ml) were made to 50% glycerol and stored at −20° C. Amplex red (AR) 5 mg was dissolved in dry dimethyl sulfoxide (DMSO) and aliquots were stored in the dark at −20° C. Amplex red was mixed in the reaction buffer (Tris 20 mM, pH 8.8) with a final substrate concentration of 0.1 mM. A total of 5 ng of the HRP or AP enzyme per ml was added to reactions for time course measurements. The substrate and enzyme were mixed just prior to the addition of the $H_2O_2$ solution. AS-MX phosphate (ASMXP) was dissolved in water, aliquoted to 1 mg per tube, lyophyllized and stored at −20° C. The ASMXP substrate was used at 1 mM final concentration. The luminol was dissolved in dry DMSO and stored in the −20° C. until dissolved in Tris pH 8.8 and reacted in the presence of 4-iodophenylboronic acid for detection on sensitive x-ray film [31].

Immunological Reactions in 96 Well Plates

The 96 well plates were coated with 250 ng of capture antibody per well in coating buffer (0.1M Na2CO3/NaCHO3 pH 9.6) on a rocking platform overnight at 4° C. The wells were blocked with 200 ul of blocking buffer (1% BSA, 1% goat serum in 1×PBS pH7.4) for 30 minutes at room temperature. The wells were briefly washed with 100 ul 1×PBS pH7.4 three times. The standard antigen or biological samples were diluted in 2× Antigen incubation buffer (0.6M NaCl in 2×PBS pH7.4 plus 1% BSA and 1% goat normal serum) to a final volume of 100 micro liters. To reduce non-specific binding, the wells were then washed three times in washing buffer (1×PBS, 0.05% Na-Deoxycholate pH7.4). The detection antibody conjugated to biotin (5 ng/well) using NHS coupling reagent [17] was applied in antibody incubation buffer (1×PBS, 0.05% Na-Deoxycholate, 1% BSA, 1% goat serum pH7.4). The wells were washed three times again with washing buffer. The substrate was reacted with the Streptavidin-AP or Streptavidin-HRP in substrate buffer (20 mM Tris pH8.8) [16]. In the case of amplex red [10] 0.1 mM $H_2O_2$ was added.

Colorimetric, Fluorescence or Chemiluminescent Detection

Oxidation of non fluorescent Amplex Red (AR) (FW 257.24) by HRP consumes stoichiometric amounts of $H_2O_2$ for the production of brightly fluorescent resorufin (FW 213.19) that can be detected colorimetrically at 570 nm or by fluorescence using excitation of 563 nm and emission of 587 nm [75]. The substrates for Alkaline phosphatase (AP) were reacted in 20 mM Tris pH 8.8 buffer and for HRP 0.1 mM $H_2O_2$ was added. The proprietary substrate Blue Phos was converted to a blue color that absorbed at 620 nm [30]. The substrates were tested in the PSA ELISA using 0.1 ng to at least 10 ng of PSA per well. In the case of chemiluminescence the limit of sensitivity for HRP-IgG was measured by dot blotting onto methanol-activated PVDF with detection by x-ray film in the presence of the enhancing agent 4-iodophenylboronic acid [31].

LC-ESI-MS/MS

A 1 ml volume of 1 mM solution of AS-MX phosphate (ASMXP) was completely dephosphorylated with 0.5 μg of AP for 1 hr to yield the ASMX enzyme product standard. The resorufin or ASMX enzyme products were diluted 10 fold in 0.1% formic for positive ionization. The standard reaction product was loaded in to a 500 ul Hamilton syringe for infusion and ionization through an electrospray source at 20 μl per minute at 3.5 kV, at 10 liters of nitrogen per minute and the transfer capillary at 250° C. The tuning files and parameters for the SIM ion and subsequent SRM transitions were established from the infusion experiment. The oxidation of amplex red [76] 258 yields the product resorufin that was assayed by SIM at 214 m/z and the fragmentation energy was manually optimized for assay by SRM using the major intense fragment at 214→186 m/z. The resorufin reporter enzyme product typically diluted 10 fold and resolved by injection through a 2 µl loop into a mobile phase of 70% acetonitrile and 30% water to a final of 0.1% acetic acid as the ionization buffer flowing at 20 µl per minute over 15 cm×300 micron ID C18 (5 micron, 300 Angstrom) column. The dephosphorylation of ASMX naphthol phosphate (FW 348) by AP was assayed by SIM at 292 m/z and SRM by the 292→171 m/z transition. The ASMX product of the reporter enzyme AP from the substrate ASMXP was diluted 10 fold and resolved by injection of 2 µl into a mobile phase of 30% acetonitrile, 40% isopropyl alcohol and 30% water flowing over 10 cm×300 micron I.D. column of normal phase resin (5 micron, 300 Angstrom). The HPLC was an Agilent 1100 connected via a liquid voltage junction to an electrospray source fitted with a metal needle [50] mounted on a linear quadruple ion trap (LTQ XL, Thermo Electron Corporation) [33].

ELIMSA

The ELIMSA reactions were performed in the non-ionic detergent deoxycholate (0.05%) to limit non-specific binding in 20 mM tris pH 8.8 buffer. The reactions were quenched by diluting the each 100 micro liter sample well by 10 fold with 0.1% formic acid in water on ice. The samples were vortexed prior to immediate analysis of 2 µl by LC-ESI-MS/MS using isocratic HPLC and SIM of the peaks. Typically the equivalent of only 0.2 microliter of the sample well (100 microliter) ELIMSA reaction was injected. The HRP-SA conjugate (5 ng) was added to 1 ml of 0.1 mM amplex red in 20 mM tris pH 8.8 with 0.1 mM $H_2O_2$. The ELIMSA reaction products were introduced on the column with a Rheodyne 1755 injector manual sample injector.

Results

Comparison of ELISA, ECL and ELIMSA Assays

Traditional ELISA reactions were first performed with HRP and AP colorimetric or fluorescent substrates to confirm that the immunological reagents in the ELISA were working well and were in agreement with previous limits of detection at about 1 ng per well. HRP directly conjugated to IgG was used to determine the detection limit of ECL reactions using luminol [31] with sensitive x-ray film that showed a detection limit of about 250 pico gram or about 10 femto mol absolute detection limit as expected (see supplement).

Amplex Red Substrate

The log linear dilution curve of the small molecule resorufin demonstrates that the HPLC-MS analysis shows a predictable relationship between signal and quantity injected as low as about 200 femto mol on column (FIG. 50). The colorimetric reaction of the HRP substrate amplex red (AR) to resorufin in a colorimetric ELISA format for PSA was found to have a detection limit of about 1 ng per well (100 µl) under the conditions tested and showed linearity to about 10 ng in good agreement with previous results [10]. The infusion of resorufin in 0.1% formic or acetic acid produced an intense spectrum line at 214 [76] that was used to tune for the product of amplex red from the HRP reporter enzyme. A time course showed that 5 ng of HRP per ml of a 0.1 mM amplex red reaction reaches its maxima by 10 to 15 minutes (FIG. 51A). The log plot of the dilution of resorufin, the product of HRP from the substrate amplex red, showed a linear relationship to the hundred of femto mol range on column (FIG. 51B). Holding the substrate constant at 0.1 mM in a 1 ml reaction and varying the free HRP-SA (40+60 kDa) conjugate enzyme showed the enzyme dependent production of resorufin was linear as low as to 0.1 ng per ml of which 1 micro liter was then diluted 10 fold with the manual injection of 2 micro liters corresponding to the equivalent of about 100 zepto mol of HRP-SA on column (FIG. 51C) or as high as 100 ng per ml (FIG. 51D). In use as an ELIMSA, the method showed that capacity to quantify on the order of 0.1 ng per well that corresponds to about 6 atto mol of PSA injected on column (FIG. 51E). The resorufin generally showed a linear function that could be fit with an $R^2$ of ~0.99 using log transformation of the quantity (log pg PSA) and log resorufin intensity in agreement with previous results [26]. The intensity results for the PSA standard curve were comparable on three separate days (FIG. 51F)

ASMX Naphthol Phosphate

The enzyme product ASMX was obtained from reacting the substrate with an excess of AP followed by serial dilution that showed the LC-ESI-MS system is sensitive to the injection of 200 femto mol on column and is log linear over about two orders of magnitude to pico mol amounts injected (FIG. 50B). The colorimetric ELISA using AP substrates such as Blue Phos [30] showed sensitivity to the 1 ng range per where the entire 100 ul was used to make the determination but many patient samples were below reliable quantification. The enzymatic product ASMX was recorded by SIM at 292 m/z and showed a characteristic increase with time (FIG. 52A). A total of 2 ml of a 1 mM solution of the ASMXP substrate was reacted with 1 micro gram of the AP enzyme for 1 hour and the dilution curve for the ASMX enzyme product showed a log linear relationship with the amount injected and was sensitive to 1 pico mol on column as determined by serial dilution (FIG. 52B). A dilution series of the free AP-SA conjugate from 0.1 ng per ml to 1 ng per ml shows log linearity (FIG. 52C) as does the curve from 1 to 20 ng per ml (FIG. 52D). The absolute sensitivity to the free enzyme probe in solution by SIM 292 [76] was 0.05 ng of the AP-SA conjugate (140 kDa+60 kDa) added to the 1 ml reaction and then after enzyme incubation was diluted 10 fold with injection of 2 µl (about 10-100 zepto mol PSA on column). The PSA ELIMSA reactions were run as low as to 0.1 ng per well that was beneath all samples in this study, and then diluted 10 fold before injecting 2 micro liters and showed typical sensitivity to the equivalent of ~6 atto mol of PSA injected on column (FIG. 52E). As previously observed with Amplex red and other enzyme assays, the response between concentration and intensity was log linear within 1-2 orders of magnitude (FIG. 52F). The ASMX curve could be fit with an $R^2$ of ~0.99 using the standard log transformation of the quantity, e.g. log pg PSA and log ASMX intensity in agreement with previous results [26].

Reproducibility

The estimated PSA levels of serum and plasma samples were compared alongside a standard of PSA in three consecutive experiments on separate days for both the AR and ASMX substrates (FIGS. 51&52, Panel FI). The results show that error that was typically within 10% of the mean value reported in pico grams per well (Table 4). The methods observed showed useful reproducibility and did not seem much more or less error prone compared to the values obtained from colorimetric ELISA.

Direct Comparison of ELIMSA Versus ELISA

Only a small part of one microliter of the ELISA plate reaction was required for the LC-MS analysis and so the direct comparison of signal per quantity of PSA analyzed shows that ELIMSA was about 1,000 fold more sensitive than ELISA in these experiments (FIG. 53). The two ELISA reactions shown reach their limit of sensitivity limit at 1 ng per well (signal approaches zero units). In contrast the ASMX and AR substrates for ELIMSA commonly showed a linear detection of standards from 100 pico g to 10 ng of PSA per 100 µl sample well where 0.2 µl was injected. Greater than one ELIMSA reaction may be analyzed in the same LC-ESI-MS/MS run by incubating different patient samples with different substrates in separate wells and running the sample products together using two independent SIM or SRM mass spectrometry protocols.

Discussion

Enzymatic and Immunological Reactions

Incubating the substrate in the appropriate reaction buffer alone produced little signal. The product was shown to require the presence of the enzyme. The signal from the enzyme product was shown to be dependent on the time of incubation. The signal was found to be dependent on enzyme concentration. Thus, the signal recorded from the LC-MS system showed all the hallmarks of an enzyme dependent reaction. In the context of a 96 well dish assay, the signal recorded by ELIMSA was dependent on the presence and amount of the PSA analyte. Taken together the simplest explanation is that the ELIMSA signal observed is the PSA dependent product of the reporter enzymes that bind to the biotin on the specific detection antibody.

Linearity

The dilution series of the enzyme products showed a log linear intensity response with log concentration clearly demonstrating that the LC-ESI-MS was inherently quantitative for these analytes in the range utilized. Previous studies have shown some peptides have log intensity plots with a linear relationship [26]. Many analytical techniques require transformation of the data to yield a linear response such as UV-VIS spectroscopy requires a ratio of incident and transmitted light where the fraction is then also log transformed in order to produce a linear relationship.

Sensitivity

Absolute amount of enzyme products such as resorufin were detectable in the femto to pico mol range and so under suitable reaction conditions a vigorous reporter enzyme producing such an ionizable product may be detected at much lower concentrations. The ELISA reactions using HRP or AP substrates showed sensitivity to the 1 ng after the entire 100 microliters of reaction was analyzed to make the determination. In contrast, injecting the equivalent of only 0.2 microliters of 0.1 ng per 100 µl sample well was required to quantify clear signals by liquid chromatography and mass spectrometry (LC-MS) corresponding to the equivalent of ~6 atto mol amounts of PSA on column. The absolute sensitivity of ELIMSA surpassed that of ELISA with fluorescent, colorimetric or ECL detection and rivaled the reported limits of RIA or electrochemical detection in terms of PSA detection or absolute sensitivity to the enzyme probe into the femto gram range with absolute amounts of AP as low as 67 amol reported [56, 58, 61, 72, 73, 74]. In most cases the sample was diluted 10 fold and only about 2 micro liters was injected so the sensitivity of ELIMSA may be increased by simply injecting more sample to reach even lower levels of detection and quantification. Similarly, greater sensitivity might be achieved by drying and/or solid phase extraction the product using organic solvents and modifiers. Moreover in these experiments a simple quadrupole mass spectrometer was employed but further sensitivity might be obtained from the use of triple quadrupole instruments [77].

Specificity

The mouse mono clonal antibodies used in this study show a high selectivity for the analyte permitting the specific detection of PSA. The requirement for the binding of both the capture and detection antibody to produce a signal apparently resulted in good specificity with little signal obtained in the control reaction. The ASMX and AR reagents, buffers and solvents were such that there was little difficulty in finding the product ions with a good signal-to-noise in the SIM mode and with sharp peaks in the isocratic LC-MS chromatogram. The enzymatic products may be obtained as reference standards to confirm the MS/MS spectral pattern. Furthermore the biochemical methods shown here could be extended for use with high-resolution mass spectrometry if isotopically labelled internal standards were commercially available.

Reproducibility and Bias

Estimates of the mean level of PSA or enzymes like AP or HRP with an error on the order of 10% of the estimated mean are demonstrated. An acceptable reproducibility was observed after log transformation of intensity values and concentrations. Absolute amounts of the enzyme products can be analyzed as a reference curve to provide quantification.

Broad Application and Importance of ELIMSA

The colorimetric or fluorescent signal intensity of the HRP substrate amplex red and the AP substrate Blue Phos were compared and it was found that ELIMSA was more sensitive than ELISA. The substrates amplex red (AR) and AS-MX naphthol phosphate (ASMXP) were useful to detect the presence of the HRP or AP labelled probes by mass spectrometry. The amplex red reagent and its enzyme product resorufin are commercially available permitting the easy estimation of absolute sensitivity. At present the most potent growth factor and signalling molecules in the cell or body have binding affinities that permit these ligand to bind their receptors in the atto molar concentration range that is at or beyond the reported results from most electrochemical detectors [47]. A quantitative analytical method that can confidently measure analytes to atto mol levels is required for biomedical and environmental testing and research. Here the equivalent of about 6 atto mol of PSA on column were detectable by ELIMSA with a capture and detection antibody in a 96 well plate. The measurement of the diluted samples showed signal to noise of 5 to 1 or better in the low atto mol range injected on column ELIMSA seems to show the absolute sensitivity to make quantifications in plasma and serum that matches or exceeds that possible from existing ELISA, electrochemical and RIA assays. The flexibility and sensitivity of mass spectrometry to distinguish and measure large numbers of compounds representing different antigens, ligands or receptors simultaneously and thus permit the quantification of multiple binding reactions at separate mass-to-charge (m/z) ratios. Thus, by combining the specificity of both a capture and a detection antibody in ELISA with the sensitivity of LC-ESI-MS/MS results in a highly selective method for measuring molecules at low concentrations.

Example 8

ELIMSA for Low Abundance Analytes

There is a need for a method to measure low abundance proteins in human blood that often cannot be directly detected by either ELISA (2) or mass spectrometry (20) when used separately: However the combination of enzymatic amplification by ELISA with detection of the enzymatic products by liquid chromatography, electrospray ionization and mass spectrometry (LC-ESI-MS) results in ultrasensitive quantification method termed ELIMSA (42). The development of ELIMSA might permit the common analysis of femto gram amounts of proteins that are found low concentrations. The enzymatic amplification is obtained from alkaline phosphatase (AP), a near perfect enzyme (43) that may be attached to the bacterial protein streptavidin (SA). Streptavidin conjugated to the reporter enzyme (AP-SA) (16) and used to detect NHS-biotinylated antibodies, ligands or probes with a high affinity (17) (FIG. 54). Enzymatic reactions were monitored by mass spectrometry (29) and the substrate PA5P has been used to generate an ionizable product for ion mobility spectrometry (44). Moreover, mass spectrometry has been used to confirm the nature of the products from an ELISA reactions (45).

PSA Model System

The prostate specific antigen (PSA) has a concentration distribution from picogram to nano gram amounts in 100 µl of normal human plasma (NHP) from men and so it is often near or below UV-VIS or ECL detection (46). The quantification of PSA over the complete range of NHP is challenging by ELISA (46) or mass spectral methods (20) and many normal samples are below the detection limit of the assay. Thus PSA is good model system to show the increased sensitivity of the ELIMSA system. In addition there are excellent experimental reasons to consider PSA as a test protein for developing more sensitive assays: the analyte PSA and the enzyme AP-SA have been used to benchmark the sensitivity of ELISA (41), direct mass spectral detection (20), and electrochemical detection (47) and so there is good historical and practical reasons to use PSA and AP-SA as the reference analytes. Furthermore there are excellent PSA calibrants and high affinity PSA capture and detection reagents available.

Linearity of PA

It has been previously shown that an enzyme linked immunosorbant assay of the colorimetric enzyme substrates amplex red and naphthol AS-MX phosphate can be measured by liquid chromatography, electrospray ionization and mass spectrometry (LC-ESI-MS) with greater sensitivity than UV-VIS or ECL based detection. The same specific PSA calibrant, capture and detection reagents used previously were tested with the identifies ELIMSA substrate PA5P (42). UV-VIS detection is agreed to be linear after taking the logarithm of the ratio of incident over transmitted light. In contrast, it has been stated that the relationship between mass spectral intensity and quantity is complex (53) and this necessitates the use of isotopic or isobaric labels. A linear relationship between log ion intensity and quantity was observed for some blood peptides or fragment ions, peptide standards, resorufin, naphthol AS-MX, and in the present experiment pyridoxamine (PA) that were all shown to be linear after simple log transformation (26, 42, 48, 49).

PA5P as a Substrate

The substrate pyridoxamine-5-phosphate (PA5P) is demonstrated to have several practical advantages over the previous AP-SA substrate AS-MX phosphate in that the enzyme product pyridoxamine (PA) is basic, ionizes readily but is also hydrophilic and elutes rapidly with a more symmetrical peak. PA5P shows a more predictable chromatography, is not strongly retained, and does not show a creeping increase in baseline over the course of measurement. The use of PA5P has an important additional advantage in that the enzyme product PA, is a metabolite that is available in $^{13}C$ isotope labeled form that can be used as an internal standard to demonstrate absolute quantification by ELIMSA. Thus to address the issue of transformation, linearity and absolute quantification in ELIMSA by LC-ESI-MS, the ELIMSA experiments were controlled with internal and external, $^{13}C$ labelled pyridoxamine ($^{13}C$ PA) standards to confirm the quantification of the enzyme product. If mass spectrometry is log linear and normal for PA, then instead of using UV-VIS spectroscopy to read the 96 well ELISA plate, the production of the colorless PA could be measured using LC-MS with a sensitive ion trap (42). The capacity to measure attomole amounts of blood proteins may have great application to biomedical research and permit the common analysis of may ultra-low abundance analytes.

Materials and Methods

Materials

The NHS-biotin coupling reagent was obtained from Pierce. The prostate specific antigen (PSA) capture and detection antibodies were purchased from Medix Biochemica (Kauniainen, Finland). The PSA calibration antigen was obtained from the Scripps Laboratory (San Diego, Calif.). The PA5P, Pyridoxamine (PA) and $^{13}C$ (PA) and all other buffers and salts were obtained from Sigma Aldrich chemical company and were of the highest quality available. The alkaline phosphatase-streptavidin (AP-SA) enzyme-probe conjugate was obtained from Jackson ImmunoResearch Laboratories (West Grove, Pa., USA). The liquid chromatography mass spectrometry grade solvents were obtained from Caledon Laboratories (Georgetown, Ontario, Canada).

Immunoassay

The PSA ELIMSA was performed as previously described in Example 3 but with the substitution of the substrate PA5P for the substrate AS-MX phosphate (42). The PA5P substrate, PSA standards, and AP-SA probe were dissolved in water on ice, aliquoted and freeze dried for day to day consistency in the assay. The plates were coated with the capture antibody in bicarbonate coating buffer prior to blocking the plates in 1% albumin and 1% goat serum in 1×PBS pH 7.4 prior to incubating the plasma in 1×PBS, 0.05% Na-deoxycholate pH 7.4 for 1 h. After washing the wells three times again with washing buffer the substrate was reacted with the streptavidin-AP or in substrate buffer (20 mM, Tris pH 8.8). Thus the PSA ELISA using the high affinity reagents described here provides a suitable model system wherein the experimental assay can be optimized and tested to ensure there is no background binding and confirm the antibodies and calibrants are working and linear in color assays before switching to ELIMSA to measure the lower standards and concentrations for normal human plasma (NHP).

Liquid Chromatography, Electrospray Ionization and Mass Spectrometry (LC-ESI-MS)

The LC-ESI-MS analysis was performed by manual injection (Rheodyne 1755) of 2 ul of the standard or sample diluted ten-fold in 0.1% acetic acid. The sample was analyzed via an Agilent 1100 high pressure liquid chromatography (HPLC) pump set at 70% acetonitrile in 0.1% acetic acid for isocratic separation over a 300 micron ID×150 mm normal phase column (5 micron particle diameter, 300 Angstrom pore) at 20 µl/min. Normal versus C18 reversed phase columns were compared and while C18 gradient provide sharper peaks it was not as convenient as the isocratic approach. The normal phase produced symmetrical peaks that were resolved from the buffer components with low back pressure and high flow rates for rapid analysis with a stable background over time. The HPLC was coupled via an electrospray source fitted with a metal needle (50) mounted on a linear quadruple ion trap (LTQ XL, Thermo Electron Corporation) (33, 51) as previously described (42). The results were log transformed and the ion intensity results analyzed for normality and linearity (48) using the R open source statistical analysis software. RESULTS Pyridoxamine Chromatography Characteristics Previously the alkaline phosphatase enzyme system was more sensitive than the HRP system that presumably suffers from a slight background chemical reaction of the $H_2O_2$ cofactor (42). However, the AP substrate AS-MX phosphate has the hydrophobic naphthol conjugate rings that show a distinct tailing in the chromatographic peaks and does not always attain peak to peak separation at a convenient injection intervals significantly increasing analysis time (FIG. 55A). In contrast, the basic and hydrophilic substrate pyridoxamine ionizes readily, shows much more symmetrical peaks and easily achieves baseline to baseline separation even at close injection intervals. Note that the ASMX substrate also suffers from and increasing background over time that required local background corrections. In contrast, pyridoxamine separates well from other buffer components with 15 cm×300 micron column flowing at 20 ul per minute that shows low back pressure and a flat baseline over the normal phase resin for rapid and simple isocratic analysis (FIG. 55B). However observing the peak intensity values of PA with concentration shows there is a sharp increase in signal with each incremental amount of PSA added to the assay around 0.1 ng PSA per well to 1 ng of PSA per well but that the signal shows some attenuation as the quantity of PSA approaches 10 ng per well (FIG. 55B). The attenuation of the signal above 1 ng observed in ELIMSA may indicate that the data needs to be mathematically transformed to provide a linear relationship between the ion intensity and quantity of PA injected for the purpose of convenient calculations.

Pyridoxamine Ion Intensity is Log Linear

A simple dilution of curve of pyridoxamine (PA) in ionization buffer reveals a log linear relationship between intensity and quantity when injected into the isocratic LC-ESI-MS/MS system. The PA product standards showed a log linear relationship between ion intensity versus absolute quantity as measured using LC-MS with single ion monitoring (SIM) at 169 [M+H] (FIG. 56A). Similarly the $^{13}C$ PA standard at SIM 172 [M+H] m/z also showed a linear relationship between ion intensity and quantity (FIG. 56B). The results indicated that LC-ESI-MS of PA is inherently linear and quantitative after simple log transformation. However since electrospray ionization is a competitive electrochemical reaction the linearity of PA in pure ionization buffer may not be the same as the ionization of PA in ELIMSA reaction buffer where there may be some complex confounding effects of the tris buffer, blocking agents, non-ionic detergents or other buffer components.

Log Linear Release of Pyridoxamine (PA) with Alkaline Phosphatase-Streptavidin (AP-SA)

Adding the biotin-specific molecular probe streptavidin, conjugated to the enzyme alkaline phosphatase (AP-SA), to the substrate PA5P in tris reaction buffer released the product PA and the biochemical reaction was essentially complete by 3 h (FIG. 57A). The AP-Streptavidin conjugate (AP-SA~190,000 g per mole) was diluted down to 0.1 ng per ml or less and then the enzyme was reacted with the substrate PA5P for 3 h to produce PA that showed a log linear intensity curve to 100 zepto mol of AP-SA on column. The enzymatic production of PA was clearly detectable with a high signal to noise ratio and low error in the baseline (FIG. 57B).

The Estimate of PA Production from ELIMSA by Internal $^{13}C$ PA Dilution

In order to demonstrate that the intensity values of PA remain linear even in the presence of background ELIMSA ionization buffer comprising 0.01% acetic acid the isotope dilution method was used to estimate the quantity of internal $^{13}C$ labelled PA that matched the production of PA from the ELIMSA. The isotope dilution method was used to estimate the average production of PA from the same replicate NHP sample (Table 4) and was found to be about 2.01 pmol PA measured against the internal $^{13}C$ PA internal isotope dilution curve (FIG. 58A, Table 4).

The Estimate PA Production by Ratio with a One-Point Calibration Internal Standard In a separate experiment the PA product from 0.2 µl of the ELIMSA reaction with an NHP sample was found to be closest to the ~1.5 pmol internal standard. Thus we estimated the amount of PA produced by a one point calibration against the addition of ~1.5 pmol $^{13}C$ PA to the NHP ELIMSA reaction sample. Thus, each replicate ELIMSA reaction was monitored at SIM 169 [M+H] alongside 1.50 pmol of the $^{13}C$ PA internal standard monitored at SIM 172 [M+H] (FIG. 58B, Table 4). Based on the one point internal calibration there was good agreement between the independent internal isotope dilution curve and the one point ratio estimate from a pooled normal sample that showed about 2.01 pmol PA versus 1.28 pmol PA, respectively (27).

Agreement Between Internal Versus External Standards

On the same day, and on the same chromatograph as the one-point calibration experiment, PA production was measured in terms of external $^{13}C$ PA and PA standard curves with the analysis of 0.2 µl analyzed from each 100 µl well. Reading the amount of pyridoxamine produced by the PSA ELIMSA against the $^{13}C$ PA (SIM 172 [M+H]) versus PA (SIM 169 [M+H]) that showed 1.58 and 2.19 of pmol on column in agreement with internal isotope dilution and internal one-point calibration (FIG. 58C, Table 4). The plot of log ion intensity of PA versus log concentration of protein complexes or standards, and the close agreement between the external versus internal standards, all demonstrated that ELIMSA by dilution and injection was quantitative to the attomole range of PSA protein complexes under analysis [0.1 ng/well PSA inject 0.2 µl=6.6 amol]. Thus when on the order of 1 attomole of PSA standard was analyzed the ELIMSA reaction produced on the order of 1 pmol amounts of PA and thus apparently achieved nearly a million fold amplification.

ELIMSA for Prostate Specific Antigen (PSA) from Normal Human Plasma (NHP)

ELIMSA was applied to measure PSA in normal human plasma (NHP) that was pre-selected to be below the detection limit of the UV-VIS ELISA assay as a test of the system under authentic conditions. The external PSA standard showed a log linear relationship between PA ion intensity versus PSA quantity and good technical reproducibility as measured by replicate analysis of a test sample using LC-MS with single ion monitoring (SIM) at 169 [M+H] m/z (FIG. 58C). Twelve randomly selected normal plasma (NHP) samples were analyzed on three independent days in a row with good agreement and fitted to the calculated normal distribution (FIG. 59). The average amount of PSA in the NHP samples was about 67.8 picograms with a standard error of about 4.3 µg from a total of 30 NHP samples (50 µl) (Table 5). The estimated PSA values showed a Guassian, i.e. Normal distribution, by the Shapiro-Wilk test (N=30, W 968499 Prob<W 0.3222) and the plotted distribution shown showed little deviation from the normal curve as shown in the quantile plot produced with the R statistical analysis system (FIG. 59). In the application of ELIMSA to PSA levels from NHP the amount of PSA in the human blood samples was not lower than 33 pico grams per well and so all of the human plasma samples are were with the limit of detection and quantification. All of the normal male plasma samples were within the limit of quantification of the assay and so were not able to establish the lower limit of ELIMSA for PSA in patient samples.

Ultra Sensitive Detection

The limit of detection of ELIMSA in use with NHP must be less than 33 picogram per well in these experiments. In order to estimate the lowest possible detection of the AP-SA enzyme conjugate a dilution series of AP-SA was made that showed a clear detection of 1 µg/ml as quantified by the injection of 0.2 micro liters (~10 zeptomole on column) at 20 µl per minute with robust electrospray and a simple ion trap (FIG. 60). At low sensitivity levels the contamination of the substrate by un-phosphorylated substrate is especially obvious. Hence it was possible to clearly detect the presence of ~1 fg of AP-SA or less at a 20 µl per minute through an electrospray source with a simple ion trap.

Discussion

Sensitivity

Direct quantification of the detection reagent AP-SA by LC-MS permits the quantification of receptor-ligand complexes to at least 1 pico gram per well range and detection of the probe to 1 pico gram per ml range from the injection 0.2 µl from the sample (i.e. ~10 zepto mol amounts of the molecular probe on column). The sensitivity was such that all normal human plasma (NHP) were well within the standards at concentrations far below the detection limit of color, fluorescence or ECL based detection (42). At present the assay seems comparable to radio-immuno metric levels of sensitivity but without the administrative burden of handling radio isotopes. The sensitivity of the assay is sufficient to detect the apparent trace contamination of the substrate with a small amount of un-phosphorylated pyridoxamine and to clearly detect the background binding of the biotinylated enzyme to the ELISA plate.

Agreement Between Independent Methods

The result with the internal $^{13}$C isotope dilution curve was in close agreement with the external PA curve and the external $^{13}$C PA curve. The one point calibration method showed the greatest divergence, but all four independent methods were within 1 digit in the same order of magnitude and so in general showed good agreement. The results with the substrate PA5P were similar to those of AS-MX and amplex red in that all three methods showed good agreement between the standard curve measured by ELISA using color versus ELIMSA at values greater than 1 ng per well. Hence there are multiple lines of evidence in agreement that LC-ESI-MS may provide for the absolute quantification of molecules such as PA after log transformation.

Absolute Quantification of PSA by ELIMSA

The linear results with the PSA external standard were consistent with the PA and $^{13}$C PA external standard curves, and the $^{13}$C PA internal isotope dilution curve. Together these several controls unambiguously demonstrated that ELIMSA can absolutely quantify proteins against an external protein standard in a manner that is similar to the absolute quantification provided by UV-VS ELISA. The PA and $^{13}$C PA ion intensity values were linear after log transformation and the calculated PSA results were normal and so ideal for ANOVA statistical analysis between experimental treatments. As the data is log transformed the line cannot pass through zero and so it is traditional to calculate the data as log (i+1) that apparently showed acceptable linearity over 1 to 3 orders of magnitude ($R^2$ of ~0.99). The results of the PSA assay measured by PA was in agreement with the estimates of PSA previously observed using the amplex red and ASMX naphthol phosphate substrates. Moreover the results of normal human plasma presented here closely match the correct order of magnitude for PSA in control patients reported in the literature. Thus, multiple lines of evidence in agreement indicate that the ELIMSA standardized against known amounts of the PSA calibrant provides an accurate absolute quantification of PSA. ELIMSA may be used to quantify proteins to at least ~1 picogram levels.

Inherent Log Linearity of LC-ESI-MS

In this study, the internal $^{13}$C PA isotope dilution curve, the external PA curve, the external $^{13}$C PA isotope standard curves and the internal $^{13}$C PA, one-point-calibration all agreed that mass spectrometry showed a linear relationship with quantity after simple log transformation.

The log linear results with PA were in agreement with log linear results from some standard peptides or peptides from blood proteins (26), resorufin and ASMX Phosphate (42), many peptides and proteins from cells (49) or protein secreted from cells into the experimental media (48). Taken together the results with small molecules, isotopic labels, and many peptides all indicate the LC-ESI-MS is linear for many pure compounds and thus may approach linearity for some from chromatographically pre-separated molecules. The experiments with iosotopic labels herein ruled out the concept that LC-ESI-MS cannot be quantitative, or that there is necessarily a complex and poorly understood relationship between ion intensity and quantity (52). The observation that the signal intensity values from mass spectrometry may be linear is consistent with the electrospray ionization process (19) that is a competitive reaction where the presence of other analytes may effect the observed intensity in unpredictable ways (53, 54). The potentially confounding effects of competition for ionization were apparently not a factor when relatively pure analyte PA, dissolved in a 1 mM tris, is efficiently resolved by high pressure liquid chromatography prior ionization, and the results closely approached log linearity. Hence molecules may be absolutely quantified by LC-ESI-MS against external standards without the use of isotopic or isobaric labels.

Absolute Quantification by Mass Spectrometry Versus UV-VIS Spectroscopy

Both UV-VIS and LC-ESI-MS require a form of log transformation to achieve a linear detector response. However the direct log transformation required for linearity and normality in mass spectrometry (16, 17, 41) is simpler than the transformation required to achieve linearity in UV-VIS: UV Visible spectroscopy requires a more complex ratio of incident and transmitted light, and this ratio is then log transformed in order to yield linear and normal data. Like UV-VIS spectroscopy, adding the same amount of different peptide sequences or molecules may lead to a different measured signal intensity; like UV-VIS spectroscopy, strong signals, well resolved from the background that is subtracted, are required to avoid a skewed distribution contaminated by noise (26, 42, 48, 49); like UV-VIS, the results are entirely dependent on the compound; like UV-VIS, the baseline and the results may be confounded by the presence of other analytes. But unlike UV-VIS, LC-ESI-MS is astonishingly sensitive and can easily measure and quantify femtomole to picomole amounts of some compounds such as PA, and can also be confirmed by internal isotope standards. After about a million fold enzyme amplification, vanishingly small amounts of ligand-receptor complexes in the zepto to attomol range may be quantified.

The use of LC-MS to measure enzyme-conjugated molecular probes is a universal system for the quantification of proteins, ligands and/or receptors at pico gram amounts or less with good signal to noise values. The demonstrated measurement of AP-SA to the 1 zepto mol is as low a quantity as the most sensitive methods claimed to date (20, 41, 47, 55-66). ELIMSA with the substrate PA5P that releases the hydrophilic and basic compound PA showed more symmetrical peaks, baseline to baseline separation even at close injection intervals and a much flatter baseline compared to the previous substrate ASMX phosphate. The experiments here with external and internal standards and isotopic dilutions clearly demonstrate that LC-MS may provide strict linear relationship between intensity and quantity after log transformation: Thus isotopic or isobaric internal standards were not required to calculate the absolute quantity of a protein or metabolite by LC-ESI-MS. All of the PSA samples in this study were within the range of this assay in the attomole amounts and all of the samples could be estimated by interpolation between known amounts. The present log linear results for PA and many other compounds after log transformation opens up broad vistas for the direct quantification of many molecules by mass spectrometry and classical linear models with statistical analysis (26, 42, 48, 49). The experiments demonstrated that enzyme-labelled probes can sensitively quantify proteins or receptor-ligand complexes to vanishingly low amounts by direct mass spectrometric analysis and will have a broad application that greatly extends the practical sensitivity of ELISA bio-molecular analysis.

TABLE 4

Agreement between internal isotope dilution, internal one-point calibration, and external PA, $^{13}$C PA alongside the results of the external PSA standard curve used to estimate the normal human plasma samples (NHP). The NHP samples had less than 0.1 ng per 100 µl and so could not be measured by colorimetric methods. The experimental set up that produced the estimates is provided in FIG. 58.

| Method | Result |
| --- | --- |
| $^{13}$C PA isotope dilution | 2.01 p mol PA |
| PA external curve | 2.19 p mol PA |
| $^{13}$C external curve | 1.58 p mol PA |
| $^{13}$C PA one point internal calibration | 1.28 p mol PA |
| PSA external curve | 57.78 pg PSA/well |

TABLE 5

The replication of the PSA pg/well analysis in 30 normal human plasma samples that were too low to estimate PSA by the colorimetric assay. The within day mean and standard error (Std Err.) is shown vertically below and the summary over all three days to the right.

|  | Day 1 | Day 2 | Day 3 | All 3 days |
| --- | --- | --- | --- | --- |
|  | 93.04 | 105.33 | 58.36 |  |
|  | 58.30 | 58.13 | 61.30 |  |
|  | 61.28 | 42.26 | 68.37 |  |
|  | 83.35 | 41.88 | 77.90 |  |
|  | 41.06 | 35.33 | 48.96 |  |
|  | 63.34 | 33.75 | 61.30 |  |
|  | 65.46 | 89.46 | 82.59 |  |
|  | 50.10 | 75.67 | 102.53 |  |
|  | 67.64 | 85.32 | 88.51 |  |
|  | 84.02 | 73.26 | 75.20 |  |
| mean | 66.67 | 64.04 | 72.5 | 67.76 |
| Std Err. | 5.07 | 8.01 | 5.06 | 4.32 |

Example 9

Mono- di- and tri-phosphorylated nucleotides were assessed as substrates using methods described in Example 3.

dNTPs, dNDPs and dMPs were used as substrates for ELIMSA using positive mode ionization.

The m/z of triphosphates are: dATP, 491.2. dCTP, 467.2. dGTP, 507.2. dTTP, 482.2, UTP 534.1

The m/z after dephosphorylation of A, C, G, T and U is: A 268: C 283: G 243; T 242; and U 214.

TABLE 6

|  | dNTPs | | dNDP | | dNMP | |
| --- | --- | --- | --- | --- | --- | --- |
|  | no enzyme | with enzyme | no enzyme | with enzyme | no enzyme | with enzyme |
| A | 11900 | 160000 | 18400 | 230000 | 11800 | 151000 |
| C | 58500 | 176000 | 60900 | 146000 | 18000 | 145000 |
| G | 753000 | 421000 | 841000 | 524000 | 861000 | 427000 |
| T | 207000 | 147000 | 209000 | 162000 | 216000 | 162000 |
| U | 24000 | 78400 | 23400 | 78300 | 17800 | 71800 |

Example 10

The combination of enzyme-linked immunosorbent assay (ELISA), where the enzyme is alkaline phosphatase and the substrate adenosine which can be monophosphate, will release the ionizable product adenosine as measured by mass spectrometry (MS). Adenosine itself can be measured to about the femto mol range by dilution and direct analysis of by liquid chromatograpy, electrospray ionization and mass spectrometry (LC-ESI-MS). However the enzyme alkaline phosphatase in the ELISA plate provides about a million fold amplification. And so the combination of the enzyme amplification together with the low detection limits of LC-ESI-MS leads to zepto mole detection limit for the low abundance human blood protein prostate specific antigen (PSA). The external PSA standard curve as measured by the enzyme product adenosine (A) produced was log linear with respect to ion intensity by single ion monitoring (SIM) 268 mz versus quantity of PSA in pico grams. With respect to adenosine itself, the internal 13C adenosine (13C A) isotope dilution curve, the internal 13C A on point calibration and external adenosine standard curves all showed very close agreement. The results of the ELIMSA assay for PSA are normal and homogenous when replicated over multiple days and the inter and intra assay variation are less than 10% of the means. The ELIMSA was observed to be sensitive and linear from 1 to 1000 picograpm per ml where only 0.2 microliters was analyzed and therefor showed about 1 femto gram and or about 1 zeptomole sensitivity.

Prostate Specific Antigen (PSA) Model System

An embodiment of ELIMSA is applied to the dectection of PSA over a range of plasma concentrations from hundred of nano grams to on the order of 1 pico grams in patients serum using the same assay. The prostate specific antigen (PSA) has a concentration distribution from picogram to nano gram amounts in 100 µl of normal human plasma (NHP) from men and so it is often near or below UV-VIS or ECL detection (46). The quantification of PSA over the complete range of NHP is challenging by ELISA (46) or mass spectral methods (20) and many normal samples are below the detection limit of the assay. Thus PSA is good model system to show the increased sensitivity of the ELIMSA system.

Linearity of LC-ESI-MS for Adenosine and 13 C Adenosine

It is demonstrated above that an enzyme linked immunosorbant assay of the colorimetric enzyme substrates amplex red and naphthol AS-MX phosphate can be measured by liquid chromatography, electropspray ionization and mass spectrometry (LC-ESI-MS) with greater sensitivity than UV-VIS or ECL based detection. Here the same specific PSA calibrant, capture and detection reagents used previously were tested with the novel ELIMSA substrate AMP (42). UV-VIS detection is agreed to be linear after taking the logarithm of the ratio of incident over transmitted light. In contrast, it has been stated that the relationship between mass spectral intensity and quantity is complex (50) and this necessitates the use of isotopic or isobaric labels. A linear relationship between log ion intensity and quantity was observed for some blood peptides or fragment ions, peptide standards, resorufin, naphthol AS-MX, and in the present experiment adenosine (A) that were all shown to be linear after simple log transformation and as described (26, 42, 48, 49).

Advantages of Adenonsine Monophosphate (AMP) Substrate

The substrate adenosine monophosphate (AMP) has several important practical advantages in that the enzyme product adenosine (A) is basic, ionizes readily but is also hydrophilic and elutes rapidly with a symmetrical peak. Adenosine shows a more predictable chromatography, is not strongly retained, and does not show a creeping increase in baseline over the course of measurement. The use of AMP has an important additional advantage in that the enzyme substrate AMP is a common metabolite that is widely available in 13C isotope labeled form that can be used as an internal standard to demonstrate absolute quantification by ELIMSA. Thus to address the issue of transformation, linearity and absolute quantification in ELIMSA by LC-ESI-MS, the ELIMSA experiments were controlled with internal, and external, 13C labelled adenosine (13C A) standards to confirm the quantification of the enzyme product. If mass spectrometry is log linear and normal for PA, then instead of using UV-VIS spectroscopy to read the 96 well ELISA plate, the production of the colorless A could be measured using LC-MS with a sensitive ion trap (42). Alkaline phosphatase (AP) is a near perfect enzyme (43) that may be conjugated by glutaraldehyde to the bacterial protein streptavidin (AP-SA) (16) and used to detect biotinylated probes (17) and, the hydrophilic substrate adenosine mono phosphate (AMP), converted by AP-SA to adenosine, resolved well in isocratic LC and ionized very efficiently in an electrospray (19).

Utility of ELIMSA

At present ECL detection is the most practical high sensitivity system for measuring analytes to low levels without the use of radioactivity and so the sensitivity of ECL was compared by two independent methods to an embodiment of ELIMSA. An attempt to determine the lower limits of sensitivity of the ELIMSA assay for blood proteins. However, PSA was successfully measured from patients with prostectomy and from female subjects while many of these ultra low samples were below detection by ECL based methods. It was previously showed that mass spectral intensity values are linear and normal for some, but not all compounds, after log transformation (26). Since the concentration of blood protein should be normally distributed, the normality of the PSA results of ELIMSA was examined. In order to demonstrate that ELIMSA was linear and accurate, the results of the PSA ELIMSA measured, were compared against external PSA standards, external adenosine standard curves, and internal 13C adenosine one point calibration. The requirement of statistical analysis by ANOVA is that the data s randomly and independently samples from a normal population. The capacity to measure attomole amounts of blood proteins with an assay that is sensitive and normal may have great application to biomedical research and permit the common analysis of may ultra-low abundance analytes for classical statistical analysis by ANOVA.

Materials and Methods

Materials

The NHS-biotin coupling reagent was obtained from Pierce. The prostate specific antigen (PSA) capture and detection antibodies were purchased from Medix Biochemica (Kauniainen, Finland). The PSA calibration antigen was obtained from the Scripps Laboratory (San Diego, Calif.). The AMP, Adenosine (A) and 13C (A) and all other buffers and salts were obtained from Sigma Aldrich chemical company and were of the highest quality available. The alkaline phosphatase-streptavidin (AP-SA) enzyme-probe conjugate was obtained from Jackson ImmunoResearch Laboratories (West Grove, Pa., USA). The liquid chromatography mass spectrometry grade solvents were obtained from Caledon Laboratories (Georgetown, Ontario, Canada).

Immunoassay

The PSA ELIMSA was performed as previously described but with the substitution of the substrate AMP for the substrate AS-MX phosphate (Example 3 and 42). The AMP substrate, PSA standards, and AP-SA probe were dissolved in water on ice, aliquoted and freeze dried for day to day consistency in the assay. The plates were coated with the capture antibody in bicarbonate coating buffer prior to blocking the plates in 1% albumin and 1% goat serum in 1×PBS pH 7.4 prior to incubating the plasma in 1×PBS, 0.05% Na-deoxycholate pH 7.4 for 1 h. After washing the wells three times again with washing buffer the substrate was reacted with the streptavidin-AP or in substrate buffer (20 mM, Tris pH 8.8). Thus the PSA ELISA using the high affinity reagents described here is an excellent model system wherein the experimental assay can be first optimized and tested to ensure there is no background binding and confirm the antibodies and calibrants are working and linear in color assays before switching to ELIMSA to measure the lower standards and concentrations for normal human plasma (NHP).

Liquid Chromatography, Electrospray Ionization and Mass Spectrometry (LC-ESI-MS)

The LC-ESI-MS analysis was performed by manual injection (Rheodyne 1755) of 2 ul of the standard or sample diluted ten-fold in 0.1% acetic acid. The sample was analyzed via an Agilent 1100 high pressure liquid chromatography (HPLC) pump set at 70% acetonitrile in 0.1% acetic acid for isocratic separation over a 300 micron ID×150 mm normal phase column (5 micron particle diameter, 300 Angstrom pore) at 20 µl/min. The normal versus C18 reversed phase columns were compared and while C18 gradient provide sharper peaks it was not as convenient as the isocratic approach. The normal phase produced symmetrical peaks that were resolved from the buffer components with low back pressure and high flow rates for rapid analysis with a stable background over time. The HPLC was coupled via an electrospray source fitted with a metal needle (50) mounted on a linear quadruple ion trap (LTQ XL, Thermo Electron Corporation) (33, 51) as previously described (42). The results were log transformed and the ion intensity results analyzed for normality and linearity (48) using the R open source statistical analysis software. A total of 0.2 micro liters of the adenosine product was injected over the normal-phase isocratic chromatogram, showing the concentration of AP from 1 to 1000 pico grams per ml (See FIG. 61A inset shows detection of as little as 1 pico gram per ml with injection of 2 micro liters ~1.0 E-20 mol on column). FIG. 61B shows the log-linear relationship between AP injected and adenosine intensity.

The reaction was diluted ten fold in 0.1% formic acid, or dried under vacuum and the adenosine product was extracted in 100 micro liters of acetone, prior to injection via HPLC connected to an electrospray source fitted with a metal needle [20] mounted on an ion trap mass spectrometer (LC-ESI-MS). The analysis was performed with an Agilent 1100 high pressure liquid chromatography pump in the isocratic mode over a 300 micron ID×150 mm normal phase column (5 micron particle diameter, 300 Angstrom pore) coupled via an electrospray source to a linear quadruple ion trap (LTQ XL, Thermo Electron Corporation) [29, 42].

Results

Adenosine Dilution Curve

The relationship between the adenosine injected and the ion intensity observed by SIM at 268 m/z [M+H] was established by the injection of adenosine dilution series over a normal-phase isocratic LC-MS. The adenosine dilution curve was linear after log transformation and as little as 50 fmol was clearly detectable by LC-ESI-MS (FIG. 61). Adenosine production showed a log linear relationship between quantity versus the intensity observed as measured using LC-MS with single ion monitoring at 268 m/z [M+H] (FIG. 61A). The plot of log intensity of adenosine [M+H] versus log concentration shows that LC-MS of the enzyme product is inherently linear to at least low femto mol amounts (FIG. 61B).

Enzymatic Reaction

To confirm the ELIMSA resulted from an enzyme dependent reaction the signal for the enzyme product adenosine was monitored by SIM 260 over time and with respect to enzyme concentration. The time course of adenosine production by AP as measured using LC-MS with SIM of adenosine at 268 m/z [M+H] showed that the enzymatic reaction was essentially complete by 3 hours (FIG. 62). After log transformation the intensity of the adenosine peak initially appeared to increase linearly over time but the enzyme reaction approached completion by 3 hours of incubation (FIG. 62B). The adenosine SIM 268 signal was dependent on the enzyme concentration: The high active enzyme AP conjugated to the bacterial protein strepavidin (AP-SA, ~190,000 g per mole) was diluted down to 1 µg per ml or less and then the enzyme was reacted with the substrate AMP to produce adenosine: Injecting 0.2 ul of a 1 pico gram per per ml solution of AP-SA is the equivalent of injecting about 200 femto gram or about 10,000 AP-SA molecules. Known absolute amounts of the alkaline phosphatase-streptavidin probe (AP-SA) from 1 to 1000 pico grams per ml were reacted with a constant excess of AMP substrate and the production of adenosine was measured by injecting 0.2 µl for LC-MS with single ion monitoring at 268 m/z [M+H] that showed clear signal at as low as 200 femto grams of AP-SA that corresponds to on the order of E4 or ten thousand AP-SA molecules or so. Thus fempto gram quantities of AP per ml could be detected by monitoring adenosine production from injection of 0.2 micro liters of sample diluted 10 fold in 0.1% formic acid for the ELIMSA that commonly showed R2 values of ~0.99 (FIG. 63). In absolute terms about 1.05 E-19 100 zepto mol amounts of AP-SA were clearly detectable with a high signal to noise ratio by LC-MS with a simple ion trap mass spectrometer (FIG. 63A) that showed a linear response after log transformation (FIG. 63B). The smallest standard is 200 atto gram which is about 105 yoctomol.

ELIMSA PSA Assay

The PSA assay was linear from 0.1 to 2.5 ng per well with an R-squared: 0.9918 (p-value: 2.062 E-06), and so for the purpose of quantifying NHP that was below detection by colorimetric or ECL, no transformation was required (FIG. 64A). The PSA assay was linear from 0.1 to 2.5 ng per well with an R-squared: 0.9918 (p-value: 2.062 E-06) and log transformation resulted in a linear relationship between intensity SIM 268 m/z versus pico grams of PSA (FIG. 64B). The assay shows a linear relationship to at least picogram amounts of PSA that are well separated from the background and recorded with a high signal to noise compared to the small error in the thickness of the TIC trace compared to the height of the peaks. The assay is sensitive enough to detect the contamination of the AMP substrate with adenosine resulting in a peak at concentration zero ng pico grams PSA that is recorded and subtracted from the SIM 268 values that are extracted from the TIC data.

ELIMSA Homogeneity and Normality

Human plasma PSA values like many continuous biological variable may be expected to show a normal distribution within a population. An aliquoted set of NHP samples was used to estimate the distributions of the PSA values obtained from the ELIMSA assay. The density plot of three replicate days showed that the calculated PSA values showed a Gaussian distribution that centered on about 150 pico grams per well (FIG. 65A). After calculating the mean and standard errors it was apparent that the assay showed accepted inter and intraday variation (FIG. 65B). The error was within 1 day was within 10% of the mean and the error between three independent days was less than 10% of the mean. The quantile plot was used to assess the normality of the entire data set that showed the PSA results from ELIMSA are within the tolerance of the predicted normal distribution shown as the diagonal solid line in the data plot (FIG. 65C). All indications were that ELIMSA results in a normal population of PSA estimates.

ELIMSA Accuracy and Linearity

The PSA standard series apparently resulted in a linear relationship between PSA quantity and intensity of the adenosine ion as measured by SIM 268 m/z. The linearity of the LC-ESI-MS assay for adenosine was tested and compared to: (i) an internal isotope dilution curve; (ii) an internal one point calibration; (iii) an external adenosine curve made from the same stock used to standardize the ELMISA, (iv) an external adenosine curve from a second adenosine stock; and, (v) an external adenosine curve made from the $^{13}$C adenosine standards.

Internal Isotope Dilution Curve

The average of 10 NHP adenosine product measurements were used to calculated the pmol of adenosine 268 m/z from the one point calibration against an internal standard of 50 pmol $^{13}$C added to the sample before LC-ESI-MS/MS. The linearity of the PSA assays was measured alongside 13C adenosine internal isotope dilution curve that showed good linearity and indicated that about 0.59 pmol of adenosine (A) was produced by the ELIMSA of the NHP sample (FIG. 66, Table 7). The average of 10 NHP adenosine product measurements were used to calculate the pmol of adenosine 268 m/z from the one point calibration against an internal standard of 50 pmol $^{13}$C added to the sample before LC-ESI-MS/MS.

Internal One Point 13C Adenosine Calibration

The production of the PSA as measured alongside 13C adenosine internal one point calibration that takes a direct ratio of the intensity of the unknown over the intensity of the known 13C internal standard to estimate the 12C adenosine produced by the ELIMSA assay. The one point calibration is based on the assumption of local linearity between intensity at SIM 268 and SIM 283 with quantity. The one point internal calibration method resulted in the estimate of 0.58 pmol adenosine was produced by the ELIMSA assay (Table 7).

External Adenosine (A) Standard, A from Enzyme-Reacted AMP, and 13C A

External adenosine and 13C adenosine standards were also used to estimate the quantity of adenosine produced from the ELIMSA of NHP samples and to independently confirm the linearity of the LC-ESI-MS assay for adenosine. The linearity of the external standard of adenosine produced by reacting the AMP with excess AP-SA showed an R-squared: 0.9994 (p-value: 2.469E-09) (FIGS. 67&68) and resulted in an estimate of 0.54 pmol Adenosine (Table 7). The linearity of the external standard of 13C adenosine purchased from SIGMA showed an R2 of 0.9998 (p-value: 1.226e-10) (FIGS. 67&68) and resulted in an estimate of 0.27 pmol adenosine. The linearity of the external standard of adenosine from SIGMA showed and R2 of 0.9986 (p-value: 2.319E-08) (FIGS. 67&68) and resulted in an estimate of 0.48 pmol adenosine (Table 7).

Comparison to ELIMSA to Abbott Architect and ECL

The sensitivity of the ELIMSA assay was compared to PSA as measured by the Abbott Architect platform ECL assay and showed excellent agreement at PSA levels above 100 picograms (FIG. 69). However below about 100 picograms per well the Abbott results plunged to near zero and no reliable result could be obtained. In contrast, the ELIMSA method provide values well separated from zero for all samples (FIG. 68). Regression of the ELIMSA results onto the Abbot Architect results for PSA showed an R2 of 0.9212 (p-value: <2.2e-16). A subsequent comparison of ELIMSA to hand made ECL detection also results in good agreement on high abundance samples with an R2 of 0.9227 for ELIMSA explained by the results obtained from ECL. (FIG. 69 inset). The home made ECL system also showed a precipitous drop in signal below about 100 picograms, was sometimes not able to quantify all samples, and some patient samples could not be distinguished from zero by ECL.

Discussion

Sensitivity

The use of ELIMSA was both more sensitive and more linear than electrochemical detection that has previously reached 67 of atto mol of AP but required at least 50 micro liters of sample volume (47, 58). Direct quantification of the generic detection reagent AP-SA by LC-MS permits the quantification of receptor-ligand complexes to at least 1 pico gram per well range and detection of the probe to 1 pico gram per ml range from the injection 0.2 µl from the sample (i.e. ~10 zepto mol amounts of the molecular probe on column). The sensitivity was such that all normal human plasma (NHP) were well within the standards at concentrations far below the detection limit of color, fluorescence or ECL based detection (42). The limit of detection of the assay for PSA could not be determined using normal samples specifically selected for low PSA values, samples from prostectomy patients or samples from female subjects and all of these samples could be clearly resolved from the background and quantified.

ELIMSA of PSA

The ELIMSA for PSA in blood measured was against an external standard curve of the PSA calibrant that showed a linear relationship between the PSA added to the ELIMSA and the log intensity of adenosine as measured by LC-ESI-MS. The log linear results with A were in agreement with log linear results from some standard peptides or peptides from blood proteins (26), resorufin and ASMX Phosphate (42), many peptides and proteins from cells (49) or protein secreted from cells into the experimental media (48). Taken together the results with small molecules, isotopic labels, and many peptides all indicate the LC-ESI-MS is inherently linear for many pure compounds and thus may approach linearity for some from chromatographically pre-separated molecules. The results with the substrate AMP were similar to those of ELIMSA using amplex red or napthol AS-MX phosphate substrates that showed good agreement with ELISA using color at values greater than 1 ng per well. Moreover the results of normal human plasma presented here closely match the correct order of magnitude for PSA in control patients reported in the literature. Thus, multiple lines of evidence in agreement indicate that the ELIMSA standardized against known amounts of the PSA calibrant provides the accurate absolute quantification of PSA. ELIMSA may be used to quantify proteins to at least ~1 picogram levels.

Linearity of LC-ESI-MS for Adenosine and 13C Adenosine

The result with the internal 13C isotope dilution curve was in close agreement with the external A curve and the external 13C A curve indicating the LC-ESI-MS assay for adenosine is linear and normal. The one point calibration method, that assumes linearity, was also in close agreement with the internal isotope dilution curve and two adenosine external standard. Hence four independent methods were within about 1 digit in the same order of magnitude and so in general showed good agreement. In this study, the internal 13C A isotope dilution curve, the external A curve, the external 13C A isotope standard curves and the internal 13C PA, one-point-calibration all supported that mass spectrometry showed a linear relationship with quantity after simple log transformation. The experiments with iosotopic labels herein dispel the belief that LC-ESI-MS cannot be quantitative, or that there is necessarily a complex and poorly understood relationship between ion intensity and quantity (24). The observation that the signal intensity values from mass spectrometry may be linear is consistent with the electrospray ionization process (19) that is a competitive reaction where the presence of other analytes may effect the observed intensity in unpredictable ways (53, 54). The potentially confounding effects of competition for ionization were apparently not a factor when relatively pure analyte PA, dissolved in a 1 mM tris, is efficiently resolved by high pressure liquid chromatography prior ionization, and the results closely approached log linearity. Hence molecules may be absolutely quantified by LC-ESI-MS against external standards without the use of isotopic or isobaric labels. Hence there are multiple lines of evidence in agreement that LC-ESI-MS may provide for the absolute quantification of molecules such as adenosine that may require log transformation to achieve linearity over a wide range of concentrations.

Homogeneity and Normality of ELIMSA

Many biological variables show a normal distribution and it might be expected that the distribution of PSA in a population of normal human plasma samples could be normally distributed. The three main pre-requisites for the comparison of clinical samples by ANOVA is random and independent sampling from a normal population. In this study the application of an ELIMSA method to analyze PSA human plasma samples (FIG. 64A) showed a normal distribution (26). The assay showed reasonable levels of error within 1 day and the error between three independent days was less than 10% of the mean. The high signal to noise ratios and low levels of error associated with the estimated means was observed below 50 pico grams per well with clear signal to the 1 pico gram range.

ELIMSA Versus ECL

This approach of direct quantification of the generic AP-SA molecular probe by LC-MS permits the routine analysis of receptor-ligand complexes with quantification of biological molecules to femto gram, i.e. zepto mol, amounts. The PSA ELIMSA easily detected to the tens of pico grams per well or less and could detect and quantify PSA that was well below the range of the commercial ECL based ELISA or a laboratory ECL assay that both showed a precipitous decline below 100 pico grams per well and was not able to detect many of the plasma PSA levels. Based on the samples tested, ELIMSA brings all patient PSA levels within the limit of quantification. The use of LC-MS to measure enzyme-conjugated molecular probes may be a system for the quantification of proteins, ligands and/or receptors at pico gram amounts or less with good signal to noise values. The demonstrated measurement of AP-SA to the 1 zepto mol is as low a quantity as the most sensitive methods claimed to date (20, 41, 47, 55-66,) but requires only commonly available micro electrospray and a simple ion trap. ELIMSA with the substrate AMP that releases the hydrophilic and basic compound A showed more symmetrical peaks, baseline to baseline separation even at close injection intervals and a much flatter baseline compared to the previous substrate ASMX phosphate and was an improvement to the method. The experiments here with external and internal standards and isotopic dilutions clearly demonstrate that LC-MS may provide linear relationship between intensity and quantity after log transformation: Thus isotopic or isobaric internal standards were not necessarily required to calculate the absolute quantity of a protein or metabolite by LC-ESI-MS. All of the PSA samples in this study were within the range of this assay in the attomole absolute amounts amounts and all of the samples could be estimated by interpolation between known standard amounts. The present log linear results for adensosine and many other compounds including peptides after log transformation opens up broad vistas for the direct quantification of many molecules by mass spectrometry and classical linear models with statistical analysis (26, 42, 48, 49). The experiments here unambiguously demonstrated that enzyme-labelled probes can sensitively quantify proteins or receptor-ligand complexes to vanishingly low amounts by direct mass spectrometric analysis and will have a broad application that greatly extends the practical sensitivity of ELISA bio-molecular analysis.

TABLE 7

Comparison of the estimated production of adenosine by ELIMSA from internal isotope dilution with a 13C AMP.

| Method | Result |
| --- | --- |
| 13C Adenosine isotope dilution | 0.59 p mol A |
| A external curve (XS AP-SA) | 0.54 p mol A |
| 13C A external curve | 0.27 p mol 13C A |
| Adenosine external curve (S) | 0.48 p mol A |
| 13C Adenosine internal ratio | 0.58 p mol A |
| PSA external curve | 0.116 pg PSA |

XS=excess

Example 11

The amplification of the protein binding signal in ELISA by the catalytic production of reporter molecules is the key to the sensitivity of ELISA. The capacity of mass spectrometry to detect femtomole to picomole amounts of molecules, together with the amplification of the signal by reporter enzymes such as the enzyme alkaline phosphatase, results in an ultra-sensitive new method described herein termed ELIMSA that measured attomole to zeptomole amounts of proteins by for example micro electrospray on a simple ion trap. In an embodiment, a ELIMSA substrate, pyridoxamine-5-phosphate (PA5P) is cleaved by the enzyme alkaline phosphatase to yield the basic and hydrophilic product pyridoxamine (PA) that elutes rapidly with a symmetrical peaks and a flat baseline. As shown herein Pyridoxamine (PA) and $^{13}$C PA were both observed to show a linear relationship between log ion intensity and quantity from picomole to femtomole amounts by liquid chromatography electrospray ionization and mass spectrometry. Four independent methods: internal $^{13}$C isotope PA dilution curves, internal $^{13}$C isotope one point calibration, external PA and $^{13}$C PA curves, all agreed within 1 digit in the same order of magnitude on the linear quantification of PA. Here as little as 1 femto gram of alkaline phosphatase bonded to the molecular probe Streptavidin (AP-SA) was detected by the release of PA that showed a log linear intensity relationship with AP-SA quantity as measured by LC-ESI-MS. Hence a mass spectrometer can be used to measure a reporter enzyme such as present in an Enzyme-linked immunosorbent assay that produces pyridoxamine against external proteins standards with great sensitivity and accuracy that provides a system for absolute quantification at 1 pico gram amounts or less.

Example 12

Amino acids as monomers such as phosphotyrosine, phosphoserine or phospho threonine (Table I) and peptides (amino acid polymers) were used as substrates FIG. 70. At least one peptide with at least one amino acid of a characteristic mass may be used as a substrate in a separate ELIMSA reaction where each reaction has a least one peptide or phosphopeptide and where the products of multiple ELIMSA assays may be analyzed at the same time at a separate mass to charge ratio (m/z). For example the peptide pT17: RRLIEDAEpYAARG (MW 1598.7) (SEQ ID NO: 14) and the peptide pT18: TSTEPQpYQPGENL (Mw 1542.5) (SEQ ID NO: 15) may de-phosphorylated by the enzyme AP in separate reactions but the two peptides may be identified by their MS or MS/MS spectra and their intensity measured by separation by liquid chromatography or other means followed by mass spectrometry. Hence at least one or more than one ELIMSA reaction may be measured at the same time or multiplexed by the use of substrates that differ in the mass of the substrate or product that may be distinguished by mass spectrometry to uniquely identify and quantify the sample reaction.

Quantification can be accomplished using internal and/or external isotope standards.

Example 13

Using methods described herein, ELIMSA assays for: myosin Light chain 2 (MLC2) made with antibodies obtained from Fitzgerald; Troponin I made with antibodies from MyBioSource (MBS); Troponin I made with antibodies from Fitzgerald; *E. coli* 0157 made with antibodies from Fitzgerald. Results are shown in FIG. 71. The experiments were all done with AMP as the substrate and at m/z SIM 268.

Example 14

The DNA vector EGFP (enhanced Green Fluorescence protein empty vector) was biotinylated to serve as a probe. The same vector was dried onto nylon hybond membranes alongside a control spot. The spots were cut and placed in 1.5 ml sample tubes. The membrane spots were washed in PBS buffer. The 1 micron gram of the biotinylated probe was added to the filter spots in 1 ml of PBS. The probe was incubated for 30 minutes. The membranes were washed 5 times in PBS. The tube was filled with 0.5 ml of 10 mM tris pH 8.8 reaction buffer. A total of 1 ug of the AP-SA enzyme was added to both the test and control membranes, incubating 30 minutes and washing 5 times. A 1 mM solution of the enzyme substrate AMP was added to the solution. After a 1 hour incubation 1 ul of the resulting reaction was analyzed by LC-ESI-MS at SIM 268 m/z. Thus DNA, was detected using a biotinylated nucleic acid polymer probe.

TABLE 8

| Probe + target | Adensoine 268 m/z control filter | Adenosine 268 m/z |
|---|---|---|
| EGFP vector biotinylated DNA probe | 1057 counts | 4156 counts |

Example 15

Short oligos AA, AAA, AAAA, CCC and CCCC were tested using methods described here. The table provides the intensity values measured in negative mode before and after enzyme. The negative mode was run isocratically in 70% Acetonitrile with 0.1% Ammonium Hydroxide.

TABLE 9

| | MW | MW dephosphorylated | Intensity before | Intensity after adding enzyme AP |
|---|---|---|---|---|
| AA | 644.4 | 564.4 | 4.84E+03 | 1.54E+04 |
| AAA | 957.6 | 877.6 | 6.30E+03 | 1.97E+04 |
| AAAA | 1270.9 | 1190.9 | 8.01E+03 | 1.20E+04 |
| CCC | 885.6 | 805.5 | 2.93E+03 | 8.79E+03 |
| CCCC | 1174.8 | 1094.8 | 7.68E+03 | 8.77E+03 |

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

TABLE I

The infusion screening results of AP and HRP substrates.

| | 0.1% FA | | | | | | 0.1% Amm | | |
|---|---|---|---|---|---|---|---|---|---|
| p nitrophenyl phosphate (AP) | SIM 138 | | Signal to noise ratio | SRM 110 | | Signal to noise ratio | SIM 138 | | Signal to noise ratio |
| | 1.69E+05 | 160000 | | 5.81E+01 | 58 | | 2.89E+05 | 280000 | |
| | 2.15E+05 | 210000 | 1 | 5.69E+01 | 55 | 1 | 2.66E+05 | 250000 | 1 |
| | 3.62E+02 | 600 | 0.002857143 | 5.59E+01 | 55 | 1 | 6.82E+05 | 680000 | 2.72 |
| | 0.1% FA | | | | | | 0.1% Amm | | |
| pyridoxamine 5 phosphate (AP) | SIM 166 | | | SRM 148 | | | SIM 166 | | |
| | 5.09E+03 | 5000 | | 1.27E+02 | 120 | | 1.82E+05 | 180000 | |
| | 2.09E+04 | 20000 | 1 | 1.72E+02 | 160 | 1 | 9.42E+04 | 94000 | 1 |
| | 1.43E+04 | 14000 | 0.7 | 2.78E+02 | 270 | 1.6875 | 2.13E+06 | 2100000 | 22.34042553 |
| | 0.1% FA | | | | | | 0.1% Amm | | |
| Sphingosine (AP) | SIM 298 | | | SRM 206 | | | SIM 297 | | |
| | 4.73E+03 | 5000 | | 4.20E+02 | 420 | | 1.23E+03 | 1200 | |
| | 1.14E+04 | 11000 | 1 | 2.06E+02 | 205 | 1 | 2.08E+03 | 2050 | 1 |
| | 6.90E+04 | 68000 | 6.181818182 | 2.19E+02 | 215 | 1.048780488 | 8.59E+03 | 8400 | 4.097560976 |
| | 0.1% FA | | | | | | 0.1% Amm | | |
| L-(+)-2-amino-6-phosphonohexanoic acid (AP) | SIM 132 | | | SRM 214 | | | SIM 133 | | |
| | 9.15E+03 | 9000 | | 1.56E+03 | 1550 | | 3.44E+02 | 360 | |
| | 1.44E+04 | 14000 | 1 | 3.18E+03 | 3100 | 1 | 4.79E+02 | 480 | 1 |
| | 3.09E+04 | 30000 | 2.142857143 | 2.57E+03 | 2050 | 0.661290323 | 9.30E+01 | 100 | 0.208333333 |
| | 0.1% FA | | | | | | 0.1% Amm | | |

TABLE I-continued

The infusion screening results of AP and HRP substrates.

| | | | | | | | | |
|---|---|---|---|---|---|---|---|---|
| O-phospho-DL-threonine (AP) | SIM 122 | | | SRM 104 | | | SIM 120 | |
| | 5.44E+05 | 540000 | | 2.61E+05 | 260000 | | 2.82E+02 | 280 |
| | 4.86E+06 | 4800000 | 1 | 5.07E+05 | 500000 | 1 | 3.31E+02 | 300 | 1 |
| | 1.87E+07 | 18000000 | 3.75 | 1.36E+06 | 1300000 | 2.6 | 5.74E+02 | 500 | 1.666666667 |
| | 0.1% FA | | | | | | 0.1% Amm | | |
| 5-Bromo-4-chloro-3-indolyl phosphate disodium salt (AP) | SIM 244 | | | SRM 226 | | | SIM 242 | |
| | 1.29E+04 | 13000 | | 9.58E+01 | 94 | | 1.99E+02 | 200 |
| | 1.40E+04 | 14000 | 1 | 2.47E+02 | 240 | 1 | 3.74E+02 | 380 | 1 |
| | 1.22E+04 | 12000 | 0.857142857 | 2.95E+02 | 290 | 1.208333333 | 1.84E+03 | 1800 | 4.736842105 |
| | 0.1% FA | | | | | | 0.1% Amm | | |
| Phenylbenzene ω-phosphono-α-amino acid (AP) | SIM 255 | | | SRM 177 | | | SIM 255 | |
| | 4.32E+04 | 43000 | | 1.48E+02 | 145 | | 2.72E+02 | 270 |
| | 4.04E+04 | 40000 | 1 | 2.45E+02 | 240 | 1 | 3.91E+02 | 390 | 1 |
| | 1.20E+04 | 11800 | 0.295 | 1.11E+02 | 110 | 0.458333333 | 8.31E+02 | 810 | 2.076923077 |
| | 0.1% FA | | | | | | 0.1% Amm | | |
| Naphthol AS-MX phosphate (AP) | SIM 292 | | | SRM 171 | | | SIM 290 | |
| | 3.95E+03 | 4000 | | 5.21E+04 | 52000 | | 2.22E+04 | 22000 |
| | 1.38E+03 | 1300 | 1 | 5.14E+04 | 51000 | 1 | 9.73E+03 | 9600 | 1 |
| | 2.86E+05 | 280000 | 215.3846154 | 1.62E+05 | 160000 | 3.137254902 | 1.96E+05 | 195000 | 20.3125 |
| | 0.1% FA | | | | | | 0.1% Amm | | |
| 4-Methylumbelliferyl phosphate (4-MUP) (AP) | SIM 231 | | | SRM 185 | | | SIM 231 | |
| | 1.98E+04 | 20000 | | 3.37E+02 | 330 | | 1.13E+02 | 110 |
| | 1.50E+04 | 15000 | 1 | 3.93E+02 | 390 | 1 | 1.20E+02 | 120 | 1 |
| | 1.36E+04 | 13500 | 0.9 | 3.09E+02 | 300 | 0.769230769 | 1.91E+02 | 190 | 1.583333333 |
| | 0.1% FA | | | | | | 0.1% Amm | | |
| Ampliflu Red DI (HRP) | SIM 214 | | | SRM 186 | | | | |
| | 1.49E+04 | 14500 | | 1.13E+02 | 110 | | | |
| | 7.63E+04 | 76000 | 1 | 2.05E+02 | 200 | 1 | | |
| | 1.16E+05 | 116000 | 1.526315789 | 1.51E+02 | 150 | 0.75 | | |
| | 0.1% FA | | | | | | | |
| Ampliflu Red Column (HRP) | SIM 214 | | | | | | | |
| | 1.07E+05 | 107000 | 1 | | | | | |
| | 8.65E+05 | 965000 | 9.018691589 | | | | | |
| | 0.1% FA | | | | | | | |
| Lumigen TMA6 DI (HRP) | SIM 272 | | | SRM 254 | | | | |
| | 3.48E+02 | 3400 | | 1.26E+02 | 125 | | | |
| | 6.93E+03 | 6800 | 1 | 1.05E+02 | 104 | 1 | | |
| | 3.04E+05 | 300000 | 44.11764706 | 2.36E+02 | 235 | 2.259615385 | | |
| | 0.1% FA | | | | | | | |
| Lumigen TMA6 Column (HRP) | SIM 272 | | | | | | | |
| | 1440000 | 1440000 | 1 | | | | | |
| | 5330000 | 5330000 | 3.701388889 | | | | | |

| | | | | 70% MeOH | | | | | |
|---|---|---|---|---|---|---|---|---|---|
| p nitrophenyl phosphate (AP) | SRM 108 | | Signal to noise ratio | SIM 138 | | Signal to noise ratio | SRM 110 | | Signal to noise ratio |
| | 7.48E+02 | 740 | | 2.20E+05 | 230000 | | 1.44E+01 | 14 | |
| | 7.24E+02 | 720 | 1 | 2.43E+05 | 240000 | 1 | 6.81E+00 | 6.8 | 1 |
| | 1.50E+03 | 1450 | 2.013888889 | 2.54E+04 | 25000 | 0.104166667 | 2.17E+00 | 2.2 | 0.323529412 |
| | | | | 70% MeOH | | | | | |
| pyridoxamine 5 phosphate (AP) | SRM 138 | | | SIM 166 | | | SRM 138 | | |
| | 5.11E+03 | 5000 | | 2.33E+04 | 23000 | | 3.20E+01 | 32 | |
| | 4.24E+03 | 4200 | 1 | 1.76E+04 | 17500 | 1 | 1.54E+01 | 15 | 1 |
| | 2.24E+03 | 2200 | 0.523809524 | 2.27E+03 | 2200 | 0.125714286 | 2.47E+02 | 240 | 16 |
| | | | | 70% MeOH | | | | | |
| Sphingosine (AP) | SRM 279 | | | SIM 297 | | | SRM 279 | | |
| | 4.00E+01 | 40 | | 9.92E+03 | 9800 | | 6.06E+01 | 60 | |
| | 4.29E+01 | 42 | 1 | 7.94E+03 | 7800 | 1 | 7.27E+01 | 72 | 1 |
| | 3.47E+01 | 34 | 0.80952381 | 1.78E+04 | 17500 | 2.243589744 | 8.89E+02 | 880 | 12.22222222 |
| | | | | 70% MeOH | | | | | |
| L-(+)-2-amino-6-phosphonohexanoic acid (AP) | SRM 113 | | | SIM 133 | | | SRM 114 | | |
| | 5.34E+01 | 53 | | 5.09E+04 | 50000 | | 1.57E+03 | 1550 | |
| | 4.96E+01 | 49 | 1 | 3.12E+04 | 31000 | 1 | 2.29E+02 | 225 | 1 |
| | 1.71E+00 | 1.7 | 0.034693878 | 9.34E+03 | 9200 | 0.296774194 | 3.26E+01 | 32 | 0.142222222 |
| | | | | 70% MeOH | | | | | |
| O-phospho-DL-threonine (AP) | SRM 74 | | | SIM 122 | | | SRM104 | | |
| | 2.55E+02 | 250 | | 1.56E+06 | 1550000 | | 1.43E+05 | 140000 | |
| | 1.77E+02 | 170 | 1 | 1.37E+07 | 13500000 | 1 | 1.70E+06 | 1650000 | 1 |
| | 2.52E+02 | 250 | 1.470588235 | 2.23E+07 | 23000000 | 1.703703704 | 2.02E+06 | 2000000 | 1.212121212 |
| | | | | 70% MeOH | | | | | |
| 5-Bromo-4-chloro-3-indolyl phosphate disodium salt (AP) | SRM 198 | | | SIM 243 | | | SRM 225 | | |
| | 1.63E+01 | 16 | | 4.96E+03 | 5000 | | 3.86E+01 | 38 | |
| | 1.66E+01 | 16 | 1 | 3.96E+03 | 4000 | 1 | 3.46E+01 | 34 | 1 |
| | 6.14E+01 | 60 | 3.75 | 1.22E+04 | 12000 | 3 | 3.88E+01 | 39 | 1.147058824 |
| | | | | 70% MeOH | | | | | |

TABLE I-continued

The infusion screening results of AP and HRP substrates.

| | | | | | | | | | |
|---|---|---|---|---|---|---|---|---|---|
| Phenylbenzene ω-phosphono-α-amino acid (AP) | SRM 237 | | | SIM 255 | | | SRM 237 | | |
| | 1.05E+01 | 10 | | 2.95E+03 | 3000 | | 1.54E+01 | 15 | |
| | 1.82E+01 | 18 | 1 | 3.13E+03 | 3000 | 1 | 2.11E+02 | 210 | 1 |
| | 3.07E+01 | 30 | 1.666666667 | 1.22E+04 70% MeOH | 12000 | 4 | 5.84E+02 | 580 | 2.761904762 |
| Naphthol AS-MX phosphate (AP) | SRM 143 | | | SIM 292 | | | SRM 171 | | |
| | 9.83E+03 | 9800 | | 3.00E+05 | 22000 | | 1.76E+05 | 175000 | |
| | 1.56E+04 | 15500 | 1 | 2.01E+05 | 200000 | 1 | 6.47E+04 | 64000 | 1 |
| | 9.57E+04 | 94000 | 6.064516129 | 8.82E+05 70% MeOH | 880000 | 4.4 | 2.53E+05 | 250000 | 3.90625 |
| 4-Methylumbelliferyl phosphate (4-MUP) (AP) | SRM 211 | | | SIM 229 | | | SRM 151 | | |
| | 3.05E+01 | 30 | | 2.57E+03 | 2500 | | 3.30E+01 | 33 | |
| | 3.07E+01 | 30 | 1 | 3.05E+03 | 3000 | 1 | 3.47E+01 | 35 | 1 |
| | 1.01E+02 | 100 | 3.333333333 | 3.24E+04 | 32000 | 10.66666667 | 3.28E+01 | 32 | 0.914285714 |

TABLE II

Oxidation of the chemilumnescent HRP substrate Lumigen ® TMA-3 in the presence of $H_2O_2$ and HRP

| | TMA-3 Substrate | | TMA-3 Product | |
|---|---|---|---|---|
| Reaction | m/z | Ion intensity | m/z | Ion intensity |
| Lumigen TMA-3 | 504.4 | 4.17 × 104 | 286.21 | 4.50 × 104 |
| Lumigen TMA-3 + H2O2 | 504.26 | 2.95 × 104 | 286.26 | 6.35 × 104 |
| Lumigen TMA-3 + H2O2 + HRP | 504.4 | 3.50 × 104 | 286.16 | 1.12 × 106 |

TABLE III

Oxidation of the chemilumiscent HRP substrate Lumigen ® TMA-6 in the presence of $H_2O_2$ and HRP.

| | TMA-6 Substrate | | TMA-6 Product | |
|---|---|---|---|---|
| Reaction | m/z | Ion intensity | m/z | Ion intensity |
| Lumigen TMA-6 | 534.59 | 1.42 × 105 | 272.21 | 4.86 × 104 |
| Lumigen TMA-6 + H2O2 | 534.61 | 1.60 × 105 | 272.13 | 3.35 × 105 |
| Lumigen TMA-6 + H2O2 + HRP | 534.44 | 8.44 × 104 | 272.16 | 3.77 × 105 |

CITATIONS FOR REFERENCES REFERRED TO IN THE SPECIFICATION

1. Low, T. L., Liu, Y. S., Putnam, F. W. (1976) Structure, function, and evolutionary relationships of Fc domains of human immunoglobulins A, G, M, and E. *Science* 191, 390-2.
2. Engvall, E., Perlman, P. (1971) Enzyme-linked immunosorbent assay (ELISA). Quantitative assay of immunoglobulin G. *Immunochemistry* 8, 871-4.
3. Van Weemen, B. K., Schuurs, A. B. (1971) Immunoassay using antigen-enzyme conjugates. *FEBS Lett* 15, 232-236.
4. Wilchek, M., Jakoby, W. B. (1974) The literature on affinity chromatography. *Methods Enzymol* 34, 3-10.
5. Pearson, T., Galfre, G., Ziegler, A., Milstein, C. (1977) A myeloma hybrid producing antibody specific for an allotypic determinant on "IgD-like" molecules of the mouse. *Eur J Immunol* 7, 684-90.
6. Bayse, G. S., Michaels, A. W., Morrison, M. (1972) The peroxidase-catalyzed oxidation of tyrosine. *Biochim Biophys Acta* 284, 34-42.
7. Gilabert, M. A., Fenoll, L. G., Garcia-Molina, F., Garcia-Ruiz, P. A., Tudela, J., Garcia-Canovas, F., Rodriguez-Lopez, J. N. (2004) Stereospecificity of horseradish peroxidase. *Biol Chem* 385, 1177-84.
8. Conyers, S. M., Kidwell, D. A. (1991) Chromogenic substrates for horseradish peroxidase. *Anal Biochem* 192, 207-11.
9. Filomeni, M., Siesto, A. J. (1951) [Micromethod for photometric determination of peroxides by reaction with luminol. Determination of hydrogen peroxide and ethyl peroxide]. *Boll Soc Ital Biol Sper* 27, 1096-8.
10. Zhou, M., Diwu, Z., Panchuk-Voloshina, N., Haugland, R. P. (1997) A stable nonfluorescent derivative of resorufin for the fluorometric determination of trace hydrogen peroxide: applications in detecting the activity of phagocyte NADPH oxidase and other oxidases. *Anal Biochem* 253, 162-8.
11. Gregory, R. P. (1966) A rapid assay for peroxidase activity. *Biochem J* 101, 582-3.
12. Groome, N. P. (1980) Superiority of ABTS over Trinder reagent as chromogen in highly sensitive peroxidase assays for enzyme linked immunoadsorbent assay. *J Clin Chem Clin Biochem* 18, 345-9.
13. Tsou, K. C., Su, B. C. (1965) A New Colorimetric Method for the Determination of Alkaline Phosphatase with Indoxyl Phosphate. *Anal Biochem* 11, 54-64.
14. Sommer, A. J. (1954) The determination of acid and alkaline phosphatase using p-nitrophenyl phosphate as substrate. *Am J Med Technol* 20, 244-53.
15. Lequin, R. M. (2005) Enzyme immunoassay (EIA)/enzyme-linked immunosorbent assay (ELISA). *Clin Chem* 51, 2415-8.
16. Chaiet, L., Wolf, F. J. (1964) The Properties of Streptavidin, a Biotin-Binding Protein Produced by Streptomycetes. *Arch Biochem Biophys* 106, 1-5.
17. Staros, J. V. (1982) N-hydroxysulfosuccinimide active esters: bis(N-hydroxysulfosuccinimide) esters of two dicarboxylic acids are hydrophilic, membrane-impermeant, protein cross-linkers. *Biochemistry* 21, 3950-5.
18. Yalow, R. S., Berson, S. A. (1960) Immunoassay of endogenous plasma insulin in man *J Clin Invest* 39, 1157-75.
19. Fenn, J. B., Mann, M., Meng, C. K., Wong, S. F., Whitehouse, C. M. (1989) Electrospray ionization for mass spectrometry of large biomolecules. *Science* 246, 64-71.
20. Kulasingam, V., Smith, C. R., Batruch, I., Buckler, A., Jeffery, D. A., Diamandis, E. P. (2008) "Product Ion Monitoring" Assay for Prostate-Specific Antigen in Serum Using a Linear Ion-Trap. *J Proteome Res* 7, 640-647.

21. Shen, Y., Kim, J., Strittmatter, E. F., Jacobs, J. M., Camp, D. G., 2nd, Fang, R., Tolie, N., Moore, R. J., Smith, R. D. (2005) Characterization of the human blood plasma proteome. *Proteomics* 5, 4034-45.
22. Selevsek, N., Matondo, M., Carbayo, M. S., Aebersold, R., Domon, B. (2011) Systematic quantification of peptides/proteins in urine using selected reaction monitoring. *Proteomics*.
23. Zhu, P., Bowden, P., Zhang, D., Marshall, J. G. (2011) Mass spectrometry of peptides and proteins from human blood. *Mass Spectrom Rev* 30, 685-732.
24. Addona, T. A., Abbatiello, S. E., Schilling, B., Skates, S. J., Mani, D. R., Bunk, D. M., Spiegelman, C. H., Zimmerman, L. J., Ham, A. J., Keshishian, H., Hall, S. C., Allen, S., Blackman, R. K., Borchers, C. H., Buck, C., Cardasis, H. L., Cusack, M. P., Dodder, N. G., Gibson, B. W., Held, J. M., Hiltke, T., Jackson, A., Johansen, E. B., Kinsinger, C. R., Li, J., Mesri, M., Neubert, T. A., Niles, R. K., Pulsipher, T. C., Ransohoff, D., Rodriguez, H., Rudnick, P. A., Smith, D., Tabb, D. L., Tegeler, T. J., Variyath, A M., Vega-Montoto, L. J., Wahlander, A., Waldemarson, S., Wang, M., Whiteaker, J. R., Zhao, L., Anderson, N. L., Fisher, S. J., Liebler, D. C., Paulovich, A. G., Regnier, F. E., Tempst, P., Carr, S. A. (2009) Multi-site assessment of the precision and reproducibility of multiple reaction monitoring-based measurements of proteins in plasma. *Nat Biotechnol* 27, 633-41.
25. Gallien, S., Duriez, E., Demeure, K., Domon, B. (2012) Selectivity of LC-MS/MS analysis: Implication for proteomics experiments. *J Proteomics*.
26. Bowden, P., Thavarajah, T., Zhu, P., McDonell, M., Thiele, H., Marshall, J. G. (2012) Quantitative statistical analysis of standard and human blood proteins from liquid chromatography, electrospray ionization, and tandem mass spectrometry. *J Proteome Res* 11, 2032-47.
27. Marshall, J., Krump, E., Lindsay, T., Downey, G., Ford, D. A., Zhu, P., Walker, P., Rubin, B. (2000) Involvement of cytosolic phospholipase A2 and secretory phospholipase A2 in arachidonic acid release from human neutrophils. *J Immunol* 164, 2084-91.
28. Burke, M. D., Mayer, R. T., Kouri, R. E. (1977) 3-methylcholanthrene-induced monooxygenase (O-deethylation) activity of human lymphocytes. Cancer Res 37, 460-3.
29. Bothner, B., Chavez, R., Wei, J., Strupp, C., Phung, Q., Schneemann, A., Siuzdak, G. (2000) Monitoring enzyme catalysis with mass spectrometry. *J Biol Chem* 275, 13455-9.
30. Luo, T., Zhang, X., Wakeel, A., Popov, V. L., McBride, J. W. (2008) A variable-length PCR target protein of *Ehrlichia chaffeensis* contains major species-specific antibody epitopes in acidic serine-rich tandem repeats. *Infect Immun* 76, 1572-80.
31. Haan, C., Behrmann, I. (2007) A cost effective non-commercial ECL-solution for Western blot detections yielding strong signals and low background. *J Immunol Methods* 318, 11-9.
32. Guzzetta, A. W., Thakur, R. A., Mylchreest, I. C. (2002) A robust micro-electrospray ionization technique for high-throughput liquid chromatography/mass spectrometry proteomics using a sanded metal needle as an emitter. *Rapid Commun Mass Spectrom* 16, 2067-72.
33. Schwartz, J. C., Senko, M. W., Syka, J. E. (2002) A two-dimensional quadrupole ion trap mass spectrometer. *J Am Soc Mass Spectrom* 13, 659-69.
34. Wuhrer M, van Remoortere A, Balog C I, Deelder A M, Hokke C H., Ligand identification of carbohydrate-binding proteins employing a biotinylated glycan binding assay and tandem mass spectrometry. Anal Biochem. 2010 Nov. 15; 406(2):132-40.
35. Zhang D W, Sun C J, Zhang F T, Xu L, Zhou Y L, Zhang X X., An electrochemical aptasensor based on enzyme linked aptamer assay. Biosens Bioelectron. 2012 Jan. 15; 31(1):363-8.
36. Mallet F, Hebrard C, Brand D, Chapuis E, Cros P, Allibert P, Besnier J M, Barin F, Mandrand B. Enzyme-linked oligosorbent assay for detection of polymerase chain reaction-amplified human immunodeficiency virus type 1. J Clin Microbiol. 1993 June; 31(6):1444-9.
37. Palermo F A, Cocci P, Angeletti M, Polzonetti-Magni A, Mosconi G. Chemosphere. PCR-ELISA detection of estrogen receptor β mRNA expression and plasma vitellogenin induction in juvenile sole (Solea solea) exposed to waterborne 4-nonylphenol. 2012 March; 86(9):919-25.
38. Kumada Y, Ohigashi Y, Emori Y, Imamura K, Omura Y, Kishimoto M. Improved lectin ELISA for glycosylation analysis of biomarkers using PS-tag-fused single-chain Fv. J Immunol Methods. 2012 Nov. 30; 385(1-2):15-22.
39. Petrosian A M, Britan A V. [Lectin-enzyme assay as a method of estimation of immunoglobulins' glycosylation]. Ukr Biokhim Zh. 2006 July-August; 78(4):151-9.
40. Darwish I A, Al-Obaid A R, Al-Malaq H A. Novel enzyme-linked immunosorbent assay for determination of fluvastatin in plasma at picogram level. Talanta. 2009 Nov. 15; 80(1):179-83.
41. Diamandis, E. P. (1988) Immunoassays with time-resolved fluorescence spectroscopy: principles and applications. *Clin Biochem* 21, 139-150.
42. Florentinus-Mefailoski, A., Safi, F., and Marshall, J. G. (2014) Enzyme Linked Immuno Mass Spectrometric Assay (ELIMSA). *J Proteomics* 96, 343-352.
43. Simopoulos, T. T., and Jencks, W. P. (1994) Alkaline phosphatase is an almost perfect enzyme. *Biochemistry* 33, 10375-10380.
44. Pris, A. D., Mondello, F. J., Wroczynski, R. J., Murray, A. J., Boudries, H., Surman, C. M., and Paxon, T. L. (2009) Improved specific biodetection with ion trap mobility spectrometry (ITMS): a 10-min, multiplexed, immunomagnetic ELISA. *Anal Chem* 81, 9948-9954.
45. Hempen, C., van Leeuwen, S. M., Luftmann, H., and Karst, U. (2005) Liquid chromatographic/mass spectrometric investigation on the reaction products in the peroxidase-catalyzed oxidation of o-phenylenediamine by hydrogen peroxide. *Anal Bioanal Chem* 382, 234-238.
46. Black, M. H., Grass, C. L., Leinonen, J., Stenman, U. H., and Diamandis, E. P. (1999) Characterization of monoclonal antibodies for prostate-specific antigen and development of highly sensitive free prostate-specific antigen assays. *Clin Chem* 45, 347-354.
47. Chikkaveeraiah, B. V., Bhirde, A. A., Morgan, N. Y., Eden, H. S., and Chen, X. (2012) Electrochemical immunosensors for detection of cancer protein biomarkers. *ACS Nano* 6, 6546-6561.
48. Florentinus, A. K., Bowden, P., Sardana, G., Diamandis, E. P., and Marshall, J. G. (2012) Identification and quantification of peptides and proteins secreted from prostate epithelial cells by unbiased liquid chromatography tandem mass spectrometry using goodness of fit and analysis of variance. *J Proteomics* 75, 1303-1317.
49. Florentinus, A. K., Jankowski, A., Petrenko, V., Bowden, P., and Marshall, J. G. (2011) The Fc receptor-cytoskeleton complex from human neutrophils. *J Proteomics* 75, 450-468.

50. Chelius, D., Huhmer, A. F., Shieh, C. H., Lehmberg, E., Traina, J. A., Slattery, T. K., and Pungor, E., Jr. (2002) Analysis of the adenovirus type 5 proteome by liquid chromatography and tandem mass spectrometry methods. *J Proteome Res* 1, 501-513.
51. Stafford, G., Jr. (2002) Ion trap mass spectrometry: a personal perspective. *J Am Soc Mass Spectrom* 13, 589-596.
52. Aebersold, R., and Maim, M. (2003) Mass spectrometry-based proteomics. *Nature* 422, 198-207.
53. Tang, K., Page, J. S., and Smith, R. D. (2004) Charge competition and the linear dynamic range of detection in electrospray ionization mass spectrometry. *J Am Soc Mass Spectrom* 15, 1416-1423.
54. Chowdhury, S. K., Katta, V., and Chait, B. T. (1990) Electrospray ionization mass spectrometric peptide mapping: a rapid, sensitive technique for protein structure analysis. *Biochem Biophys Res Commun* 167, 686-692.
55. Salehpour, M., Possnert, G., and Bryhni, H. (2008) Subattomole sensitivity in biological accelerator mass spectrometry. *Anal Chem* 80, 3515-3521.
56. Liu, G., Wang, J., Kim, J., Jan, M. R., and Collins, G. E. (2004) Electrochemical coding for multiplexed immunoassays of proteins. *Anal Chem* 76, 7126-7130.
57. Lohmann, W., Hayen, H., and Karst, U. (2008) Covalent Protein Modification by Reactive Drug Metabolites Using Online Electrochemistry/Liquid Chromatography/Mass Spectrometry. *Anal Chem.*
58. Munge, B., Liu, G., Collins, G., and Wang, J. (2005) Multiple enzyme layers on carbon nanotubes for electrochemical detection down to 80 DNA copies. Anal Chem 77, 4662-4666.
59. Rozet, E., Morello, R., Lecomte, F., Martin, G. B., Chiap, P., Crommen, J., Boos, K. S., and Hubert, P. (2006) Performances of a multidimensional on-line SPE-LC-ECD method for the determination of three major catecholamines in native human urine: validation, risk and uncertainty assessments. *J Chromatogr B Analyt Technol Biomed Life Sci* 844, 251-260.
60. Takatsy, A., Boddi, K., Nagy, L., Nagy, G., Szabo, S., Marko, L., Wittmann, I., Ohmacht, R., Ringer, T., Bonn, G. K., Gjerde, D., and Szabo, Z. (2009) Enrichment of Amadori products derived from the nonenzymatic glycation of proteins using microscale boronate affinity chromatography. *Anal Biochem* 393, 8-22.
61. Tang, C. K., Vaze, A., and Rusling, J. F. (2012) Fabrication of immunosensor microwell arrays from gold compact discs for detection of cancer biomarker proteins. *Lab Chip* 12, 281-286.
62. Valentini, F., Compagnone, D., Gentili, A., and Palleschi, G. (2002) An electrochemical ELISA procedure for the screening of 17beta-estradiol in urban waste waters. *Analyst* 127, 1333-1337.
63. Zhang, S., Yang, J., and Lin, J. (2008) 3,3'-diaminobenzidine (DAB)-H2O2-HRP voltammetric enzyme-linked immunoassay for the detection of carcionembryonic antigen. Bioelectrochemistry 72, 47-52.
64. Shi, T., Sun, X., Gao, Y., Fillmore, T. L., Schepmoes, A. A., Zhao, R., He, J., Moore, R. J., Kagan, J., Rodland, K. D., Liu, T., Liu, A. Y., Smith, R. D., Tang, K., Camp, D. G., 2nd, and Qian, W. J. (2013) Targeted quantification of low ng/mL level proteins in human serum without immunoaffinity depletion. *J Proteome Res* 12, 3353-3361.
65. Cook, D. B., and Self, C. H. (1993) Determination of one thousandth of an attomole (1 zeptomole) of alkaline phosphatase: application in an immunoassay of proinsulin. *Clin Chem* 39, 965-971.
66. Kricka, L. J. (1993) Ultrasensitive immunoassay techniques. *Clin Biochem* 26, 325-331.
67. Tucholska, M., Bowden, P., Jacks, K., Zhu, P., Furesz, S., Dumbrovsky, M., Marshall, J. (2009) Human Serum Proteins Fractionated by Preparative Partition Chromatography Prior to LC-ESI-MS/MS. *J Proteome Res* 8, 1143-55.
68. Bowden, P., Pendrak, V., Zhu, P., Marshall, J. G. (2010) Meta sequence analysis of human blood peptides and their parent proteins. *J Proteomics* 73, 1163-75.
69. Bowden, P., Beavis, R., Marshall, J. (2009) Tandem mass spectrometry of human tryptic blood peptides calculated by a statistical algorithm and captured by a relational database with exploration by a general statistical analysis system. *J Proteomics* 73, 103-11.
70. Florentinus, A. K., Bowden, P., Barbisan, V., Marshall, J. (2012) Capture and qualitative analysis of the activated Fc receptor complex from live cells. *Curr Protoc Protein Sci Chapter* 19, Unit 19 22.
71. Jankowski, A., Zhu, P., Marshall, J. G. (2008) Capture of an activated receptor complex from the surface of live cells by affinity receptor chromatography. *Anal Biochem* 380, 235-48.
72. Lerner, M. B., D'Souza, J., Pazina, T., Dailey, J., Goldsmith, B. R., Robinson, M. K., Johnson, A. T. (2012) Hybrids of a genetically engineered antibody and a carbon nanotube transistor for detection of prostate cancer biomarkers. *ACS Nano* 6, 5143-9.
73. Munge, B. S., Coffey, A. L., Doucette, J. M., Somba, B. K., Malhotra, R., Patel, V., Gutkind, J. S., Rusling, J. F. (2011) Nanostructured immunosensor for attomolar detection of cancer biomarker interleukin-8 using massively labeled superparamagnetic particles. *Angew Chem Int Ed Engl* 50, 7915-8.
74. Jie, G. F., Liu, P., Zhang, S. S. (2010) Highly enhanced electrochemiluminescence of novel gold/silica/CdSe-CdS nanostructures for ultrasensitive immunoassay of protein tumor marker. *Chem Commun (Carob)* 46, 1323-5.
75. Guilbault, G. G. (1975) Fluorometric determination of dehydrogenase activity using resorufin. *Methods Enzymol* 41, 53-6.
76. Shibata, A., Morioka, I., Ashi, C., Nagasaki, S., Tode, C., Morikawa, S., Miwa, A., Enomoto, M., Saiki, K., Yokoyama, N., Takeuchi, A., Matsuo, M. (2009) Identification of N-acetyl Proline-Glycine-Proline (acPGP) in human serum of adults and newborns by liquid chromatography-tandem mass spectrometry. *Clin Chim Acta.*
77. Yost, R. A., Enke, C. G. (1979) Triple quadrupole mass spectrometry for direct mixture analysis and structure elucidation. *Anal Chem* 51, 1251-64

The invention claimed is:

1. A method of detecting a target substance comprising the steps:

I.
   a. obtaining a sample for detecting the target substance;
   b. immobilizing the target substance to a solid phase directly by binding the target substance to the solid phase, optionally by adsorption to the solid phase; or immobilizing the target substance to the solid phase indirectly by a capture molecule, coupled to the solid phase that binds the target substance;
   c. incubating the immobilized target substance with a reporter enzyme detection probe in solution under conditions for forming a target: enzyme detection probe complex;
   d. washing the solid phase to remove any unbound reporter enzyme detection probe;
   e. incubating the target: enzyme detection probe complex with a reporter enzyme detection probe substrate in a substrate reaction solution to generate one or more ionizable products; and
   f. detecting one or more of the one or more ionizable products using mass spectrometry (MS); or II.
   a. contacting a sample for detecting the target substance with an immobilized antibody specific for the target substance to produce an immobilized target substance, when the sample comprises a target substance;
   b. contacting the immobilized target substance with a reporter enzyme detection probe, wherein the reporter enzyme detection probe has enzyme activity and wherein the reporter enzyme detection probe is able to bind specifically to the immobilized target substance or a primary detection agent specifically bound to the immobilized target substance, the primary detection agent permitting the reporter enzyme detection probe to bind the immobilized target substance indirectly through the primary detection agent;
   c. contacting the immobilized reporter enzyme detection probe with a substrate which reacts with the enzymatic activity of the reporter enzyme detection probe to generate one or more ionizable products for a period of time; and
   d. detecting one or more of the ionizable products using MS.

2. The method of claim 1 separating the one or more ionizable products prior to detection using MS; optionally wherein the separation is by liquid chromatography.

3. The method of claim 1, wherein the step of detecting the one or more ionizable products using MS comprises ionizing the one or more ionizable products, by electrospray ionization (ESI), MALDI, chemical ionization, electron impact, laser desorption, electrical ionization, or heat ionization to produce one or more product ions with a selected signal to noise ratio, and subjecting the one or more product ions to MS, wherein the selected signal to noise ratio is at least 3, at least 4, at least 5, at least 6, or at least 10.

4. The method of claim 1, wherein the MS is selected from electrospray ionization tandem MS (ESI-MS/MS) or matrix-assisted laser desorption/ionization time-of-flight (MALDI-TOF); and/or wherein detection using MS comprises recording product ion intensity by single ion monitoring (SIM) and/or product ion parent to fragment transition by single reagent monitoring (SRM).

5. The method of claim 1, wherein the reporter enzyme detection probe comprises a primary target binding moiety or a secondary target binding moiety and an enzyme comprising enzymatic activity, wherein the secondary target binding moiety is covalently bound to the reporter enzyme; optionally wherein the reporter enzyme is a phosphatase, lyase, hydrolase, synthase, synthetase, oxidoreductase, dehydrogenase, oxidase, transferease, isomerase, ligase, protease, proteinase, peroxidase, glucose oxidase, myeloperoxidase, oxidase, monooxygenase, cytochrome, decarboxylase, lipase, caspase, amylase, peptidase, transaminase, kinase, DNA or RNA polymerase, restriction enzyme, klenow fragment, or DNA ligase; wherein the primary target binding moiety that binds specifically to the target substance is a binding polypeptide, an aptamer or a nucleic acid; wherein the secondary target binding moiety that comprises avidin, streptavidin, or is a secondary antibody.

6. The method of claim 5, wherein the primary target binding moiety that binds specifically to the target substance is an antibody or an antibody fragment, optionally wherein the antibody is a monoclonal antibody, polyclonal antibody, chimeric antibody, monospecific antibody, dimer or multimer.

7. The method of claim 1, wherein the substrate is readily ionizable under ESI-MS/MS or MALDI-TOF and generates a product ion characterized by a high signal to noise ratio, and the substrate is selected from:
   a. a phosphorylated nucleoside, phosphorylated nucleotide, phosphorylated alkaloid, phosphorylated amino acid, phosphorylated amino acid polymer, or phosphorylated metabolite when the enzyme is alkaline phosphatase (AP);
   b. a compound selected from phenols, amines, amides, aromatic compounds, olefin halogenations, luminol, pyrogallol, 2,2'-azino-bis(3-ethylbenzothiazoline-6-sulphonic acid (ABTS), 10-acetyl-3,7-dihydroxyphenoxazine or resazurin when the reporter enzyme is horseradish peroxidase (HRP); and
   c. opiates, detergents, dye precursor, alcohols, or matrix.

8. The method of claim 7, wherein the substrate is selected from pyridoxamine-5-phosphate (PA5P), p-nitrophenyl phosphate (PNPP), 10-acetyl-3,7-dihydroxyphenoxazine, resazurin, naphthol ASMX phosphate, luminol or other chemiluminescent HRP substrates, sphingosine, 4MUP, L-(+)-2-amino-6-phosphonohexanoic acid, 5-Bromo-4-chloro-3-indolyl phosphate (BCIP), phenylbenzene ω phosphono-α-amino acid, O-phospho-DL-threonine, adenosine monophosphate (AMP), AR (3-amino-9-ethylcarbazole), 4-CN (4-Chloro-1-Naphtol), DAB (3,3'-DiAminoBenzimidine), OPD (o-Phenylene Diamine), TMB (3,3",5,5"-tetramethylbenzidine), pNPP (p-Nitrophenyl Phosphate), NBT (nitroblue tetrazolium), INT (p-iodonitrotetrazolium), MUP (4-Methylumbelliferyl Phosphate), FDP (Fluorescein DiPhosphate), or pyrogallol.

9. The method of claim 1, wherein the substrate reaction solution in step d) comprises Tris buffer, having a pH of about 7 to about 10; and/or wherein the substrate reaction solution comprises a non-ionic non polymeric detergent, deoxycholate, rapigest, octyl-beta-glucopyranoside, octylglucopyranoside, chaps, big chap, non-ionic acid labile surfactants, glucosides, n-Octyl-β-D-glucopyranoside n-Nonyl-β-D-glucopyranoside thioglucosides, n-Octyl-β-D-thioglucopyranoside maltosides, n-Decyl-β-D-maltopyranoside, n-Dodecyl-β-D-maltopyranoside, n-Undecyl-β-D-maltopyranoside, n-Tridecyl-β-D-maltopyranoside, cymal-5, cymal-6, thiomaltosides, n-Dodecyl-β-D-thiomaltopyranoside, alkyl glycosides, octyl glucose neopentyl glycol, polyoxyethylene glycols, NP40, C8E4, C8E5, C10E5, C12E8, and/or C12E9.

10. The method of claim 8, wherein the substrate reaction solution further comprises 4-iodophenylboronic acid when the substrate comprises luminol.

11. The method of claim 1, wherein the step of immobilizing the target substance comprises: coupling a capture molecule to the solid phase by incubating the solid phase with the capture molecule in coating solution, blocking the solid phase with blocking solution, adding the target substance to the solid phase in antigen incubation solution and removing any unbound target substance; wherein the step of incubating the immobilized target substance with a reporter enzyme detection probe in solution under conditions for forming target: enzyme detection probe complexes comprises: incubating the immobilized target substance with primary detection agent and/or reporter enzyme detection probe in detection probe incubation solution; and/or wherein the capture molecule is coupled to the solid phase in a coating solution optionally comprising $Na_2CO_3/NaCHO_3$.

12. The method of claim 1, wherein the target: enzyme detection probe complex is incubated with a reporter enzyme detection probe substrate in a substrate reaction solution to generate one or more ionizable products for a period of time less than 72 hours, less than 24 hours, less than 12 hours, less than 60 minutes, less than 50 minutes, less than 40 minutes, less than 30 minutes, less than 20 minutes, less than 15 min, less than 10 min, less than 5 min, less than 2 min, or less than 1 min.

13. The method of claim 4, wherein the product ion is assayed by SIM and/or SRM using an optimized fragmentation energy and m/z range.

14. The method of claim 8, wherein the substrate is AMP, ADP or ATP and one or the ionizable products generated comprises adenosine, the product ion of which is assayed by SIM at 268 m/z; or the substrate is CMP, CDP or CTP and one or the ionizable products generated comprises cytosine, the product ion of which is assayed by SIM at 283 m/z; or the substrate is AR and one of the one or more ionizable products generated comprises resorufin, the product ion of which is assayed by SIM at 214 m/z and SRM using the major intense fragment at 214-186 m/z; or wherein the substrate is naphthol ASMX phosphate and one of the one or more ionizable products generated comprises dephosphorylated naphthol ASMX, the product ion of which is assayed by SIM at 292 m/z and SRM using the major intense fragment at 292-171 m/z or the substrate is PA5P and one or the ionizable products generated comprises PA, the product ion of which is assayed by SIM at 169 m/z.

15. The method of claim 1, wherein the solid phase is a reaction vessel, and wherein the surface is metal, gold, stainless steel, plastic, glass, silica, polycarbonate, polyester, PVDF, nitrocellulose, cellulose, polystyrene, polymer, iron, magnetic, coated magnetic, and/or fullerene.

16. A method of quantifying the amount of the target substance in a sample comprising the steps:
 a. detecting a target substance according to the method of claim 1; and
 b. quantifying the amount of target substance in the sample based on the intensity of the signal for one or more of the products detected by mass spectrometry.

17. The method of claim 16, wherein the quantification comprises comparing the intensity of the signal for one or more products against signal intensities generated using known quantities of the target substance, under similar conditions.

18. The method of claim 16, wherein the sample is a biological sample, industrial product or environmental sample.

19. The method of claim 16, wherein the target substance is a biopolymer selected from a polypeptide, polynucleotide, lipid, carbohydrate or combination thereof or wherein the target substance is an organism, optionally a microbial species, plant cell, animal cell, fungus, mycoplasma, virus, or bacteria.

20. The method of claim 1, wherein the method is for detecting a plurality of target substances, and each target substance forms a target: enzyme detection probe complex with a different reporter enzyme detection probe.

21. The method of claim 1, wherein the target substance is in or expected to be in the sample in the femtomol, attomol, zeptomol or yoctomol range.

22. The method of claim 5, wherein the reporter enzyme is alkaline phosphatase, horseradish peroxidase, trypsin, or cytochrome C monooxygenase.

23. The method of claim 7, wherein the phosphorylated nucleoside is AMP or CMP and the phosphorylated nucleotide is ATP or CTP.

24. The method of claim 8, wherein the substrate is selected from:
 a. 10-acetyl-3,7-dihydroxyphenoxazine, resazurin, luminol or other chemiluminescent HRP substrates, when the reporter enzyme detection probe comprises HRP; or
 b. naphthol ASMX phosphate, PA5P, AMP, or PNPP, when the reporter enzyme detection probe comprises AP.

25. The method of claim 18, wherein the biological sample is a blood sample, urine sample, fecal sample, effusate or tissue sample.

26. The method of claim 2, wherein the liquid chromatography is high-performance liquid chromatography (HPLC) selected from nanoflow liquid chromatography, partition chromatography, normal-phase chromatography, displacement chromatography, reversed-phase chromatography (RPC), size-exclusion chromatography, Ion-exchange chromatography, bioaffinity chromatography, aqueous normal-phase chromatography, nanoflow liquid chromatography or ultra high performance liquid chromatography (UPLC).

27. The method of claim 19, wherein the biopolymer is a polypeptide selected from a tumour marker, autoantigen, hormone, chemokine, cytokine, cardiac protein or bacteria.

28. The method of claim 27, wherein the tumour marker is prostate specific antigen (PSA) or the cardiac protein is Troponin T; and the bacteria is an *E. Coli* species, *Salmonella* species, *Pseudomonas* species, or anthrax species.

* * * * *

SEQUENCE LISTING

<160> NUMBER OF SEQ ID NOS: 15

<210> SEQ ID NO 1
<211> LENGTH: 6

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n can be adenosine monophosphate, adenosine
      diphosphate or adenosine triphosphate

<400> SEQUENCE: 1 naaaaa                                                                    6

<210> SEQ ID NO 2
<211> LENGTH: 6
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n can be adenosine, adenosine monophosphate or
      adenosine diphosphate

<400> SEQUENCE: 2 naaaaa                                                                    6

<210> SEQ ID NO 3
<211> LENGTH: 7
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is adenosine monophosphate

<400> SEQUENCE: 3 naaaaaa                                                                   7

<210> SEQ ID NO 4
<211> LENGTH: 7
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is adenosine

<400> SEQUENCE: 4 naaaaaa                                                                   7

<210> SEQ ID NO 5
<211> LENGTH: 6
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is adenosine monophosphate

<400> SEQUENCE: 5 nttttt                                                                    6
```

```
<210> SEQ ID NO 6
<211> LENGTH: 8
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is adenosine

<400> SEQUENCE: 6 nttttttt                                                                  8

<210> SEQ ID NO 7
<211> LENGTH: 8
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is adenosine monophosphate

<400> SEQUENCE: 7 nggggggg                                                                  8

<210> SEQ ID NO 8
<211> LENGTH: 9
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is adenosine monophosphate

<400> SEQUENCE: 8 ncccccccc                                                                 9

<210> SEQ ID NO 9
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is adenosine monophosphate

<400> SEQUENCE: 9
natcgatcga tcg                                                           13

<210> SEQ ID NO 10
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is guanosine monophosphate

<400> SEQUENCE: 10 naaaaaaaaa                                                               10
```

```
<210> SEQ ID NO 11
<211> LENGTH: 9
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is cytidine triphosphate

<400> SEQUENCE: 11 naaaaaaaa                                                               9

<210> SEQ ID NO 12
<211> LENGTH: 9
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is uridine monophosphate

<400> SEQUENCE: 12 ngccgttaa                                                               9

<210> SEQ ID NO 13
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is adenosine monophosphate
<220> FEATURE:
<221> NAME/KEY: misc_feature
<222> LOCATION: (2)..(2)
<223> OTHER INFORMATION: n can be a, c, g or t
<220> FEATURE:
<221> NAME/KEY: misc_feature
<222> LOCATION: (3)..(3)
<223> OTHER INFORMATION: n can be a, c, g or t
<220> FEATURE:
<221> NAME/KEY: misc_feature
<222> LOCATION: (4)..(4)
<223> OTHER INFORMATION: n can be absent or present and can be a, c, g
     or t when present
<220> FEATURE:
<221> NAME/KEY: misc_feature
<222> LOCATION: (5)..(5)
<223> OTHER INFORMATION: n can be absent or present and can be a, c, g
     or t when present
<220> FEATURE:
<221> NAME/KEY: misc_feature
<222> LOCATION: (6)..(6)
<223> OTHER INFORMATION: n can be absent or present and can be a, c, g
     or t when present
<220> FEATURE:
<221> NAME/KEY: misc_feature
<222> LOCATION: (7)..(7)
<223> OTHER INFORMATION: n can be absent or present and can be a, c, g
     or t when present
<220> FEATURE:
<221> NAME/KEY: misc_feature
<222> LOCATION: (8)..(8)
<223> OTHER INFORMATION: n can be absent or present and can be a, c, g
     or t when present
<220> FEATURE:
<221> NAME/KEY: misc_feature
```

```
<222> LOCATION: (9)..(9)
<223> OTHER INFORMATION: n can be absent or present and can be a, c, g
      or t when present
<220> FEATURE:
<221> NAME/KEY: misc_feature
<222> LOCATION: (10)..(10)
<223> OTHER INFORMATION: n can be absent or present and can be a, c, g
      or t when present
<220> FEATURE:
<221> NAME/KEY: misc_feature
<222> LOCATION: (11)..(11)
<223> OTHER INFORMATION: n can be absent or present and can be a, c, g
      or t when present
<220> FEATURE:
<221> NAME/KEY: misc_feature
<222> LOCATION: (12)..(12)
<223> OTHER INFORMATION: n can be absent or present and can be a, c, g
      or t when present
<220> FEATURE:
<221> NAME/KEY: misc_feature
<222> LOCATION: (13)..(13)
<223> OTHER INFORMATION: n can be absent or present and can be a, c, g
      or t when present
<220> FEATURE:
<221> NAME/KEY: misc_feature
<222> LOCATION: (14)..(14)
<223> OTHER INFORMATION: n can be absent or present and can be a, c, g
      or t when present
<220> FEATURE:
<221> NAME/KEY: misc_feature
<222> LOCATION: (15)..(15)
<223> OTHER INFORMATION: n can be absent or present and can be a, c, g
      or t when present
<220> FEATURE:
<221> NAME/KEY: misc_feature
<222> LOCATION: (16)..(16)
<223> OTHER INFORMATION: n can be absent or present and can be a, c, g
      or t when present

<400> SEQUENCE: 13
nnnnnnnnnn nnnnnn                                                     16

<210> SEQ ID NO 14
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is phosphorylated tyrosine

<400> SEQUENCE: 14

Arg Arg Leu Ile Glu Asp Ala Glu Xaa Tyr Ala Ala Arg Gly
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is phosphorylated tyrosine

<400> SEQUENCE: 15

Thr Ser Thr Glu Pro Gln Xaa Tyr Gln Pro Gly Glu Asn Leu
1               5                   10
```